US010465213B2

(12) United States Patent
Liao et al.

(10) Patent No.: US 10,465,213 B2
(45) Date of Patent: Nov. 5, 2019

(54) MICROORGANISMS AND METHODS FOR THE PRODUCTION OF FATTY ACIDS AND FATTY ACID DERIVED PRODUCTS

(71) Applicant: Cargill, Incorporated, Wayzata, MN (US)

(72) Inventors: Hans Liao, Superior, CO (US); Eileen Spindler, Lafayette, CO (US); Joseph R. Warner, San Clemente, CA (US); Michael Louie, Broomfield, CO (US); Wendy Ribble, Arvada, CO (US); Brittany Prather, Boulder, CO (US); Ron Evans, Boulder, CO (US); Tanya E. W. Lipscomb, Boulder, CO (US); Michael D. Lynch, Westminster, CO (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/083,924

(22) Filed: Mar. 29, 2016

(65) Prior Publication Data

US 2016/0340700 A1 Nov. 24, 2016

Related U.S. Application Data

(63) Continuation of application No. 13/963,858, filed on Aug. 9, 2013, now abandoned.

(60) Provisional application No. 61/682,138, filed on Aug. 10, 2012, provisional application No. 61/682,127, filed on Aug. 10, 2012.

(51) Int. Cl.

| | |
|---|---|
| ***C12N 9/04*** | (2006.01) |
| ***C12N 9/10*** | (2006.01) |
| ***C12N 9/12*** | (2006.01) |
| ***C12P 7/64*** | (2006.01) |
| ***C12P 7/04*** | (2006.01) |
| ***C12P 7/44*** | (2006.01) |
| ***C12N 1/21*** | (2006.01) |
| ***C12R 1/19*** | (2006.01) |
| ***C12N 15/52*** | (2006.01) |
| ***C12P 7/40*** | (2006.01) |
| ***C12N 9/02*** | (2006.01) |

(52) U.S. Cl.

CPC ............ *C12P 7/6409* (2013.01); *C12N 9/001* (2013.01); *C12N 9/0006* (2013.01); *C12N 9/1029* (2013.01); *C12N 15/52* (2013.01); *C12P 7/04* (2013.01); *C12P 7/40* (2013.01); *C12R 1/19* (2013.01); *C12Y 101/01157* (2013.01); *C12Y 103/01009* (2013.01); *C12Y 203/01194* (2013.01)

(58) Field of Classification Search

None

See application file for complete search history.

(56) References Cited

U.S. PATENT DOCUMENTS

| | | | |
|---|---|---|---|
| 2,406,889 | A | 10/1946 | Short et al. |
| 2,464,768 | A | 3/1949 | Griffin et al. |
| 2,469,701 | A | 5/1949 | Redmon et al. |
| 2,798,053 | A | 7/1957 | Brown et al. |
| 3,687,885 | A | 8/1972 | Murray et al. |
| 3,872,037 | A | 3/1975 | MacLeod |
| 3,875,101 | A | 4/1975 | MacLeod |
| 3,891,591 | A | 6/1975 | Chang et al. |
| 3,904,685 | A | 9/1975 | Shahidi |
| 3,915,921 | A | 10/1975 | Schlatzer |
| 4,029,577 | A | 6/1977 | Godlewski et al. |
| 4,268,641 | A | 5/1981 | Koenig et al. |
| 4,301,266 | A | 11/1981 | Muenster et al. |
| 4,431,547 | A | 2/1984 | Dubin et al. |
| 4,666,983 | A | 5/1987 | Tsubakimoto et al. |
| 4,685,915 | A | 8/1987 | Hasse et al. |
| 4,708,997 | A | 11/1987 | Stanley et al. |
| 4,734,478 | A | 3/1988 | Tsubakimoto et al. |
| 4,857,610 | A | 8/1989 | Pauen et al. |
| 4,952,505 | A | 8/1990 | Cho |
| 4,985,518 | A | 1/1991 | Alexander et al. |
| 5,009,653 | A | 4/1991 | Osborn |
| 5,093,472 | A | 3/1992 | Bresciani |
| 51,356,177 | | 8/1992 | Yamaguchi et al. |
| 5,145,906 | A | 9/1992 | Chambers et al. |
| 5,180,798 | A | 1/1993 | Nakamura et al. |
| 5,252,474 | A | 10/1993 | Macneil et al. |

(Continued)

FOREIGN PATENT DOCUMENTS

| | | | |
|---|---|---|---|
| CA | 2520795 | A1 | 10/2004 |
| CA | 2591599 | A1 | 7/2006 |

(Continued)

OTHER PUBLICATIONS

Okamura et al., Unprecedented acetoacetyl-coenzyme A synthesizing enzyme of thiolase superfamily involved in the mevalonate pathway, Proc. Natl. Acad. Sci. USA, 2010, 107, 11265-70.*

(Continued)

*Primary Examiner* — Robert B Mondesi

*Assistant Examiner* — Todd M Epstein

(57) ABSTRACT

This invention relates to metabolically engineered microorganism strains, such as bacterial strains, in which there is an increased utilization of malonyl-CoA for production of a fatty acid or fatty acid derived product, wherein the modified microorganism produces fatty acyl-CoA intermediates via a malonyl-CoA dependent but malonyl-ACP independent mechanism.

9 Claims, 7 Drawing Sheets

Specification includes a Sequence Listing.

(56) References Cited

U.S. PATENT DOCUMENTS 5,274,073 A 12/1993 Gruber et al.
5,331,059 A 7/1994 Engelhardt et al.
5,342,899 A 8/1994 Graham et al.
5,350,799 A 9/1994 Woodrum et al.
5,426,199 A 6/1995 Lundquist
5,470,928 A 11/1995 Harwood et al.
5,487,989 A 1/1996 Fowler et al.
5,510,307 A 4/1996 Narayanan et al.
5,510,526 A 4/1996 Baniel et al.
5,558,656 A 9/1996 Bergman
5,616,496 A 4/1997 Draths et al.
5,723,639 A 3/1998 Datta et al.
5,817,870 A 10/1998 Haas et al.
5,827,255 A 10/1998 Crainic
5,876,983 A 3/1999 Suzuki et al.
6,004,773 A 12/1999 Yoshihara et al.
6,013,494 A 1/2000 Picataggio et al.
6,087,140 A 7/2000 Cameron et al.
6,117,658 A 9/2000 Dennis et al.
6,143,538 A 11/2000 Somerville et al.
6,284,495 B1 9/2001 Sato et al.
6,297,319 B1 10/2001 Nagasuna et al.
6,306,636 B1 10/2001 Haselkorn et al.
6,355,412 B1 3/2002 Stewart et al.
6,472,188 B1 10/2002 Lee et al.
6,489,508 B1 12/2002 Van Gansbeghe et al.
6,509,156 B1 1/2003 Stewart et al.
6,534,679 B2 3/2003 Eyal et al.
6,586,229 B1 7/2003 Ben-Bassat et al.
6,593,116 B1 7/2003 Huisman et al.
6,623,944 B2 9/2003 Rieping
6,709,919 B2 3/2004 Tu et al.
6,723,799 B2 4/2004 Higley et al.
6,852,517 B1 2/2005 Suthers et al.
6,960,455 B2 11/2005 Akhverdian et al.
7,090,998 B2 8/2006 Ishikawa et al.
7,118,896 B2 10/2006 Kalscheuer et al.
7,141,154 B2 11/2006 Lin et al.
7,153,663 B2 12/2006 Payne et al.
7,166,743 B2 1/2007 Whitehouse et al.
7,186,541 B2 3/2007 Buckel et al.
7,186,856 B2 3/2007 Meng et al.
7,223,587 B2 5/2007 Sanchez et al.
7,279,598 B2 10/2007 Meng et al.
7,285,406 B2 10/2007 Payne et al.
7,309,597 B2 12/2007 Gokarn et al.
7,326,557 B2 2/2008 San et al.
7,358,071 B2 4/2008 Payne et al.
7,393,676 B2 7/2008 Buckel et al.
7,524,660 B2 4/2009 Caimi et al.
7,538,247 B2 5/2009 Craciun et al.
7,638,316 B2 12/2009 Buckel et al.
7,678,869 B2 3/2010 Matyjaszewski et al.
7,687,661 B2 3/2010 Lilga et al.
7,803,620 B2 9/2010 Zirkle et al.
7,826,975 B2 11/2010 Maranas et al.
7,833,761 B2 11/2010 Terashita et al.
7,846,688 B2 12/2010 Gill et al.
7,943,362 B2 5/2011 Frost
7,987,056 B2 7/2011 Gill et al.
8,048,624 B1 11/2011 Lynch et al.
8,076,111 B2 12/2011 Fukui et al.
8,097,439 B2 1/2012 Alibhai et al.
8,110,093 B2 2/2012 Friedman et al.
8,110,670 B2 2/2012 Valle et al.
8,183,028 B2 5/2012 Schirmer et al.
8,268,599 B2 9/2012 Schirmer et al.
8,283,143 B2 10/2012 Valle et al.
8,313,934 B2 11/2012 Bhatia et al.
8,323,924 B2 12/2012 Schirmer et al.
8,372,610 B2 2/2013 Haliburton et al.
8,377,666 B2 2/2013 Niu et al.
8,467,975 B2 6/2013 Ryan et al.
8,530,221 B2 9/2013 Hu et al.
8,535,916 B2 9/2013 Del et al.
8,597,922 B2 12/2013 Rude et al.
8,652,816 B2 2/2014 Lynch et al.
8,658,404 B2 2/2014 Rude et al.
8,753,840 B2 6/2014 Vermaas et al.
8,809,027 B1 8/2014 Mercogliano et al.
8,835,137 B2 9/2014 Cross et al.
8,859,259 B2 10/2014 Rude
8,883,464 B2 11/2014 Gill et al.
9,388,419 B2 7/2016 Gill et al.
9,428,778 B2 8/2016 Gill et al.
9,447,438 B2 9/2016 Louie et al.
9,587,231 B2 3/2017 Trinh et al.
9,944,959 B2 * 4/2018 Grammann ........... C12P 7/6436
2002/0081684 A1 6/2002 Grobler et al.
2002/0164729 A1 11/2002 Skraly et al.
2003/0004375 A1 1/2003 Mizrahi et al.
2003/0087381 A1 5/2003 Gokarn et al.
2003/0101486 A1 5/2003 Facciotti et al.
2003/0158441 A1 8/2003 Zhong et al.
2003/0159175 A1 8/2003 Ghulam et al.
2003/0191146 A1 10/2003 Kabbash et al.
2003/0211131 A1 11/2003 Martin et al.
2003/0233675 A1 12/2003 Cao et al.
2003/0235892 A1 12/2003 Katz et al.
2004/0009466 A1 1/2004 Maranas et al.
2004/0076982 A1 4/2004 Gokarn et al.
2004/0077090 A1 4/2004 Short
2004/0152174 A1 6/2004 Cervn et al.
2004/0152159 A1 8/2004 Causey et al.
2004/0209337 A1 10/2004 Frost et al.
2004/0210087 A1 10/2004 Meng et al.
2004/0214294 A1 10/2004 Rieping
2005/0003481 A1 1/2005 Gabriel et al.
2005/0054060 A1 3/2005 Chateau et al.
2005/0196758 A1 9/2005 Rock et al.
2005/0221457 A1 10/2005 Tsobanakis et al.
2005/0221466 A1 10/2005 Liao et al.
2005/0222458 A1 10/2005 Craciun et al.
2005/0233031 A1 10/2005 Hughes et al.
2005/0239179 A1 10/2005 Skraly et al.
2005/0272135 A1 12/2005 Datta et al.
2005/0283029 A1 12/2005 Meng et al.
2006/0014977 A1 1/2006 Miller et al.
2006/0068468 A1 3/2006 Knopf et al.
2006/0084098 A1 4/2006 Gill et al.
2006/0166342 A1 7/2006 Taoka et al.
2007/0010708 A1 1/2007 Ness et al.
2007/0027342 A1 2/2007 Meng et al.
2007/0031918 A1 2/2007 Dunson et al.
2007/0087403 A1 4/2007 Bestel-Corre et al.
2007/0092957 A1 4/2007 Donaldson et al.
2007/0107080 A1 5/2007 Liao et al.
2007/0141574 A1 6/2007 Keasling et al.
2007/0148749 A1 6/2007 Yasuda et al.
2007/0184524 A1 8/2007 Gokarn et al.
2007/0219390 A1 9/2007 Zacher et al.
2007/0245431 A1 10/2007 Metz et al.
2007/0270494 A1 11/2007 Metz et al.
2007/0281343 A9 12/2007 Arslanian
2008/0076167 A1 3/2008 Gokarn et al.
2008/0124785 A1 5/2008 Liao et al.
2008/0182308 A1 7/2008 Donaldson et al.
2008/0193989 A1 8/2008 Verser et al.
2008/0199926 A1 8/2008 Burgard et al.
2008/0274523 A1 11/2008 Renninger et al.
2009/0017514 A1 1/2009 Datta et al.
2009/0023006 A1 1/2009 Bub et al.
2009/0031453 A1 1/2009 Jessen et al.
2009/0053783 A1 2/2009 Gokarn et al.
2009/0076297 A1 3/2009 Bogan et al.
2009/0082286 A1 3/2009 Huang et al.
2009/0111151 A1 4/2009 Julien et al.
2009/0148914 A1 6/2009 Causey et al.
2009/0203097 A1 8/2009 Flint et al.
2009/0234146 A1 9/2009 Cooney et al.
2009/0246141 A1 10/2009 Hirai et al.
2009/0291480 A1 11/2009 Jessen et al.
2009/0298144 A1 12/2009 Tsobanakis et al.
2009/0305369 A1 12/2009 Donaldson et al.

(56) References Cited

U.S. PATENT DOCUMENTS

| | | | |
|---|---|---|---|
| 2009/0325248 | A1 | 12/2009 | Marx et al. |
| 2010/0021978 | A1 | 1/2010 | Burk et al. |
| 2010/0028962 | A1 | 2/2010 | Hu et al. |
| 2010/0037329 | A1 | 2/2010 | Frommer et al. |
| 2010/0064381 | A1 | 3/2010 | Zou et al. |
| 2010/0068773 | A1 | 3/2010 | Eggeling et al. |
| 2010/0099910 | A1 | 4/2010 | Meng et al. |
| 2010/0113822 | A1 | 5/2010 | Craciun et al. |
| 2010/0151536 | A1 | 6/2010 | Baynes et al. |
| 2010/0170148 | A1* | 7/2010 | Steen ........................ C12P 7/24 44/605 |
| 2010/0186117 | A1 | 7/2010 | Fabijanski et al. |
| 2010/0210017 | A1 | 8/2010 | Gill et al. |
| 2010/0257777 | A1 | 10/2010 | Sanchez-Riera et al. |
| 2010/0257778 | A1 | 10/2010 | Gaertner et al. |
| 2010/0261239 | A1 | 10/2010 | Soucaille et al. |
| 2010/0274033 | A1 | 10/2010 | Sanchez-Riera et al. |
| 2010/0285549 | A1 | 11/2010 | Muramatsu et al. |
| 2010/0291644 | A1 | 11/2010 | Marx et al. |
| 2011/0020883 | A1* | 1/2011 | Roessler .................. C12N 9/16 435/134 |
| 2011/0038364 | A1 | 2/2011 | Monsieux et al. |
| 2011/0072714 | A1 | 3/2011 | Gaertner et al. |
| 2011/0089016 | A1 | 4/2011 | Winkelaar et al. |
| 2011/0124063 | A1 | 5/2011 | Lynch et al. |
| 2011/0125118 | A1 | 5/2011 | Lynch et al. |
| 2011/0144377 | A1 | 6/2011 | Eliot et al. |
| 2011/0159558 | A1 | 6/2011 | Grady et al. |
| 2011/0162259 | A1 | 7/2011 | Gaertner et al. |
| 2011/0171702 | A1 | 7/2011 | Reinecke et al. |
| 2011/0183382 | A1 | 7/2011 | Schmalisch et al. |
| 2011/0183388 | A1 | 7/2011 | Sabirova et al. |
| 2011/0183391 | A1 | 7/2011 | Frost et al. |
| 2011/0190513 | A1 | 8/2011 | Lynch et al. |
| 2011/0214979 | A1 | 9/2011 | Chen et al. |
| 2011/0244575 | A1 | 10/2011 | Lipscomb et al. |
| 2011/0275851 | A1 | 11/2011 | Orjuela et al. |
| 2011/0281314 | A1 | 11/2011 | Lynch et al. |
| 2012/0041232 | A1 | 2/2012 | Lynch et al. |
| 2012/0058530 | A1 | 3/2012 | Zhang et al. |
| 2012/0116108 | A1 | 5/2012 | Basu et al. |
| 2012/0129231 | A1 | 5/2012 | Wang et al. |
| 2012/0135481 | A1 | 5/2012 | Jessen et al. |
| 2012/0240289 | A1 | 9/2012 | Feussner et al. |
| 2012/0244586 | A1 | 9/2012 | Gokarn et al. |
| 2012/0244588 | A1 | 9/2012 | Park et al. |
| 2012/0264902 | A1 | 10/2012 | Lipscomb et al. |
| 2012/0329110 | A1 | 12/2012 | Kim et al. |
| 2013/0071893 | A1 | 3/2013 | Lynch |
| 2013/0078684 | A1 | 3/2013 | Holtzapple et al. |
| 2013/0078686 | A1 | 3/2013 | Holtzapple et al. |
| 2013/0122541 | A1 | 5/2013 | Lynch et al. |
| 2013/0122562 | A1 | 5/2013 | Aldor et al. |
| 2013/0189787 | A1 | 7/2013 | Lynch et al. |
| 2013/0316413 | A1 | 11/2013 | Gonzalez et al. |
| 2013/0345470 | A1 | 12/2013 | Tengler et al. |
| 2014/0051136 | A1 | 2/2014 | Liao et al. |
| 2014/0121118 | A1 | 5/2014 | Warner |
| 2014/0135526 | A1 | 5/2014 | Lynch et al. |
| 2014/0215904 | A1 | 8/2014 | Pandey et al. |
| 2014/0242648 | A1* | 8/2014 | Ochiai ............... A61K 31/7088 435/134 |
| 2014/0309451 | A1 | 10/2014 | Tengler et al. |
| 2014/0330032 | A1* | 11/2014 | Lynch .................... C12N 9/001 554/1 |
| 2015/0044746 | A1 | 2/2015 | Meerman et al. |
| 2015/0056651 | A1 | 2/2015 | Gill et al. |
| 2015/0056669 | A1 | 2/2015 | Louie et al. |
| 2015/0056684 | A1 | 2/2015 | Gill et al. |
| 2015/0057455 | A1 | 2/2015 | Harkrader et al. |
| 2015/0064754 | A1 | 3/2015 | Louie et al. |
| 2015/0072384 | A1 | 3/2015 | Mercogliano et al. |
| 2015/0072399 | A1 | 3/2015 | Lipscomb et al. |
| 2015/0119601 | A1 | 4/2015 | Louie et al. |
| 2015/0299679 | A1 | 10/2015 | Da et al. |
| 2016/0060663 | A1 | 3/2016 | Grammann et al. |
| 2016/0090576 | A1 | 3/2016 | Garg et al. |
| 2016/0257975 | A1 | 9/2016 | Lynch et al. |
| 2016/0340700 | A1 | 11/2016 | Liao et al. |
| 2016/0362710 | A9 | 12/2016 | Lee et al. |

FOREIGN PATENT DOCUMENTS

| | | | |
|---|---|---|---|
| CA | 2654133 | A1 | 12/2007 |
| CN | 101573451 | A | 11/2009 |
| CN | 101679924 | A | 3/2010 |
| DE | 102008002309 | A1 | 12/2009 |
| EP | 1124789 | B1 | 9/2004 |
| EP | 1036190 | B1 | 5/2005 |
| EP | 1305439 | B1 | 6/2006 |
| EP | 1124979 | B1 | 8/2006 |
| EP | 1731604 | A1 | 12/2006 |
| EP | 1105514 | B1 | 2/2008 |
| EP | 1778840 | B1 | 6/2008 |
| EP | 1975236 | A2 | 10/2008 |
| EP | 1654212 | B1 | 7/2009 |
| EP | 2133420 | A1 | 12/2009 |
| EP | 1706457 | B1 | 2/2012 |
| EP | 3103867 | A1 | 12/2016 |
| GB | 2473755 | B | 9/2011 |
| KR | 2007096348 | | 10/2007 |
| KR | 20120108538 | A | 10/2012 |
| WO | 9821339 | A1 | 5/1998 |
| WO | 9855442 | A1 | 12/1998 |
| WO | 9914343 | A1 | 3/1999 |
| WO | 0039287 | A2 | 7/2000 |
| WO | 0056693 | A1 | 9/2000 |
| WO | 0061740 | A1 | 10/2000 |
| WO | 0116346 | A1 | 3/2001 |
| WO | 0138284 | A1 | 5/2001 |
| WO | 0208428 | A2 | 1/2002 |
| WO | 0234784 | A2 | 5/2002 |
| WO | 0242418 | A2 | 5/2002 |
| WO | 02090312 | A1 | 11/2002 |
| WO | 03040690 | A2 | 5/2003 |
| WO | 03062173 | A2 | 7/2003 |
| WO | 03082795 | A2 | 10/2003 |
| WO | 2004018621 | A2 | 3/2004 |
| WO | 2004033646 | A2 | 4/2004 |
| WO | 2005003074 | A1 | 1/2005 |
| WO | 2005047498 | A1 | 5/2005 |
| WO | 2005105770 | A2 | 11/2005 |
| WO | 2005118719 | A2 | 12/2005 |
| WO | 2006034156 | A2 | 3/2006 |
| WO | 2006052871 | A2 | 5/2006 |
| WO | 2006052914 | A2 | 5/2006 |
| WO | 2006121755 | A2 | 11/2006 |
| WO | 2007012078 | A1 | 1/2007 |
| WO | 2007030830 | A2 | 3/2007 |
| WO | 2007042494 | A2 | 4/2007 |
| WO | 2007047680 | A2 | 4/2007 |
| WO | 2007093848 | A2 | 8/2007 |
| WO | 2007106903 | A2 | 9/2007 |
| WO | 2007130745 | A1 | 11/2007 |
| WO | 2007136762 | A2 | 11/2007 |
| WO | 2008021765 | A2 | 2/2008 |
| WO | 2008023039 | A1 | 2/2008 |
| WO | 2008027742 | A1 | 3/2008 |
| WO | 2008028002 | A1 | 3/2008 |
| WO | 2008072920 | A1 | 6/2008 |
| WO | 2008089102 | A2 | 7/2008 |
| WO | 2008091627 | A2 | 7/2008 |
| WO | 2008145737 | A1 | 12/2008 |
| WO | 2008149951 | A1 | 12/2008 |
| WO | 2009006430 | A1 | 1/2009 |
| WO | 2009031737 | A1 | 3/2009 |
| WO | 2009036095 | A1 | 3/2009 |
| WO | 2009062190 | A2 | 5/2009 |
| WO | 2009089457 | A1 | 7/2009 |
| WO | 2009094485 | A1 | 7/2009 |
| WO | 2009111513 | A1 | 9/2009 |
| WO | 2009111672 | A1 | 9/2009 |
| WO | 12009121066 | A1 | 10/2009 |
| WO | 2009143401 | A2 | 11/2009 |

(56) References Cited

FOREIGN PATENT DOCUMENTS

| | | | | |
|---|---|---|---|---|
| WO | 2009151342 A1 | | 12/2009 | |
| WO | 2010006076 A2 | | 1/2010 | |
| WO | 2010011874 A2 | | 1/2010 | |
| WO | 2010017230 A2 | | 2/2010 | |
| WO | 2010031083 A2 | | 3/2010 | |
| WO | 2010105095 A1 | | 9/2010 | |
| WO | 2011002892 A2 | | 1/2011 | |
| WO | 2011008565 A1 | | 1/2011 | |
| WO | WO 2011038364 A1 | * | 3/2011 | ............ A61L 15/24 |
| WO | 2011063304 A1 | | 5/2011 | |
| WO | 2011063363 A2 | | 5/2011 | |
| WO | 2011094457 A1 | | 8/2011 | |
| WO | 2012017083 A1 | | 2/2012 | |
| WO | 2012019175 A2 | | 2/2012 | |
| WO | 2012050931 A2 | | 4/2012 | |
| WO | 2012054400 A1 | | 4/2012 | |
| WO | WO 2012129450 A1 | * | 9/2012 | ............ C12N 9/001 |
| WO | 2012135760 A1 | | 10/2012 | |
| WO | 2012177726 A1 | | 12/2012 | |
| WO | 2013003608 A1 | | 1/2013 | |
| WO | 2013039563 A1 | | 3/2013 | |
| WO | 2013126855 A1 | | 8/2013 | |
| WO | 2013152051 A2 | | 10/2013 | |
| WO | 2013152052 A2 | | 10/2013 | |
| WO | 2013192450 A1 | | 12/2013 | |
| WO | 2013192451 A1 | | 12/2013 | |
| WO | 2013192453 A1 | | 12/2013 | |
| WO | 2014026162 A1 | | 2/2014 | |
| WO | 2014042693 A1 | | 3/2014 | |
| WO | 2014145096 A1 | | 9/2014 | |
| WO | 2014145297 A1 | | 9/2014 | |
| WO | 2014145332 A1 | | 9/2014 | |
| WO | 2014145334 A1 | | 9/2014 | |
| WO | 2014145343 A1 | | 9/2014 | |
| WO | 2014145344 A2 | | 9/2014 | |
| WO | 2014146026 A1 | | 9/2014 | |
| WO | 2014146047 A1 | | 9/2014 | |
| WO | 2014198831 A1 | | 12/2014 | |
| WO | 2015010103 A2 | | 1/2015 | |

OTHER PUBLICATIONS

Lee et al., Fatty acid synthesis by elongases in trypanosomes, Cell, 2006, 126, 691-99.*

Dellomonaco et al., Engineered reversal of the beta-oxidation cycle for the synthesis of fuels and chemicals, Nature, 2011, 476, 335-59.*

Machado et al., A selection platform for carbon chain elongation using the CoA-dependent pathway to produce linear higher alcohols, Metabolic Eng., 2012, 14, 504-11.*

Jing et al., Phylogenetic and experimental characterization of an acyl-ACP thioesterase family reveals significant diversity in enzymatic specificity and activity, BMC Biochem., 2011, 12, 44.*

Alerts, Bruce et al., "Molecular Biology of the Cell", 3rd Ed. Garland Publishing. New York, 1994, 42-45 66-74.

Arthur, et al., "Contribution of VanY D,D-carboxypeptidase to glycopeptide resistance in Enterococcus faecalis by hydrolysis of peptidoglycan precursors", Antimicrob: Agents Chemother. 38(9), Sep. 1994, 1899-1903.

Bailey, James F., et al., "Biochemical Engineering Fundamentals", 2nd Ed. McGraw Hill, New York, entire book for purposes indicated and Chapter 9, 1986. 533-657.

Beguin , et al., "The biological degradation of cellulose", FEMS Microbiol Rev. Jan. 1994; 13(1)25-58.

Beisson, Frederic , et al., "*Arabidopsis* Genes Involved in Acyl Lipid Metabolism. A 2003 Census of the Candidates, a Study of Distribution of Expressed Sequence Tags in Organs and a Web-Based Database", Plant Physiol. 132(2), Jun. 2003, 681-97.

Bellion, Edward , at al., "Methylamine Utilization in Yeast and Bacteria: Studies Using in vivo NMR", Micro b. Growth C1 Compd. (Int. Symp.) 7th Editors: Murrell, J. Coliin, Kelly, Don P. Publisher: Intercept. Andover. UK, 1993, 415-32.

Bowie, James U., et al., "Deciphering the Message in Protein Sequences: Tolerance to Amino Acid Substitutions", Science 247(4948), Mar. 16, 1990, 1306-10.

Bressler , et al., "Studies on the mechanism of fatty acid synthesis. XI. The product of the reaction and the role of sulfhydryl groups in the synthesis of fatty acids", J. Biol Chem. vol. 237, May 1962, 1441-1448.

Brock, Thomas D., "Biotechnology: A Textbook of Industrial Microbiology", Second Edition Sinauer Associates, Inc, Sunderland, Mass., 1989.

Brosius, Jurgen , et al., "Spacing of the -10 and -35 Regions in tac Promoter. Effect on its in vivo activity", J Biol Chem. 260(6). Mar. 25, 1985, 3539-41.

Brutlag, Douglas L., et al., "Improved sensitivity of biological sequence database searches", Comput Appl Biosel. 6(3), Mar. 25, 1990. 237-45.

Coleman, Rosalind A., et al., "Enzymes triacylglycerol synthesis and their regulation", Prog Lipid Res. 43(2), Mar. 2004, 134-74.

Cowan, Peter J., et al., "Characterization of the Major Promoter for the Plasmid-Encoded Sucrose Genes scrY scrA, and scrB", J Bacteriol. 173(23), Dec. 1991, 7464-70.

Daniel, Jaiyanth , et al., "Induction of a Novel Class of Diacylglycerol Acyltransferases and Triacylglycerol Accumulation in Mycobacterium tuberculosis as It Goes into a Dormancy-Like State in Culture", J Bacteriol. 186(15), Aug. 2004, 5017-30.

Davis, Mark S., et al., "Overproduction of Acetyl-CoA Carboxylase Activity Increases the Rate of Fatty Acid Biosynthesis in *Escherichia coli*", The Journal of Biological Chemistry (2000), vol. 275, pp. 28593-28598, 2000, 28593-28598.

De Boer, Herman A., et al.. "The tac promoter: A functional hybrid derived from the trp and lac promoters", Natl Acad Sci USA. 80(1), Jan. 1983, 21-5.

Denic , et al., "A Molecular Caliper Mechanism for Determining Very Long-Chain Fatty Acid Length", vol. 130, Issue 4, Aug. 24, 2007, Aug. 24, 2007, 663-377.

Dittrich, Franziska , et al., "Fatty acid elongsation in yeast. Biochemical characteristics of the enzyme system and isolation of elongation-defective mutants", Eur J Biochem. 252(3), Mar. 15, 1998, 477-85.

Dohr, Olaf , et al., "Engineering of a functional human NADH-dependent cytochrome P450 system", Proc Natl Acad Sci USA. 98(1), Jan. 2, 2001, 81-6.

Elvin, Christopher M , et al., "Modified bacteriophage lambda promoter vector for overproduction of proteins in *Escherichia coli*", Gene. 87(1), Mar. 1, 1990, 123-6.

Eppink, Michel H. M., et al., "Switch of Coenzyme Specificity of p-Hydroxybenzoate Hydroxylase", J Mol Biol. 292(1), Sep. 10, 1999, 87-96.

Fleming , et al., "Extracellular enzyme synthesis in a sporulation-deficient strain of Bacillus licheniformis", Appl Environ Microbiol. Nov. 1995, 61 (11):3775-3780.

Freshney , "Culture of animal cells : a manual of basic technique", Journal of Chemical Technology and Biotechnology, 2nd Edition, 1987.

Fujimoto , et al., "pAM401-Based Shuttle Vectors That Enable Overexpression of Promoterless Genes and One-Step Purification of Tag Fusion Proteins Directly from *Enterococcus faecalis*", doi: 10.1128/AEM.67.3.1262-1267.2001 Appl. Environ. Microbiol. Mar. 2001 vol. 87 No. 3 1262-1267.

Gronenborn, Bruno , "Overproduction of Phage Lambda Repressor under Control of the lac Promotor of *Escherichia coli*", Mol Gen Genet. 148(3), Nov. 17, 1976. 243-50.

Guzman, L. M., et al., "Tight regulation, modulation, and high-level expression by vectors containing the arabinose PBAD promoter", J Bacteriol. 177(14), Jul. 1995, 4121-30.

Haldimann, Andreas , et al., "Use of New Methods for Construction of Tightly Regulated Arabinose and Rhamnose Promoter Fusions in Studies of the *Escherichia coli* Phosphate Regulon", J Bacteriol. 180(5). Mar. 1998, 1277-89.

Hall, Neil , et al., "Structure-function analysis of NADPH: nitrate reductase from Aspergillus nidulans: analysis of altered pyridine nucleotide specificity in vivo", Microbiology. 146 (Pt.6) Jun. 2000, 1399-406.

(56) References Cited

OTHER PUBLICATIONS

Heath, Richard J. et al.,"Enoyl-Acyl Carrier Protein Reductase (fabl) Plays a Determinant Role in Completing Cycles of Fatty Acid Elongation in *Escherichia coli*", J Biol Chem. 270(44). Nov. 3, 1995, 26538-42.
Katavic, Vesna , et al., "Alteration of Seed Fatty Acid Composition by an Ethyl Methanesulfonate-Induced Mutation in *Arabidopsis thaliana* Affecting Diacylglycerol Acyltransferase Activity". Plant Physiol. 108(1), May 1995, 399-409.
Kinney, Anthony J., "Manipulating flux through plant metabolic pathways", Curr Opin Plant Biol. 1(2), Apr. 1998, 173-8.
Kleerebezem , et al., "Controlled gene expression systems for lactic acid bacteria: transferable nisin-inducible expression cassettes for Lactococcus, Leuconostoc, and Lactobacillus spp", Appl Environ Microbiol. Nov. 1997:63 (11):4581-4584.
Kunin , et al., "A comparative analysis of the inventive step standard in the European and Japanese patent office from an US perspective", IP Litigator, Jan./Feb. 2008, 15-23.
Lassner, Michael W., et al., "Lysophosphatidic Acid Acyltransferase from Meadowfoam Mediates Insertion of Erucic Acid at the sn-2 Position of Triacylglycerol in Transgenic Rapeseed Oil", Plant Physiol. 109(4), Dec. 1995, 1389-94.
Li, Jianguo , et al., "Chronic intermittent hypoxia upregulates genes of lipid biosynthesis in obese mice", J Appl Physiol. 99(5), Nov. 2005, 1643-8.
Lilly, Mariska , et al., "The effect of increased yeast alcohol acetyltransferase and esterase activity on the flavour profiles of wine and distillates", Yeast. 23(9), Jul. 15, 2006, 641-59.
Lioa , et al., "Metabolic engineering for a malonyl-CoA-dependent pathway for fatty acid production in *Escherichia coli* (abstract)", SIMB Annual Meeting & Exhibition. Aug. 12-16, 2012. Washington Hilton, Washington, DC, Available at http://sim.confex.com/sim/2012/webprogram/Paper23197.html, Aug. 2012.
Magnuson, Kelly , et al., "Regulation of fatty acid biosynthesis in *Escherichia coli*", Microbiological Reviews, vol. 57, No. 3, 1993, 522-42.
Mandaokar, Ajin , et al., "Transcriptional regulators of stamen development in *Arabidopsis* identified by transcriptional profiling", Plant J. 46(6), Jun. 2006, 984-1008.
McCabe, Warren L., et al., "Unit Operations of Chemical Engineering", 5th Ed., W.L. McGraw Hill, New York, 1993.
Nelson, David L., et al.,"Principles of Biochemistry 3rd Ed.", Worth Publishers New York, 2000, 527-658.
Nicholson, Donald , "Lipid Metabolism Graphic Design—IUBMB—Nicholson", 2002, 1 page.
Nugent, Patricia , "Development of Improved Chemicals and Plastics from Oilseeds. Final technical report", The Dow Chemical Company. DE-FC36-01ID14213, Jul. 31, 2006.
Ohmiya , et al., "Structure of Cellulases and Their Applications", Biotechnol. Genet. Eng. Rev., vol. 14, 1997, 365-414.
O'Sullivan , et al., "High- and low-copy-number Lactococcus shuttle cloning vectors with features for clone screening", Gene. Volume 137, Issue 2, Dec. 31, 1993, pp. 227-231.
Papanikolaou, Seraphim , et al., "Lipid production by Yarrowia lipolytica growing on industrial glycerol in a single-stage continuous culture", Bioresour Technol. 82(1), Mar. 2002, 43-9.
Renault , et al., "Plasmid vectors for Gram-positive bacteria switching from high to low copy number", Gene. vol. 183, Issues 1-2, 1996, pp. 175-182.
Saerens, S. M. G , et al., "Parameters Affecting Ethyl Ester Production by Saccharomyces cerevisiae during Fermentation", Appl Environ Microbiol 74(2), Jan. 2008, 454-61.
Sambrook and Russell , "Molecular Cloning: A Laboratory Manual", Third Edition (vols. 1-3). Cold Spring Harbor Laboratory Press, Cold Spring Harbor, N.Y., 2001.
Schmid, Katherine M., et al., "Lipid Metabolism in Plants", Biochemistry of Lipids, Lipoproteins and memebranes, Ch 4, 2002, 93-126.
Hondorp , et al., "Oxidation of cysteine 645 of cobalamin-independent methionine synthase causes a methionine limitation in *Escherichia coli*", J Bacteriol. May 2009;191(10):3407-10. Epub Mar 13, 2009.
Hugler , et al., "Malonyl-Coenzyme A Reductase from Chloroflexus aurantiacus, a Key Enzyme of the 3-Hydroxypropionate Cycle for Autotrophic CO2 Fixation", J Bacteriol May 2002;184(9):2404-2410.
Ikuo Miyahisa , et al., "Efficient production of (2S)-flavanones by *Escherichia coli* containing an artificial biosynthetic gene cluster", Applied Microbiology and Biotechnology, Springer, Berlin, DE, (Sep. 1, 2005), vol. 68, No. 4, doi:10.1007/S00253-005-1916-3, ISSN 1432-0614, pp. 498-504, XP019331939.
Ivanova , et al., "Genome sequence of Bacillus cereus and comparative analysis with Bacillus anthracis", Nature. May 1, 2003;423(6935):87-91.
James, Ethan S., et al., "Expression of two *Escherichia coli* acetyl-CoA carboxylase subunits is autoregulated", J Biol Chem. 279(4), Jan. 23, 2004, 2520-7.
Jan Podkowinski , et al., "Opinions Acetyl-coenzyme A carboxylase—an attractive enzyme for biotechnology", Biotechnologia. PL, (Jan. 1, 2011), vol. 4, doi:10.5114/bta.2011.46549, ISSN 0860-7796, pp. 321-335, XP055303418.
Jenkins , et al., "Genetic and molecular characterization of the genes involved in short-chain fatty acid degradation in *Escherichia coli*: the ato system", J Bacteriol. Jan. 1987; 169(1): 42-52.
Jiang , et al., "Biosynthetic pathways for 3-hydroxypropionic acid production", Appl Microbiol Biotechnol. Apr. 2009;82(6):995-1003.
Jiang , et al., "Cloning and Expression of aroG Gene of *E. coli* and Its Co-expression with pheA and tyrB Genes", 1998;30(6):593-596. (in Chinese with English abstract).
Joike , et al., "Amino acid substitutions affecting catalytic activity and subunit interactions of aminodeoxychorismate synthase in *E. coli*", Abstracts of the General Meeting of the American Society for Microbiology. 2002; 102:275-276, and 102nd General Meeting of the American Society for Microbiology; Salt Lake, UT, USA; May 19-23, 2002.
Juliano Alves , et al., "Cloning, expression, and enzymatic activity ofandacetyl-coenzyme A carboxylases", Analytical Biochemistry, Academic Press Inc. New York, vol. 417, No. 1, doi:10.1016/J.AB.2011.05.041, ISSN 0003-2697, (May 25, 2011), pp. 103-111, (Jun. 1, 2011), XP028245778.
Jung , et al., "Jung et al., Wax-deficient antherl is involved in cuticle and wax production in rice anther walls and is required for pollen development", and is required for pollen development, Plant Cell, Nov. 2006, vol. 18, No. 11, pp. 3015-3032.
Kapol , et al., "Purification and characterization of 2-oxoglutarate decarboxylase of Leuconostoc oenos", Journal of General Microbiology 136 (1990), 1497-1499.
Katsuyama, Yohei , et al., "Production of curcuminoids by *Escherichia coli* carrying an artificial biosynthesis pathway", Microbiology. 154(Pt 9), Sep. 2008, 2620-8.
Kern , et al., "Engineering primary metabolic pathways of industrial micro-organisms", J Biotechnol. Mar. 30, 2007;129(1):6-29. Epub Dec. 2, 2006.
Kiatpapan, Pornpimon , et al., "Molecular Characterization of Lactobacillus plantarum Genes for B-Ketoacyl-Acyl Carrier Protein Synthase III (fabH) and Acetyl Coenzyme a Carboxylase (accBCDA), Which Are Essential for Fatty Acid Biosynthesis", Appl Environ Microbiol. 67(1), Jan. 2001, 426-33.
Kim, Youngnyun , et al., "Construction of an *Escherichia coli* K-12 Mutant for Homoethanologenic Fermentation of Glucose or Xylose without Foreign Genes", Appl Environ Microbiol. 73(6), Mar. 2007, 1766-71.
Kim, Youngnyun , et al., "Dihydrolipoamide Dehydrogenase Mutation Alters the NADH Sensitivity of Pyruvate Dehydrogenase Complex of *Escherichia coli* K-12", J Bacteriol. 190(11), Jun. 2008, 3851-8.
Kim , et al., "Effect of Overexpression of Actinobacillus succinogenes Phosphoenolpyruvate Carboxykinase on Succinate Production in *Escherichia coli*", Appl. Environ. Microbiol. vol. 70 No. 2, Feb. 2004, 1238-1241.

(56) References Cited

OTHER PUBLICATIONS

Kim, Joong Kyun, et al., "Extractive Recovery of Products from Fermentation Broths", Biotechnol. Bioprocess Eng, 4, 1999, 1-11.
Kim, Kwang-Seo , et al., "The Rut Pathway for Pyrimidine Degradation: Novel Chemistry and Toxicity Problems", J Bacteriol. 192(16), Aug. 2010, 4089-102.
Kimchi-Sarfaty , et al., "A "Silent" Polymorphism in the MDR1 Gene Changes Substrate Specificity", Science. Science 315(5811):, Jan. 26, 2007, 525-8.
Kisselev , "Polypeptide Release Factors in Prokaryotes and Eukaryotes: Same Function, Different Structure", Structure. 10(1), Jan. 2002, 8-9.
Kizer, Lance , et al., "Application of Functional Genomics to Pathway Optimization for Increased Isoprenoid Production", Appl Environ Microbiol. 74(10), May 2008, 3229-41.
Kleerebezem , et al., "The qmeA (ts) mutation of *Escherichia coli* is localized in the fabl gene, which encodes enoyl-ACP reductase.", Res Microbiol, 147(8), Oct. 1996, 609-13.
Knothe, Gerhard , et al., "Biodiesel and renewable diesel: A comparison", Progress in Energy and Combustion Science. vol. 36, No. 3 XP026919218, Jun. 1, 2010, 364-373.
Kozliak , et al., "Expression of proteins encoded by the *Escherichia coli* cyn operon: carbon dioxide-enhanced degradation of carbonic anhydrase", J Bacteriol. 176(18), Sep. 1994, 5711-7.
Kozliak , et al., "Role of bicarbonate/CO2 in the inhibition of *Escherichia coli* growth by cyanate", J. Bacteriol. vol. 177 No. 11, Jun. 1995, 3213-3219.
Kroeger, Jasmin K., et al., "A spectrophotometric assay for measuring acetyl-coenzyme A carboxylase", Anal Biochem. 411(1), Apr. 1, 2011, 100-5.
Kurcok , et al., "Reactions of13-lactones with potassium alkoxides and their complexes with 18-crown-6 in aprotic solvents", Journal of Organic Chemistry. 58(16), 1993, 4219-4220.
Kwon , et al., "A physiology study of *Escherichia coli* overexpressing phosphoenolpyruvate carboxykinase", Biosci. Biotechnol. Biochem., 72 (4), 2008, 1138-1141.
Kwon , et al., "Influence of gluconeogenic phosphoenolpyruvate carboxykinase (PCK) expression on succinic acid fermentation in *Escherichia coli* under high bicarbonate condition", Journal of Microbiology and Biotechnology 16(9)., Sep. 2006, 1448-1452.
Lambert , et al., "Cre-lox-Based System for Multiple Gene Deletions and Selectable-Marker Removal in Lactobacillus plantarum", AEM, vol. 73, No. 4, Jan. 1, 1900, 1126-1135.
Langlois , et al., "A new preparation of trifluoromethanesulfinate salts", Journal of Fluorine Chemistry. 128(7), 2007, 851-856.
Leeper, Stephen A., "Membrane Separations in the Recovery of Biofuels and Biochemicals: An Update Review", Separation and Purification Technology, Norman N. Li and Joseph M. Calo, Eds., Marcel Dekker, 1992, 99-194.
Lennen , et al., "A process for microbial hydrocarbon synthesis: Overproduction of fatty acids in *Escherichia coli* and catalytic conversion to alkanes", Biotechnol Bioeng. vol. 106, Issue 2, Jun. 1, 2010, 193-202.
Leonard, Effendi , et at, "Engineering Central Metabolic Pathways for High-Level Flavonoid Production in *Escherichia coli*", Appl Environ Microbiol. 73(12), Jun. 2007, 3877-86.
Li, Wang , et al., "Characterization of two temperature-inducible promoters newly isolated from B. subtilis", Biochem Biophys Res Commun. 358(4), Jul. 13, 2007, 1148-53.
Li , et al., "Effect of poxB gene knockout on metabolism in *Escherichia coli* based on growth characteristics and enzyme activities", World Journal of Microbiology and Biotechnology. vol. 23, Issue 4, Apr. 2007, 573-580.
Liang , et al., "Fe2(SO4)3.4H20/concentrated H2SO4: an efficient catalyst for esterification", Journal of Chemical Research, Synopses. 3, 2004, 226-227.
Lipscomb , et al., "Poster—Understanding production of 3-Hydroxypropionic Acid (3¬3 HP) in a genomic context.", OPX Biotechnologies. Metabolic Engineering, Sep. 17, 2008.
Lu, Xuefeng , et al., "Overproduction of free fatty acids in *E. coli*: Implications for biodiesel production", Metab Eng. 10(6), Nov. 2008, 333-9.
Lutke-Eversloh , et al., "Feedback inhibition of chorismate mutase/prephenate dehydrogenase (TyrA) of *Escherichia coli*: generation and characterization of tyrosine-insensitive mutants", Appl Environ Microbiol. vol. 71 no. 11, Nov. 2005, 7224-8.
Lynch , "Rapid optimization of microorganisms for the cost superior production of chemicals & fuels", OPX Biotechnologies, Sep. 15, 2008.
Lynch, M. , et al., "SCALEs: multiscale analysis of library enrichment. Nat Methods", Nat Methods. 4(1)., Jan. 2007, 87-93.
Martin , et al., "Engineering a mevalonate pathway in *Escherichia coli* for production of terpenoids", Nat Biotechnol. 21(7)., Jul. 2003, 796-802.
Masayuki , et al., "Expression of Clostridium acetobutylicum butanol synthetic genes in *Escherichia coli*", Applied Microbiology and Biotechnology, Jan. 2008, vol. 77, Issue 6, pp. 1305-1316.
Meades, Glen , et al., "A tale of two functions: enzymatic activity and translational repression by carboxyltransferase", Nucleic Acids Res. 38(4), Mar. 2010, 1217-27.
Mehta , et al., "Aminotransferases: demonstration of homology and division into evolutionary subgroups", Eur J Biochem. 214(2), Jun. 1, 1993, 549-61.
Meng, Xin , et al., "Increasing fatty acid production in *E. coli* by simulating the lipid accumulation of oleaginous microorganisms", Journal of Industrial Microbiology and Biotechnology. 38(8), 2011, 919-925.
Cheng , et al., "Mammalian wax biosynthesis: I. Identification of two fatty acyl-Coenzyme A reductases with different substrate specificities and tissue distributions", Journal of Biological Chemistry, Sep. 3, 2004, vol. 279, No. 36, pp. 37789-37797.
Chica, Roberto A., et al., "Semi-rational approaches to engineering enzyme activity: combining the benefits of directed evolution and rational design", Curr Opin Biotechnol. 16(4), Aug. 2005, 378-84.
Cho , et al., "Simultaneous synthesis of enantiomerically pure (S)-amino acids and (R)¬amines using coupled transaminase reactions", Biotechnol Bioeng. Mar. 30, 2003;81(7):783-9.
Choi-Rhee, Eunjoo , et al., "The Biotin Carboxylase-Biotin Carboxyl Carrier Protein Complex of *Escherichia coli* Acetyl-CoA Carboxylase", J Biol Chem. 278(33), Aug. 15, 2003, 30806-12.
Chotani , et al., "The commercial production of chemicals using pathway engineering", Biochim Biophys Acta. Dec. 29, 2000;1543(2):434-455. . . .
Cleusix , et al., "Inhibitory activity spectrum of reuterin produced by Lactobacillus reuteri against intestinal bacteria", BMC Microbiology, 7: 101, Nov. 12, 2007, 9 Pages.
Crameri , et al., "DNA shuffling of a family of genes from diverse species accelerates directed evolution", Nature. Jan. 15, 1998;391(6664):288-91.
Cronan , et al., "Genetic and biochemical analyses of pantothenate biosynthesis in *Escherichia coli* and *Salmonella typhimurium*.", J Bacteriol. Mar. 1982;149(3):916-22.
Cronan, J.E , "Beta-Alanine Synthesis in *Escherichia coli*", J Bacteriol. Mar. 1980;141(3):1291-7.
Cronk , et al., "Cloning, crystallization and preliminary characterization of a beta-carbonic anhydrase from *Escherichia coli*", Acta Crystallogr D Biol Crystallogr. Sep. 2000;56(Pt 9):1176-9.
Daley , Daniel O., et al., "Global Topology Analysis of the *Escherichia coli* Inner Membrane Proteome", Science. 308 (5726), May 27, 2005, 1321-3.
Daruwala , et al., "Menaquinone (vitamin K2) biosynthesis: overexpression, purification, and characterization of a new isochorismate synthase from *Escherichia coli*", J. Bacteriol. 179(10), May 1997, 3133-8.
Datsenko, Kirill A., et al., "One-step inactivation of chromosomal genes in *Escherichia coli* K-12 using PCR products", Proc Natl Acad Sci USA. 97(12), Jun. 6, 2000, 6640-5.
Datta, Simanti , et al., "A set of recombineering plasmids for gram-negative bacteria", Gene. 379, Sep. 1, 2006, 109-15.
De Mendoza , et al., "Thermal regulation of membrane lipid fluidity in bacteria", Trends Biochem. Sci. 1983; 8:49-52.

(56) References Cited

OTHER PUBLICATIONS

Dell'Aquila , et al., "Acid-base balance in peritoneal dialysis", J Nephrol. Mar.-Apr. 2006;19 Suppl 9:S104-7.
Demmer, Ulrike , et al., "Structural Basis for a Bispecific NADP and CoA Binding Site in an Archaeal Malonyl-Coenzyme A Reductase", J Biol Chem. 288(9), Mar. 1, 1990, 6363-70.
Den , et al., "Enzymatic Conversion of13-Hydroxypropionate to Malonic Semialdehyde*", J Biol Chem Jul. 1959;234 (7):1666-1671.
Deshpande, Mukund V., "Ethanol Production from Cellulose by Coupled Saccharification/Fermentation using Saccharomyces cerevisiae and Cellulase Complex from Sclerotium rolfsii UV-8 Mutant", Appl Biochem Biotechnol. 36 (3), 1992, 227-34.
Devos, Damien , et al., "Practical Limits of Function Prediction", Proteins. 41(1), Oct. 1, 2000, 98-107.
Dewick, P. , "Chapter 4. The Shikimate Pathway: Aromatic Amino Acids and Phenylpropanoids", Medicinal Natural Products: A Biosynthetic Approach, Second Edition(2002): 121-166.
Diaz , et al., "Characterization of the hca cluster encoding the dioxygenolytic pathway for initial catabolism of 3-phenylpropionic acid in *Escherichia coli* K-12", J Bacteriol. Jun. 1998;180(11):2915-23.
Doroshenko, Vera G., et al., "Pho regulon promoter-mediated transcription of the key pathway gene aroGFbr improves the performance of an L-phenylalanine-producing *Escherichia coli* strain", Applied Microbiology and Biotechnology 88, 2010, 1287-1295.
Drake , et al., "Structure of the EntB Multidomain Nonribosomal Peptide Synthetase and Functional Analysis of Its Interaction with the EntE Adenylation Domain", Chem Biol. Apr. 2006;13(4):409-19.
Duncan , et al., "Lactate-utilizing bacteria, isolated from human feces, that produce butyrate as a major fermentation product", Appl Environ Microbiol. Oct. 2004;70(10):5810-7.
Duncan , et al., "The overexpression and complete amino acid sequence of *Escherichia coli* 3-dehydroquinase", Biochem J. Sep. 1, 1986:238(2):475-83.
Epstein , et al., "Oil: A Life Cycle Analysis of its Health and Environmental Impacts", The Center for Health and the Global Environment, Harvard Medical School, Mar. 2002. www.med.harvard.edu/chge/oil.html.
Erb , et al., "Carboxylation mechanism and stereochemistry of crotonyl-CoA carboxylase/reductase, a carboxylating enoyl-thioester reductase", Proc Nati Acad Sci U S A. Jun. 2, 2009; 106(22): 8871-8876. Published online May 20, 2009. doi: 10.1073/pnas.0903939106, 8871-8876.
Farmer , et al., "Improving lycopene production in *Escherichia coli* by engineering metabolic control", Nat Biotechnol. May 2000;18(5):533-7.
Felce , Jeremy, et al., "Carbonic Anhydrases Fused to Anion Transporters of the SulP Family Evidence for a Novel Type of Bicarbonate Transporter", J Mol Microbiol Biotechnol. 8(3), 2004, 169-76.
Fernando , et al., "Biorefineries: current status, challenges and future direction", Energ. Fuel. May 2006; 20:1727-1737.
Figge , "Methionine biosynthesis is *Escherichia coli* and Corynebacterium glutamicum", Microbiol Monogro. 2007; 5:163-193.
Fodor, et al., "Light-Directed, Spatially Addressable Parallel Chemical Synthesis", Science. Feb. 15, 1991;251 (4995):767-73.
Fowler, Zachary L., et al., "Increased Malonyl Coenzyme A Biosynthesis by Tuning the *Escherichia coli* Metabolic Network and Its Application to Flavanone Production", Appl Environ Microbiol. 75(18), Sep. 2009, 5831-9.
Funa , et al., "A novel quinone-forming monooxygenase family involved in modification of aromatic polyketides", J Biol Chem. Apr. 15, 2005;280(15):14514-23. Epub Feb. 8, 2005.
Gietz, R. Daniel , et al., "Transformation of Yeast by Lithium Acetate/Single-Stranded Carrier DNA/Polyethylene Glycol Method", Methods Enzymol, 350, 2002, 87-96.
Giladi , et al., "FolM, a new chromosomally encoded dihydrofolate reductase in *Escherichia coli.*", J Bacteriol. 185 (23), Dec. 2003, 7015-8.
Gilbert, Walter , et al., "Useful Proteins from Recombinant Bacteria", Sci Am. 242(4), Apr. 1980, 74-94.
Gill , et al., "Genome-wide screening for trait conferring genes using DNA microarrays", Proc Natl Acad Sci U S A. May 14, 2002;99(10):7033-8. Epub May 7, 2002.
Ginkel , et al., "Identification and cloning of the *Mycobacterium avium* folA gene, required for dihydrofolate reductase activity", FEMS Microbiology Letters. vol. 156, Issue 1, Nov. 1, 1997, 69-78.
Gokarn , et al., "Metabolic analysis of *Escherichia coli* in the presence and absence of the carboxylating enzymes phosphoenolpyruvate carboxylase and pyruvate carboxylase", Appl Environ Microbiol. May 2000;66(5):1844-50.
Goodwin , et al., "Purification and characterization of methylmalonate-semialdehyde dehydrogenase from rat liver. Identity to malonate-semialdehyde dehydrogenase", J Biol Chem. Sep. 5, 1989;264(25):14965-71.
Gray , et al., "Monofunctional chorismate mutase from Bacillus subtilis: purification of the protein, molecular cloning of the gene, and overexpression of the gene product in *Escherichia coli*", Biochemistry. Jan. 16, 1990;29(2):376-83.
Gu , et al., "Polyketide Decarboxylative Chain Termination Preceded by O-Sulfonation in Curacin A Biosynthesis", J Am Chem Soc. Nov. 11, 2009; 131(44): 16033-16035, doi: 10.1021/ja9071578.
Gulmezian , et al., "Genetic Evidence for an Interaction of the UbiG O-Methyltransferase with UbiX in *Escherichia coli* Coenzyme Q Biosynthesis", J Bacteriol. Sep. 2006;188(17):6435-9.
Hatzimanikatis , et al., "Exploring the diversity of complex metabolic networks", Bioinformatics, Apr. 15, 2005;21 (8):1603-9. Epub Dec. 21, 2004.
He , et al., "A T42M Substitution in Bacterial 5-Enolpyruvyishikimate-3-phosphate Synthase (EPSPS) Generates Enzymes with Increased Resistance to Glyphosate", Biosci Biotechnol Biochem. vol. 67, 2003—Issue 6, 1405-1409.
Helge, Jans , et al., "Fatty acid synthesis in *Escherichia coli* and its applications towards the production of fatty acid based biofuels", Biotechnology for Biofuels, vol. 7, No. 1, XP-021173667, Jan. 9, 2014.
Henry , et al., "Discovery of novel routes for the biosynthesis of industrial chemicals: 3¬Hydroxypropanoate. Slides", AICHE Annual Meeting. Nov. 8, 2007. Salt Lake City, UT.
Herter , "Autotrophic CO2 Fixation by Chloroflexus aurantiacus: Study of Glyoxylate Formation and Assimilation via the 3-Hydroxypropionate Cycle", J Bacteriol Jul. 2001;183(14):4305-4316.
Meng , et al., "Nucleotide sequence of the *Escherichia coli* cad operon: a system for neutralization of low extracellular pH.", J. Bacteriol. vol. 174 No. 8, Apr. 1992, 2659-2669.
Milton , et al., "In vitro mutagenesis and overexpression of the *Escherichia coli* trpA gene and the partial characterization of the resultant tryptophan synthase mutant alpha-subunits", Biol Chem. 261(35), Dec. 15, 1986, 16604-15.
Mohan Raj , et al., "Effect of process parameters on 3-hydroxypropionic acid production from glycerol using a recombinant *Escherichia coli*", Appl Microbiol Biotechnol. 84(4), Sep. 2009, 649-57.
Moreau , et al., "Diversion of the metabolic flux from pyruvate dehydrogenase to pyruvate oxidase decreases oxidative stress during glucose metabolism in nongrowing *Escherichia coli* cells incubated under aerobic, phosphate starvation conditions", J Bacteriol. 186(21), Nov. 2004, 7364-8.
Muday , et al., "The tyrosine repressor negatively regulates aroH expression in *Escherichia coli*", 173(12), Jun. 1991, 3930-2.
Nackley , et al., "Human Catechol-O-Methyltransferase Haplotypes Modulate Protein Expression by Altering mRNA Secondary Structure", Science. 314(5807)., Dec. 22, 2006, 1930-3.
Nichols , "Cloning and sequencing of *Escherichia coli* ubiC and purification of chorismate lyase", J Bacteriol. 174 (16), Aug. 1992, 5309-16.

(56) References Cited

OTHER PUBLICATIONS

Ohnishi , et al., "A novel methodology employing Corynebacterium glutamicum genome information to generate a new L-lysine-producing mutant", Appl Microbiol Biotechnol. 58(2), Feb. 2002, 217-23.
Oliveira , et al., "Cloning and Overexpression in Soluble Form of Functional Shikimate Kinase and 5-Enolpyruvylshikimate 3-Phosphate Synthase Enzymes from *Mycobacterium tuberculosis*", Protein Expr Purif. 22(3)., Aug. 2001, 430-5.
Orjuela , et al., "Presentation: Recovery of succinic acid from fermentative broth through esterification with ethanol", Department of Chemical Engineering and Materials Science. Michigan State University. East Lansing, Michigan 48824, Jun. 29, 2010.
Ozcelik , et al., "Metabolic engineering of aromatic group amino acid pathway in Bacillus subtilis for L-phenylalanine production", Chemical Engineering Science 59(22-23):, 2004, 5019-5026.
Parikh , et al., "Directed evolution of RuBisCO hypermorphs through genetic selection in engineered *E.coli*", Protein Eng Des Sel. 19(3), Mar. 2006, 113-9.
Park , et al., "Production of alternatives to fuel oil from organic waste by the alkane-producing", Vibrio furnissii MI, Journal of Applied Microbiology, 2005, vol. 98, No. 2, pp. 324-331.
Patnaik , et al., "Genome shuffling of Lactobacillus for improved acid tolerance", Nat Biotechnol, 20(7), Jul. 2002, 707-12.
Pohl , et al., "A new perspective on thiamine catalysis", Curr Opin Biotechnol. 15(4), Aug. 2004, 335-42.
Ponce , et al., "Cloning of the Two Pyruvate Kinase Isoenzyme StructuralGenes from *Escherichia coli*: the Relative Roles of These Enzymes in Pyruvate Biosynthesis.", J Bacterial. 177(19), Oct. 1995, 5719-22.
Popp, J. , "Sequence and overexpression of the menD gene from *Escherichia coli*", J Bacteriol. 171(8), Aug. 1989, 4349-54.
Prather, Kristala L, et al., "De novo biosynthetic pathways: rational design of microbial chemical factories", Curr Opin Biotechnol 19(5), Oct. 19, 2008, 468-74.
Price-Carter , et al., "Polyphosphate kinase protects *Salmonella enterica* from weak organic acid stress", Journal of Bacteriology. 187, 2005, 3088-3099.
Ramalinga , et al., "A mild and efficient method for esterification and transesterification catalyzed by iodine", Tetrahedron Letters. 43(5), 2002, 879-882.
Ramey , et al., "Poster—Translation of genomics data into useful metabolic engineering strategies: construction of a 3-hydroxypropionic acid tolerant *E. coli*", 2010.
Ramilo , et al. "Overexpression, purification, and characterization of tyrosine-sensitive 3-deoxy-D-arabino-heptulosonic acid 7-phosphate synthase from *Escherichia coli*", Protein Expr Purif. 9(2), Mar. 1997, 253-61.
Rathnasingh , et al., "Development and evaluation of efficient recombinant *Escherichia coli* strains for the production of 3-hydroxypropionic acid from glycerol", Biotechnol Bioeng. 104(4). doi: 10.1002/bit.22429., Nov. 1, 2009, 729-39.
Rathnasingh, Chelladurai , et al., "Production of 3-hydroxypropionic acid via malonyl-COA pathway using recombinant *Escherichia coli* strains", J Biotechnol. 157(4), Feb. 20, 2012, 633-40.
Ray , et al., "Mutational analysis of the catalytic and feedback sites of the tryptophan-sensitive 3-deoxy-D-arabino-heptulosonate-7-phosphate synthase of *Escherichia coli*", J Bacteriol. 170(12), Dec. 1988, 5500-6.
Rodriguez , et al., "Structure-cytoprotective activity relationship of simple molecules containing an alpha, beta-unsaturated carbonyl system", J Med Chem. 40(12), Jun. 6, 1997, 1827-34.
Roe , et al., "Inhibition of *Escherichia coli* growth by acetic acid: a problem with methionine biosynthesis and homocysteine toxicity", Microbiology. 148(Pt 7), Jul. 2002, 2215-2222.
Sadowski, M. I., et al., "The sequence-structure relationship and protein function prediction", Current Opinion in Structural Biology 19, 2009, 357-362.
Saier , et al., "The catabolite repressor/activator (Cra) protein of enteric bacteria", J Bacteriol. 178(12), Jun. 1996, 3411-7.
Salis, Howard M., et al., "Automated Design of Synthetic Ribosome Binding Sites to Precisely Control Protein Expression", Nat Biotechnol 27(10), Oct. 2009, 946-50.
Sauna , et al., "Silent polymorphisms speak: how they affect pharmacogenomics and the treatment of cancer", Cancer Research. 67(20), Oct. 15, 2007, 9609-12.
Schmidt-Dannert , et al., "Molecular breeding of carotenoid biosynthetic pathways", Nat Biotechnol. 18(7), Jul. 2000, 750-3.
Seffernick, Jennifer L., et al., "Melamine Deaminase and Atrazine Chlorohydrolase: 98 Percent Identical but Functionally Different", J Bacteriol. 183(8), Apr. 2001, 2405-10.
Sen, S. , et al., "Developments in Directed Evolution for Improving Enzyme Functions", Appl Biochem Biotechnol. 143 (3), Dec. 2007, 212-23.
Service , "Sugary Recipe Boosts Grow-Your-Own Plastics", Science. 312(5782), Jun. 30, 2006, 1861.
Shelden, Megan C., et al., "Membrane topology of the cyanobacterial bicarbonate transporter, BicA, a member of the SulP (SLC26A) family", Molecular Membrane Biology vol. 27(1), 2010, 12-22.
Singh , et al., "Genes restoring redox balance in fermentation-deficient *E. coli* NZN111", Metabolic Engineering. vol. 11, Issue 6, Nov. 2009, 347-354.
Singh, Raushan Kumar, et al., "Protein Engineering Approaches in the Post-Genomic Era", Curr Protein Pept Sci. 18, 2017, 1-11.
Skerra, Arne , "Use of the tetracycline promoter for the tightly regulated production of a murine antibody fragment in *Escherichia coli*", Gene. 151(1-2), Dec. 30, 1994, 131-5.
Smirnova, N. , et al., "Engineered Fatty Acid Biosynthesis in Streptomyces by Altered Catalytic Function of B-Ketoacyl-Acyl Carrier Protein Synthase III", Journal of Bacteriology, vol. 1183, no. 7., Apr. 2001, 2335-2342 & 2335, 2336.
Sousa, Silvino , et al., "The ARO4 gene of Candida albicans encodes a tyrosine-sensitive DAHP synthase: evolution, functional conservation and phenotype of Aro3p-, Aro4p-deficient mutants", Microbiology 148(Pt5), 2002, 1291-1303.
Stephanie C. Weatherly , "Expression and characterization of recombinant fungal acetyl-CoA carboxylase and isolation of a soraphen-binding domain", Biochemical Journal, GB, (May 15, 2004), vol. 380, No. 1, doi:10.1042/ bj20031960, ISSN 0264-6021, pp. 105-110, XP055302533, May 15, 2004.
Stephanopoulos , et al., "Challenges in engineering microbes for biofuels production", Science. 315(5813), Feb. 9, 2007, 801-4.
Stephanopoulos , et al., "Network Rigidity and Metabolic Engineering in Metabolite Overproduction", Science. 252(5013), Jun. 21, 1991, 1675-81.
Stephens , et al., "Mitochondrial fatty acid synthesis in Trypanosoma brucei", Journal of Biological Chemistry, vol. 282, No. 7, Feb. 16, 2007, 4427-36.
Stim , et al., "Nucleotide sequence of the adi gene, which encodes the biodegradative acid-induced arginine decarboxylase of *Escherichia coli*", J Bacteriol. 175(5), Mar. 1993, 1221-34.
Straathoff , et al., "Feasibility of acrylic acid production by fermentation", Appl Microbiol Biotechnol.67(6), Jun. 2005, 727-34.
Strauss , et al., "Enzymes of a novel autotrophic CO2 fixation pathway in the phototrophic bacterium Chloroflexus aurantiacus, the 3-hydroxypropionate cycle", Eur J Biochem. 215(3), Aug. 1,1993, 633-43.
Sun , et al., "ZrOC12 x 8H20: an efficient, cheap and reusable catalyst for the esterification of acrylic acid and other carboxylic acids with equimolar amounts of alcohols", Molecules. 11(4):, Apr. 10, 2006, 263-71.
Takamizawa , et al., "Beta-Hydroxypropionic Acid Production by *Byssochlamys* Sp. Grown on Acrylic Acid", Appl Microbiol Biotechnol. 40, 1993, 196-200.
Stone, Scot J., et al., "Lipids and Lipoproteins: Lipopenia and Skin Barrier Abnormalities in DGAT2-deficient Mice.", J Biol Chem. 279(12), Mar. 19, 2004, 11767-76.
Stryer , "Biochemistry", 4th Ed. Freeman and Co., New York., 1995, 463-650.
Studier, William F., et al., "Use of Bacteriophage T7 RNA Polymerase to Direct Selective High-level Expression of Cloned Genes", J Mol Biol. 189(1), May 5, 1900, 113-30.

(56) References Cited

OTHER PUBLICATIONS

Subrahmanyam, Satyanarayana , et al., "Overproduction of a Functional Fatty Acid Biosynthetic Enzyme Blocks Fatty Acid Synthesis in *Escherichia coli*", J Bacteriol. 180(17), Sep. 1998, 4596-602.
Suh, Mi Chung, et al., "Cuticular Lipid Composition, Surface Structure, and Gene Expression in *Arabidopsis* Stem Epidermis", Plant Physiol. 139(4), Dec. 13, 2005, 1649-65.
Sulter, G. J. et al., "Proliferation and metabolic significance of peroxisomes in Candida boldinii during growth on D-alanine or oleic acid as the sole carbon source", Arch Microbiol. 153(5), 1990, 485-9.
Taghavi , et al., "Electroporation of Alcaligenes eutrophus with (mega) plasmids and genomic DNA fragments", Appl Environ Microbiol. Oct. 1994; 60(10): 3585-3591.
Tanimoto , et al., "Analysis of the Conjugal Transfer System of the Pheromone-Independent Highly Transferable Enterococcus Plasmid pMG1: Identification of a tra Gene (traA) Up-Regulated during Conjugation", doi: 10.1128/JB,184.20,5800-5804.2002 J. Bacteriol. Oct. 2002 vol. 184 No. 20 5800-5804.
Van Kranenburg , et al., "Functional Analysis of Three Plasmids from Lactobacillus planetarum", doi: 10.1128/AEM.713.1223-1230. 2005 Appl. Environ. Microbiol. Mar. 2005 vol. 71 No. 3 1223-1230.
Vilcheze , et al., "Inactivation of the inhA-Encoded Fatty Acid Synthase ll (FASII) Enoyl-Acyl Carrier Protein Reductase induces Accumulation of the FASI End Products and Cell Lysis of Mycobacterium smegmatis", doi: 10.1128/JB.182.14.4059-4067. 2000 J. Bacteriol. vol. 182 No. 14, Jul. 2000, 4059-4067.
Wyckoff , et al., "Characterization and sequence analysis of a stable cryptic plasmid from Enterococcus faecium 226 and development of a stable cloning vector", Appl Environ Microbiol. Apr. 1996; 62(4): 1481-1486.
Zha, Wenjuan , et al., "Improving cellular malonyl-CoA in *Escherichia coli* via metabolic engineering", Metab Eng. 11(3), May 2009, 192-8.
"Agriculture Project Fact Sheet", U.S. Department of Energy, Office of Industrial Technologies, Jul. 2001.
"BMC Biochemistry", vol. 12, No. 44, pp. 1-16, 2011, 1-16.
"Energetics Incorporated. 2003. Industrial Bioproducts: Today and Tomorrow. U.S. Department of Energy, Office of Energy Efficiency and Renewable Energy, Office of the Biomass Program, Washington, D.C.".
i "GenBank Accession No. AAC74497.1; Apr. 24, 2007. 2 pgs,".
"GenBank Accession No. NP 415816.1; available 1997".
"GenBank Accession No. NP 415933.1; available 1997".
"GenBank Accession No. NP 418045.4; available 1997".
"GenBank Accession No. X81461", AF473544, Sep. 7, 1994.
"GenBank Accession No. AAS20429.1", Jan. 19, 2004.
"International Search Report and Written Opinion for PCT Application No. US2012/030209".
"NCBI Reference Sequence: NP_414657.1", Jan. 16, 1997.
"NCBI Reference Sequence: NP_415792.1", Jan. 16, 1997.
"NCBI Reference Sequence: NP_416366.1", Jan. 16, 1997.
"NCBI Reference Sequence: NP_418812.1", Jan. 16, 1997.
"NCBI Reference Sequence: WP_011957906.1", Jun. 6, 2007.
"NCBI Reference Sequence: WP_012121415.1", Sep. 4, 2007.
"NCBI Reference Sequence: WP_012616528.1", Dec. 29, 2008.
"NCBI Reference Sequence: YP_001636209.1", Dec. 21, 2007.
"NCBI Reference Sequence: ZP_01039179.1", Jan. 16, 2006.
"NCBI Reference Sequence: ZP_01626393.1", Dec. 15, 2006.
"NCBI Reference Sequence: ZP_04957196.1", Sep. 15, 2008.
"NCBI Reference Sequence: ZP_05125944.1", Sep. 15, 2008.
"Nexant, Inc. Chemsystems Perp Program, Acrylic Acid, 08/09-3", Jul. 2010.
Abdel-Hamid, Ahmed M., et al., "Coordinate Expression of the Acetyl Coenzyme A Carboxylase Genes, accB and accC, Is Necessary for Normal Regulation of Biotin Synthesis in *Escherichia coli*", J Bacteriol. 189(2), Jan. 2007, 369-76.
Alber , et al., "Malonyl-coenzyme A reductase in the modified 3-hydroxypropionate cycle for autotrophic carbon fixation in archaeal *Metallosphaera* and *Sulfolobus* spp.", spp. J Bacteriol. Dec. 2006;188(24):8551-9.
Anagnostopoulos, C. , et al., "Requirements for Transformation in Bacillus Subtilis", J Bacteriol. 81(5), May 1961, 741-6.
Anton , et al., "Sequencing and Overexpression of the *Escherichia Coli* Aroe Gene Encoding Shikimate Dehydrogenase", Biochem J. Jan. 15, 1988;249(2):319-26.
Armstrong, S. M., et al., "Abiotic conversion of dihydrophloroglucinol to resorcinol", Canadian Journal of Microbiology. 39(9), 1993, 899-902.
Asano , et al., "A new enzymatic method of acrylamide production", Agricultural and Biological Chemistry. 46(5), 1982, 1183-1189.
Baek, Jong Hwan, et al., "Novel gene members in the Pho regulon of *Escherichia coli*", FEMS Microbiol Lett. 264 (1), Nov. 2006, 104-9.
Bailey , et al., "Inverse metabolic engineering: A strategy for directed genetic engineering of useful phenotypes", BBiotechnol Bioeng. 79(5), Sep. 5, 2002, 568-79.
Bailey , et al., "Toward a science of metabolic engineering", Science;252(5013):, Jun. 21, 1991, 1668-75.
Barbin , et al., "Induction of specific base-pair substitutions in *E. coli* trpA mutants by chloroethylene oxide, a carcinogenic vinyl chloride metabolite", Mutat Res. Nov.-Dec. 1985;152(2-3):147-56.
Bastian , et al., "Engineered ketol-acid reductoisomerase and alcohol dehydrogenase enable anaerobic 2-methylpropan-l-ol production at theoretical yield in *Escherichia coli*", Metab Eng. May 2011;13(3):345-52.
Ben-Aroya, Shay , et al., "Toward a Comprehensive Temperature-Sensitive Mutant Repository of the Essential Genes of Saccharomyces cerevisiae", Molecular Cell. 30, 2008, 248-258.
Bergler , et al., "Sequences of the envM gene and of two mutated alleles in *Escherichia coli*", J Gen Microbiol. Oct. 1992;138(10):2093-100.
Bergler , et al., "The enoyl-[acyl-carrier-protein] reductase (Fabl) of *Escherichia coli*, which catalyzes a key regulatory step in fatty acid biosynthesis, accepts NADH and NADPH as cofactors and is inhibited by palmitoyl-CoA", Eur J Biochem. 242(3), Dec. 15, 1996, 689-94.
Bloch , et al., "Control mechanisms in the synthesis of saturated fatty acids", Annu Rev Biochem. 46, 1977, 263-98.
Bonner , et al., "A core catalytic domain of the TyrA protein family: arogenate dehydrogenase from Synechocystis", Biochem J. 382(Pt 1), Aug. 15, 2004, 279-91.
Bonner, William M., et al., "Purification and Properties of Fatty Acyl Thioesterase I from *Escherichia coli*", J Biol Chem. 247(10), Mar. 25, 1972, 3123-33.
Borgaro, Janine G., et al., "Substrate Recognition by B-Ketoacyl-ACP Synthases", Biochemistry. 50(49), Dec. 13, 2011, 10678-86.
Branden, Carl , et al., "Introduction to Protein Structure", Garland Publishing Inc., New York, 1991, 247.
Brock , et al., "Naturally occurring adenines within mRNA coding sequences affect ribosome binding and expression in *Escherichia coli*", J Bacteriol. Jan. 2007;189(2):501-10. Epub Nov. 3, 2006.
Broun, Pierre , et al., "Catalytic Plasticity of Fatty Acid Modification Enzymes Underlying Chemical Diversity of Plant Lipids", Science. 282(5392), Nov. 13, 1998, 1315-7.
Brown , et al., "Synthesis of labeled acrylamide and N-methylolacrylamide (NMA): 15N-acrylamide, 13C-NMA, 15N-NMA, and 13C, 15N-NMA", Journal of labelled compounds & radiopharmaceuticals. 48(14):1031-1039., Nov. 14, 2005.
Bunch , et al., "The IdhA gene encoding the fermentative lactate dehydrogenase of *Escherichia coli*", Microbiology. Jan. 1997;143 ( Pt 1):187-95.
Canada , et al., "Directed evolution of toluene ortho-monooxygenase for enhanced 1¬naphthol synthesis and chlorinated ethene degradation", J Bacteriol. Jan. 2002;184(2):344-9.
Chang , et al., "Acetate metabolism in a pta mutant of *Escherichia coli* W3110: importance of maintaining acetyl coenzyme A flux for growth and survival", J Bacteriol. Nov. 1999;181(21):6656-63.

(56) References Cited

OTHER PUBLICATIONS

Chang , et al., "Probable polyketide synthase/thioesterase. NCBI Direct Submission, Accession Number: GI50082961", Jun. 14, 2004.
Chao , et al., "Selective production of L-aspartic acid and L-phenylalanine by coupling reactions of aspartase and aminotransferase in *Escherichia coli*", Enzyme Microb Technol. 27(1-2), Jul. 1, 2000, 19-25.
Takamura , et al., "Changes in the intracellular concentration of acetyl-CoA and malonyl-CoA in relation to the carbon and energy metabolism of *Escherichia coli* K12", J Gen Microbiol. 134(8), Aug. 1988, 2249-53.
Tian , et al., "*Mycobacterium tuberculosis* appears to lack an alpha-ketoglutarate dehydrogenase and encodes pyruvate dehydrogenase in widely separated genes", Mol Microbiol. 57(3), Aug. 2005, 859-68.
Tian , et al., "Variant tricarboxylic acid cycle in *Mycobacterium tuberculosis*: Identification of alpha-ketoglutarate decarboxylase", Proc Natl Acad Sci U S A. 102(30), Jul. 26, 2005, 10670-5.
Tomar, A. , "Master Thesis. Production of Pyruvate by *Escherichia Coli* Using Metabolic Engineering", The University of Georgia, May 2002, 1-171.
Tunnicliff, et al., "The inhibition by substrate analogues of gamma-aminobutyrate aminotransferase from mitochondria of different subcellular fractions of rat brain", Can J Biochem. 55(4), Apr. 1977, 479-84.
Turlin , et al., "3-phenylpropionate catabolism and the *Escherichia coli* oxidative stress response", Res Microbiol. 156(3), Apr. 2005, 312-21.
Valentin H E , et al., "Production of poly(3-hydroxybutyrate-co-4-hydroxybutyrate) in recombinant *Escherichia coli* grown on glucose", Journal of Biotechnology, Elsevier Science Publishers, Amsterdam, NL. Elsevier Science Publishers, Amsterdam, NL, vol. 58, No. 1, doi:10.1016/S0168-1656(97)00127-2, ISSN 0168-1656, XP004126101, Oct. 2, 1997, 33-38.
Vedantam , et al., "Characterization of mutations contributing to sulfathiazole resistance in *Escherichia coli*", Antimicrob Agents Chemother. 42(1), Jan. 1998, 88-93.
Wankat, Phillip C., "Separation Process Engineering, Equilibrium Staged Separations", P.C. Wankat, Prentice Hall, Englewood Cliffs. NJ. USA., 1988.
Warnecke , et al., "A genomics approach to improve the analysis and design of strain selections", Metab Eng. 10 (3-4), May-Jul. 2008, 154-65.
Warnecke , et al., "Engineering of Organic Acid Tolerance Genes in *E. coli* for Biorefinery Applications", 2006 AlChE Annual meeting in San Francisco, California, Nov. 12-17, 2006, https://aiche.confex.comlaiche/2006/techprogram/P67122.HTM.
Warnecke , et al., "Identification of a 21 amino acid peptide conferring 3¬hydroxypropionic acid stress-tolerance to *Escherichia coli*", Biotechnol Bioeng.109(5). doi: 10.1002/bit.24398., May 2012, 1347-52.
Warnecke , et al., "Organic acid toxicity, tolerance, and production in *Escherichia coli* biorefining applications.", Microbial Cell Factories. 4(25), 2005, 1-8.
Warnecke , et al., "Rapid dissection of a complex phenotype through genomic-scale mapping of fitness altering genes", Metab Eng. 12(3), May 2010, 241-50.
Wasewar , et al., "Fermentation of Glucose to Lactic Acid Coupled with Reactive Extraction: A Review.", Ind. Eng. Chem. Res. 43, 2004, 5969-5982.
Waterson , et al., "Enoyl coenzyme A hydratase (crotonase). Catalytic properties of crotonase and its possible regulatory role in fatty acid oxidation", J Biol Chem. 247(16), Aug. 25, 1972, 5258-65.
Weilbacher , et al., "A novel sRNA component of the carbon storage regulatory system of *Escherichia coil.*", Molecular Microbiology, vol. 48, No. 3, [online] [Retrieved on Jul. 11, 2007]. [Retrieved from the intemet: http://www.blackwell-synergy.com/links/doi/10.1046/1.1365-2958.2003.03459.x/full/], May 2003, 657-670.
Welch , et al., "Extensive mosaic structure revealed by the complete genome sequence of uropathogenic *Escherichia coli.*", Proc Natl Acad Sci U S A. 99(26), Dec. 24, 2002, 17020-4.
Werpy , et al., "Top Value Added Chemicals From Biomass, Volume 1—Results of Screening for Potential candidates From Sugars and Synthesis Gas", Pacific Northwest National Laboratory. U.S. Department of Energy, Aug. 2004.
Whisstock , et al., "Prediction of protein function from protein sequence and structure", Q Rev Biophys. 36(3), Aug. 2003, 307-40.
White , et al., "The overexpression, purification and complete amino acid sequence of chorismate synthase from *Escherichia coli* K12 and its comparison with the enzyme from Neurospora crassa", Biochem J. 251(2), Apr. 15, 1988, 313-22.
Winkler, Christoph K., et al., "Asymmetric bioreduction of activated alkenes to industrially relevant optically active compounds", J Biotechnol. 162(4), Dec. 31, 2012, 381-9.
Wishart , et al., "A single mutation converts a novel phosphotyrosine binding domain into a dual-specificity phosphatase", J Biol Chem. 270(45), Nov. 10, 1995, 26782-5.
Witkowski , et al., "Conversion of a beta-ketoacyl synthase to a malonyl decarboxylase by replacement of the active-site cysteine with glutamine.", Biochemistry. 38(36), Sep. 7, 1999, 11643-50.
Xie, Dongming , et al., "Microbial Synthesis of Triacetic Acid Lactone", Biotechnol Bioeng. 93(4), Mar. 5, 2006, 727-36.
Xu , et al., "English Translation: Principles and Experiments of Biotechnology", China Minzu University Press. (English Translation), Jul. 2006, 229-231.
Xu, Xiaowei , "Fatty acid synthase inhibitors: research advances", Journal of international pharmaceutical research. vol. 36 (2). (English abstract), 2009, 105-108, 120.
Yee , et al., "On the role of helix 0 of the tryptophan synthetase alpha chain of *Escherichia coli.*", J Biol Chem. 271(25), Jun. 21, 1996, 14754-63.
Yiming Ren , et al., "Molecular Iodine in Ionic Liquid: A Green Catalytic System for Esterification and Transesterification", Synthetic Communications. 40(11), 2010, 1670-1676.
Yoshida , et al., "Identification of PhoB binding sites of the yibD and ytfK promoter regions in *Escherichia coli.*", J Microbiol. 49(2), Apr. 2011, 285-289.
Zhang , et al., "Inhibiting bacterial fatty acid synthesis", J. Biol. Chem. 281(26), Jun. 30, 2006, 17541-17544.
Zhao , "Binding of two flaviolin substrate molecules, oxidative coupling, and crystal structure of Streptamyces coelicolor A3(2) cytochrome P450 158A2.", J Biol Chem. 280(12), Mar. 25, 2005, 11599-607.
Zhou , et al., "Interdomain communication between the thiolation and thioesterase domains of EntF explored by combinatorial mutagenesis and selection", Chem Biol. 13(8), Aug. 2006, 869-79.

* cited by examiner

SEQUENCE LISTING

```
<160> NUMBER OF SEQ ID NOS: 19

<210> SEQ ID NO 1
<211> LENGTH: 5367
<212> TYPE: DNA
```

<213> ORGANISM: Escherichia coli

<400> SEQUENCE: 1
ggcgaatggg acgcgccctg tagcggcgca ttaagcgcgg cgggtgtggt ggttacgcgc 60
agcgtgaccg ctacacttgc cagcgcccta gcgcccgctc ctttcgcttt cttcccttcc 120
tttctcgcca cgttcgccgg ctttccccgt caagctctaa atcgggggct ccctttaggg 180
ttccgattta gtgctttacg gcacctcgac cccaaaaaac ttgattaggg tgatggttca 240
cgtagtgggc catcgccctg atagacggtt tttcgccctt tgacgttgga gtccacgttc 300
tttaatagtg gactcttgtt ccaaactgga acaacactca accctatctc ggtctattct 360
tttgatttat aagggatttt gccgatttcg gcctattggt taaaaaatga gctgatttaa 420
caaaaattta acgcgaattt taacaaaata ttaacgttta caatttcagg tggcactttt 480
cggggaaatg tgcgcggaac ccctatttgt ttatttttct aaatacattc aaatatgtat 540
ccgctcatga attaattctt agaaaaactc atcgagcatc aaatgaaact gcaatttatt 600
catatcagga ttatcaatac catatttttg aaaaagccgt ttctgtaatg aaggagaaaa 660
ctcaccgagg cagttccata ggatggcaag atcctggtat cggtctgcga ttccgactcg 720
tccaacatca atacaaccta ttaatttccc ctcgtcaaaa ataaggttat caagtgagaa 780
atcaccatga gtgacgactg aatccggtga gaatggcaaa agtttatgca tttctttcca 840
gacttgttca acaggccagc cattacgctc gtcatcaaaa tcactcgcat caaccaaacc 900
gttattcatt cgtgattgcg cctgagcgag acgaaatacg cgatcgctgt taaaaggaca 960
attacaaaca ggaatcgaat gcaaccggcg caggaacact gccagcgcat caacaatatt 1020
ttcacctgaa tcaggatatt cttctaatac ctggaatgct gttttcccgg ggatcgcagt 1080
ggtgagtaac catgcatcat caggagtacg gataaaatgc ttgatggtcg gaagaggcat 1140
aaattccgtc agccagttta gtctgaccat ctcatctgta acatcattgg caacgctacc 1200
tttgccatgt ttcagaaaca actctggcgc atcgggcttc ccatacaatc gatagattgt 1260
cgcacctgat tgcccgacat tatcgcgagc ccatttatac ccatataaat cagcatccat 1320
gttggaattt aatcgcggcc tagagcaaga cgtttcccgt tgaatatggc tcataacacc 1380
ccttgtatta ctgtttatgt aagcagacag ttttattgtt catgaccaaa atcccttaac 1440
gtgagttttc gttccactga gcgtcagacc ccgtagaaaa gatcaaagga tcttcttgag 1500
atcctttttt tctgcgcgta atctgctgct tgcaaacaaa aaaaccaccg ctaccagcgg 1560
tggtttgttt gccggatcaa gagctaccaa ctctttttcc gaaggtaact ggcttcagca 1620
gagcgcagat accaaatact gtccttctag tgtagccgta gttaggccac cacttcaaga 1680
actctgtagc accgcctaca tacctcgctc tgctaatcct gttaccagtg gctgctgcca 1740
gtggcgataa gtcgtgtctt accgggttgg actcaagacg atagttaccg gataaggcgc 1800
agcggtcggg ctgaacgggg ggttcgtgca cacagcccag cttggagcga acgacctaca 1860
ccgaactgag atacctacag cgtgagctat gagaaagcgc cacgcttccc gaagggagaa 1920
aggcggacag gtatccggta agcggcaggg tcggaacagg agagcgcacg agggagcttc 1980 caggggaaa cgcctggtat ctttatagtc ctgtcgggtt tcgccacctc tgacttgagc 2040
gtcgattttt gtgatgctcg tcaggggggc ggagcctatg gaaaaacgcc agcaacgcgg 2100
cctttttacg gttcctggcc ttttgctggc cttttgctca catgttcttt cctgcgttat 2160
cccctgattc tgtggataac cgtattaccg cctttgagtg agctgatacc gctcgccgca 2220
gccgaacgac cgagcgcagc gagtcagtga gcgaggaagc ggaagagcgc ctgatgcggt 2280

-continued

```
atttctcct tacgcatctg tgcggtattt cacaccgcat atatggtgca ctctcagtac   2340
aatctgctct gatgccgcat agttaagcca gtatacactc cgctatcgct acgtgactgg   2400
gtcatggctg cgccccgaca cccgccaaca cccgctgacg cgccctgacg ggcttgtctg   2460
ctcccggcat ccgcttacag acaagctgtg accgtctccg ggagctgcat gtgtcagagg   2520
ttttcaccgt catcaccgaa acgcgcgagg cagctgcggt aaagctcatc agcgtggtcg   2580
tgaagcgatt cacagatgtc tgcctgttca tccgcgtcca gctcgttgag tttctccaga   2640
agcgttaatg tctggcttct gataaagcgg gccatgttaa gggcggtttt ttcctgtttg   2700
gtcactgatg cctccgtgta agggggattt ctgttcatgg gggtaatgat accgatgaaa   2760
cgagagagga tgctcacgat acgggttact gatgatgaac atgcccggtt actggaacgt   2820
tgtgagggta aacaactggc ggtatggatg cggcgggacc agagaaaaat cactcagggt   2880
caatgccagc gcttcgttaa tacagatgta ggtgttccac agggtagcca gcagcatcct   2940
gcgatgcaga tccggaacat aatggtgcag ggcgctgact tccgcgtttc cagactttac   3000
gaaacacgga aaccgaagac cattcatgtt gttgctcagg tcgcagacgt tttgcagcag   3060
cagtcgcttc acgttcgctc gcgtatcggt gattcattct gctaaccagt aaggcaaccc   3120
cgccagccta gccgggtcct caacgacagg agcacgatca tgcgcacccg tggggccgcc   3180
atgccggcga taatggcctg cttctcgccg aaacgtttgg tggcgggacc agtgacgaag   3240
gcttgagcga gggcgtgcaa gattccgaat accgcaagcg acaggccgat catcgtcgcg   3300
ctccagcgaa agcggtcctc gccgaaaatg acccagagcg ctgccggcac ctgtcctacg   3360
agttgcatga taaagaagac agtcataagt gcggcgacga tagtcatgcc ccgcgcccac   3420
cggaaggagc tgactgggtt gaaggctctc aagggcatcg gtcgagatcc cggtgcctaa   3480
tgagtgagct aacttacatt aattgcgttg cgctcactgc ccgctttcca gtcgggaaac   3540
ctgtcgtgcc agctgcatta atgaatcggc caacgcgcgg ggagaggcgg tttgcgtatt   3600
gggcgccagg gtggtttttc ttttcaccag tgagacgggc aacagctgat tgcccttcac   3660
cgcctggccc tgagagagtt gcagcaagcg gtccacgctg gtttgcccca gcaggcgaaa   3720
atcctgtttg atggtggtta acggcgggat ataacatgag ctgtcttcgg tatcgtcgta   3780
tcccactacc gagatatccg caccaacgcg cagcccggac tcggtaatgg cgcgcattgc   3840
gcccagcgcc atctgatcgt tggcaaccag catcgcagtg ggaacgatgc cctcattcag   3900
catttgcatg gtttgttgaa aaccggacat ggcactccag tcgccttccc gttccgctat   3960
cggctgaatt tgattgcgag tgagatattt atgccagcca gccagacgca gacgcgccga   4020
gacagaactt aatgggcccg ctaacagcgc gatttgctgg tgacccaatg cgaccagatg   4080
ctccacgccc agtcgcgtac cgtcttcatg ggagaaaata atactgttga tgggtgtctg   4140
gtcagagaca tcaagaaata acgccggaac attagtgcag gcagcttcca cagcaatggc   4200
atcctggtca tccagcggat agttaatgat cagcccactg acgcgttgcg cgagaagatt   4260
gtgcaccgcc gctttacagg cttcgacgcc gcttcgttct accatcgaca ccaccacgct   4320
ggcacccagt tgatcggcgc gagatttaat cgccgcgaca atttgcgacg gcgcgtgcag   4380
ggccagactg gaggtggcaa cgccaatcag caacgactgt ttgcccgcca gttgttgtgc   4440
cacgcggttg ggaatgtaat tcagctccgc catcgccgct tccacttttt cccgcgtttt   4500
cgcagaaacg tggctggcct ggttcaccac gcgggaaacg gtctgataag agacaccggc   4560
atactctgcg acatcgtata acgttactgg tttcacattc accaccctga attgactctc   4620
```

```
ttccgggcgc tatcatgcca taccgcgaaa ggttttgcgc cattcgatgg tgtccgggat   4680

ctcgacgctc tcccttatgc gactcctgca ttaggaagca gcccagtagt aggttgaggc   4740

cgttgagcac cgccgccgca aggaatggtg catgcaagga gatggcgccc aacagtcccc   4800

cggccacggg gcctgccacc atacccacgc cgaaacaagc gctcatgagc ccgaagtggc   4860

gagcccgatc ttccccatcg gtgatgtcgg cgatataggc gccagcaacc gcacctgtgg   4920

cgccggtgat gccggccacg atgcgtccgg cgtagaggat cgagatctcg atcccgcgaa   4980

attaatacga ctcactatag gggaattgtg agcggataac aattcccctc tagaaataat   5040

tttgtttaac tttaagaagg agatatacca tgggcagcag ccatcatcat catcatcaca   5100

gcagcggcct ggtgccgcgc ggcagccata tggctagcat gactggtgga cagcaaatgg   5160

gtcgggatcc gaattcgagc tccgtcgaca agcttgcggc cgcactcgag caccaccacc   5220

accaccactg agatccggct gctaacaaag cccgaaagga agctgagttg gctgctgcca   5280

ccgctgagca ataactagca taaccccttg gggcctctaa acgggtcttg aggggttttt   5340

tgctgaaagg aggaactata tccggat                                       5367
```

<210> SEQ ID NO 2
<211> LENGTH: 4008
<212> TYPE: DNA
<213> ORGANISM: Escherichia coli

<400> SEQUENCE: 2

```
ggggaattgt gagcggataa caattcccct gtagaaataa ttttgtttaa ctttaataag     60

gagatatacc atgggcagca gccatcacca tcatcaccac agccaggatc cgaattcgag    120

ctcggcgcgc ctgcaggtcg acaagcttgc ggccgcataa tgcttaagtc gaacagaaag    180

taatcgtatt gtacacggcc gcataatcga aattaatacg actcactata ggggaattgt    240

gagcggataa caattcccca tcttagtata ttagttaagt ataagaagga gatatacata    300

tggcagatct caattggata tcggccggcc acgcgatcgc tgacgtcggt accctcgagt    360

ctggtaaaga aaccgctgct gcgaaatttg aacgccagca catggactcg tctactagcg    420

cagcttaatt aacctaggct gctgccaccg ctgagcaata actagcataa ccccttgggg    480

cctctaaacg ggtcttgagg ggttttttgc tgaaacctca ggcatttgag aagcacacgg    540

tcacactgct tccggtagtc aataaaccgg taaaccagca atagacataa gcggctattt    600

aacgaccctg ccctgaaccg acgaccgggt cgaatttgct ttcgaatttc tgccattcat    660

ccgcttatta tcacttattc aggcgtagca ccaggcgttt aagggcacca ataactgcct    720

taaaaaaatt acgccccgcc ctgccactca tcgcagtact gttgtaattc attaagcatt    780

ctgccgacat ggaagccatc acagacggca tgatgaacct gaatcgccag cggcatcagc    840

accttgtcgc cttgcgtata atatttgccc atagtgaaaa cgggggcgaa gaagttgtcc    900

atattggcca cgtttaaatc aaaactggtg aaactcaccc agggattggc tgagacgaaa    960

aacatattct caataaaccc tttagggaaa taggccaggt tttcaccgta acacgccaca   1020

tcttgcgaat atatgtgtag aaactgccgg aaatcgtcgt ggtattcact ccagagcgat   1080

gaaaacgttt cagtttgctc atggaaaacg gtgtaacaag ggtgaacact atcccatatc   1140

accagctcac cgtctttcat tgccatacgg aactccggat gagcattcat caggcgggca   1200

agaatgtgaa taaaggccgg ataaaacttg tgcttatttt tctttacggt ctttaaaaag   1260

gccgtaatat ccagctgaac ggtctggtta taggtacatt gagcaactga ctgaaatgcc   1320

tcaaaatgtt ctttacgatg ccattgggat atatcaacgg tggtatatcc agtgattttt   1380
```

-continued ttctccattt tagcttcctt agctcctgaa aatctcgata actcaaaaaa tacgcccggt 1440
agtgatctta tttcattatg gtgaaagttg gaacctctta cgtgccgatc aacgtctcat 1500
tttcgccaaa agttggccca gggcttcccg gtatcaacag ggacaccagg atttatttat 1560
tctgcgaagt gatcttccgt cacaggtatt tattcggcgc aaagtgcgtc gggtgatgct 1620
gccaacttac tgatttagtg tatgatggtg tttttgaggt gctccagtgg cttctgtttc 1680
tatcagctgt ccctcctgtt cagctactga cggggtggtg cgtaacggca aaagcaccgc 1740
cggacatcag cgctagcgga gtgtatactg gcttactatg ttggcactga tgagggtgtc 1800
agtgaagtgc ttcatgtggc aggagaaaaa aggctgcacc ggtgcgtcag cagaatatgt 1860
gatacaggat atattccgct tcctcgctca ctgactcgct acgctcggtc gttcgactgc 1920
ggcgagcgga aatggcttac gaacggggcg gagatttcct ggaagatgcc aggaagatac 1980
ttaacaggga agtgagaggg ccgcggcaaa gccgtttttc cataggctcc gcccccctga 2040
caagcatcac gaaatctgac gctcaaatca gtggtggcga aacccgacag gactataaag 2100
ataccaggcg tttccccctgg cggctccctc gtgcgctctc ctgttcctgc ctttcggttt 2160
accggtgtca ttccgctgtt atggccgcgt ttgtctcatt ccacgcctga cactcagttc 2220
cgggtaggca gttcgctcca agctggactg tatgcacgaa ccccccgttc agtccgaccg 2280
ctgcgcctta tccggtaact atcgtcttga gtccaacccg gaaagacatg caaaagcacc 2340
actggcagca gccactggta attgatttag aggagttagt cttgaagtca tgcgccggtt 2400
aaggctaaac tgaaaggaca agttttggtg actgcgctcc tccaagccag ttacctcggt 2460
tcaaagagtt ggtagctcag agaaccttcg aaaaaccgcc ctgcaaggcg gttttttcgt 2520
tttcagagca agagattacg cgcagaccaa aacgatctca agaagatcat cttattaatc 2580
agataaaata tttctagatt tcagtgcaat ttatctcttc aaatgtagca cctgaagtca 2640
gccccatacg atataagttg taattctcat gttagtcatg ccccgcgccc accggaagga 2700
gctgactggg ttgaaggctc tcaagggcat cggtcgagat cccggtgcct aatgagtgag 2760
ctaacttaca ttaattgcgt tgcgctcact gcccgctttc cagtcgggaa acctgtcgtg 2820
ccagctgcat taatgaatcg gccaacgcgc ggggagaggc ggtttgcgta ttgggcgcca 2880
gggtggtttt tcttttcacc agtgagacgg gcaacagctg attgcccttc accgcctggc 2940
cctgagagag ttgcagcaag cggtccacgc tggtttgccc cagcaggcga aaatcctgtt 3000
tgatggtggt taacggcggg atataacatg agctgtcttc ggtatcgtcg tatcccacta 3060
ccgagatgtc cgcaccaacg cgcagcccgg actcggtaat ggcgcgcatt gcgcccagcg 3120
ccatctgatc gttggcaacc agcatcgcag tgggaacgat gccctcattc agcatttgca 3180
tggtttgttg aaaaccggac atggcactcc agtcgccttc ccgttccgct atcggctgaa 3240
tttgattgcg agtgagatat ttatgccagc cagccagacg cagacgcgcc gagacagaac 3300
ttaatgggcc cgctaacagc gcgatttgct ggtgacccaa tgcgaccaga tgctccacgc 3360
ccagtcgcgt accgtcttca tgggagaaaa taatactgtt gatgggtgtc tggtcagaga 3420
catcaagaaa taacgccgga acattagtgc aggcagcttc cacagcaatg gcatcctggt 3480
catccagcgg atagttaatg atcagcccac tgacgcgttg cgcgagaaga ttgtgcaccg 3540
ccgctttaca ggcttcgacg ccgcttcgtt ctaccatcga caccaccacg ctggcaccca 3600
gttgatcggc gcgagattta atcgccgcga caatttgcga cggcgcgtgc agggccagac 3660
tggaggtggc aacgccaatc agcaacgact gtttgcccgc cagttgttgt gccacgcggt 3720

```
tgggaatgta attcagctcc gccatcgccg cttccacttt ttcccgcgtt ttcgcagaaa   3780

cgtggctggc ctggttcacc acgcgggaaa cggtctgata agagacaccg gcatactctg   3840

cgacatcgta taacgttact ggtttcacat tcaccaccct gaattgactc tcttccgggc   3900

gctatcatgc cataccgcga aaggttttgc gccattcgat ggtgtccggg atctcgacgc   3960

tctcccttat gcgactcctg cattaggaaa ttaatacgac tcactata                4008
```

<210> SEQ ID NO 3
<211> LENGTH: 7376
<212> TYPE: DNA
<213> ORGANISM: Escherichia coli

<400> SEQUENCE: 3

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140

taaattccgt cagccagttt agtctgacca tctcatctgt aacatcattg gcaacgctac   1200

ctttgccatg tttcagaaac aactctggcg catcgggctt cccatacaat cgatagattg   1260

tcgcacctga ttgcccgaca ttatcgcgag cccatttata cccatataaa tcagcatcca   1320

tgttggaatt taatcgcggc ctagagcaag acgtttcccg ttgaatatgg ctcataacac   1380

cccttgtatt actgtttatg taagcagaca gttttattgt tcatgaccaa aatcccttaa   1440

cgtgagtttt cgttccactg agcgtcagac cccgtagaaa agatcaaagg atcttcttga   1500

gatccttttt ttctgcgcgt aatctgctgc ttgcaaacaa aaaaaccacc gctaccagcg   1560

gtggtttgtt tgccggatca agagctacca actctttttc cgaaggtaac tggcttcagc   1620

agagcgcaga taccaaatac tgtccttcta gtgtagccgt agttaggcca ccacttcaag   1680

aactctgtag caccgcctac atacctcgct ctgctaatcc tgttaccagt ggctgctgcc   1740

agtggcgata agtcgtgtct taccgggttg gactcaagac gatagttacc ggataaggcg   1800

cagcggtcgg gctgaacggg gggttcgtgc acacagccca gcttggagcg aacgacctac   1860
```

```
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
```

-continued

```
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atggcgatta agagttttaa tgaaattatc   5100
atgaaggtaa agagcaaaga aatgaaaaaa gttgctgttg ctgtagcaca agacgagcca   5160
gtacttgaag cagtaagaga tgctaagaaa aatggtattg cagatgctat tcttgttgga   5220
gaccatgacg aaatcgtgtc aatcgcgctt aaaataggaa tggatgtaaa tgattttgaa   5280
atagtaaacg agcctaacgt taagaaagct gctttaaagg cagtagagct tgtatcaact   5340
ggaaaagctg atatggtaat gaagggactt gtaaatacag caactttctt aagatctgta   5400
ttaaacaaag aagttggact tagaacagga aaaactatgt ctcacgttgc agtatttgaa   5460
actgagaaat ttgatagact attattttta acagatgttg ctttcaatac ttatcctgaa   5520
ttaaaggaaa aaattgatat agtaaacaat tcagttaagg ttgcacatgc aataggaatt   5580
gaaaatccaa aggttgctcc aatttgtgca gttgaggtta taaaccctaa aatgccatca   5640
acacttgatg cagcaatgct ttcaaaaatg agtgacagag gacaaattaa aggttgtgta   5700
gttgacggac ctttagcact tgatatagct ttatcagaag aagcagcaca tcataaggga   5760
gtaacaggag aagttgctgg aaaagctgat atcttcttaa tgccaaacat agaaacagga   5820
aatgtaatgt ataagacttt aacatataca actgattcaa aaaatggagg aatcttagtt   5880
ggaacttctg caccagttgt tttaacttca agagctgaca gccatgaaac aaaaatgaac   5940
tctatagcac ttgcagcttt agttgcaggc aataaataaa ttaaagttaa gtggaggaat   6000
gttaacatgt atagattact aataatcaat cctggctcga cctcaactaa aattggtatt   6060
tatgacgatg aaaaagagat atttgagaag actttaagac attcagctga agagatagaa   6120
aaatataaca ctatatttga tcaatttcaa ttcagaaaga atgtaatttt agatgcgtta   6180
aaagaagcaa acatagaagt aagttcttta aatgctgtag ttggaagagg cggactctta   6240
aagccaatag taagtggaac ttatgcagta aatcaaaaaa tgcttgaaga ccttaaagta   6300
ggagttcaag gtcagcatgc gtcaaatctt ggtggaatta ttgcaaatga aatagcaaaa   6360
gaaataaatg ttccagcata catagttgat ccagttgttg tggatgagct tgatgaagtt   6420
tcaagaatat caggaatggc tgacattcca agaaaaagta tattccatgc attaaatcaa   6480
aaagcagttg ctagaagata tgcaaaagaa gttggaaaaa aatacgaaga tcttaattta   6540
atcgtagtcc acatgggtgg aggtacttca gtaggtactc ataaagatgg tagagtaata   6600
```

-continued

```
gaagttaata atacacttga tggagaaggt ccattctcac cagaaagaag tggtggagtt   6660
ccaataggag atcttgtaag attgtgcttc agcaacaaat atacttatga agaagtaatg   6720
aaaaagataa acggcaaagg cggagttgtt agttacttaa atactatcga ttttaaggct   6780
gtagttgata aagctcttga aggagataag aaatgtgcac ttatatatga agctttcaca   6840
ttccaggtag caaaagagat aggaaaatgt tcaaccgttt taaaaggaaa tgtagatgca   6900
ataatcttaa caggcggaat tgcgtacaac gagcatgtat gtaatgccat agaggataga   6960
gtaaaattca tagcacctgt agttagatat ggtggagaag atgaacttct tgcacttgca   7020
gaaggtggac ttagagtttt aagaggagaa gaaaaagcta aggaatacaa ataataaagt   7080
cataaataat ataatataac cagtacccat gtttataaaa cttttgccct ggtaccatat   7140
ggctagcatg actggtggac agcaaatggg tcgggatccg aattcgagct ccgtcgacaa   7200
gcttgcggcc gcactcgagc accaccacca ccaccactga gatccggctg ctaacaaagc   7260
ccgaaaggaa gctgagttgg ctgctgccac cgctgagcaa taactagcat aaccccttgg   7320
ggcctctaaa cgggtcttga ggggtttttt gctgaaagga ggaactatat ccggat       7376
```

<210> SEQ ID NO 4
<211> LENGTH: 7868
<212> TYPE: DNA
<213> ORGANISM: Escherichia coli

<400> SEQUENCE: 4

```
atcggccggc cacgcgatcg ctgacgtcgg taccctcgag tctggtaaag aaaccgctgc     60
tgcgaaattt gaacgccagc acatggactc gtctactagc gcagcttaat taacctaggc    120
tgctgccacc gctgagcaat aactagcata accccttggg gcctctaaac gggtcttgag    180
gggttttttg ctgaaacctc aggcatttga gaagcacacg gtcacactgc ttccggtagt    240
caataaaccg gtaaaccagc aatagacata agcggctatt taacgaccct gccctgaacc    300
gacgaccggg tcgaatttgc tttcgaattt ctgccattca tccgcttatt atcacttatt    360
caggcgtagc accaggcgtt taagggcacc aataactgcc ttaaaaaaat tacgccccgc    420
cctgccactc atcgcagtac tgttgtaatt cattaagcat tctgccgaca tggaagccat    480
cacagacggc atgatgaacc tgaatcgcca gcggcatcag caccttgtcg ccttgcgtat    540
aatatttgcc catagtgaaa acgggggcga agaagttgtc catattggcc acgtttaaat    600
caaaactggt gaaactcacc cagggattgg ctgagacgaa aaacatattc tcaataaacc    660
ctttagggaa ataggccagg ttttcaccgt aacacgccac atcttgcgaa tatatgtgta    720
gaaactgccg gaaatcgtcg tggtattcac tccagagcga tgaaaacgtt tcagtttgct    780
catggaaaac ggtgtaacaa gggtgaacac tatcccatat caccagctca ccgtctttca    840
ttgccatacg gaactccgga tgagcattca tcaggcgggc aagaatgtga ataaaggccg    900
gataaaactt gtgcttattt ttctttacgg tctttaaaaa ggccgtaata tccagctgaa    960
cggtctggtt ataggtacat tgagcaactg actgaaatgc ctcaaaatgt tctttacgat   1020
gccattggga tatatcaacg gtggtatatc cagtgatttt tttctccatt ttagcttcct   1080
tagctcctga aaatctcgat aactcaaaaa atacgcccgg tagtgatctt atttcattat   1140
ggtgaaagtt ggaacctctt acgtgccgat caacgtctca ttttcgccaa aagttggccc   1200
agggcttccc ggtatcaaca gggacaccag gatttattta ttctgcgaag tgatcttccg   1260
tcacaggtat ttattcggcg caaagtgcgt cgggtgatgc tgccaactta ctgatttagt   1320
```

-continued

```
gtatgatggt gtttttgagg tgctccagtg gcttctgttt ctatcagctg tccctcctgt   1380
tcagctactg acggggtggt gcgtaacggc aaaagcaccg ccggacatca gcgctagcgg   1440
agtgtatact ggcttactat gttggcactg atgagggtgt cagtgaagtg cttcatgtgg   1500
caggagaaaa aaggctgcac cggtgcgtca gcagaatatg tgatacagga tatattccgc   1560
ttcctcgctc actgactcgc tacgctcggt cgttcgactg cggcgagcgg aaatggctta   1620
cgaacggggc ggagatttcc tggaagatgc caggaagata cttaacaggg aagtgagagg   1680
gccgcggcaa agccgttttt ccataggctc cgcccccctg acaagcatca cgaaatctga   1740
cgctcaaatc agtggtggcg aaacccgaca ggactataaa gataccaggc gtttccccctg   1800
gcggctccct cgtgcgctct cctgttcctg cctttcggtt taccggtgtc attccgctgt   1860
tatggccgcg tttgtctcat tccacgcctg acactcagtt ccgggtaggc agttcgctcc   1920
aagctggact gtatgcacga acccccccgtt cagtccgacc gctgcgcctt atccggtaac   1980
tatcgtcttg agtccaaccc ggaaagacat gcaaaagcac cactggcagc agccactggt   2040
aattgattta gaggagttag tcttgaagtc atgcgccggt taaggctaaa ctgaaaggac   2100
aagttttggt gactgcgctc ctccaagcca gttacctcgg ttcaaagagt tggtagctca   2160
gagaaccttc gaaaaaccgc cctgcaaggc ggttttttcg ttttcagagc aagagattac   2220
gcgcagacca aaacgatctc aagaagatca tcttattaat cagataaaat atttctagat   2280
ttcagtgcaa tttatctctt caaatgtagc acctgaagtc agccccatac gatataagtt   2340
gtaattctca tgttagtcat gccccgcgcc caccggaagg agctgactgg gttgaaggct   2400
ctcaagggca tcggtcgaga tcccggtgcc taatgagtga gctaacttac attaattgcg   2460
ttgcgctcac tgcccgcttt ccagtcggga aacctgtcgt gccagctgca ttaatgaatc   2520
ggccaacgcg cggggagagg cggtttgcgt attgggcgcc agggtggttt ttcttttcac   2580
cagtgagacg ggcaacagct gattgccctt caccgcctgg ccctgagaga gttgcagcaa   2640
gcggtccacg ctggtttgcc ccagcaggcg aaaatcctgt ttgatggtgg ttaacggcgg   2700
gatataacat gagctgtctt cggtatcgtc gtatcccact accgagatgt ccgcaccaac   2760
gcgcagcccg gactcggtaa tggcgcgcat tgcgcccagc gccatctgat cgttggcaac   2820
cagcatcgca gtgggaacga tgccctcatt cagcatttgc atggtttgtt gaaaaccgga   2880
catggcactc cagtcgcctt cccgttccgc tatcggctga atttgattgc gagtgagata   2940
tttatgccag ccagccagac gcagacgcgc cgagacagaa cttaatgggc ccgctaacag   3000
cgcgatttgc tggtgaccca atgcgaccag atgctccacg cccagtcgcg taccgtcttc   3060
atgggagaaa ataatactgt tgatgggtgt ctggtcagag acatcaagaa ataacgccgg   3120
aacattagtg caggcagctt ccacagcaat ggcatcctgg tcatccagcg gatagttaat   3180
gatcagccca ctgacgcgtt gcgcgagaag attgtgcacc gccgctttac aggcttcgac   3240
gccgcttcgt tctaccatcg acaccaccac gctggcaccc agttgatcgg cgcgagattt   3300
aatcgccgcg acaatttgcg acggcgcgtg cagggccaga ctggaggtgg caacgccaat   3360
cagcaacgac tgtttgcccg ccagttgttg tgccacgcgg ttgggaatgt aattcagctc   3420
cgccatcgcc gcttccactt tttcccgcgt tttcgcagaa acgtggctgg cctggttcac   3480
cacgcgggaa acggtctgat aagagacacc ggcatactct gcgacatcgt ataacgttac   3540
tggtttcaca ttcaccaccc tgaattgact ctcttccggg cgctatcatg ccataccgcg   3600
aaaggttttg cgccattcga tggtgtccgg gatctcgacg ctctccctta tgcgactcct   3660
gcattaggaa attaatacga ctcactatag gggaattgtg agcggataac aattcccctg   3720
```

```
tagaaataat tttgtttaac tttaataagg agatatacag gaggaaaaac catggtcatc   3780
gtcagcgcgg ctcgtacggc tgttggcagc ttcaatggcg cgttcgcaag caccccagct   3840
cacgatctgg gtgccgcggt gattgaggcg gtcgttgcgc gtgcgggtat tgataaagcg   3900
gatgtcagcg aaaccattct gggtcaggtt ctgacggctg gccagggtca gaatcctgcc   3960
cgtcaagcgc acattaaggc aggtctgccg caagaaagcg ctgcctggtc catcaaccag   4020
gtgtgtggta gcggtctgcg tgcagtcgct ctggctgccc agcatgtcca actgggtgac   4080
gcgtcgattg tggtggcggg tggtcaggag aatatgagcc tgagcccgca tgtggcacat   4140
ttgcgtgcag gccagaagat gggtgatctg tcgttcattg acagcatgat taaggatggt   4200
ctgtgggatg ccttcaatgg ttaccacatg ggccaaactg cggaaaatgt tgcggcgaaa   4260
tggcaaatct cccgcgacat gcaggatgaa tttgcagtcg cctctcaaaa caaagccgag   4320
gccgcacaaa aagcgggtcg ttttgcagac gaaattgtcc cgtttgtgat taagacccgt   4380
aaaggtgatg ttacggtgga tgcagatgag tatatccgcc acggcgcgac cctggatgca   4440
atggctaagc tgcgcccagc gttcatcaag gacggtactg tgaccgcggc aaatgcatcg   4500
ggcatcaatg acggtgccgc tgcggtgctg gtgatgagcg cggaagaggc tgagaagcgc   4560
ggtttgagcc cgctggcgcg tattgcaagc tatgccaccg cgggtctgga cccgtcgatt   4620
atgggcgtcg gtccgattca cgccagccgc aaagcgctgg aaaaggcagg ttggaaagtt   4680
ggtgatctgg acctggtcga ggcaaacgag gcgttcgccg ctcaagcctg tgccgtgaat   4740
aaggatatgg gttgggaccc gagcatcgtt aatgtgaatg gtggtgcaat cgcgatcggc   4800
catccgatcg gcgcaagcgg tgcacgcgtt ctgaacacgc tgctgtttga aatgcagcgc   4860
cgcaatgcga agaaaggttt ggctaccctg tgcattggcg gtggtatggg tgtcgccatg   4920
tgcctggagc gtccgtagta acacatctgc agcgtcggat acgaggagga ataaaccatg   4980
aaaaaggtat gtgttatagg tgcaggtact atgggttcag gaattgctca ggcatttgca   5040
gctaaaggat ttgaagtagt attaagagat attaaagatg aatttgttga tagaggatta   5100
gattttatca ataaaaatct ttctaaatta gttaaaaaag gaaagataga agaagctact   5160
aaagttgaaa tcttaactag aatttccgga acagttgacc ttaatatggc agctgattgc   5220
gatttagtta tagaagcagc tgttgaaaga atggatatta aaaagcagat tttgctgac    5280
ttagacaata tatgcaagcc agaaacaatt cttgcatcaa atacatcatc actttcaata   5340
acagaagtgg catcagcaac taaaagacct gataaggtta taggtatgca tttctttaat   5400
ccagctcctg ttatgaagct tgtagaggta ataagaggaa tagctacatc acaagaaact   5460
tttgatgcag ttaaagagac atctatagca ataggaaaag atcctgtaga agtagcagaa   5520
gcaccaggat ttgttgtaaa tagaatatta ataccaatga ttaatgaagc agttggtata   5580
ttagcagaag gaatagcttc agtagaagac atagataaag ctatgaaact tggagctaat   5640
cacccaatgg gaccattaga attaggtgat tttataggtc ttgatatatg tcttgctata   5700
atggatgttt tatactcaga aactggagat tctaagtata gaccacatac attacttaag   5760
aagtatgtaa gagcaggatg gcttggaaga aaatcaggaa aaggtttcta cgattattca   5820
aaataagttt acaggatctg cagggaggag gaaatcatgg agttgaacaa cgttattctg   5880
gagaaagaag gcaaggtggc ggttgtcacc attaaccgtc caaaggccct gaacgctctg   5940
aactcggata ccctgaaaga gatggattac gttattggcg agattgagaa tgacagcgaa   6000
gtgctggctg tgattctgac cggtgcgggt gagaagagct ttgtcgcggg tgcggacatc   6060
```

-continued

```
agcgagatga aagaaatgaa caccatcgaa ggccgtaagt tcggtattct gggcaacaag   6120

gtgtttcgtc gtctggaact gctggagaaa cctgtcattg ctgccgtgaa cggtttcgcg   6180

ctgggcggtg gttgcgagat cgctatgagc tgcgatattc gtatcgcatc gtccaacgca   6240

cgctttggtc aaccggaggt cggtctgggt atcactccgg gtttcggcgg tacgcaacgt   6300

ctgagccgcc tggttggcat gggcatggcg aaacagttga ttttcacggc acagaacatt   6360

aaggcggatg aggcgctgcg tattggtctg gtgaataagg tcgttgagcc aagcgaactg   6420

atgaataccg cgaaagaaat tgcgaacaag atcgttagca atgccccggt ggccgttaag   6480

ctgtcgaaac aggcaatcaa ccgtggcatg cagtgtgaca tcgacaccgc cctggcgttt   6540

gagagcgagg cgtttggtga gtgcttctcc accgaggacc aaaaggatgc gatgaccgcg   6600

ttcattgaga aacgcaagat cgagggtttc aagaatcgtt aatagaggag gataggaggt   6660

tttcatatga ttgtgaaacc gatggtccgt aataatatct gtctgaatgc tcacccgcag   6720

ggctgtaaaa aaggcgtgga agatcaaatt gaatatacca aaaaacgtat tacggcagaa   6780

gtgaaagccg gcgcaaaagc tccgaaaaac gtgctggttc tgggttgcag caatggctat   6840

ggtctggctt ctcgcattac cgcggccttt ggctacggtg cagctacgat cggcgttagt   6900

ttcgaaaaag caggttccga aaccaaatat ggcacgccgg gttggtacaa caatctggct   6960

tttgatgaag cggccaaacg tgaaggcctg tatagtgtca ccattgatgg tgacgcgttc   7020

tccgatgaaa ttaaagcaca ggtgatcgaa gaagcgaaga aaaaaggcat taaatttgac   7080

ctgatcgttt acagcctggc atctccggtc cgtaccgatc cggacacggg tatcatgcat   7140

aaatctgtgc tgaaaccgtt tggcaaaacc ttcacgggta aaaccgttga tccgttcacg   7200

ggcgaactga aagaaattag cgcggaaccg gccaacgatg aagaagcagc tgcgaccgtc   7260

aaagtgatgg gcggtgaaga ctgggaacgt tggatcaaac agctgagtaa agaaggcctg   7320

ctggaagaag gttgcattac cctggcgtat tcctacatcg gcccggaagc aacccaagct   7380

ctgtatcgca aaggcacgat tggtaaagcg aaagaacatc tggaagcgac cgcccaccgt   7440

ctgaacaaag aaaatccgtc aatccgcgcc ttcgtttcgg tcaataaagg tctggttacc   7500

cgtgcatcag ctgtgattcc ggttatcccg ctgtacctgg catcgctgtt taaagtcatg   7560

aaagaaaaag gcaaccatga aggttgtatt gaacagatca cccgcctgta tgccgaacgt   7620

ctgtaccgca aagatggtac gattccggtg gacgaagaaa atcgtattcg catcgatgac   7680

tgggaactgg aagaagatgt ccaaaaagcc gtgagcgccc tgatggaaaa agttaccggc   7740

gaaaacgcgg aatctctgac ggatctggcc ggttatcgtc acgactttct ggcgagtaat   7800

ggttttgatg ttgaaggcat taactacgaa gctgaagtgg aacgctttga tcgcatttga   7860

tctagaat                                                             7868
```

<210> SEQ ID NO 5
<211> LENGTH: 6196
<212> TYPE: DNA
<213> ORGANISM: Escherichia coli

<400> SEQUENCE: 5

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300
```

```
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
```

```
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
```

```
ttttgtttaa ctttaagaag gagatatacc atgttcttca ccccgccgca actgcaaaaa   5100
ctggaacagg attggaatgg tctggctgtc cgtgactgga tgatcgcaaa tgtggatgtg   5160
gttctgtata tttcatttct gtacctgggc tttgtcttca tcggtccgaa actgttcgcc   5220
aaactggttg gcacgaaccc ggcggcggcg gcggcgggtg cacgtagcgc agatggcacc   5280
ggttctccga ttgtgcgtcg cagtatggtc gtgtggaatc tggcgctgag catttttagc   5340
atcttcggca cctccacggt taccccggtc ctgctgcgca acctggctaa taaaggcttt   5400
tatggtgcga cgtgcgattt taaagaaacc gaattttaca ccacgaacgt tggcttttgg   5460
atgggtattt tcgccctgag caaaatcccg gaactggtgg ataccatttt tctggtgctg   5520
caaggcaaac aagaactgcc gttcctgcat tggtatcatc acgtcacggt gctgctgttt   5580
tcttggcaca cctattgtgt tggtagctct gcgtacatct gggtcgccgc aatgaattat   5640
tcagtgcatt cggttatgta tctgtacttc gctctggctg cgctgggtta taagcgtgtg   5700
gtccgcccgc tggcgccgta cattacgatt atccagatcc tgcaaatggt ggttggctgc   5760
tatgtgacca tctttgctct gcaagaactg cacggtgaag gcggtcgtgg ttgtggtgtg   5820
agcccggcaa acatgcgcat tcaactggtt atgtatgcat cctatctgta cctgttttca   5880
aaaatgttcg tggcatcgta catccgtccg ccgaaacgcc cgaccgttgg tggtccgagc   5940
agcacggcgg gcgtctcaaa cggttctgtg gaaaagaaag tgaaataacc taatgcaggg   6000
aattcgagct ccgtcgacaa gcttgcggcc gcactcgagc accaccacca ccaccactga   6060
gatccggctg ctaacaaagc ccgaaaggaa gctgagttgg ctgctgccac cgctgagcaa   6120
taactagcat aaccccttgg ggcctctaaa cgggtcttga ggggtttttt gctgaaagga   6180
ggaactatat ccggat                                                   6196
```

<210> SEQ ID NO 6
<211> LENGTH: 8959
<212> TYPE: DNA
<213> ORGANISM: Escherichia coli

<400> SEQUENCE: 6

```
ccttgccagc ccgtggatat gtggacgatg gccgcgagcg gccaccggct ggctcgcttc     60
gctcggcccg tggacaaccc tgctggacaa gctgatggac aggctgcgcc tgcccacgag    120
cttgaccaca gggattgccc accggctacc cagccttcga ccacataccc accggctcca    180
actgcgcggc ctgcggcctt gccccatcaa ttttttaat tttctctggg gaaaagcctc     240
cggcctgcgg cctgcgcgct tcgcttgccg gttggacacc aagtggaagg cgggtcaagg    300
ctcgcgcagc gaccgcgcag cggcttggcc ttgacgcgcc tggaacgacc caagcctatg    360
cgagtggggg cagtcgaagg cgaagcccgc ccgcctgccc cccgagcctc acggcggcga    420
gtgcgggggt tccaaggggg cagcgccacc ttgggcaagg ccgaaggccg cgcagtcgat    480
caacaagccc cggaggggcc actttttgcc ggaggggggag ccgcgccgaa ggcgtggggg   540
aaccccgcag gggtgccctt ctttgggcac caaagaacta gatatagggc gaaatgcgaa    600
agacttaaaa atcaacaact taaaaaaggg gggtacgcaa cagctcattg cggcaccccc    660
cgcaatagct cattgcgtag gttaaagaaa atctgtaatt gactgccact tttacgcaac    720
gcataattgt tgtcgcgctg ccgaaaagtt gcagctgatt gcgcatggtg ccgcaaccgt    780
gcggcaccct accgcatgga gataagcatg gccacgcagt ccagagaaat cggcattcaa    840
gccaagaaca agcccggtca ctgggtgcaa acggaacgca aagcgcatga ggcgtgggcc    900
```

```
gggcttattg cgaggaaacc cacggcggca atgctgctgc atcacctcgt ggcgcagatg    960
ggccaccaga acgccgtggt ggtcagccag aagacacttt ccaagctcat cggacgttct   1020
ttgcggacgg tccaatacgc agtcaaggac ttggtggccg agcgctggat ctccgtcgtg   1080
aagctcaacg gccccggcac cgtgtcggcc tacgtggtca atgaccgcgt ggcgtggggc   1140
cagccccgcg accagttgcg cctgtcggtg ttcagtgccg ccgtggtggt tgatcacgac   1200
gaccaggacg aatcgctgtt ggggcatggc gacctgcgcc gcatcccgac cctgtatccg   1260
ggcgagcagc aactaccgac cggccccggc gaggagccgc ccagccagcc cggcattccg   1320
ggcatggaac cagacctgcc agccttgacc gaaacggagg aatgggaacg gcgcgggcag   1380
cagcgcctgc cgatgcccga tgagccgtgt tttctggacg atggcgagcc gttggagccg   1440
ccgacacggg tcacgctgcc gcgccggtag tacgtacccg gaattgccag ctggggcgcc   1500
ctctggtaag gttgggaagc cctgcaaagt aaactggatg gctttcttgc cgccaaggat   1560
ctgatggcgc aggggatcaa gctctgatca agagacagga tgaggatcgt ttcgatgaag   1620
cagcgtatta cagtgacagt tgacagcgac agctatcagt tgctcaaggc atatgatgtc   1680
aatatctccg gtctggtaag cacaaccatg cagaatgaag cccgtcgtct gcgtgccgaa   1740
cgctggaaag cggaaaatca ggaagggatg gctgaggtcg cccggtttat tgaaatgaac   1800
ggctcttttg ctgacgagaa cagggactgg tgaaatgcag tttaaggttt acacctataa   1860
aagagagagc cgttatcgtc tgtttgtgga tgtacagagc gatattattg acacgcccgg   1920
gcgacggatg gtgatccccc tggccagtgc acgtctgctg tcagataaag tctcccgtga   1980
actttacccg gtggtgcata tcggggatga aagctggcgc atgatgacca ccgatatggc   2040
cagtgtgccg gtctccgtta tcggggaaga agtggctgat ctcagccacc gcgaaaatga   2100
catcaaaaac gccattaacc tgatgttctg gggaatataa atcctagacg aattctctag   2160
tagaggttcc aactttcacc ataatgaaat aagatcacta ccgggcgtat tttttgagtt   2220
atcgagattt tcaggagcta aggaagctaa aatggagaaa aaaatcactg gatataccac   2280
cgttgatata tcccaatggc atcgtaaaga acattttgag gcatttcagt cagttgctca   2340
atgtacctat aaccagaccg ttcagctgga tattacggcc tttttaaaga ccgtaaagaa   2400
aaataagcac aagttttatc cggcctttat tcacattctt gcccgcctga tgaatgctca   2460
tccggaattc cgtatggcaa tgaaagacgg tgagctggtg atatgggata gtgttcaccc   2520
ttgttacacc gttttccatg agcaaactga aacgttttca tcgctctgga gtgaatacca   2580
cgacgatttc cggcagtttc tacacatata ttcgcaagat gtggcgtgtt acggtgaaaa   2640
cctggcctat ttccctaaag ggtttattga gaatatgttt ttcgtctcag ccaatccctg   2700
ggtgagtttc accagttttg atttaaacgt ggccaatatg gacaacttct tcgcccccgt   2760
tttcaccatg ggcaaatatt atacgcaagg cgacaaggtg ctgatgccgc tggcgattca   2820
ggttcatcat gccgtttgtg atggcttcca tgtcggcaga atgcttaatg aattacaaca   2880
gtactgcgat gagtggcagg gcggggcgta aagatcttct cgacgctctc ccttatgcga   2940
ctcctgcatt aggaaattaa tacgactcac tataggggaa ttgtgagcgg ataacaattc   3000
ccctgtagaa ataattttgt ttaactttaa taaggagata taccatggcg gcggacaccc   3060
tgctgatcct gggcgactcc ctgtcggcgg gctaccgcat gtcggcgtcg gcggcgtggc   3120
cggcgctgct gaacgacaag tggcagtcca agacctcggt ggtcaacgcc tcgatcagcg   3180
gcgacacgag ccagcagggc ctggcccgcc tgccggcgct gctgaagcag caccagccgc   3240
gctgggtgct ggtcgagctg ggcggcaacg acggcctgcg cggcttccag ccgcagcaga   3300
```

-continued

```
ccgaacagac gctgcgccag atcctgcagg acgtgaaggc cgcgaacgcc gagccgctgc   3360
tgatgcagat ccgcctgccg gcgaactacg gccgtcgcta caacgaggcc ttctccgcga   3420
tctacccgaa gctggccaag gaattcgacg tgccgctgct gccgttcttc atggaggaag   3480
tctacctgaa gccgcagtgg atgcaggacg acggcatcca cccgaaccgc gacgcgcagc   3540
cgttcatcgc cgactggatg gccaagcaac tgcagccgct ggtcaaccac gactcctgaa   3600
tttaaatccc ttatgcgact cctgcattag gaaattaata cgactcacta taggggaatt   3660
gtgagcggat aacaattccc ctgtagaaat aattttgttt aactttaata aggagatata   3720
ccatgacgga tgtccgcttt cgtatcattg gcacgggcgc ttacgtcccg gaacgcattg   3780
tcagcaacga cgaagtcggc gcaccggctg gtgtggatga cgattggatt acgcgtaaaa   3840
ccggtatccg ccagcgtcgc tgggcggccg acgatcaagc aacgagcgat ctggctaccg   3900
cagctggtcg tgcagcactg aaagcagctg gcattacgcc ggaacagctg accgtcatcg   3960
cagtggctac ctctacgccg gaccgtccgc agccgccgac cgcggcctat gttcaacatc   4020
acctgggtgc aaccggcacg gcagcttttg atgttaacgc tgtgtgcagc ggtacggttt   4080
tcgcgctgag ctctgttgcc ggcaccctgg tctatcgtgg cggttacgca ctggtcattg   4140
gtgctgatct gtactcacgt atcctgaatc cggcggaccg caaaaccgtg gttctgttcg   4200
gcgatggtgc gggcgcgatg gtgctgggcc cgaccagcac cggcaccggt ccgattgtgc   4260
gtcgcgttgc actgcatacg tttggcggtc tgaccgatct gatccgtgtt ccggccggcg   4320
gttcccgcca gccgctggac accgatggtc tggacgcagg cctgcaatat tttgcgatgg   4380
atggccgcga agtccgtcgc ttcgtgaccg aacatctgcc gcagctgatt aaaggttttc   4440
tgcacgaagc gggcgtggat gcggcggata ttagccattt cgtgccgcac caagccaacg   4500
gtgtgatgct ggacgaagtt tttggcgaac tgcatctgcc gcgtgcaacc atgcaccgta   4560
cggtggaaac ctacggtaat acgggcgcag ctagtattcc gatcacgatg gatgcggccg   4620
ttcgtgcagg ttccttccgt ccgggcgaac tggttctgct ggcgggcttt ggcggcggta   4680
tggcggcttc gtttgctctg attgaatggt gacctaatgc aggctgcagg cggatacgag   4740
gaggaataaa ccatgaaaaa ggtatgtgtt ataggtgcag gtactatgggttcaggaatt   4800
gctcaggcat ttgcagctaa aggatttgaa gtagtattaa gagatattaa agatgaattt   4860
gttgatagag gattagattt tatcaataaa aatctttcta aattagttaa aaaaggaaag   4920
atagaagaag ctactaaagt tgaaatctta actagaattt ccggaacagt tgaccttaat   4980
atggcagctg attgcgattt agttatagaa gcagctgttg aaagaatgga tattaaaaag   5040
cagatttttg ctgacttaga caatatatgc aagccagaaa caattcttgc atcaaataca   5100
tcatcacttt caataacaga agtggcatca gcaactaaaa gacctgataa ggttataggt   5160
atgcatttct ttaatccagc tcctgttatg aagcttgtag aggtaataag aggaatagct   5220
acatcacaag aaacttttga tgcagttaaa gagacatcta tagcaatagg aaaagatcct   5280
gtagaagtag cagaagcacc aggatttgtt gtaaatagaa tattaatacc aatgattaat   5340
gaagcagttg gtatattagc agaaggaata gcttcagtag aagacataga taaagctatg   5400
aaacttggag ctaatcaccc aatgggacca ttagaattag gtgattttat aggtcttgat   5460
atatgtcttg ctataatgga tgttttatac tcagaaactg gagattctaa gtatagacca   5520
catacattac ttaagaagta tgtaagagca ggatggcttg gaagaaaatc aggaaaaggt   5580
ttctacgatt attcaaaata agtttacagg atctgcaggg aggaggaaat catggagttg   5640
```

-continued

```
aacaacgtta ttctggagaa agaaggcaag gtggcggttg tcaccattaa ccgtccaaag   5700
gccctgaacg ctctgaactc ggataccctg aaagagatgg attacgttat tggcgagatt   5760
gagaatgaca gcgaagtgct ggctgtgatt ctgaccggtg cgggtgagaa gagctttgtc   5820
gcgggtgcgg acatcagcga gatgaaagaa atgaacacca tcgaaggccg taagttcggt   5880
attctgggca acaaggtgtt tcgtcgtctg gaactgctgg agaaacctgt cattgctgcc   5940
gtgaacggtt tcgcgctggg cggtggttgc gagatcgcta tgagctgcga tattcgtatc   6000
gcatcgtcca acgcacgctt tggtcaaccg gaggtcggtc tgggtatcac tccgggtttc   6060
ggcggtacgc aacgtctgag ccgcctggtt ggcatgggca tggcgaaaca gttgattttc   6120
acggcacaga acattaaggc ggatgaggcg ctgcgtattg gtctggtgaa taaggtcgtt   6180
gagccaagcg aactgatgaa taccgcgaaa gaaattgcga acaagatcgt tagcaatgcc   6240
ccggtggccg ttaagctgtc gaaacaggca atcaaccgtg gcatgcagtg tgacatcgac   6300
accgccctgg cgtttgagag cgaggcgttt ggtgagtgct tctccaccga ggaccaaaag   6360
gatgcgatga ccgcgttcat tgagaaacgc aagatcgagg gtttcaagaa tcgttaatag   6420
aggaggatag gaggttttca tatgattgtg aaaccgatgg tccgtaataa tatctgtctg   6480
aatgctcacc cgcagggctg taaaaaaggc gtggaagatc aaattgaata taccaaaaaa   6540
cgtattacgg cagaagtgaa agccggcgca aaagctccga aaaacgtgct ggttctgggt   6600
tgcagcaatg gctatggtct ggcttctcgc attaccgcgg cctttggcta cggtgcagct   6660
acgatcggcg ttagtttcga aaaagcaggt tccgaaacca aatatggcac gccgggttgg   6720
tacaacaatc tggcttttga tgaagcggcc aaacgtgaag gcctgtatag tgtcaccatt   6780
gatggtgacg cgttctccga tgaaattaaa gcacaggtga tcgaagaagc gaagaaaaaa   6840
ggcattaaat ttgacctgat cgtttacagc ctggcatctc cggtccgtac cgatccggac   6900
acgggtatca tgcataaatc tgtgctgaaa ccgtttggca aaaccttcac gggtaaaacc   6960
gttgatccgt tcacgggcga actgaaagaa attagcgcgg aaccggccaa cgatgaagaa   7020
gcagctgcga ccgtcaaagt gatgggcggt gaagactggg aacgttggat caaacagctg   7080
agtaaagaag gcctgctgga agaaggttgc attaccctgg cgtattccta catcggcccg   7140
gaagcaaccc aagctctgta tcgcaaaggc acgattggta aagcgaaaga acatctggaa   7200
gcgaccgccc accgtctgaa caaagaaaat ccgtcaatcc gcgccttcgt ttcggtcaat   7260
aaaggtctgg ttacccgtgc atcagctgtg attccggtta tcccgctgta cctggcatcg   7320
ctgtttaaag tcatgaaaga aaaaggcaac catgaaggtt gtattgaaca gatcacccgc   7380
ctgtatgccg aacgtctgta ccgcaaagat ggtacgattc cggtggacga agaaaatcgt   7440
attcgcatcg atgactggga actggaagaa gatgtccaaa aagccgtgag cgccctgatg   7500
gaaaaagtta ccggcgaaaa cgcggaatct ctgacggatc tggccggtta tcgtcacgac   7560
tttctggcga gtaatggttt tgatgttgaa ggcattaact acgaagctga agtggaacgc   7620
tttgatcgca tttgatctag agaattcgtc aacgaattca agcttgatat cattcaggac   7680
gagcctcaga ctccagcgta actggactga aaacaaacta aagcgccctt gtggcgcttt   7740
agttttgttc cgctcatgat aataatggtt tcttagacgt caggtggcac ttttcgggga   7800
aatgtgcgcg cccgcgttcc tgctggcgct gggcctgttt ctggcgctgg acttcccgct   7860
gttccgtcag cagcttttcg cccacggcct tgatgatcgc ggcggccttg gcctgcatat   7920
cccgattcaa cggccccagg gcgtccagaa cgggcttcag gcgctcccga aggtctcggg   7980
ccgtctcttg ggcttgatcg gccttcttgc gcatctcacg cgctcctgcg gcggcctgta   8040
```

-continued gggcaggctc ataccccctgc cgaaccgctt ttgtcagccg gtcggccacg gcttccggcg 8100
tctcaacgcg ctttgagatt cccagctttt cggccaatcc ctgcggtgca taggcgcgtg 8160
gctcgaccgc ttgcgggctg atggtgacgt ggcccactgg tggccgctcc agggcctcgt 8220
agaacgcctg aatgcgcgtg tgacgtgcct tgctgccctc gatgccccgt tgcagcccta 8280
gatcggccac agcggccgca aacgtggtct ggtcgcgggt catctgcgct ttgttgccga 8340
tgaactcctt ggccgacagc ctgccgtcct gcgtcagcgg caccacgaac gcggtcatgt 8400
gcgggctggt ttcgtcacgg tggatgctgg ccgtcacgat gcgatccgcc ccgtacttgt 8460
ccgccagcca cttgtgcgcc ttctcgaaga acgccgcctg ctgttcttgg ctggccgact 8520
tccaccattc cgggctggcc gtcatgacgt actcgaccgc caacacagcg tccttgcgcc 8580
gcttctctgg cagcaactcg cgcagtcggc ccatcgcttc atcggtgctg ctggccgccc 8640
agtgctcgtt ctctggcgtc ctgctggcgt cagcgttggg cgtctcgcgc tcgcggtagg 8700
cgtgcttgag actggccgcc acgttgccca ttttcgccag cttcttgcat cgcatgatcg 8760
cgtatgccgc catgcctgcc cctccctttt ggtgtccaac cggctcgacg gggcagcgc 8820 aaggcggtgc ctccggcggg ccactcaatg cttgagtata ctcactagac tttgcttcgc 8880
aaagtcgtga ccgcctacgg cggctgcggc gccctacggg cttgctctcc gggcttcgcc 8940
ctgcgcggtc gctgcgctc 8959

<210> SEQ ID NO 7
<211> LENGTH: 4334
<212> TYPE: DNA
<213> ORGANISM: Escherichia coli

<400> SEQUENCE: 7
ctgatggaca ggctgcgcct gcccacgagc ttgaccacag ggattgccca ccggctaccc 60
agccttcgac cacataccca ccggctccaa ctgcgcggcc tgcggccttg ccccatcaat 120
ttttttaatt ttctctgggg aaaagcctcc ggcctgcggc ctgcgcgctt cgcttgccgg 180
ttggacacca agtggaaggc gggtcaaggc tcgcgcagcg accgcgcagc ggcttggcct 240
tgacgcgcct ggaacgaccc aagcctatgc gagtgggggc agtcgaaggc gaagcccgcc 300
cgcctgcccc ccgagcctca cggcggcgag tgcgggggtt ccaagggggc agcgccacct 360
tgggcaaggc cgaaggccgc gcagtcgatc aacaagcccc ggaggggcca ctttttgccg 420
gagggggagc cgcgccgaag gcgtggggga accccgcagg ggtgcccttc tttgggcacc 480
aaagaactag atatagggcg aaatgcgaaa gacttaaaaa tcaacaactt aaaaaagggg 540
ggtacgcaac agctcattgc ggcacccccc gcaatagctc attgcgtagg ttaaagaaaa 600
tctgtaattg actgccactt ttacgcaacg cataattgtt gtcgcgctgc cgaaaagttg 660
cagctgattg cgcatggtgc cgcaaccgtg cggcacccta ccgcatggag ataagcatgg 720
ccacgcagtc cagagaaatc ggcattcaag ccaagaacaa gcccggtcac tgggtgcaaa 780
cggaacgcaa agcgcatgag gcgtgggccg ggcttattgc gaggaaaccc acggcggcaa 840
tgctgctgca tcacctcgtg gcgcagatgg gccaccagaa cgccgtggtg gtcagccaga 900
agacactttc caagctcatc ggacgttctt tgcggacggt ccaatacgca gtcaaggact 960
tggtggccga gcgctggatc tccgtcgtga agctcaacgg ccccggcacc gtgtcggcct 1020
acgtggtcaa tgaccgcgtg gcgtggggcc agccccgcga ccagttgcgc ctgtcggtgt 1080
tcagtgccgc cgtggtggtt gatcacgacg accaggacga atcgctgttg ggcatggcg 1140

-continued

```
acctgcgccg catcccgacc ctgtatccgg gcgagcagca actaccgacc ggccccggcg   1200
aggagccgcc cagccagccc ggcattccgg gcatggaacc agacctgcca gccttgaccg   1260
aaacggagga atgggaacgg cgcgggcagc agcgcctgcc gatgcccgat gagccgtgtt   1320
ttctggacga tggcgagccg ttggagccgc cgacacgggt cacgctgccg cgccggtagt   1380
acgtacccgg aattgccagc tggggcgccc tctggtaagg ttgggaagcc ctgcaaagta   1440
aactggatgg ctttcttgcc gccaaggatc tgatggcgca ggggatcaag ctctgatcaa   1500
gagacaggat gaggatcgtt tcgatgaagc agcgtattac agtgacagtt gacagcgaca   1560
gctatcagtt gctcaaggca tatgatgtca atatctccgg tctggtaagc acaaccatgc   1620
agaatgaagc ccgtcgtctg cgtgccgaac gctggaaagc ggaaaatcag gaagggatgg   1680
ctgaggtcgc ccggtttatt gaaatgaacg gctcttttgc tgacgagaac agggactggt   1740
gaaatgcagt ttaaggttta cacctataaa agagagagcc gttatcgtct gtttgtggat   1800
gtacagagcg atattattga cacgcccggg cgacggatgg tgatccccct ggccagtgca   1860
cgtctgctgt cagataaagt ctcccgtgaa ctttacccgg tggtgcatat cggggatgaa   1920
agctggcgca tgatgaccac cgatatggcc agtgtgccgg tctccgttat cggggaagaa   1980
gtggctgatc tcagccaccg cgaaaatgac atcaaaaacg ccattaacct gatgttctgg   2040
ggaatataaa tcctagacga attctctagt agaggttcca actttcacca taatgaaata   2100
agatcactac cgggcgtatt ttttgagtta tcgagatttt caggagctaa ggaagctaaa   2160
atggagaaaa aaatcactgg atataccacc gttgatatat cccaatggca tcgtaaagaa   2220
cattttgagg catttcagtc agttgctcaa tgtacctata accagaccgt tcagctggat   2280
attacggcct ttttaaagac cgtaaagaaa aataagcaca agttttatcc ggcctttatt   2340
cacattcttg cccgcctgat gaatgctcat ccggaattcc gtatggcaat gaaagacggt   2400
gagctggtga tatgggatag tgttcaccct tgttacaccg ttttccatga gcaaactgaa   2460
acgttttcat cgctctggag tgaataccac gacgatttcc ggcagtttct acacatatat   2520
tcgcaagatg tggcgtgtta cggtgaaaac ctggcctatt tccctaaagg gtttattgag   2580
aatatgtttt tcgtctcagc caatccctgg gtgagtttca ccagttttga tttaaacgtg   2640
gccaatatgg acaacttctt cgcccccgtt ttcaccatgg gcaaatatta tacgcaaggc   2700
gacaaggtgc tgatgccgct ggcgattcag gttcatcatg ccgtttgtga tggcttccat   2760
gtcggcagaa tgcttaatga attacaacag tactgcgatg agtggcaggg cggggcgtaa   2820
agatctggat ccccctcaag tcaaaagcct ccggtcggag gcttttgact ttctgctatg   2880
gaggtcaggt atgatttaaa tggtcagtat tgagcgatat ctagagaatt cgtcaacgaa   2940
ttcaagcttg atatcattca ggacgagcct cagactccag cgtaactgga ctgaaaacaa   3000
actaaagcgc ccttgtggcg ctttagtttt gttccgctca tgataataat ggtttcttag   3060
acgtcaggtg gcacttttcg gggaaatgtg cgcgcccgcg ttcctgctgg cgctgggcct   3120
gtttctggcg ctggacttcc cgctgttccg tcagcagctt ttcgcccacg gccttgatga   3180
tcgcggcggc cttggcctgc atatcccgat tcaacggccc cagggcgtcc agaacgggct   3240
tcaggcgctc ccgaaggtct cgggccgtct cttgggcttg atcggccttc ttgcgcatct   3300
cacgcgctcc tgcggcggcc tgtagggcag gctcataccc ctgccgaacc gcttttgtca   3360
gccggtcggc cacggcttcc ggcgtctcaa cgcgctttga gattcccagc ttttcggcca   3420
atccctgcgg tgcataggcg cgtggctcga ccgcttgcgg gctgatggtg acgtggccca   3480
ctggtggccg ctccagggcc tcgtagaacg cctgaatgcg cgtgtgacgt gccttgctgc   3540
```

```
cctcgatgcc ccgttgcagc cctagatcgg ccacagcggc cgcaaacgtg gtctggtcgc   3600

gggtcatctg cgctttgttg ccgatgaact ccttggccga cagcctgccg tcctgcgtca   3660

gcggcaccac gaacgcggtc atgtgcgggc tggtttcgtc acggtggatg ctggccgtca   3720

cgatgcgatc cgccccgtac ttgtccgcca gccacttgtg cgccttctcg aagaacgccg   3780

cctgctgttc ttggctggcc gacttccacc attccgggct ggccgtcatg acgtactcga   3840

ccgccaacac agcgtccttg cgccgcttct ctggcagcaa ctcgcgcagt cggcccatcg   3900

cttcatcggt gctgctggcc gcccagtgct cgttctctgg cgtcctgctg gcgtcagcgt   3960

tgggcgtctc gcgctcgcgg taggcgtgct tgagactggc cgccacgttg cccattttcg   4020

ccagcttctt gcatcgcatg atcgcgtatg ccgccatgcc tgcccctccc ttttggtgtc   4080

caaccggctc gacgggggca gcgcaaggcg gtgcctccgg cgggccactc aatgcttgag   4140

tatactcact agactttgct tcgcaaagtc gtgaccgcct acggcggctg cggcgcccta   4200

cgggcttgct ctccgggctt cgccctgcgc ggtcgctgcg ctcccttgcc agcccgtgga   4260

tatgtggacg atggccgcga gcggccaccg gctggctcgc ttcgctcggc ccgtggacaa   4320

ccctgctgga caag                                                     4334
```

<210> SEQ ID NO 8
<211> LENGTH: 5024
<212> TYPE: DNA
<213> ORGANISM: Escherichia coli

<400> SEQUENCE: 8

```
caaaaaaccc ctcaagaccc gtttagaggc cccaaggggt tatgctagtt attgctcagc     60

ggtggcagca gcctaggtta attaagctgc gctagtagac gagtccatgt gctggcgttc    120

aaatttcgca gcagcggttt ctttaccaga ctcgaaaatt caggagtcgt ggttgaccag    180

cggctgcagt tgcttggcca tccagtcggc gatgaacggc tgcgcgtcgc ggttcgggtg    240

gatgccgtcg tcctgcatcc actgcggctt caggtagact tcctccatga agaacggcag    300

cagcggcacg tcgaattcct tggccagctt cgggtagatc gcggagaagg cctcgttgta    360

gcgacggccg tagttcgccg gcaggcggat ctgcatcagc agcggctcgg cgttcgcggc    420

cttcacgtcc tgcaggatct ggcgcagcgt ctgttcggtc tgctgcggct ggaagccgcg    480

caggccgtcg ttgccgccca gctcgaccag cacccagcgc ggctggtgct gcttcagcag    540

cgccggcagg cgggccaggc cctgctggct cgtgtcgccg ctgatcgagg cgttgaccac    600

cgaggtcttg gactgccact tgtcgttcag cagcgccggc cacgccgccg acgccgacat    660

gcggtagccc gccgacaggg agtcgcccag gatcagcagg gtgtccgccg ccatggtata    720

tctccttatt aaagttaaac aaaattattt ctacagggga attgttatcc gctcacaatt    780

cccctatagt gagtcgtatt aatttcctaa tgcaggagtc gatcattcag gacgagcctc    840

agactccagc gtaactggac tgaaaacaaa ctaaagcgcc cttgtggcgc tttagttttg    900

ttccgctcat gataataatg gtttcttaga cgtcaggtgg cacttttcgg ggaaatgtgc    960

gcgcccgcgt tcctgctggc gctgggcctg tttctggcgc tggacttccc gctgttccgt   1020

cagcagcttt tcgcccacgg ccttgatgat cgcggcggcc ttggcctgca tatcccgatt   1080

caacggcccc agggcgtcca gaacgggctt caggcgctcc cgaaggtctc gggccgtctc   1140

ttgggcttga tcggccttct tgcgcatctc acgcgctcct gcggcggcct gtagggcagg   1200

ctcatacccc tgccgaaccg cttttgtcag ccggtcggcc acggcttccg gcgtctcaac   1260
```

-continued

```
gcgctttgag attcccagct tttcggccaa tccctgcggt gcataggcgc gtggctcgac   1320
cgcttgcggg ctgatggtga cgtggcccac tggtggccgc tccagggcct cgtagaacgc   1380
ctgaatgcgc gtgtgacgtg ccttgctgcc ctcgatgccc cgttgcagcc ctagatcggc   1440
cacagcggcc gcaaacgtgg tctggtcgcg ggtcatctgc gctttgttgc cgatgaactc   1500
cttggccgac agcctgccgt cctgcgtcag cggcaccacg aacgcggtca tgtgcgggct   1560
ggtttcgtca cggtggatgc tggccgtcac gatgcgatcc gccccgtact tgtccgccag   1620
ccacttgtgc gccttctcga agaacgccgc ctgctgttct tggctggccg acttccacca   1680
ttccgggctg gccgtcatga cgtactcgac cgccaacaca gcgtccttgc gccgcttctc   1740
tggcagcaac tcgcgcagtc ggcccatcgc ttcatcggtg ctgctggccg cccagtgctc   1800
gttctctggc gtcctgctgg cgtcagcgtt gggcgtctcg cgctcgcggt aggcgtgctt   1860
gagactggcc gccacgttgc ccattttcgc cagcttcttg catcgcatga tcgcgtatgc   1920
cgccatgcct gcccctccct tttggtgtcc aaccggctcg acgggggcag cgcaaggcgg   1980
tgcctccggc gggccactca atgcttgagt atactcacta gactttgctt cgcaaagtcg   2040
tgaccgccta cggcggctgc ggcgccctac gggcttgctc tccgggcttc gccctgcgcg   2100
gtcgctgcgc tcccttgcca gcccgtggat atgtggacga tggccgcgag cggccaccgg   2160
ctggctcgct tcgctcggcc cgtggacaac cctgctggac aagctgatgg acaggctgcg   2220
cctgcccacg agcttgacca cagggattgc ccaccggcta cccagccttc gaccacatac   2280
ccaccggctc caactgcgcg gcctgcggcc ttgccccatc aattttttta attttctctg   2340
gggaaaagcc tccggcctgc ggcctgcgcg cttcgcttgc cggttggaca ccaagtggaa   2400
ggcgggtcaa ggctcgcgca gcgaccgcgc agcggcttgg ccttgacgcg cctggaacga   2460
cccaagccta tgcgagtggg ggcagtcgaa ggcgaagccc gcccgcctgc cccccgagcc   2520
tcacggcggc gagtgcgggg gttccaaggg ggcagcgcca ccttgggcaa ggccgaaggc   2580
cgcgcagtcg atcaacaagc cccggagggg ccactttttg ccggaggggg agccgcgccg   2640
aaggcgtggg ggaaccccgc aggggtgccc ttctttgggc accaaagaac tagatatagg   2700
gcgaaatgcg aaagacttaa aaatcaacaa cttaaaaaag gggggtacgc aacagctcat   2760
tgcggcaccc cccgcaatag ctcattgcgt aggttaaaga aaatctgtaa ttgactgcca   2820
cttttacgca acgcataatt gttgtcgcgc tgccgaaaag ttgcagctga ttgcgcatgg   2880
tgccgcaacc gtgcggcacc ctaccgcatg gagataagca tggccacgca gtccagagaa   2940
atcggcattc aagccaagaa caagcccggt cactgggtgc aaacggaacg caaagcgcat   3000
gaggcgtggg ccgggcttat tgcgaggaaa cccacggcgg caatgctgct gcatcacctc   3060
gtggcgcaga tgggccacca gaacgccgtg gtggtcagcc agaagacact ttccaagctc   3120
atcggacgtt ctttgcggac ggtccaatac gcagtcaagg acttggtggc cgagcgctgg   3180
atctccgtcg tgaagctcaa cggccccggc accgtgtcgg cctacgtggt caatgaccgc   3240
gtggcgtggg gccagccccg cgaccagttg cgcctgtcgg tgttcagtgc cgccgtggtg   3300
gttgatcacg acgaccagga cgaatcgctg ttggggcatg gcgacctgcg ccgcatcccg   3360
accctgtatc cgggcgagca gcaactaccg accggccccg gcgaggagcc gcccagccag   3420
cccggcattc cgggcatgga accagacctg ccagccttga ccgaaacgga ggaatgggaa   3480
cggcgcgggc agcagcgcct gccgatgccc gatgagccgt gttttctgga cgatggcgag   3540
ccgttggagc cgccgacacg ggtcacgctg ccgcgccggt agtacgtacc cggaattgcc   3600
agctggggcg ccctctggta aggttgggaa gccctgcaaa gtaaactgga tggctttctt   3660
```

gccgccaagg atctgatggc gcaggggatc aagctctgat caagagacag gatgaggatc 3720
gtttcgatga agcagcgtat tacagtgaca gttgacagcg acagctatca gttgctcaag 3780
gcatatgatg tcaatatctc cggtctggta agcacaacca tgcagaatga agcccgtcgt 3840
ctgcgtgccg aacgctggaa agcggaaaat caggaaggga tggctgaggt cgcccggttt 3900
attgaaatga acggctcttt tgctgacgag aacagggact ggtgaaatgc agtttaaggt 3960
ttacacctat aaaagagaga gccgttatcg tctgtttgtg gatgtacaga gcgatattat 4020
tgacacgccc gggcgacgga tggtgatccc cctggccagt gcacgtctgc tgtcagataa 4080
agtctcccgt gaactttacc cggtggtgca tatcggggat gaaagctggc gcatgatgac 4140
caccgatatg gccagtgtgc cggtctccgt tatcggggaa gaagtggctg atctcagcca 4200
ccgcgaaaat gacatcaaaa acgccattaa cctgatgttc tggggaatat aaatcctaga 4260
cgaattctct agtagaggtt ccaactttca ccataatgaa ataagatcac taccgggcgt 4320
attttttgag ttatcgagat tttcaggagc taaggaagct aaaatggaga aaaaaatcac 4380
tggatatacc accgttgata tatcccaatg gcatcgtaaa gaacattttg aggcatttca 4440
gtcagttgct caatgtacct ataaccagac cgttcagctg gatattacgg cctttttaaa 4500
gaccgtaaag aaaaataagc acaagtttta tccggccttt attcacattc ttgcccgcct 4560
gatgaatgct catccggaat tccgtatggc aatgaaagac ggtgagctgg tgatatggga 4620
tagtgttcac ccttgttaca ccgttttcca tgagcaaact gaaacgtttt catcgctctg 4680
gagtgaatac cacgacgatt tccggcagtt tctacacata tattcgcaag atgtggcgtg 4740
ttacggtgaa aacctggcct atttccctaa agggtttatt gagaatatgt ttttcgtctc 4800
agccaatccc tgggtgagtt tcaccagttt tgatttaaac gtggccaata tggacaactt 4860
cttcgccccc gttttcacca tgggcaaata ttatacgcaa ggcgacaagg tgctgatgcc 4920
gctggcgatt caggttcatc atgccgtttg tgatggcttc catgtcggca gaatgcttaa 4980
tgaattacaa cagtactgcg atgagtggca gggcggggcg taaa 5024

<210> SEQ ID NO 9
<211> LENGTH: 4245
<212> TYPE: DNA
<213> ORGANISM: Escherichia coli

<400> SEQUENCE: 9
gaattccgga tgagcattca tcaggcgggc aagaatgtga ataaaggccg gataaaactt 60
gtgcttattt ttctttacgg tctttaaaaa ggccgtaata tccagctgaa cggtctggtt 120
ataggtacat tgagcaactg actgaaatgc ctcaaaatgt tctttacgat gccattggga 180
tatatcaacg gtggtatatc cagtgatttt tttctccatt ttagcttcct tagctcctga 240
aaatctcgat aactcaaaaa atacgcccgg tagtgatctt atttcattat ggtgaaagtt 300
ggaacctctt acgtgccgat caacgtctca ttttcgccaa aagttggccc agggcttccc 360
ggtatcaaca gggacaccag gatttattta ttctgcgaag tgatcttccg tcacaggtat 420
ttattcggcg caaagtgcgt cgggtgatgc tgccaactta ctgatttagt gtatgatggt 480
gtttttgagg tgctccagtg gcttctgttt ctatcagctg tccctcctgt tcagctactg 540
acggggtggt gcgtaacggc aaaagcaccg ccggacatca gcgctagcgg agtgtatact 600
ggcttactat gttggcactg atgagggtgt cagtgaagtg cttcatgtgg caggagaaaa 660
aaggctgcac cggtgcgtca gcagaatatg tgatacagga tatattccgc ttcctcgctc 720

-continued

```
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atatcgtcca ttccgacagc atcgccagtc actatggcgt gctgctagcg ctatatgcgt   1740
tgatgcaatt tctatgcgca cccgttctcg gagcactgtc cgaccgcttt ggccgccgcc   1800
cagtcctgct cgcttcgcta cttggagcca ctatcgacta cgcgatcatg gcgaccacac   1860
ccgtcctgtg gatcctctac gccggacgca tcgtggccgg catcaccggc gccacaggtg   1920
cggttgctgg cgcctatatc gccgacatca ccgatgggga agatcgggct cgccacttcg   1980
ggctcatgag cgcttgtttc ggcgtgggta tggtggcagg ccccgtggcc gggggactgt   2040
tgggcgccat ctccttgcat gcaccattcc ttgcggcggc ggtgctcaac ggcctcaacc   2100
tactactggg ctgcttccta atgcaggagt cgcataaggg agagcgtcga ccgatgccct   2160
tgagagcctt caacccagtc agctccttcc ggtgggcgcg gggcatgact atcgtcgccg   2220
cacttatgac tgtcttcttt atcatgcaac tcgtaggaca ggtgccggca gcgctctggg   2280
tcattttcgg cgaggaccgc tttcgctgga gcgcgacgat gatcggcctg tcgcttgcgg   2340
tattcggaat cttgcacgcc ctcgctcaag ccttcgtcac tggtcccgcc accaaacgtt   2400
tcggcgagaa gcaggccatt atcgccggca tggcggccga cgcgctgggc tacgtcttgc   2460
tggcgttcgc gacgcgaggc tggatggcct tccccattat gattcttctc gcttccggcg   2520
gcatcgggat gcccgcgttg caggccatgc tgtccaggca ggtagatgac gaccatcagg   2580
gacagcttca aggatcgctc gcggctctta ccagcctaac ttcgatcact ggaccgctga   2640
tcgtcacggc gatttatgcc gcctcggcga gcacatggaa cgggttggca tggattgtag   2700
gcgccgccct ataccttgtc tgcctccccg cgttgcgtcg cggtgcatgg agccgggcca   2760
cctcgacctg aatggaagcc ggcggcacct cgctaacgga ttcaccactc caagaattgg   2820
agccaatcaa ttcttgcgga gaactgtgaa tgcgcaaacc aacccttggc agaacatatc   2880
catcgcgtcc gccatctcca gcagccgcac gcggcgcatc tcgggcagcg ttgggtcctg   2940
gccacgggtg cgcatgatcg tgctcctgtc gttgaggacc cggctaggct ggcggggttg   3000
ccttactggt tagcagaatg aatcaccgat acgcgagcga acgtgaagcg actgctgctg   3060
caaaacgtct gcgacctgag caacaacatg aatggtcttc ggtttccgtg tttcgtaaag   3120
```

tctggaaacg cggaagtccc ctacgtgctg ctgaagttgc ccgcaacaga gagtggaacc 3180
aaccggtgat accacgatac tatgactgag agtcaacgcc atgagcggcc tcatttctta 3240
ttctgagtta caacagtccg caccgctgtc cggtagctcc ttccggtggg cgcggggcat 3300
gactatcgtc gccgcactta tgactgtctt ctttatcatg caactcgtag gacaggtgcc 3360
ggcagcgccc aacagtcccc cggccacggg gcctgccacc atacccacgc cgaaacaagc 3420
gccctgcacc attatgttcc ggatctgcat cgcaggatgc tgctggctac cctgtggaac 3480
acctacatct gtattaacga agcgctaacc gtttttatca ggctctggga ggcagaataa 3540
atgatcatat cgtcaattat tacctccacg ggagagcct gagcaaactg gcctcaggca 3600
tttgagaagc acacggtcac actgcttccg gtagtcaata aaccggtaaa ccagcaatag 3660
acataagcgg ctatttaacg accctgccct gaaccgacga ccgggtcgaa tttgctttcg 3720
aatttctgcc attcatccgc ttattatcac ttattcaggc gtagcaccag gcgtttaagg 3780
gcaccaataa ctgccttaaa aaaattacgc cccgccctgc cactcatcgc agtactgttg 3840
taattcatta agcattctgc cgacatggaa gccatcacag acggcatgat gaacctgaat 3900
cgccagcggc atcagcacct tgtcgccttg cgtataatat ttgcccatgg tgaaaacggg 3960
ggcgaagaag ttgtccatat tggccacgtt taaatcaaaa ctggtgaaac tcacccaggg 4020
attggctgag acgaaaaaca tattctcaat aaacccttta gggaaatagg ccaggttttc 4080
accgtaacac gccacatctt gcgaatatat gtgtagaaac tgccggaaat cgtcgtggta 4140
ttcactccag agcgatgaaa acgtttcagt ttgctcatgg aaaacggtgt aacaagggtg 4200
aacactatcc catatcacca gctcaccgtc tttcattgcc atacg 4245

<210> SEQ ID NO 10
<211> LENGTH: 9542
<212> TYPE: DNA
<213> ORGANISM: Escherichia coli

<400> SEQUENCE: 10
ccttgccagc ccgtggatat gtggacgatg gccgcgagcg gccaccggct ggctcgcttc 60
gctcggcccg tggacaaccc tgctggacaa gctgatggac aggctgcgcc tgcccacgag 120
cttgaccaca gggattgccc accggctacc cagccttcga ccacataccc accggctcca 180
actgcgcggc ctgcggcctt gccccatcaa tttttttaat tttctctggg gaaaagcctc 240
cggcctgcgg cctgcgcgct tcgcttgccg gttggacacc aagtggaagg cgggtcaagg 300
ctcgcgcagc gaccgcgcag cggcttggcc ttgacgcgcc tggaacgacc caagcctatg 360
cgagtggggg cagtcgaagg cgaagcccgc ccgcctgccc cccgagcctc acggcggcga 420
gtgcgggggt tccaaggggg cagcgccacc ttgggcaagg ccgaaggccg cgcagtcgat 480
caacaagccc cggaggggcc actttttgcc ggagggggag ccgcgccgaa ggcgtggggg 540
aaccccgcag gggtgccctt ctttgggcac caaagaacta gatatagggc gaaatgcgaa 600
agacttaaaa atcaacaact taaaaaaggg gggtacgcaa cagctcattg cggcaccccc 660
cgcaatagct cattgcgtag gttaaagaaa atctgtaatt gactgccact tttacgcaac 720
gcataattgt tgtcgcgctg ccgaaaagtt gcagctgatt gcgcatggtg ccgcaaccgt 780
gcggcaccct accgcatgga gataagcatg gccacgcagt ccagagaaat cggcattcaa 840
gccaagaaca agcccggtca ctgggtgcaa acggaacgca aagcgcatga ggcgtgggcc 900
gggcttattg cgaggaaacc cacggcggca atgctgctgc atcacctcgt ggcgcagatg 960

-continued

```
ggccaccaga acgccgtggt ggtcagccag aagacacttt ccaagctcat cggacgttct   1020
ttgcggacgg tccaatacgc agtcaaggac ttggtggccg agcgctggat ctccgtcgtg   1080
aagctcaacg gccccggcac cgtgtcggcc tacgtggtca atgaccgcgt ggcgtggggc   1140
cagccccgcg accagttgcg cctgtcggtg ttcagtgccg ccgtggtggt tgatcacgac   1200
gaccaggacg aatcgctgtt ggggcatggc gacctgcgcc gcatcccgac cctgtatccg   1260
ggcgagcagc aactaccgac cggcccccggc gaggagccgc ccagccagcc cggcattccg   1320
ggcatggaac cagacctgcc agccttgacc gaaacggagg aatgggaacg gcgcgggcag   1380
cagcgcctgc cgatgcccga tgagccgtgt tttctggacg atggcgagcc gttggagccg   1440
ccgacacggg tcacgctgcc gcgccggtag tacgtacccg gaattgccag ctggggcgcc   1500
ctctggtaag gttgggaagc cctgcaaagt aaactggatg gctttcttgc cgccaaggat   1560
ctgatggcgc aggggatcaa gctctgatca agagacagga tgaggatcgt ttcgatgaag   1620
cagcgtatta cagtgacagt tgacagcgac agctatcagt tgctcaaggc atatgatgtc   1680
aatatctccg gtctggtaag cacaaccatg cagaatgaag cccgtcgtct gcgtgccgaa   1740
cgctggaaag cggaaaatca ggaagggatg gctgaggtcg cccggtttat tgaaatgaac   1800
ggctcttttg ctgacgagaa cagggactgg tgaaatgcag tttaaggttt acacctataa   1860
aagagagagc cgttatcgtc tgtttgtgga tgtacagagc gatattattg acacgcccgg   1920
gcgacggatg gtgatccccc tggccagtgc acgtctgctg tcagataaag tctcccgtga   1980
actttacccg gtggtgcata tcggggatga aagctggcgc atgatgacca ccgatatggc   2040
cagtgtgccg gtctccgtta tcggggaaga agtggctgat ctcagccacc gcgaaaatga   2100
catcaaaaac gccattaacc tgatgttctg gggaatataa atcctagacg aattctctag   2160
tagaggttcc aactttcacc ataatgaaat aagatcacta ccgggcgtat tttttgagtt   2220
atcgagattt tcaggagcta aggaagctaa aatgaaatct aacaatgcgc tcatcgtcat   2280
cctcggcacc gtcaccctgg atgctgtagg cataggcttg gttatgccgg tactgccggg   2340
cctcttgcgg gatatcgtcc attccgacag catcgccagt cactatggcg tgctgctagc   2400
gctatatgcg ttgatgcaat ttctatgcgc acccgttctc ggagcactgt ccgaccgctt   2460
tggccgccgc ccagtcctgc tcgcttcgct acttggagcc actatcgact acgcgatcat   2520
ggcgaccaca cccgtcctgt ggatcctcta cgccggacgc atcgtggccg gcatcaccgg   2580
cgccacaggt gcggttgctg gcgcctatat cgccgacatc accgatgggg aagatcgggc   2640
tcgccacttc gggctcatga gcgcttgttt cggcgtgggt atggtggcag gccccgtggc   2700
cgggggactg ttgggcgcca tctccttgca tgcaccattc cttgcggcgg cggtgctcaa   2760
cggcctcaac ctactactgg gctgcttcct aatgcaggag tcgcataagg gagagcgtcg   2820
accgatgccc ttgagagcct tcaacccagt cagctccttc cggtgggcgc ggggcatgac   2880
tatcgtcgcc gcacttatga ctgtcttctt tatcatgcaa ctcgtaggac aggtgccggc   2940
agcgctctgg gtcattttcg gcgaggaccg ctttcgctgg agcgcgacga tgatcggcct   3000
gtcgcttgcg gtattcggaa tcttgcacgc cctcgctcaa gccttcgtca ctggtcccgc   3060
caccaaacgt ttcggcgaga agcaggccat tatcgccggc atggcggccg acgcgctggg   3120
ctacgtcttg ctggcgttcg cgacgcgagg ctggatggcc ttccccatta tgattcttct   3180
cgcttccggc ggcatcggga tgcccgcgtt gcaggccatg ctgtccaggc aggtagatga   3240
cgaccatcag ggacagcttc aaggatcgct cgcggctctt accagcctaa cttcgatcac   3300
tggaccgctg atcgtcacgg cgatttatgc cgcctcggcg agcacatgga acgggttggc   3360
```

-continued

```
atggattgta ggcgccgccc tataccttgt ctgcctcccc gcgttgcgtc gcggtgcatg   3420
gagccgggcc acctcgacct gaatggaagg gatccccctc aagtcaaaag cctccggtcg   3480
gaggcttttg acttagatct tctcgacgct ctcccttatg cgactcctgc attaggaaat   3540
taatacgact cactataggg gaattgtgag cggataacaa ttcccctgta gaaataattt   3600
tgtttaactt taataaggag atataccatg gcggcggaca ccctgctgat cctgggcgac   3660
tccctgtcgg cgggctaccg catgtcggcg tcggcggcgt ggccggcgct gctgaacgac   3720
aagtggcagt ccaagacctc ggtggtcaac gcctcgatca gcggcgacac gagccagcag   3780
ggcctggccc gcctgccggc gctgctgaag cagcaccagc cgcgctgggt gctggtcgag   3840
ctgggcggca acgacggcct gcgcggcttc cagccgcagc agaccgaaca gacgctgcgc   3900
cagatcctgc aggacgtgaa ggccgcgaac gccgagccgc tgctgatgca gatccgcctg   3960
ccggcgaact acggccgtcg ctacaacgag gccttctccg cgatctaccc gaagctggcc   4020
aaggaattcg acgtgccgct gctgccgttc ttcatggagg aagtctacct gaagccgcag   4080
tggatgcagg acgacggcat ccacccgaac cgcgacgcgc agccgttcat cgccgactgg   4140
atggccaagc aactgcagcc gctggtcaac cacgactcct gaatttaaat cccttatgcg   4200
actcctgcat taggaaatta atacgactca ctataggga attgtgagcg gataacaatt   4260
cccctgtaga aataattttg tttaacttta ataaggagat ataccatgac ggatgtccgc   4320
tttcgtatca ttggcacggg cgcttacgtc ccggaacgca ttgtcagcaa cgacgaagtc   4380
ggcgcaccgg ctggtgtgga tgacgattgg attacgcgta aaaccggtat ccgccagcgt   4440
cgctgggcgg ccgacgatca agcaacgagc gatctggcta ccgcagctgg tcgtgcagca   4500
ctgaaagcag ctggcattac gccggaacag ctgaccgtca tcgcagtggc tacctctacg   4560
ccggaccgtc cgcagccgcc gaccgcggcc tatgttcaac atcacctggg tgcaaccggc   4620
acggcagctt ttgatgttaa cgctgtgtgc agcggtacgg ttttcgcgct gagctctgtt   4680
gccggcaccc tggtctatcg tggcggttac gcactggtca ttggtgctga tctgtactca   4740
cgtatcctga atccggcgga ccgcaaaacc gtggttctgt tcggcgatgg tgcgggcgcg   4800
atggtgctgg gcccgaccag caccggcacc ggtccgattg tgcgtcgcgt tgcactgcat   4860
acgtttggcg gtctgaccga tctgatccgt gttccggccg gcggttcccg ccagccgctg   4920
gacaccgatg gtctggacgc aggcctgcaa tattttgcga tggatggccg cgaagtccgt   4980
cgcttcgtga ccgaacatct gccgcagctg attaaaggtt ttctgcacga agcgggcgtg   5040
gatgcggcgg atattagcca tttcgtgccg caccaagcca acggtgtgat gctggacgaa   5100
gtttttggcg aactgcatct gccgcgtgca accatgcacc gtacggtgga aacctacggt   5160
aatacgggcg cagctagtat tccgatcacg atggatgcgg ccgttcgtgc aggttccttc   5220
cgtccgggcg aactggttct gctggcgggc tttggcggcg gtatggcggc ttcgtttgct   5280
ctgattgaat ggtgacctaa tgcaggctgc aggcggatac gaggaggaat aaaccatgaa   5340
aaaggtatgt gttataggtg caggtactat gggttcagga attgctcagg catttgcagc   5400
taaaggattt gaagtagtat taagagatat taaagatgaa tttgttgata gaggattaga   5460
ttttatcaat aaaaatcttt ctaaattagt taaaaaagga aagatagaag aagctactaa   5520
agttgaaatc ttaactagaa tttccggaac agttgacctt aatatggcag ctgattgcga   5580
tttagttata gaagcagctg ttgaaagaat ggatattaaa aagcagattt ttgctgactt   5640
agacaatata tgcaagccag aaacaattct tgcatcaaat acatcatcac tttcaataac   5700
```

-continued

```
agaagtggca tcagcaacta aaagacctga taaggttata ggtatgcatt tctttaatcc   5760
agctcctgtt atgaagcttg tagaggtaat aagaggaata gctacatcac aagaaacttt   5820
tgatgcagtt aaagagacat ctatagcaat aggaaaagat cctgtagaag tagcagaagc   5880
accaggattt gttgtaaata gaatattaat accaatgatt aatgaagcag ttggtatatt   5940
agcagaagga atagcttcag tagaagacat agataaagct atgaaacttg gagctaatca   6000
cccaatggga ccattagaat taggtgattt tataggtctt gatatatgtc ttgctataat   6060
ggatgtttta tactcagaaa ctggagattc taagtataga ccacatacat tacttaagaa   6120
gtatgtaaga gcaggatggc ttggaagaaa atcaggaaaa ggtttctacg attattcaaa   6180
ataagtttac aggatctgca gggaggagga aatcatggag ttgaacaacg ttattctgga   6240
gaaagaaggc aaggtggcgg ttgtcaccat taaccgtcca aaggccctga acgctctgaa   6300
ctcggatacc ctgaaagaga tggattacgt tattggcgag attgagaatg acagcgaagt   6360
gctggctgtg attctgaccg gtgcgggtga gaagagcttt gtcgcgggtg cggacatcag   6420
cgagatgaaa gaaatgaaca ccatcgaagg ccgtaagttc ggtattctgg gcaacaaggt   6480
gtttcgtcgt ctggaactgc tggagaaacc tgtcattgct gccgtgaacg gtttcgcgct   6540
gggcggtggt tgcgagatcg ctatgagctg cgatattcgt atcgcatcgt ccaacgcacg   6600
ctttggtcaa ccggaggtcg gtctgggtat cactccgggt ttcggcggta cgcaacgtct   6660
gagccgcctg gttggcatgg gcatggcgaa acagttgatt ttcacggcac agaacattaa   6720
ggcggatgag gcgctgcgta ttggtctggt gaataaggtc gttgagccaa gcgaactgat   6780
gaataccgcg aaagaaattg cgaacaagat cgttagcaat gccccggtgg ccgttaagct   6840
gtcgaaacag gcaatcaacc gtggcatgca gtgtgacatc gacaccgccc tggcgtttga   6900
gagcgaggcg tttggtgagt gcttctccac cgaggaccaa aaggatgcga tgaccgcgtt   6960
cattgagaaa cgcaagatcg agggtttcaa gaatcgttaa tagaggagga taggaggttt   7020
tcatatgatt gtgaaaccga tggtccgtaa taatatctgt ctgaatgctc acccgcaggg   7080
ctgtaaaaaa ggcgtggaag atcaaattga atataccaaa aaacgtatta cggcagaagt   7140
gaaagccggc gcaaaagctc cgaaaaacgt gctggttctg ggttgcagca atggctatgg   7200
tctggcttct cgcattaccg cggcctttgg ctacggtgca gctacgatcg gcgttagttt   7260
cgaaaaagca ggttccgaaa ccaaatatgg cacgccgggt tggtacaaca atctggcttt   7320
tgatgaagcg gccaaacgtg aaggcctgta tagtgtcacc attgatggtg acgcgttctc   7380
cgatgaaatt aaagcacagg tgatcgaaga agcgaagaaa aaaggcatta aatttgacct   7440
gatcgtttac agcctggcat ctccggtccg taccgatccg gacacgggta tcatgcataa   7500
atctgtgctg aaaccgtttg gcaaaacctt cacgggtaaa accgttgatc cgttcacggg   7560
cgaactgaaa gaaattagcg cggaaccggc caacgatgaa gaagcagctg cgaccgtcaa   7620
agtgatgggc ggtgaagact gggaacgttg gatcaaacag ctgagtaaag aaggcctgct   7680
ggaagaaggt tgcattaccc tggcgtattc ctacatcggc ccggaagcaa cccaagctct   7740
gtatcgcaaa ggcacgattg gtaaagcgaa agaacatctg gaagcgaccg cccaccgtct   7800
gaacaaagaa aatccgtcaa tccgcgcctt cgtttcggtc aataaaggtc tggttacccg   7860
tgcatcagct gtgattccgg ttatcccgct gtacctggca tcgctgttta aagtcatgaa   7920
agaaaaaggc aaccatgaag gttgtattga acagatcacc cgcctgtatg ccgaacgtct   7980
gtaccgcaaa gatggtacga ttccggtgga cgaagaaaat cgtattcgca tcgatgactg   8040
ggaactggaa gaagatgtcc aaaaagccgt gagcgccctg atggaaaaag ttaccggcga   8100
```

aaacgcggaa tctctgacgg atctggccgg ttatcgtcac gactttctgg cgagtaatgg 8160
ttttgatgtt gaaggcatta actacgaagc tgaagtggaa cgctttgatc gcatttgatc 8220
tagagaattc gtcaacgaat tcaagcttga tatcattcag gacgagcctc agactccagc 8280
gtaactggac tgaaaacaaa ctaaagcgcc cttgtggcgc tttagttttg ttccgctcat 8340
gataataatg gtttcttaga cgtcaggtgg cacttttcgg ggaaatgtgc gcgcccgcgt 8400
tcctgctggc gctgggcctg tttctggcgc tggacttccc gctgttccgt cagcagcttt 8460
tcgcccacgg ccttgatgat cgcggcggcc ttggcctgca tatcccgatt caacggcccc 8520
agggcgtcca gaacgggctt caggcgctcc cgaaggtctc gggccgtctc ttgggcttga 8580
tcggccttct tgcgcatctc acgcgctcct gcggcggcct gtagggcagg ctcatacccc 8640
tgccgaaccg cttttgtcag ccggtcggcc acggcttccg gcgtctcaac gcgctttgag 8700
attcccagct tttcggccaa tccctgcggt gcataggcgc gtggctcgac cgcttgcggg 8760
ctgatggtga cgtggcccac tggtggccgc tccagggcct cgtagaacgc ctgaatgcgc 8820
gtgtgacgtg ccttgctgcc ctcgatgccc cgttgcagcc ctagatcggc cacagcggcc 8880
gcaaacgtgg tctggtcgcg ggtcatctgc gctttgttgc cgatgaactc cttggccgac 8940
agcctgccgt cctgcgtcag cggcaccacg aacgcggtca tgtgcgggct ggtttcgtca 9000
cggtggatgc tggccgtcac gatgcgatcc gccccgtact tgtccgccag ccacttgtgc 9060
gccttctcga agaacgccgc ctgctgttct tggctggccg acttccacca ttccgggctg 9120
gccgtcatga cgtactcgac cgccaacaca gcgtccttgc gccgcttctc tggcagcaac 9180
tcgcgcagtc ggcccatcgc ttcatcggtg ctgctggccg cccagtgctc gttctctggc 9240
gtcctgctgg cgtcagcgtt gggcgtctcg cgctcgcggt aggcgtgctt gagactggcc 9300
gccacgttgc ccattttcgc cagcttcttg catcgcatga tcgcgtatgc cgccatgcct 9360
gcccctccct tttggtgtcc aaccggctcg acgggggcag cgcaaggcgg tgcctccggc 9420
gggccactca atgcttgagt atactcacta gactttgctt cgcaaagtcg tgaccgccta 9480
cggcggctgc ggcgccctac gggcttgctc tccgggcttc gccctgcgcg gtcgctgcgc 9540
tc 9542

<210> SEQ ID NO 11
<211> LENGTH: 6862
<212> TYPE: DNA
<213> ORGANISM: Escherichia coli

<400> SEQUENCE: 11
gacgaattct ctagatgcat gatcgtgctc ctgtcgttga ggacccggct aggctggcgg 60
ggttgcctta ctggttagca gaatgaatca ccgatacgcg agcgaacgtg aagcgactgc 120
tgctgcaaaa cgtctgcgac ctgagcaaca acatgaatgg tcttcggttt ccgtgtttcg 180
taaagtctgg aaacgcggaa gtcccctacg tgctgctgaa gttgcccgca acagagagtg 240
gaaccaaccg gtgataccac gatactatga ctgagagtca acgccatgag cggcctcatt 300
tcttattctg agttacaaca gtccgcaccg ctgtccggta gctccttccg gtgggcgcgg 360
ggcatgacta tcgtcgccgc acttatgact gtcttcttta tcatgcaact cgtaggacag 420
gtgccggcag cgcccaacag tcccccggcc acggggcctg ccaccatacc cacgccgaaa 480
caagcgccct gcaccattat gttccggatc tgcatcgcag gatgctgctg gctaccctgt 540
ggaacaccta catctgtatt aacgaagcgc taaccgtttt tatcaggctc tgggaggcag 600

-continued

```
aataaatgat catatcgtca attattacct ccacggggag agcctgagca aactggcctc    660
aggcatttga gaagcacacg gtcacactgc ttccggtagt caataaaccg gtaaaccagc    720
aatagacata agcggctatt taacgaccct gccctgaacc gacgaccggg tcgaatttgc    780
tttcgaattt ctgccattca tccgcttatt atcacttatt caggcgtagc accaggcgtt    840
taagggcacc aataactgcc ttaaaaaaat tacgccccgc cctgccactc atcgcagtac    900
tgttgtaatt cattaagcat tctgccgaca tggaagccat cacagacggc atgatgaacc    960
tgaatcgcca gcggcatcag caccttgtcg ccttgcgtat aatatttgcc catagtgaaa   1020
acgggggcga agaagttgtc catattggcc acgtttaaat caaaactggt gaaactcacc   1080
cagggattgg ctgagacgaa aaacatattc tcaataaacc ctttagggaa ataggccagg   1140
ttttcaccgt aacacgccac atcttgcgaa tatatgtgta gaaactgccg gaaatcgtcg   1200
tggtattcac tccagagcga tgaaaacgtt tcagtttgct catggaaaac ggtgtaacaa   1260
gggtgaacac tatcccatat caccagctca ccgtctttca ttgccatacg gaactccgga   1320
tgagcattca tcaggcgggc aagaatgtga ataaaggccg gataaaactt gtgcttattt   1380
ttctttacgg tctttaaaaa ggccgtaata tccagctgaa cggtctggtt ataggtacat   1440
tgagcaactg actgaaatgc ctcaaaatgt tctttacgat gccattggga tatatcaacg   1500
gtggtatatc cagtgatttt tttctccatt ttagcttcct tagctcctga aaatctcgat   1560
aactcaaaaa atacgcccgg tagtgatctt atttcattat ggtgaaagtt ggaacctctt   1620
acgtgccgat caacgtctca ttttcgccaa aagttggccc agggcttccc ggtatcaaca   1680
gggacaccag gatttattta ttctgcgaag tgatcttccg tcacaggtat ttattcggcg   1740
caaagtgcgt cgggtgatgc tgccaactta ctgatttagt gtatgatggt gtttttgagg   1800
tgctccagtg gcttctgttt ctatcagctg tccctcctgt tcagctactg acggggtggt   1860
gcgtaacggc aaaagcaccg ccggacatca gcgctagcgg agtgtatact ggcttactat   1920
gttggcactg atgagggtgt cagtgaagtg cttcatgtgg caggagaaaa aaggctgcac   1980
cggtgcgtca gcagaatatg tgatacagga tatattccgc ttcctcgctc actgactcgc   2040
tacgctcggt cgttcgactg cggcgagcgg aaatggctta cgaacggggc ggagatttcc   2100
tggaagatgc caggaagata cttaacaggg aagtgagagg gccgcggcaa agccgttttt   2160
ccataggctc cgcccccctg acaagcatca cgaaatctga cgctcaaatc agtggtggcg   2220
aaacccgaca ggactataaa gataccaggc gtttccccct ggcggctccc tcgtgcgctc   2280
tcctgttcct gcctttcggt ttaccggtgt cattccgctg ttatggccgc gtttgtctca   2340
ttccacgcct gacactcagt tccgggtagg cagttcgctc caagctggac tgtatgcacg   2400
aaccccccgt tcagtccgac cgctgcgcct tatccggtaa ctatcgtctt gagtccaacc   2460
cggaaagaca tgcaaaagca ccactggcag cagccactgg taattgattt agaggagtta   2520
gtcttgaagt catgcgccgg ttaaggctaa actgaaagga caagttttgg tgactgcgct   2580
cctccaagcc agttacctcg gttcaaagag ttggtagctc agagaacctt cgaaaaaccg   2640
ccctgcaagg cggttttttc gttttcagag caagagatta cgcgcagacc aaaacgatct   2700
caagaagatc atcttattaa tcagataaaa tatttctaga tttcagtgca atttatctct   2760
tcaaatgtag cacctgaagt cagccccata cgatataagt tgtaattctc atgtttgaca   2820
gcttatcatc gatacagtcc agttacgctg gagtctgagg ctcgtcctga atgatatgcg   2880
gcctccacgt gcgtaattgt gctgatctct tatatagctg ctctcattat ctctctaccc   2940
tgaagtgact ctctcacctg taaaaataat atctcacagg cttaatagtt tcttaataca   3000
```

-continued

```
aagcctgtaa aacgtcagga taacttctgt gtaggaggat aatccatgag tctgaacttc   3060
ctggacttcg agcagccgat cgccgaactg gaggcgaaga ttgacagcct gaccgcggtt   3120
agccgtcaag atgagaaact ggacattaac atcgacgaag aggtccaccg tttgcgtgag   3180
aagtctgttg aactgactcg caaaatcttt gctgatttgg gcgcatggca gattgcccag   3240
ttggctcgcc acccacaacg cccatatacc ctggactacg tgcgcctggc gtttgacgag   3300
ttcgacgaac tggcaggcga ccgcgcctat gcggacgata aagcaattgt cggcggtatt   3360
gctcgtttgg atggccgtcc ggtgatgatt atcggccatc aaaaaggccg cgagacaaag   3420
gaaaagattc gtcgtaattt cggaatgccg gcaccggagg gctaccgcaa ggccctgcgt   3480
ctgatgcaaa tggccgaacg ctttaagatg ccgattatca cgttcattga tacgcctggt   3540
gcgtacccag gcgttggtgc ggaagagcgt ggtcagagcg aggccatcgc acgtaacctg   3600
cgtgagatgt ctcgtctggg tgtgccggtc gtttgcaccg tgattggcga gggcggtagc   3660
ggtggtgcgt tggcgatcgg tgtcggtgat aaggtcaaca tgctgcaata cagcacgtac   3720
agcgtcatta gcccggaagg ttgcgcttcc attctgtgga agagcgcgga taaagcacca   3780
ttggcagcgg aagcgatggg tatcatcgca ccgcgtctga aagaactgaa gttgattgat   3840
tctatcatcc cggaaccgct gggcggtgct caccgtaatc cggaggcgat ggcagccagc   3900
ctgaaggccc agctgctggc ggacctggcg gatctggacg tgctgagcac ggaggatctg   3960
aaaaaccgtc gctatcagcg cttgatgagc tatggctacg cctaaggtac ctttatcaat   4020
ttatttaagg aggactctta agatgagctg gatcgagcgc atcaagagca acatcacccc   4080
gacccgcaag gcgagcatcc ctgaaggcgt ctggaccaaa tgcgatagct gcggtcaggt   4140
tttgtatcgt gcggagctgg agcgtaacct ggaagtgtgc ccgaaatgcg accatcacat   4200
gcgtatgacc gctcgtaatc gtctgcatag cctgctggat gagggcagcc tggtcgagct   4260
gggtagcgaa ctggaaccga aagatgttct gaaattccgt gattccaaga agtataagga   4320
tcgtttggca tctgcacaaa aagaaaccgg tgagaaggac gcactggttg ttatgaaagg   4380
caccctgtat ggtatgccgg ttgttgctgc ggcgttcgag tttgcgttta tgggtggcag   4440
catgggttcc gtggtgggcg cacgctttgt gcgtgccgtg gagcaggcgc tggaggataa   4500
ctgtcctctg atttgtttca gcgcgagcgg tggtgcgcgt atgcaagagg ccctgatgag   4560
cctgatgcag atggcaaaaa cctcggcagc cctggcgaag atgcaagaac gcggcctgcc   4620
gtacatttcc gtcctgaccg accctacgat gggcggtgtc agcgccagct ttgcgatgct   4680
gggtgatttg aacatcgcag agccgaaggc tctgattggt tttgctggtc cgcgtgttat   4740
tgaacagacg gttcgcgaaa agttgccgcc tggtttccag cgcagcgagt tcctgattga   4800
gaaaggtgcc atcgacatga tcgttcgccg tccagaaatg cgtctgaaac tggcgagcat   4860
tctggcgaaa ttgatgaatc tgccggctcc gaatcctgaa gcaccgcgtg agggtgtcgt   4920
ggttccgccg gtcccggacc aagagccgga ggcttaatta accaaattag aagtatttta   4980
tttagaggag gtagccatgg acatccgcaa gatcaagaag ctgatcgaac tggtggaaga   5040
gtctggcatc agcgagctgg agatcagcga aggtgaagag agcgtccgta tttcccgtgc   5100
ggcaccggca gcgagctttc cggttatgca gcaagcatac gccgctccga tgatgcaaca   5160
gccggcacag agcaacgccg ctgcaccggc gaccgttcca agcatggagg caccggcagc   5220
ggccgagatt tcgggtcata tcgtgcgtag cccgatggtg ggcaccttct atcgcacgcc   5280
gtcgccggac gcaaaagcct tcatcgaagt cggccagaag gtcaatgtcg gcgacacgct   5340
```

gtgtatcgtt gaggcaatga aaatgatgaa ccagattgaa gcggataaga gcggtactgt 5400
taaagcgatc ctggtggaat ccggccagcc tgttgagttc gatgaaccgc tggttgtgat 5460
cgagtaagag ctccggatat acggggaaga acaaggggtg tacatgctgg acaagatcgt 5520
catcgccaac cgcggcgaaa tcgccctgcg catcttgcgc gcgtgtaaag agctgggcat 5580
taagactgtt gccgtgcatt ccagcgcaga ccgcgacctg aagcatgttc tgctggccga 5640
cgaaacggtt tgcatcggtc cggcaccgag cgtgaaaagc tatctgaaca tcccggccat 5700
catctctgcg gcagagatca ccggtgcagt ggcgattcat ccgggctacg gtttcctgag 5760
cgagaacgct aactttgctg aacaagtgga gcgtagcggt ttcatcttca ttggccctaa 5820
ggcggagacg attcgcctga tgggcgacaa agtgagcgcc attgcagcga tgaaaaaggc 5880
cggtgtgccg tgtgttccgg gcagcgatgg tccgctgggt gacgatatgg acaagaaccg 5940
tgccatcgct aaacgtattg gctacccggt cattatcaaa gcctctggtg gtggcggtgg 6000
ccgtggtatg cgtgtcgtcc gtggtgatgc ggaactggcg caaagcatca gcatgacccg 6060
tgcggaagcc aaagcggcgt tctctaacga tatggtgtat atggagaagt atctggagaa 6120
tccgcgccac gttgaaatcc aagttctggc ggatggtcag ggcaatgcga tctacttggc 6180
agaacgtgat tgctccatgc aacgccgtca tcagaaggtg gtggaagagg caccggctcc 6240
gggtattacg ccggaactgc gtcgctacat cggtgagcgc tgtgcgaaag cgtgtgtgga 6300
cattggttac cgtggtgcgg gtacgtttga gttcctgttc gaaaatggtg agttttactt 6360
cattgaaatg aatacccgca tccaggttga gcacccggtg accgagatga ttactggcgt 6420
tgatctgatc aaagagcaac tgcgcattgc ggctggtcag ccgctgtcga tcaagcaaga 6480
agaggtgcac gttcgtggtc acgcggtcga gtgccgtatc aatgcggagg acccgaatac 6540
ctttctgccg agccctggta agatcactcg ttttcacgcg ccaggtggtt ttggcgttcg 6600
ttgggagtct cacatctacg ccggttacac cgtgccgccg tactatgaca gcatgattgg 6660
taaactgatc tgctatggcg aaaatcgtga tgtcgcgatc gcccgcatga aaaacgcgct 6720
gcaagagctg atcattgatg gcattaagac caatgtggat ttgcagatcc gcattatgaa 6780
cgacgagaat ttccagcacg gcggtacgaa cattcactac ctggaaaaga aactgggcct 6840
gcaagagaaa taactgcaga gg 6862

<210> SEQ ID NO 12
<211> LENGTH: 5988
<212> TYPE: DNA
<213> ORGANISM: Escherichia coli

<400> SEQUENCE: 12
agatctcgat cccgcgaaat taatacgact cactataggg gaattgtgag cggataacaa 60
ttcccctcta gaaataattt tgtttaactt taagaaggag atataccatg ggaaagttca 120
aaaagaagtt taagattggc cgcatgcacg tggacccgtt caattacatt tcgatgcgct 180
acctggtggc gctgatgaac gaagtggcgt tcgaccaggc cgaaattctg gagaaggaca 240
tcgatatgaa aaatctgcgc tggatcattt actcgtggga tatccagatt gaaaacaata 300
tccgcctggg cgaagagatc gagattacca cgatcccgac ccacatggac aagttctacg 360
cgtatcgcga ttttattgtc gagtcccgcg gcaacatcct ggcccgcgcg aaagccacct 420
tcctgctgat ggacatcacg cgcctgcgcc cgatcaagat tccgcagaac ctgagcctgg 480
cctacggcaa agaaaatccg atcttcgaca tttatgatat ggagatccgc aacgacctgg 540
cgtttatccg cgatattcag ctgcgtcgcg ccgacctgga taacaatttc catatcaaca 600
atgcggtgta ctttgacctg attaaggaaa ccgtcgatat ctatgacaag gatatcagct 660
acattaaact gatctatcgc aacgagattc gcgacaagaa acagatccag gcgttcgccc 720
gtcgcgaaga caaatcgatc gattttgccc tgcgcggcga ggacggccgc gattattgcc 780
tgggcaagat caaaacgaat gtgtaaattt aaatattgga tcggatccga attcgagctc 840
cgtcgacaag cttgcggccg cactcgagca ccaccaccac caccactgag atccggctgc 900
taacaaagcc cgaaaggaag ctgagttggc tgctgccacc gctgagcaat aactagcata 960
accccttggg gcctctaaac gggtcttgag gggttttttg ctgaaaggag gaactatatc 1020
cggattggcg aatgggacgc gccctgtagc ggcgcattaa gcgcggcggg tgtggtggtt 1080
acgcgcagcg tgaccgctac acttgccagc gccctagcgc ccgctccttt cgctttcttc 1140
ccttcctttc tcgccacgtt cgccggcttt ccccgtcaag ctctaaatcg ggggctccct 1200
ttagggttcc gatttagtgc tttacggcac ctcgacccca aaaaacttga ttagggtgat 1260
ggttcacgta gtgggccatc gccctgatag acggtttttc gccctttgac gttggagtcc 1320
acgttcttta atagtggact cttgttccaa actggaacaa cactcaaccc tatctcggtc 1380
tattcttttg atttataagg gattttgccg atttcggcct attggttaaa aaatgagctg 1440
atttaacaaa aatttaacgc gaattttaac aaaatattaa cgtttacaat ttcaggtggc 1500
acttttcggg gaaatgtgcg cggaacccct atttgtttat ttttctaaat acattcaaat 1560
atgtatccgc tcatgaatta attcttagaa aaactcatcg agcatcaaat gaaactgcaa 1620
tttattcata tcaggattat caataccata tttttgaaaa agccgtttct gtaatgaagg 1680
agaaaactca ccgaggcagt tccataggat ggcaagatcc tggtatcggt ctgcgattcc 1740
gactcgtcca acatcaatac aacctattaa tttcccctcg tcaaaaataa ggttatcaag 1800
tgagaaatca ccatgagtga cgactgaatc cggtgagaat ggcaaaagtt tatgcatttc 1860
tttccagact tgttcaacag gccagccatt acgctcgtca tcaaaatcac tcgcatcaac 1920
caaaccgtta ttcattcgtg attgcgcctg agcgagacga aatacgcgat cgctgttaaa 1980
aggacaatta caaacaggaa tcgaatgcaa ccggcgcagg aacactgcca gcgcatcaac 2040
aatattttca cctgaatcag gatattcttc taatacctgg aatgctgttt tcccggggat 2100
cgcagtggtg agtaaccatg catcatcagg agtacggata aaatgcttga tggtcggaag 2160
aggcataaat tccgtcagcc agtttagtct gaccatctca tctgtaacat cattggcaac 2220
gctacctttg ccatgtttca gaaacaactc tggcgcatcg ggcttcccat acaatcgata 2280
gattgtcgca cctgattgcc cgacattatc gcgagcccat ttatacccat ataaatcagc 2340
atccatgttg gaatttaatc gcggcctaga gcaagacgtt tcccgttgaa tatggctcat 2400
aacacccctt gtattactgt ttatgtaagc agacagtttt attgttcatg accaaaatcc 2460
cttaacgtga gttttcgttc cactgagcgt cagaccccgt agaaaagatc aaaggatctt 2520
cttgagatcc tttttttctg cgcgtaatct gctgcttgca aacaaaaaaa ccaccgctac 2580
cagcggtggt ttgtttgccg gatcaagagc taccaactct ttttccgaag gtaactggct 2640
tcagcagagc gcagatacca aatactgtcc ttctagtgta gccgtagtta ggccaccact 2700
tcaagaactc tgtagcaccg cctacatacc tcgctctgct aatcctgtta ccagtggctg 2760
ctgccagtgg cgataagtcg tgtcttaccg ggttggactc aagacgatag ttaccggata 2820
aggcgcagcg gtcgggctga acggggggtt cgtgcacaca gcccagcttg gagcgaacga 2880
cctacaccga actgagatac ctacagcgtg agctatgaga aagcgccacg cttcccgaag 2940

-continued

```
ggagaaaggc ggacaggtat ccggtaagcg gcagggtcgg aacaggagag cgcacgaggg   3000
agcttccagg gggaaacgcc tggtatcttt atagtcctgt cgggtttcgc cacctctgac   3060
ttgagcgtcg atttttgtga tgctcgtcag gggggcggag cctatggaaa aacgccagca   3120
acgcggcctt tttacggttc ctggcctttt gctggccttt tgctcacatg ttctttcctg   3180
cgttatcccc tgattctgtg gataaccgta ttaccgcctt tgagtgagct gataccgctc   3240
gccgcagccg aacgaccgag cgcagcgagt cagtgagcga ggaagcggaa gagcgcctga   3300
tgcggtattt tctccttacg catctgtgcg gtatttcaca ccgcatatat ggtgcactct   3360
cagtacaatc tgctctgatg ccgcatagtt aagccagtat acactccgct atcgctacgt   3420
gactgggtca tggctgcgcc ccgacacccg ccaacacccg ctgacgcgcc ctgacgggct   3480
tgtctgctcc cggcatccgc ttacagacaa gctgtgaccg tctccgggag ctgcatgtgt   3540
cagaggtttt caccgtcatc accgaaacgc gcgaggcagc tgcggtaaag ctcatcagcg   3600
tggtcgtgaa gcgattcaca gatgtctgcc tgttcatccg cgtccagctc gttgagtttc   3660
tccagaagcg ttaatgtctg gcttctgata aagcgggcca tgttaagggc ggtttttttcc  3720
tgtttggtca ctgatgcctc cgtgtaaggg ggatttctgt tcatgggggt aatgataccg   3780
atgaaacgag agaggatgct cacgatacgg gttactgatg atgaacatgc ccggttactg   3840
gaacgttgtg agggtaaaca actggcggta tggatgcggc gggaccagag aaaaatcact   3900
cagggtcaat gccagcgctt cgttaataca gatgtaggtg ttccacaggg tagccagcag   3960
catcctgcga tgcagatccg gaacataatg gtgcagggcg ctgacttccg cgtttccaga   4020
ctttacgaaa cacggaaacc gaagaccatt catgttgttg ctcaggtcgc agacgttttg   4080
cagcagcagt cgcttcacgt tcgctcgcgt atcggtgatt cattctgcta accagtaagg   4140
caaccccgcc agcctagccg ggtcctcaac gacaggagca cgatcatgcg cacccgtggg   4200
gccgccatgc cggcgataat ggcctgcttc tcgccgaaac gtttggtggc gggaccagtg   4260
acgaaggctt gagcgagggc gtgcaagatt ccgaataccg caagcgacag gccgatcatc   4320
gtcgcgctcc agcgaaagcg gtcctcgccg aaaatgaccc agagcgctgc cggcacctgt   4380
cctacgagtt gcatgataaa gaagacagtc ataagtgcgg cgacgatagt catgccccgc   4440
gcccaccgga aggagctgac tgggttgaag gctctcaagg gcatcggtcg agatcccggt   4500
gcctaatgag tgagctaact tacattaatt gcgttgcgct cactgcccgc tttccagtcg   4560
ggaaacctgt cgtgccagct gcattaatga atcggccaac gcgcggggag aggcggtttg   4620
cgtattgggc gccagggtgg tttttctttt caccagtgag acgggcaaca gctgattgcc   4680
cttcaccgcc tggccctgag agagttgcag caagcggtcc acgctggttt gccccagcag   4740
gcgaaaatcc tgtttgatgg tggttaacgg cgggatataa catgagctgt cttcggtatc   4800
gtcgtatccc actaccgaga tatccgcacc aacgcgcagc ccggactcgg taatggcgcg   4860
cattgcgccc agcgccatct gatcgttggc aaccagcatc gcagtgggaa cgatgccctc   4920
attcagcatt tgcatggttt gttgaaaacc ggacatggca ctccagtcgc cttcccgttc   4980
cgctatcggc tgaatttgat tgcgagtgag atatttatgc cagccagcca gacgcagacg   5040
cgccgagaca gaacttaatg ggcccgctaa cagcgcgatt tgctggtgac ccaatgcgac   5100
cagatgctcc acgcccagtc gcgtaccgtc ttcatgggag aaaataatac tgttgatggg   5160
tgtctggtca gagacatcaa gaaataacgc cggaacatta gtgcaggcag cttccacagc   5220
aatggcatcc tggtcatcca gcggatagtt aatgatcagc ccactgacgc gttgcgcgag   5280
aagattgtgc accgccgctt tacaggcttc gacgccgctt cgttctacca tcgacaccac   5340
```

cacgctggca cccagttgat cggcgcgaga tttaatcgcc gcgacaattt gcgacggcgc 5400
gtgcagggcc agactggagg tggcaacgcc aatcagcaac gactgtttgc ccgccagttg 5460
ttgtgccacg cggttgggaa tgtaattcag ctccgccatc gccgcttcca ctttttcccg 5520
cgttttcgca gaaacgtggc tggcctggtt caccacgcgg gaaacggtct gataagagac 5580
accggcatac tctgcgacat cgtataacgt tactggtttc acattcacca ccctgaattg 5640
actctcttcc gggcgctatc atgccatacc gcgaaaggtt ttgcgccatt cgatggtgtc 5700
cgggatctcg acgctctccc ttatgcgact cctgcattag gaagcagccc agtagtaggt 5760
tgaggccgtt gagcaccgcc gccgcaagga atggtgcatg caaggagatg gcgcccaaca 5820
gtcccccggc cacggggcct gccaccatac ccacgccgaa acaagcgctc atgagcccga 5880
agtggcgagc ccgatcttcc ccatcggtga tgtcggcgat ataggcgcca gcaaccgcac 5940
ctgtggcgcc ggtgatgccg gccacgatgc gtccggcgta gaggatcg 5988

<210> SEQ ID NO 13
<211> LENGTH: 7687
<212> TYPE: DNA
<213> ORGANISM: Escherichia coli

<400> SEQUENCE: 13
cgctgacgtc ggtaccctcg agtctggtaa agaaaccgct gctgcgaaat ttgaacgcca 60
gcacatggac tcgtctacta gcgcagctta attaacctag gctgctgcca ccgctgagca 120
ataactagca taaccccttg gggcctctaa acgggtcttg aggggttttt tgctgaaacc 180
tcaggcattt gagaagcaca cggtcacact gcttccggta gtcaataaac cggtaaacca 240
gcaatagaca taagcggcta tttaacgacc ctgccctgaa ccgacgaccg ggtcgaattt 300
gctttcgaat ttctgccatt catccgctta ttatcactta ttcaggcgta gcaccaggcg 360
tttaagggca ccaataactg ccttaaaaaa attacgcccc gccctgccac tcatcgcagt 420
actgttgtaa ttcattaagc attctgccga catggaagcc atcacagacg gcatgatgaa 480
cctgaatcgc cagcggcatc agcaccttgt cgccttgcgt ataatatttg cccatagtga 540
aaacgggggc gaagaagttg tccatattgg ccacgtttaa atcaaaactg gtgaaactca 600
cccagggatt ggctgagacg aaaaacatat tctcaataaa ccctttaggg aaataggcca 660
ggttttcacc gtaacacgcc acatcttgcg aatatatgtg tagaaactgc cggaaatcgt 720
cgtggtattc actccagagc gatgaaaacg tttcagtttg ctcatggaaa acggtgtaac 780
aagggtgaac actatcccat atcaccagct caccgtcttt cattgccata cggaactccg 840
gatgagcatt catcaggcgg gcaagaatgt gaataaaggc cggataaaac ttgtgcttat 900
ttttctttac ggtctttaaa aaggccgtaa tatccagctg aacggtctgg ttataggtac 960
attgagcaac tgactgaaat gcctcaaaat gttctttacg atgccattgg gatatatcaa 1020
cggtggtata tccagtgatt tttttctcca ttttagcttc cttagctcct gaaaatctcg 1080
ataactcaaa aaatacgccc ggtagtgatc ttatttcatt atggtgaaag ttggaacctc 1140
ttacgtgccg atcaacgtct cattttcgcc aaaagttggc ccagggcttc ccggtatcaa 1200
cagggacacc aggatttatt tattctgcga agtgatcttc cgtcacaggt atttattcgg 1260
cgcaaagtgc gtcgggtgat gctgccaact tactgattta gtgtatgatg gtgtttttga 1320
ggtgctccag tggcttctgt ttctatcagc tgtccctcct gttcagctac tgacggggtg 1380
gtgcgtaacg gcaaaagcac cgccggacat cagcgctagc ggagtgtata ctggcttact 1440

-continued

```
atgttggcac tgatgagggt gtcagtgaag tgcttcatgt ggcaggagaa aaaaggctgc   1500
accggtgcgt cagcagaata tgtgatacag gatatattcc gcttcctcgc tcactgactc   1560
gctacgctcg gtcgttcgac tgcggcgagc ggaaatggct tacgaacggg gcggagattt   1620
cctggaagat gccaggaaga tacttaacag ggaagtgaga gggccgcggc aaagccgttt   1680
ttccataggc tccgcccccc tgacaagcat cacgaaatct gacgctcaaa tcagtggtgg   1740
cgaaacccga caggactata aagataccag gcgtttcccc tggcggctcc ctcgtgcgct   1800
ctcctgttcc tgcctttcgg tttaccggtg tcattccgct gttatggccg cgtttgtctc   1860
attccacgcc tgacactcag ttccgggtag gcagttcgct ccaagctgga ctgtatgcac   1920
gaaccccccg ttcagtccga ccgctgcgcc ttatccggta actatcgtct tgagtccaac   1980
ccggaaagac atgcaaaagc accactggca gcagccactg gtaattgatt tagaggagtt   2040
agtcttgaag tcatgcgccg gttaaggcta aactgaaagg acaagttttg gtgactgcgc   2100
tcctccaagc cagttacctc ggttcaaaga gttggtagct cagagaacct tcgaaaaacc   2160
gccctgcaag gcggtttttt cgttttcaga gcaagagatt acgcgcagac caaaacgatc   2220
tcaagaagat catcttatta atcagataaa atatttctag atttcagtgc aatttatctc   2280
ttcaaatgta gcacctgaag tcagccccat acgatataag ttgtaattct catgttagtc   2340
atgccccgcg cccaccggaa ggagctgact gggttgaagg ctctcaaggg catcggtcga   2400
gatcccggtg cctaatgagt gagctaactt acattaattg cgttgcgctc actgcccgct   2460
ttccagtcgg gaaacctgtc gtgccagctg cattaatgaa tcggccaacg cgcggggaga   2520
ggcggtttgc gtattgggcg ccagggtggt ttttcttttc accagtgaga cgggcaacag   2580
ctgattgccc ttcaccgcct ggccctgaga gagttgcagc aagcggtcca cgctggtttg   2640
ccccagcagg cgaaaatcct gtttgatggt ggttaacggc gggatataac atgagctgtc   2700
ttcggtatcg tcgtatccca ctaccgagat gtccgcacca acgcgcagcc cggactcggt   2760
aatggcgcgc attgcgccca gcgccatctg atcgttggca accagcatcg cagtgggaac   2820
gatgccctca ttcagcattt gcatggtttg ttgaaaaccg gacatggcac tccagtcgcc   2880
ttcccgttcc gctatcggct gaatttgatt gcgagtgaga tatttatgcc agccagccag   2940
acgcagacgc gccgagacag aacttaatgg gcccgctaac agcgcgattt gctggtgacc   3000
caatgcgacc agatgctcca cgcccagtcg cgtaccgtct tcatgggaga aaataatact   3060
gttgatgggt gtctggtcag agacatcaag aaataacgcc ggaacattag tgcaggcagc   3120
ttccacagca atggcatcct ggtcatccag cggatagtta atgatcagcc cactgacgcg   3180
ttgcgcgaga agattgtgca ccgccgcttt acaggcttcg acgccgcttc gttctaccat   3240
cgacaccacc acgctggcac ccagttgatc ggcgcgagat ttaatcgccg cgacaatttg   3300
cgacggcgcg tgcagggcca gactggaggt ggcaacgcca atcagcaacg actgtttgcc   3360
cgccagttgt tgtgccacgc ggttgggaat gtaattcagc tccgccatcg ccgcttccac   3420
tttttcccgc gttttcgcag aaacgtggct ggcctggttc accacgcggg aaacggtctg   3480
ataagagaca ccggcatact ctgcgacatc gtataacgtt actggtttca cattcaccac   3540
cctgaattga ctctcttccg ggcgctatca tgccataccg cgaaaggttt tgcgccattc   3600
gatggtgtcc gggatctcga cgctctccct tatgcgactc ctgcattagg aaattaatac   3660
gactcactat aggggaattg tgagcggata acaattcccc tgtagaaata attttgttta   3720
actttaataa ggagatatac catgacggat gtccgctttc gtatcattgg cacgggcgct   3780
tacgtcccgg aacgcattgt cagcaacgac gaagtcggcg caccggctgg tgtggatgac   3840
```

-continued

```
gattggatta cgcgtaaaac cggtatccgc cagcgtcgct gggcggccga cgatcaagca   3900
acgagcgatc tggctaccgc agctggtcgt gcagcactga aagcagctgg cattacgccg   3960
gaacagctga ccgtcatcgc agtggctacc tctacgccgg accgtccgca gccgccgacc   4020
gcggcctatg ttcaacatca cctgggtgca accggcacgg cagcttttga tgttaacgct   4080
gtgtgcagcg gtacggtttt cgcgctgagc tctgttgccg gcaccctggt ctatcgtggc   4140
ggttacgcac tggtcattgg tgctgatctg tactcacgta tcctgaatcc ggcggaccgc   4200
aaaaccgtgg ttctgttcgg cgatggtgcg ggcgcgatgg tgctgggccc gaccagcacc   4260
ggcaccggtc cgattgtgcg tcgcgttgca ctgcatacgt ttggcggtct gaccgatctg   4320
atccgtgttc cggccggcgg ttcccgccag ccgctggaca ccgatggtct ggacgcaggc   4380
ctgcaatatt ttgcgatgga tggccgcgaa gtccgtcgct tcgtgaccga acatctgccg   4440
cagctgatta aaggttttct gcacgaagcg ggcgtggatg cggcggatat tagccatttc   4500
gtgccgcacc aagccaacgg tgtgatgctg gacgaagttt ttggcgaact gcatctgccg   4560
cgtgcaacca tgcaccgtac ggtggaaacc tacggtaata cgggcgcagc tagtattccg   4620
atcacgatgg atgcggccgt tcgtgcaggt tccttccgtc cgggcgaact ggttctgctg   4680
gcgggctttg gcggcggtat ggcggcttcg tttgctctga ttgaatggtg acctaatgca   4740
ggctgcaggc ggatacgagg aggaataaac catgaaaaag gtatgtgtta taggtgcagg   4800
tactatgggt tcaggaattg ctcaggcatt tgcagctaaa ggatttgaag tagtattaag   4860
agatattaaa gatgaatttg ttgatagagg attagatttt atcaataaaa atctttctaa   4920
attagttaaa aaaggaaaga tagaagaagc tactaaagtt gaaatcttaa ctagaatttc   4980
cggaacagtt gaccttaata tggcagctga ttgcgattta gttatagaag cagctgttga   5040
aagaatggat attaaaaagc agatttttgc tgacttagac aatatatgca agccagaaac   5100
aattcttgca tcaaatacat catcactttc aataacagaa gtggcatcag caactaaaag   5160
acctgataag gttataggta tgcatttctt taatccagct cctgttatga agcttgtaga   5220
ggtaataaga ggaatagcta catcacaaga aacttttgat gcagttaaag agacatctat   5280
agcaatagga aaagatcctg tagaagtagc agaagcacca ggatttgttg taaatagaat   5340
attaatacca atgattaatg aagcagttgg tatattagca gaaggaatag cttcagtaga   5400
agacatagat aaagctatga aacttggagc taatcaccca atgggaccat tagaattagg   5460
tgattttata ggtcttgata tatgtcttgc tataatggat gttttatact cagaaactgg   5520
agattctaag tatagaccac atacattact taagaagtat gtaagagcag gatggcttgg   5580
aagaaaatca ggaaaaggtt tctacgatta ttcaaaataa gtttacagga tctgcaggga   5640
ggaggaaatc atggagttga acaacgttat tctggagaaa gaaggcaagg tggcggttgt   5700
caccattaac cgtccaaagg ccctgaacgc tctgaactcg gataccctga aagagatgga   5760
ttacgttatt ggcgagattg agaatgacag cgaagtgctg gctgtgattc tgaccggtgc   5820
gggtgagaag agctttgtcg cgggtgcgga catcagcgag atgaaagaaa tgaacaccat   5880
cgaaggccgt aagttcggta ttctgggcaa caaggtgttt cgtcgtctgg aactgctgga   5940
gaaacctgtc attgctgccg tgaacggttt cgcgctgggc ggtggttgcg agatcgctat   6000
gagctgcgat attcgtatcg catcgtccaa cgcacgcttt ggtcaaccgg aggtcggtct   6060
gggtatcact ccgggtttcg gcggtacgca acgtctgagc cgcctggttg gcatgggcat   6120
ggcgaaacag ttgattttca cggcacagaa cattaaggcg gatgaggcgc tgcgtattgg   6180
```

```
tctggtgaat aaggtcgttg agccaagcga actgatgaat accgcgaaag aaattgcgaa   6240

caagatcgtt agcaatgccc cggtggccgt taagctgtcg aaacaggcaa tcaaccgtgg   6300

catgcagtgt gacatcgaca ccgccctggc gtttgagagc gaggcgtttg gtgagtgctt   6360

ctccaccgag gaccaaaagg atgcgatgac cgcgttcatt gagaaacgca agatcgaggg   6420

tttcaagaat cgttaataga ggaggatagg aggttttcat atgattgtga aaccgatggt   6480

ccgtaataat atctgtctga atgctcaccc gcagggctgt aaaaaaggcg tggaagatca   6540

aattgaatat accaaaaaac gtattacggc agaagtgaaa gccggcgcaa aagctccgaa   6600

aaacgtgctg gttctgggtt gcagcaatgg ctatggtctg gcttctcgca ttaccgcggc   6660

ctttggctac ggtgcagcta cgatcggcgt tagtttcgaa aaagcaggtt ccgaaaccaa   6720

atatggcacg ccgggttggt acaacaatct ggcttttgat gaagcggcca aacgtgaagg   6780

cctgtatagt gtcaccattg atggtgacgc gttctccgat gaaattaaag cacaggtgat   6840

cgaagaagcg aagaaaaaag gcattaaatt tgacctgatc gtttacagcc tggcatctcc   6900

ggtccgtacc gatccggaca cgggtatcat gcataaatct gtgctgaaac cgtttggcaa   6960

aaccttcacg ggtaaaaccg ttgatccgtt cacgggcgaa ctgaaagaaa ttagcgcgga   7020

accggccaac gatgaagaag cagctgcgac cgtcaaagtg atgggcggtg aagactggga   7080

acgttggatc aaacagctga gtaaagaagg cctgctggaa gaaggttgca ttaccctggc   7140

gtattcctac atcggcccgg aagcaaccca agctctgtat cgcaaaggca cgattggtaa   7200

agcgaaagaa catctggaag cgaccgccca ccgtctgaac aaagaaaatc cgtcaatccg   7260

cgccttcgtt tcggtcaata aaggtctggt tacccgtgca tcagctgtga ttccggttat   7320

cccgctgtac ctggcatcgc tgtttaaagt catgaaagaa aaaggcaacc atgaaggttg   7380

tattgaacag atcacccgcc tgtatgccga acgtctgtac cgcaaagatg gtacgattcc   7440

ggtggacgaa gaaaatcgta ttcgcatcga tgactgggaa ctggaagaag atgtccaaaa   7500

agccgtgagc gccctgatgg aaaaagttac cggcgaaaac gcggaatctc tgacggatct   7560

ggccggttat cgtcacgact ttctggcgag taatggtttt gatgttgaag gcattaacta   7620

cgaagctgaa gtggaacgct ttgatcgcat ttgatctaga atatcggccg gccacgcgat   7680

cgctgac                                                             7687
```

```
<210> SEQ ID NO 14
<211> LENGTH: 415
<212> TYPE: PRT
<213> ORGANISM: Escherichia coli

<400> SEQUENCE: 14

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
```

```
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Ile Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ala Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415


<210> SEQ ID NO 15
<211> LENGTH: 307
<212> TYPE: PRT
<213> ORGANISM: Escherichia coli

<400> SEQUENCE: 15

Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60
```

-continued

```
Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Glu Trp Arg
            180                 185                 190

Leu Ile Ser Gly Lys Thr Gln Asn Asp Arg Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300

Ser Glu Lys
305


<210> SEQ ID NO 16
<211> LENGTH: 477
<212> TYPE: PRT
<213> ORGANISM: Escherichia coli

<400> SEQUENCE: 16

Met Thr Gln Ser Arg Leu His Ala Ala Gln Asn Ala Leu Ala Lys Leu
1               5                   10                  15

His Glu Arg Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Glu Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125
```

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Val Ala Lys Asp Gly Arg
        275                 280                 285

Arg Ile Val Ile Gly Trp Met Asp Met Trp Glu Ser Pro Met Pro Ser
    290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Ile Ser Pro Arg Thr Ile Ser Asn Lys
            340                 345                 350

Tyr Val Leu Gln Glu Asn Ala Gln Ala Val Glu Ile Gln Leu Gln Trp
        355                 360                 365

Ala Leu Lys Asn Ser Asp Ala Glu His Tyr Gly Leu Gln Leu Gly Ala
    370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
                405                 410                 415

Pro Gln Gly Asp Met Leu Ala Leu Arg Ile Phe Ile Asp Thr Ser Ser
            420                 425                 430

Val Glu Val Phe Ile Asn Asp Gly Glu Ala Val Met Ser Ser Arg Ile
        435                 440                 445

Tyr Pro Gln Pro Glu Glu Arg Glu Leu Ser Leu Tyr Ala Ser His Gly
    450                 455                 460

Val Ala Val Leu Gln His Gly Ala Leu Trp Gln Leu Gly
465                 470                 475

<210> SEQ ID NO 17
<211> LENGTH: 8268
<212> TYPE: DNA
<213> ORGANISM: Escherichia coli

<400> SEQUENCE: 17
ccttgccagc ccgtggatat gtggacgatg gccgcgagcg gccaccggct ggctcgcttc 60
gctcggcccg tggacaaccc tgctggacaa gctgatggac aggctgcgcc tgcccacgag 120

-continued

```
cttgaccaca gggattgccc accggctacc cagccttcga ccacataccc accggctcca    180
actgcgcggc ctgcggcctt gccccatcaa ttttttaat tttctctggg gaaaagcctc    240
cggcctgcgg cctgcgcgct tcgcttgccg gttggacacc aagtggaagg cgggtcaagg    300
ctcgcgcagc gaccgcgcag cggcttggcc ttgacgcgcc tggaacgacc caagcctatg    360
cgagtggggg cagtcgaagg cgaagcccgc ccgcctgccc cccgagcctc acggcggcga    420
gtgcgggggt tccaaggggg cagcgccacc ttgggcaagg ccgaaggccg cgcagtcgat    480
caacaagccc cggaggggcc actttttgcc ggaggggggag ccgcgccgaa ggcgtggggg    540
aaccccgcag gggtgccctt ctttgggcac caaagaacta gatatagggc gaaatgcgaa    600
agacttaaaa atcaacaact taaaaaaggg gggtacgcaa cagctcattg cggcaccccc    660
cgcaatagct cattgcgtag gttaaagaaa atctgtaatt gactgccact tttacgcaac    720
gcataattgt tgtcgcgctg ccgaaaagtt gcagctgatt gcgcatggtg ccgcaaccgt    780
gcggcaccct accgcatgga gataagcatg gccacgcagt ccagagaaat cggcattcaa    840
gccaagaaca agcccggtca ctgggtgcaa acggaacgca aagcgcatga ggcgtgggcc    900
gggcttattg cgaggaaacc cacggcggca atgctgctgc atcacctcgt ggcgcagatg    960
ggccaccaga acgccgtggt ggtcagccag aagacacttt ccaagctcat cggacgttct   1020
ttgcggacgg tccaatacgc agtcaaggac ttggtggccg agcgctggat ctccgtcgtg   1080
aagctcaacg gccccggcac cgtgtcggcc tacgtggtca atgaccgcgt ggcgtggggc   1140
cagccccgcg accagttgcg cctgtcggtg ttcagtgccg ccgtggtggt tgatcacgac   1200
gaccaggacg aatcgctgtt ggggcatggc gacctgcgcc gcatcccgac cctgtatccg   1260
ggcgagcagc aactaccgac cggccccggc gaggagccgc ccagccagcc cggcattccg   1320
ggcatggaac cagacctgcc agccttgacc gaaacggagg aatgggaacg gcgcgggcag   1380
cagcgcctgc cgatgcccga tgagccgtgt tttctggacg atggcgagcc gttggagccg   1440
ccgacacggg tcacgctgcc gcgccggtag tacgtacccg gaattgccag ctggggcgcc   1500
ctctggtaag gttgggaagc cctgcaaagt aaactggatg gctttcttgc cgccaaggat   1560
ctgatggcgc aggggatcaa gctctgatca agagacagga tgaggatcgt ttcgatgaag   1620
cagcgtatta cagtgacagt tgacagcgac agctatcagt tgctcaaggc atatgatgtc   1680
aatatctccg gtctggtaag cacaaccatg cagaatgaag cccgtcgtct gcgtgccgaa   1740
cgctggaaag cggaaaatca ggaagggatg gctgaggtcg cccggtttat tgaaatgaac   1800
ggctcttttg ctgacgagaa cagggactgg tgaaatgcag tttaaggttt acacctataa   1860
aagagagagc cgttatcgtc tgtttgtgga tgtacagagc gatattattg acacgcccgg   1920
gcgacggatg gtgatccccc tggccagtgc acgtctgctg tcagataaag tctcccgtga   1980
actttacccg gtggtgcata tcggggatga aagctggcgc atgatgacca ccgatatggc   2040
cagtgtgccg gtctccgtta tcggggaaga agtggctgat ctcagccacc gcgaaaatga   2100
catcaaaaac gccattaacc tgatgttctg gggaatataa atcctagacg aattctctag   2160
tagaggttcc aactttcacc ataatgaaat aagatcacta ccgggcgtat tttttgagtt   2220
atcgagattt tcaggagcta aggaagctaa aatggagaaa aaaatcactg gatataccac   2280
cgttgatata tcccaatggc atcgtaaaga acattttgag gcatttcagt cagttgctca   2340
atgtacctat aaccagaccg ttcagctgga tattacggcc tttttaaaga ccgtaaagaa   2400
aaataagcac aagttttatc cggcctttat tcacattctt gcccgcctga tgaatgctca   2460
tccggaattc cgtatggcaa tgaaagacgg tgagctggtg atatgggata gtgttcaccc   2520
```

-continued

```
ttgttacacc gttttccatg agcaaactga aacgttttca tcgctctgga gtgaatacca   2580
cgacgatttc cggcagtttc tacacatata ttcgcaagat gtggcgtgtt acggtgaaaa   2640
cctggcctat ttccctaaag ggtttattga gaatatgttt ttcgtctcag ccaatccctg   2700
ggtgagtttc accagttttg atttaaacgt ggccaatatg gacaacttct tcgcccccgt   2760
tttcaccatg ggcaaatatt atacgcaagg cgacaaggtg ctgatgccgc tggcgattca   2820
ggttcatcat gccgtttgtg atggcttcca tgtcggcaga atgcttaatg aattacaaca   2880
gtactgcgat gagtggcagg gcggggcgta aaaaatccct tatgcgactc ctgcattagg   2940
aaattaatac gactcactat aggggaattg tgagcggata acaattcccc tgtagaaata   3000
attttgttta actttaataa ggagatatac catgacggat gtccgctttc gtatcattgg   3060
cacgggcgct tacgtcccgg aacgcattgt cagcaacgac gaagtcggcg caccggctgg   3120
tgtggatgac gattggatta cgcgtaaaac cggtatccgc cagcgtcgct gggcggccga   3180
cgatcaagca acgagcgatc tggctaccgc agctggtcgt gcagcactga aagcagctgg   3240
cattacgccg gaacagctga ccgtcatcgc agtggctacc tctacgccgg accgtccgca   3300
gccgccgacc gcggcctatg ttcaacatca cctgggtgca accggcacgg cagcttttga   3360
tgttaacgct gtgtgcagcg gtacggtttt cgcgctgagc tctgttgccg gcaccctggt   3420
ctatcgtggc ggttacgcac tggtcattgg tgctgatctg tactcacgta tcctgaatcc   3480
ggcggaccgc aaaaccgtgg ttctgttcgg cgatggtgcg ggcgcgatgg tgctgggccc   3540
gaccagcacc ggcaccggtc cgattgtgcg tcgcgttgca ctgcatacgt ttggcggtct   3600
gaccgatctg atccgtgttc cggccggcgg ttcccgccag ccgctggaca ccgatggtct   3660
ggacgcaggc ctgcaatatt ttgcgatgga tggccgcgaa gtccgtcgct tcgtgaccga   3720
acatctgccg cagctgatta aaggttttct gcacgaagcg ggcgtggatg cggcggatat   3780
tagccatttc gtgccgcacc aagccaacgg tgtgatgctg gacgaagttt ttggcgaact   3840
gcatctgccg cgtgcaacca tgcaccgtac ggtggaaacc tacggtaata cgggcgcagc   3900
tagtattccg atcacgatgg atgcggccgt tcgtgcaggt tccttccgtc cgggcgaact   3960
ggttctgctg gcgggctttg gcggcggtat ggcggcttcg tttgctctga ttgaatggtg   4020
acctaatgca ggctgcaggc ggatacgagg aggaataaac catgaaaaag gtatgtgtta   4080
taggtgcagg tactatgggt tcaggaattg ctcaggcatt tgcagctaaa ggatttgaag   4140
tagtattaag agatattaaa gatgaatttg ttgatagagg attagatttt atcaataaaa   4200
atctttctaa attagttaaa aaaggaaaga tagaagaagc tactaaagtt gaaatcttaa   4260
ctagaatttc cggaacagtt gaccttaata tggcagctga ttgcgattta gttatagaag   4320
cagctgttga aagaatggat attaaaaagc agatttttgc tgacttagac aatatatgca   4380
agccagaaac aattcttgca tcaaatacat catcactttc aataacagaa gtggcatcag   4440
caactaaaag acctgataag gttataggta tgcatttctt taatccagct cctgttatga   4500
agcttgtaga ggtaataaga ggaatagcta catcacaaga aacttttgat gcagttaaag   4560
agacatctat agcaatagga aaagatcctg tagaagtagc agaagcacca ggatttgttg   4620
taaatagaat attaatacca atgattaatg aagcagttgg tatattagca gaaggaatag   4680
cttcagtaga agacatagat aaagctatga aacttggagc taatcaccca atgggaccat   4740
tagaattagg tgattttata ggtcttgata tatgtcttgc tataatggat gttttatact   4800
cagaaactgg agattctaag tatagaccac atacattact taagaagtat gtaagagcag   4860
```

-continued

```
gatggcttgg aagaaaatca ggaaaaggtt tctacgatta ttcaaaataa gtttacagga   4920
tctgcaggga ggaggaaatc atggagttga acaacgttat tctggagaaa gaaggcaagg   4980
tggcggttgt caccattaac cgtccaaagg ccctgaacgc tctgaactcg gataccctga   5040
aagagatgga ttacgttatt ggcgagattg agaatgacag cgaagtgctg gctgtgattc   5100
tgaccggtgc gggtgagaag agctttgtcg cgggtgcgga catcagcgag atgaaagaaa   5160
tgaacaccat cgaaggccgt aagttcggta ttctgggcaa caaggtgttt cgtcgtctgg   5220
aactgctgga gaaacctgtc attgctgccg tgaacggttt cgcgctgggc ggtggttgcg   5280
agatcgctat gagctgcgat attcgtatcg catcgtccaa cgcacgcttt ggtcaaccgg   5340
aggtcggtct gggtatcact ccgggtttcg gcggtacgca acgtctgagc cgcctggttg   5400
gcatgggcat ggcgaaacag ttgattttca cggcacagaa cattaaggcg gatgaggcgc   5460
tgcgtattgg tctggtgaat aaggtcgttg agccaagcga actgatgaat accgcgaaag   5520
aaattgcgaa caagatcgtt agcaatgccc cggtggccgt taagctgtcg aaacaggcaa   5580
tcaaccgtgg catgcagtgt gacatcgaca ccgccctggc gtttgagagc gaggcgtttg   5640
gtgagtgctt ctccaccgag gaccaaaagg atgcgatgac cgcgttcatt gagaaacgca   5700
agatcgaggg tttcaagaat cgttaataga ggaggatagg aggttttcat atgattgtga   5760
aaccgatggt ccgtaataat atctgtctga atgctcaccc gcagggctgt aaaaaaggcg   5820
tggaagatca aattgaatat accaaaaaac gtattacggc agaagtgaaa gccggcgcaa   5880
aagctccgaa aaacgtgctg gttctgggtt gcagcaatgg ctatggtctg gcttctcgca   5940
ttaccgcggc ctttggctac ggtgcagcta cgatcggcgt tagtttcgaa aaagcaggtt   6000
ccgaaaccaa atatggcacg ccgggttggt acaacaatct ggcttttgat gaagcggcca   6060
aacgtgaagg cctgtatagt gtcaccattg atggtgacgc gttctccgat gaaattaaag   6120
cacaggtgat cgaagaagcg aagaaaaaag gcattaaatt tgacctgatc gtttacagcc   6180
tggcatctcc ggtccgtacc gatccggaca cgggtatcat gcataaatct gtgctgaaac   6240
cgtttggcaa aaccttcacg ggtaaaaccg ttgatccgtt cacgggcgaa ctgaaagaaa   6300
ttagcgcgga accggccaac gatgaagaag cagctgcgac cgtcaaagtg atgggcggtg   6360
aagactggga acgttggatc aaacagctga gtaaagaagg cctgctggaa gaaggttgca   6420
ttaccctggc gtattcctac atcggcccgg aagcaaccca agctctgtat cgcaaaggca   6480
cgattggtaa agcgaaagaa catctggaag cgaccgccca ccgtctgaac aaagaaaatc   6540
cgtcaatccg cgccttcgtt tcggtcaata aaggtctggt tacccgtgca tcagctgtga   6600
ttccggttat cccgctgtac ctggcatcgc tgtttaaagt catgaaagaa aaaggcaacc   6660
atgaaggttg tattgaacag atcacccgcc tgtatgccga acgtctgtac cgcaaagatg   6720
gtacgattcc ggtggacgaa gaaaatcgta ttcgcatcga tgactgggaa ctggaagaag   6780
atgtccaaaa agccgtgagc gccctgatgg aaaaagttac cggcgaaaac gcggaatctc   6840
tgacggatct ggccggttat cgtcacgact ttctggcgag taatggtttt gatgttgaag   6900
gcattaacta cgaagctgaa gtggaacgct ttgatcgcat ttgatctaga gaattcgtca   6960
acgaattcaa gcttgatatc attcaggacg agcctcagac tccagcgtaa ctggactgaa   7020
aacaaactaa agcgcccttg tggcgcttta gttttgttcc gctcatgata ataatggttt   7080
cttagacgtc aggtggcact tttcggggaa atgtgcgcgc ccgcgttcct gctggcgctg   7140
ggcctgtttc tggcgctgga cttcccgctg ttccgtcagc agcttttcgc ccacggcctt   7200
gatgatcgcg gcggccttgg cctgcatatc ccgattcaac ggccccaggg cgtccagaac   7260
```

```
gggcttcagg cgctcccgaa ggtctcgggc cgtctcttgg gcttgatcgg ccttcttgcg   7320

catctcacgc gctcctgcgg cggcctgtag ggcaggctca tacccctgcc gaaccgcttt   7380

tgtcagccgg tcggccacgg cttccggcgt ctcaacgcgc tttgagattc ccagcttttc   7440

ggccaatccc tgcggtgcat aggcgcgtgg ctcgaccgct tgcgggctga tggtgacgtg   7500

gcccactggt ggccgctcca gggcctcgta gaacgcctga atgcgcgtgt gacgtgcctt   7560

gctgccctcg atgccccgtt gcagccctag atcggccaca gcggccgcaa acgtggtctg   7620

gtcgcgggtc atctgcgctt tgttgccgat gaactccttg gccgacagcc tgccgtcctg   7680

cgtcagcggc accacgaacg cggtcatgtg cgggctggtt tcgtcacggt ggatgctggc   7740

cgtcacgatg cgatccgccc cgtacttgtc cgccagccac ttgtgcgcct tctcgaagaa   7800

cgccgcctgc tgttcttggc tggccgactt ccaccattcc gggctggccg tcatgacgta   7860

ctcgaccgcc aacacagcgt ccttgcgccg cttctctggc agcaactcgc gcagtcggcc   7920

catcgcttca tcggtgctgc tggccgccca gtgctcgttc tctggcgtcc tgctggcgtc   7980

agcgttgggc gtctcgcgct cgcggtaggc gtgcttgaga ctggccgcca cgttgcccat   8040

tttcgccagc ttcttgcatc gcatgatcgc gtatgccgcc atgcctgccc ctcccttttg   8100

gtgtccaacc ggctcgacgg gggcagcgca aggcggtgcc tccggcgggc cactcaatgc   8160

ttgagtatac tcactagact ttgcttcgca aagtcgtgac cgcctacggc ggctgcggcg   8220

ccctacgggc ttgctctccg ggcttcgccc tgcgcggtcg ctgcgctc                8268
```

<210> SEQ ID NO 18
<211> LENGTH: 5385
<212> TYPE: DNA
<213> ORGANISM: Escherichia coli

<400> SEQUENCE: 18

```
gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gtttttttgcg ccgacatcat aacggttctg gcaaatattc   180

tgaaatgagc tgttgacaat taatcatccg gctcgtataa tgtgtggaat tgtgagcgga    240

taacaatttc acacaggaaa cagcgccgct gagaaaaagc gaagcggcac tgctctttaa    300

caatttatca gacaatctgt gtgggcactc gaccggaatt atcgattaac tttattatta    360

aaaattaaag aggtatatat taatgtatcg attaaataag gaggaataaa ccatgaccac    420

tctgtgccgc cctagcgtta gcgtcccgga acacgtgatt accatggagg aaacgctgga    480

actggcgcgt cgtcgtcata cggatcatcc gcagctgccg ctggctttgc gtctgatcga    540

gaataccggc gtgcgcactc gtcacattgt tcagccaatt gaggacacgc tggagcatcc    600

gggtttcgag gaccgcaaca aagtctatga acgtgaagcc aagagccgcg ttccggctgt    660

gatccagcgt gccctggacg atgcagaact gctggctacg gatattgatg ttatcatcta    720

cgtgagctgc acgggtttta tgatgccgag cctgaccgcg tggttgatta acgagatggg    780

tttcgactcc accacccgtc aaatcccgat tgcgcagctg ggttgtgcag cgggtggtgc    840

ggcgatcaac cgtgcccatg atttttgcac cgcgtacccg gaagccaatg cactgatcgt    900

cgcttgcgaa ttctgtagcc tgtgctatca gccgaccgac ttgggtgtgg gtagcttgct    960

gtgcaacggt ctgttcggcg atggcattgc agcggccgtg gttcgcggtc gtggtggcac   1020

cggtgttcgc ctggaacgta atggttctta cctgattccg aaaaccgaag attggattat   1080
```

-continued

```
gtatgatgtg aaggcgacgg gtttccattt tctgctggac aagcgtgtcc cggcgaccat   1140
ggaaccgttg gctccggcac tgaaagagct ggctggtgag cacggctggg acgccagcga   1200
tctggacttc tacattgtgc acgcgggtgg tccgcgtatt ctggatgacc tgagcacctt   1260
tctggaagtc gaccctcacg cattccgctt ttcccgtgca acgctgacgg agtacggcaa   1320
tatcgcaagc gcggttgttt tggacgcact gcgtcgtctg ttcgacgagg gtggtgttga   1380
ggaaggcgca cgcggcttgc tggcgggttt tggtccgggt attactgcag aaatgagcct   1440
gggttgttgg cagaccgccg atgttcgtcg cggcatccgc caagatgtga cccgcacggc   1500
ggcacgtggc gttagccgcc gtgtgcgtca agcttggctg ttttggcgga tgagagaaga   1560
ttttcagcct gatacagatt aaatcagaac gcagaagcgg tctgataaaa cagaatttgc   1620
ctggcggcag tagcgcggtg gtcccacctg accccatgcc gaactcagaa gtgaaacgcc   1680
gtagcgccga tggtagtgtg gggtctcccc atgcgagagt agggaactgc caggcatcaa   1740
ataaaacgaa aggctcagtc gaaagactgg gcctttcgtt ttatctgttg tttgtcggtg   1800
aacgctctcc tgagtaggac aaatccgccg ggagcggatt tgaacgttgc gaagcaacgg   1860
cccggagggt ggcgggcagg acgcccgcca taaactgcca ggcatcaaat taagcagaag   1920
gccatcctga cggatggcct ttttgcgttt ctacaaactc tttttgttta tttttctaaa   1980
tacattcaaa tatgtatccg ctcatgagac aataaccctg ataaatgctt caataatatt   2040
gaaaaaggaa gagtatgagt attcaacatt tccgtgtcgc ccttattccc ttttttgcgg   2100
cattttgcct tcctgttttt gctcacccag aaacgctggt gaaagtaaaa gatgctgaag   2160
atcagttggg tgcacgagtg ggttacatcg aactggatct caacagcggt aagatccttg   2220
agagttttcg ccccgaagaa cgttttccaa tgatgagcac ttttaaagtt ctgctatgtg   2280
gcgcggtatt atcccgtgtt gacgccgggc aagagcaact cggtcgccgc atacactatt   2340
ctcagaatga cttggttgag tactcaccag tcacagaaaa gcatcttacg gatggcatga   2400
cagtaagaga attatgcagt gctgccataa ccatgagtga taacactgcg gccaacttac   2460
ttctgacaac gatcggagga ccgaaggagc taaccgcttt tttgcacaac atgggggatc   2520
atgtaactcg ccttgatcgt tgggaaccgg agctgaatga agccatacca aacgacgagc   2580
gtgacaccac gatgcctgta gcaatggcaa caacgttgcg caaactatta actggcgaac   2640
tacttactct agcttcccgg caacaattaa tagactggat ggaggcggat aaagttgcag   2700
gaccacttct gcgctcggcc cttccggctg gctggtttat tgctgataaa tctggagccg   2760
gtgagcgtgg gtctcgcggt atcattgcag cactggggcc agatggtaag ccctcccgta   2820
tcgtagttat ctacacgacg gggagtcagg caactatgga tgaacgaaat agacagatcg   2880
ctgagatagg tgcctcactg attaagcatt ggtaactgtc agaccaagtt tactcatata   2940
tactttagat tgatttaaaa cttcattttt aatttaaaag gatctaggtg aagatccttt   3000
ttgataatct catgaccaaa atcccttaac gtgagttttc gttccactga gcgtcagacc   3060
ccgtagaaaa gatcaaagga tcttcttgag atcctttttt tctgcgcgta atctgctgct   3120
tgcaaacaaa aaaaccaccg ctaccagcgg tggtttgttt gccggatcaa gagctaccaa   3180
ctctttttcc gaaggtaact ggcttcagca gagcgcagat accaaatact gtccttctag   3240
tgtagccgta gttaggccac cacttcaaga actctgtagc accgcctaca tacctcgctc   3300
tgctaatcct gttaccagtg gctgctgcca gtggcgataa gtcgtgtctt accgggttgg   3360
actcaagacg atagttaccg gataaggcgc agcggtcggg ctgaacgggg ggttcgtgca   3420
cacagcccag cttggagcga acgacctaca ccgaactgag atacctacag cgtgagctat   3480
```

-continued gagaaagcgc cacgcttccc gaagggagaa aggcggacag gtatccggta agcggcaggg 3540
tcggaacagg agagcgcacg agggagcttc caggggggaaa cgcctggtat ctttatagtc 3600
ctgtcgggtt tcgccacctc tgacttgagc gtcgattttt gtgatgctcg tcaggggggc 3660
ggagcctatg gaaaaacgcc agcaacgcgg cctttttacg gttcctggcc ttttgctggc 3720
cttttgctca catgttcttt cctgcgttat cccctgattc tgtggataac cgtattaccg 3780
cctttgagtg agctgatacc gctcgccgca gccgaacgac cgagcgcagc gagtcagtga 3840
gcgaggaagc ggaagagcgc ctgatgcggt attttctcct tacgcatctg tgcggtattt 3900
cacaccgcat atggtgcact ctcagtacaa tctgctctga tgccgcatag ttaagccagt 3960
atacactccg ctatcgctac gtgactgggt catggctgcg ccccgacacc cgccaacacc 4020
cgctgacgcg ccctgacggg cttgtctgct cccggcatcc gcttacagac aagctgtgac 4080
cgtctccggg agctgcatgt gtcagaggtt ttcaccgtca tcaccgaaac gcgcgaggca 4140
gcagatcaat tcgcgcgcga aggcgaagcg gcatgcattt acgttgacac catcgaatgg 4200
tgcaaaacct ttcgcggtat ggcatgatag cgcccggaag agagtcaatt cagggtggtg 4260
aatgtgaaac cagtaacgtt atacgatgtc gcagagtatg ccggtgtctc ttatcagacc 4320
gtttcccgcg tggtgaacca ggccagccac gtttctgcga aaacgcggga aaaagtggaa 4380
gcggcgatgg cggagctgaa ttacattccc aaccgcgtgg cacaacaact ggcgggcaaa 4440
cagtcgttgc tgattggcgt tgccacctcc agtctggccc tgcacgcgcc gtcgcaaatt 4500
gtcgcggcga ttaaatctcg cgccgatcaa ctgggtgcca gcgtggtggt gtcgatggta 4560
gaacgaagcg gcgtcgaagc ctgtaaagcg gcggtgcaca atcttctcgc gcaacgcgtc 4620
agtgggctga tcattaacta tccgctggat gaccaggatg ccattgctgt ggaagctgcc 4680
tgcactaatg ttccggcgtt atttcttgat gtctctgacc agacacccat caacagtatt 4740
attttctccc atgaagacgg tacgcgactg ggcgtggagc atctggtcgc attgggtcac 4800
cagcaaatcg cgctgttagc gggcccatta agttctgtct cggcgcgtct gcgtctggct 4860
ggctggcata aatatctcac tcgcaatcaa attcagccga tagcggaacg ggaaggcgac 4920
tggagtgcca tgtccggttt tcaacaaacc atgcaaatgc tgaatgaggg catcgttccc 4980
actgcgatgc tggttgccaa cgatcagatg gcgctgggcg caatgcgcgc cattaccgag 5040
tccgggctgc gcgttggtgc ggatatctcg gtagtgggat acgacgatac cgaagacagc 5100
tcatgttata tcccgccgtc aaccaccatc aaacaggatt ttcgcctgct ggggcaaacc 5160
agcgtggacc gcttgctgca actctctcag ggccaggcgg tgaagggcaa tcagctgttg 5220
cccgtctcac tggtgaaaag aaaaaccacc ctggcgccca atacgcaaac cgcctctccc 5280
cgcgcgttgg ccgattcatt aatgcagctg gcacgacagg tttcccgact ggaaagcggg 5340
cagtgagcgc aacgcaatta atgtgagtta gcgcgaattg atctg 5385

<210> SEQ ID NO 19
<211> LENGTH: 286
<212> TYPE: PRT
<213> ORGANISM: Escherichia coli

<400> SEQUENCE: 19

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

-continued

```
Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285
```

MICROORGANISMS AND METHODS FOR THE PRODUCTION OF FATTY ACIDS AND FATTY ACID DERIVED PRODUCTS

CROSS-REFERENCE TO RELATED APPLICATIONS

This application is a continuation of and claims the benefit of priority to U.S. patent application Ser. No. 13/963,858, filed Aug. 9, 2013 and to provisional applications: U.S. Application No. 61/682,127 filed on Aug. 10, 2012 and U.S. Application No. 61/682,138 filed on Aug. 10, 2012, the benefit of priority of each of which is claimed hereby, and each of which are incorporated by reference herein in its entirety.

STATEMENT AS TO FEDERALLY SPONSORED RESEARCH

This invention was made with Government support under DE-AR0000088 awarded by the United States Department of Energy. The Government has certain rights in this invention.

SEQUENCE LISTING

This document incorporates by reference herein an electronic sequence listing text file, which is filed in electronic format via EFS-Web. The text file is named "1561487.TXT," is 143,360 bytes, and was created on Mar. 29, 2016.

FIELD OF THE INVENTION

This invention relates to metabolically engineered microorganisms, such as bacterial strains, in which there is an increased utilization of malonyl-CoA for production of a fatty acid or fatty acid derived product, through a malonyl-CoA dependent, but malonyl-ACP independent metabolic pathway. These products may include aldehydes, alcohols, alkanes, alkenes, and diacids and further downstream products made from such chemical products. Also, genetic modifications may be made to provide one or more chemical products.

INCORPORATION BY REFERENCE

All applications, patents, and publications listed herein are hereby incorporated by reference in their entirety and for all purposes.

BACKGROUND OF THE INVENTION

With increasing acceptance that petroleum hydrocarbon supplies are decreasing and their costs are ultimately increasing, interest has increased for developing and improving industrial microbial systems for production of chemicals and fuels. Such industrial microbial systems could completely or partially replace the use of petroleum hydrocarbons for production of certain chemicals.

Numerous chemicals are produced through such means, ranging from antibiotic and anti-malarial pharmaceutical products to fine chemicals to fuels such as ethanol. However, there is still a commercial need in modified microorganisms that are adapted to produce a chemical product having malonyl-CoA as a substrate in the microbial production pathway of that chemical product, such as but not limited to various fatty acids and fatty acid derived products.

SUMMARY OF THE INVENTION

According to one embodiment, the invention is directed to a method for producing a fatty acid or fatty acid derived product including but not limited to a fatty acid, an alcohol, aldehyde, alkane, alkene or diacid, said method comprising i) combining a carbon source and a microorganism cell culture to produce such fatty acid or fatty acid derived product, wherein a) said cell culture comprises an inhibitor of fatty acid synthase or said microorganism is genetically modified for reduced enzymatic activity in the microorganism's fatty acid synthase pathway; or b) wherein said microorganism is genetically modified for increased enzymatic activity in the microorganism's malonyl-CoA dependent, malonyl-ACP independent, fatty acyl-CoA metabolic pathway ("MDMIFAA") This pathway is also referred to herein as malonyl-CoA dependent, but malonyl-ACP independent, fatty acyl-CoA metabolic pathway. Such increase in the microorganism's malonyl-CoA dependent, malonyl-ACP independent fatty acyl-CoA metabolic pathway can be achieved by an increased activity or expression of a gene or a pathway comprising an acetoacetyl-CoA synthase, a ketoacyl-CoA synthase (or elongase), an enoyl-CoA reductase, a ketoacyl-CoA reductase and/or a 3-hydroxyacyl-CoA dehydratase in combination with a decrease in expression or activity of acetoacetyl-CoA thiolase. Alternatively, increased activity in the microorganism's malonyl-CoA dependent, malonyl-ACP independent fatty acyl-CoA metabolic pathway can be achieved by an increased expression of a gene or a pathway comprising an acetoacetyl-CoA synthase, a ketoacyl-CoA thiolase, a enoyl-CoA reductase, a ketoacyl-CoA reductase and/or a 3-hydroxyacyl-CoA dehydratase in combination with a decrease in expression or activity of acetoacetyl-CoA thiolase. In various aspects, the carbon source provided to the micro-organism has a ratio of carbon-14 to carbon-12 of about $1.0\times10^{-14}$ or greater.

The carbon source according to the invention may be predominantly glucose, sucrose, fructose, dextrose, lactose, xylose, other cellulosic sugars or a combination thereof. Alternatively, the carbon source is glycerol.

In various embodiments, the increase in production of the fatty acid or fatty acid derived product is at least 20 percent, at least 50 percent, at least 75 percent, at least 100 percent, or at least 150 percent above the production of the product in a microorganism that does not comprise the genetic modifications and/or culture system features of the invention.

In certain embodiments, the cell culture comprises an inhibitor of fatty acid synthase or the microorganism is genetically modified for reduced enzymatic activity in the microorganism's fatty acid synthase pathway. For example, the inhibitor of a fatty acid synthase may be selected from the group consisting of thiolactomycin, triclosan, cerulenin, thienodiazaborine, isoniazid, and analogs thereof. Included within the invention are embodiments where the cell culture comprises a genetically modified microorganism. The genetically modified microorganism can be modified for a trait selected from reduced enzymatic activity in the microorganism's fatty acid synthase pathway, increased enzymatic activity in one or more enzymes of the malonyl-CoA dependent, malonyl-ACP independent fatty acyl-CoA metabolic pathway, increased enzymatic activity in the microorganism's fatty acyl-CoA thioesterase activity, increased enzymatic activity in the microorganism's acetoacetyl-CoA synthase activity, decreased enzymatic activity in the microorganism's acetoacetyl-CoA thiolase activity, increased enzymatic activity in the microorganism's acetyl-CoA carboxylase pathway, and combinations thereof. For example, the genetically modified microorganism can be modified for reduced enzymatic activity in the microorganism's fatty acid synthase pathway. Alternatively, the reduced enzymatic activity is a reduction in enzymatic activity in an enzyme selected from the group consisting of beta-ketoacyl-ACP reductase, 3-hydroxyacyl-ACP dehydratase, or enoyl-ACP reductase. In various aspects, the reduced enzymatic activity in the microorganism's fatty acid synthase pathway occurs via introduction of a heterologous nucleic acid sequence coding for an inducible promoter operably linked to a sequence coding for a enzyme in the fatty acid synthase pathway or homolog thereof, or a heterologous nucleic acid sequence coding for an enzyme in the fatty acid synthase pathway or homolog thereof with reduced activity. In various aspects, the enzyme in the fatty acid synthase pathway or homolog thereof is a polypeptide with temperature-sensitive beta-ketoacyl-ACP or temperature-sensitive enoyl-ACP reductase activity. In *E. coli*, these temperature-sensitive mutant genes could include $fabI^{ts}$(S241F), $fabB^{ts}$(A329V) or $fabD^{ts}$(W257Q).

In various embodiments, the increased enzymatic activity in the microorganism's malonyl-CoA dependent, but malonyl-ACP independent fatty acyl-CoA metabolic pathway may occur via increased expression of feedback resistant enzymes including pantothenate kinase or pyruvate dehydrogenase. In *E. coli*, these feedback resistant mutant genes could include coaA(R106A) and lpd(E354K) respectively.

In various embodiments, the increased enzymatic activity in the microorganism's malonyl-CoA dependent, malonyl-ACP independent fatty acyl-CoA metabolic pathway may occur via increased expression of a pathway comprising an acetoacetyl-CoA synthase, a ketoacyl-CoA thiolase, a enoyl-CoA reductase, a ketoacyl-CoA reductase and a 3-hydroxyacyl-CoA dehydratase. The enoyl-CoA reductase can either utilize the cofactor NADH or NADPH or alternatively both NADPH and NADH. In addition, the ketoacyl-CoA reductase can either utilize the cofactor NADH or NADPH or alternatively both NADPH and NADH.

In various embodiments, the increased enzymatic activity in the microorganism's malonyl-CoA dependent, but malonyl-ACP independent fatty acyl-CoA metabolic pathway may occur via increased expression of a pathway comprising an acetoacetyl-CoA synthase, a ketoacyl-CoA synthase (or elongase), an enoyl-CoA reductase, a ketoacyl-CoA reductase and a 3-hydroxyacyl-CoA dehydratase. The enoyl-CoA reductase can either utilize the cofactor NADH or NADPH or alternatively both NADPH and NADH. In addition, the ketoacyl-CoA reductase can either utilize the cofactor NADH or NADPH or alternatively both NADPH and NADH.

In various embodiments, the increased production of fatty acid or fatty acid derived products through the microorganism's malonyl-CoA dependent, but malonyl-ACP independent fatty acyl-CoA metabolic pathway can occur through reduction in the acetoacetyl-CoA thiolase activity, either via gene deletion, disruption or genetic mutation.

In various embodiments, the increased production of fatty acid or fatty acid derived products through the microorganism's malonyl-CoA dependent, but malonyl-ACP independent fatty acyl-CoA metabolic pathway can occur through reduction in trigger factor activity or in the activity of a molecular chaperone involved in cell division, either via gene deletion, disruption or genetic mutation of an microorganisms tig gene.

Increased enzymatic activity in the microorganism's NADPH-dependent transhydrogenase pathway may occur by introduction of a heterologous nucleic acid sequence coding for a polypeptide encoding nucleotide transhydrogenase activity.

In various embodiments, the increased production of fatty acid or fatty acid derived products through the microorganism's malonyl-CoA dependent, but malonyl-ACP independent fatty acyl-CoA metabolic pathway can occur through reduction in fatty acid beta-oxidation activity including but not limited to a reduction in fatty acyl-CoA synthetase or ligase activity via gene deletion, disruption or genetic mutation.

In various embodiments the increased production of fatty acids or fatty acid derived products can be achieved via overexpression of an enzyme having acetyl-CoA carboxylase activity.

In various embodiments, the increased intracellular bicarbonate levels occurs by introduction of a heterologous nucleic acid sequence coding for a polypeptide having cyanase and/or carbonic anhydrase activity.

In various embodiments, the increased production of fatty acids may occur by increasing levels of fatty acyl-CoA thioesterase activity.

In various embodiments, the increased chain length specificity of a fatty acid product may occur by increasing levels of chain length specific fatty acyl-CoA thioesterase activity and decreasing the activity of fatty acyl-CoA thioesterase activity on undesired fatty acid chain lengths.

In various embodiments, the increased chain length specificity of fatty acid or fatty acid derived product may occur by increasing levels of chain length specific ketoacyl-CoA thiolase, enoyl-CoA reductase, ketoacyl-CoA reductase or 3-hydroxyacyl-CoA dehydratase activities either individually or in combination. The enoyl-CoA reductase can either utilize the cofactor NADH or NADPH or alternatively both NADPH and NADH. In addition, the ketoacyl-CoA reductase can either utilize the cofactor NADH or NADPH or alternatively both NADPH and NADH In various embodiments, the increased chain length specificity of fatty acid or fatty acid derived product may occur by increasing levels of chain length specific ketoacyl-CoA synthase (or elongase), enoyl-CoA reductase, ketoacyl-CoA reductase or 3-hydroxyacyl-CoA dehydratase activities either individually or in combination. The enoyl-CoA reductase can either utilize the cofactor NADH or NADPH or alternatively both NADPH and NADH. In addition, the ketoacyl-CoA reductase can either utilize the cofactor NADH or NADPH or alternatively both NADPH and NADH.

In various embodiments, the increased chain length specificity of fatty acid production may occur by increasing levels of chain length specific fatty acyl-CoA thioesterase activity and decreasing the activity of fatty acyl-CoA thioesterase activity on undesired chain lengths.

Within the scope of the invention are genetically modified microorganism, wherein the microorganism is capable of producing a fatty acid or fatty acid derived product at a specific rate selected from the rates of greater than 0.05 g/gDCW-hr, 0.08 g/gDCW-hr. greater than 0.1 g/gDCW-hr. greater than 0.13 g/gDCW-hr. greater than 0.15 g/gDCW-hr. greater than 0.175 g/gDCW-hr, greater than 0.2 g/gDCW-hr, greater than 0.25 g/gDCW-hr, greater than 0.3 g/gDCW-hr, greater than 0.35 g/gDCW-hr. greater than 0.4 g/gDCW-hr. greater than 0.45 g/gDCW-hr. or greater than 0.5 g/gDCW-hr.

In various embodiments, the invention includes a culture system comprising a carbon source in an aqueous medium and a genetically modified microorganism according to any one of claims herein, wherein said genetically modified microorganism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10.000 L, greater than 50,000 L, greater than 100.000 L or greater than 200.000 L, and such as when the volume of the aqueous medium is greater than 250 L and contained within a steel vessel.

Variously, the carbon source for such culture systems is selected from dextrose, sucrose, a pentose, a polyol, a hexose, both a hexose and a pentose, and combinations thereof, the pH of the aqueous medium is less than 7.5, the culture system is aerated, such as at an oxygen transfer rate selected from i) greater than 5 mmole/L-hr of oxygen and less than 200 mmole/L-hr oxygen; ii) greater than 5 mmole/L-hr of oxygen and less than 100 mmole/L-hr oxygen; iii) greater than 5 mmole/L-hr of oxygen and less than 80 mmole/L-hr oxygen; and iv) greater than 5 mmole/L-hr of oxygen and less than 50 mmole/L-hr oxygen.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are utilized, and the accompanying drawings of which:

Figure 1:
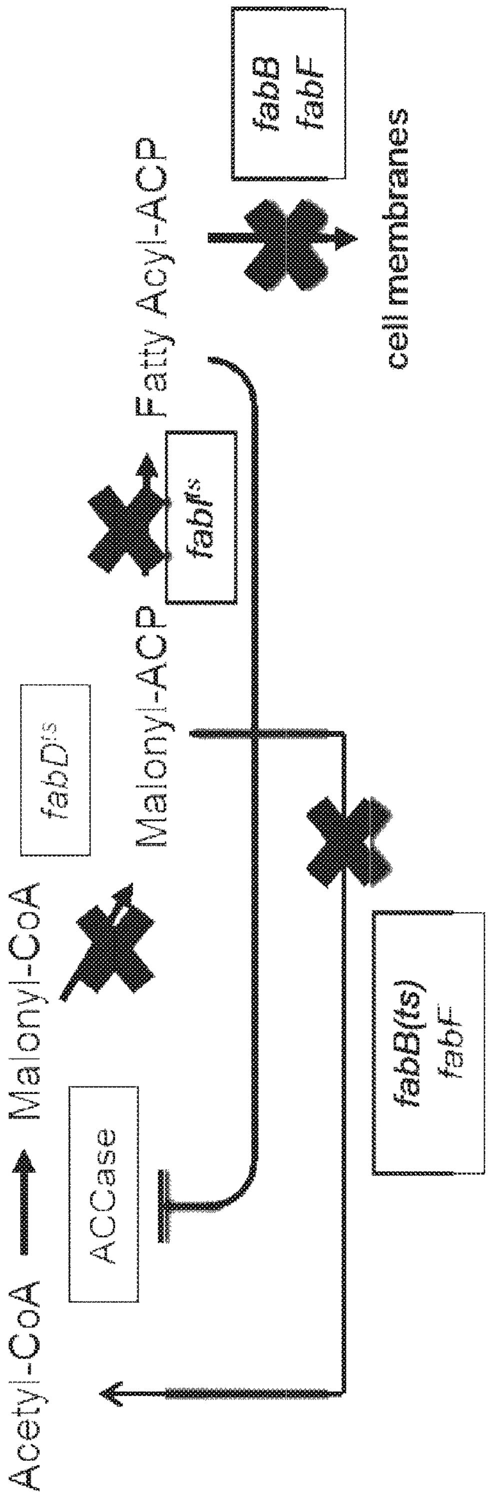
FIG. 1 depicts metabolic pathways of a microorganism related to aspects of the present invention, more particularly related to genetic modifications for increasing flux through the intermediate malonyl-CoA.

TABLES also are provided herein and are part of the specification.

DETAILED DESCRIPTION OF THE INVENTION

The present invention is related to various production methods and/or genetically modified microorganisms that have utility for fermentative production of various chemical products, to methods of making such chemical products that utilize populations of these microorganisms in vessels, and to systems for chemical production that employ these microorganisms and methods. Among the benefits of the present invention is increased specific productivity when such microorganisms produce a chemical product during a fermentation event or cycle. The present invention provides production techniques and/or genetically modified microorganisms to produce a chemical product of interest, such as a fatty acid or fatty acid derived product with one or more means for modulating conversion of malonyl-CoA to fatty acyl molecules, wherein the production pathway comprises an enzymatic conversion step that uses malonyl-CoA as a substrate but does not use malonyl-ACP as a substrate. The means for modulating conversion of malonyl-CoA to fatty acyl molecules is effective to balance carbon flow to microbial biomass with carbon flow to chemical product, and surprisingly affords achievement of elevated specific productivity rates. In particular, fatty acid or fatty acid derived products are produced in a manner dependent on a microorganism's malonyl-CoA dependent and malonyl-ACP independent fatty acid production pathway, in combination with the inhibition of a microorganism's malonyl-ACP dependent fatty acid synthase pathway. The microorganism's malonyl-CoA dependent and malonyl-ACP independent fatty acid production pathway comprises one of two pathways. The first alternative comprises increased expression of a pathway comprising an acetoacetyl-CoA synthase, a ketoacyl-CoA thiolase, an enoyl-CoA reductase, a ketoacyl-CoA reductase and a 3-hydroxyacyl-CoA dehydratase and optionally decreased activity of acetoacetyl-CoA thiolase activity. The second alternative comprises increased expression of a pathway comprising an acetoacetyl-CoA synthase, a ketoacyl-CoA synthase (or elongase), an enoyl-CoA reductase, a ketoacyl-CoA reductase and a 3-hydroxyacyl-CoA dehydratase and optionally decreased activity of acetoacetyl-CoA thiolase activity. These pathways are used to produce intracellular fatty acyl-CoA products.

A microorganism's intracellular fatty acyl-CoA product may be in turn on converted to a chemical product including a fatty acid or fatty acid derived product including but not limited to alcohols, aldehydes, alpha olefins and alkanes.

One chemical product may be a fatty acid of any chain length from 4 to greater than 18 carbons. This group of chemical products includes: butyrate or butyric acid, hexanoate or hexanoic acid, octanoate or octanoic acid, decanoate or decanoic acid, dodecanoate or dodecanoic acid, myristate or myristic acid, palmitate or palmitic acid, palmitoleate or plamitoleic acid, stearate or stearic acid, and oleate or oleic acid. These fatty acid products may be produced from a fatty acyl-CoA intermediate via the activity of a fatty acyl-CoA thioesterase. Alternatively, these fatty acids may be produced from a fatty acyl-CoA intermediate via concerted activities of a fatty acyl-CoA phosphotransferase first producing a fatty acyl-phosphate and then the action of a fatty acid kinase operating to produce a fatty acid from the fatty acyl-phosphate.

Another chemical product may be a fatty aldehyde of any chain length from 4 to greater than 18 carbons. This group of chemical products includes: butanal, hexanal octanal, decanal, octanal, decanal, dodecanal, myristaldehyde, palmitaldehyde, palmitoleic aldehyde, stearaldehyde and oleic aldehyde. These aldehyde products may be produced from a fatty acyl-CoA intermediate via the activity of a fatty acyl-CoA reductase or acyl-CoA reductase. Production strains making fatty acids may also be used to produce fatty aldehydes.

Another chemical product may be a fatty alcohol of any chain length from 4 to greater than 18 carbons. This group of chemical products includes: butanol, hexanol, octanol, decanol, dodecanol, C14 fatty alcohol, C16 fatty alcohol or C18 fatty alcohol. These fatty acid products may be produced from a fatty aldehyde via the activity of an aldehyde reductase. Production strains making fatty acids may also be used to produce fatty alcohols by expressing genes encoding enzymes that convert fatty acyl-CoA or free fatty acids to fatty alcohols. Examples of these enzymes include an alcohol-forming acyl-CoA reductase (EC 1.2.1.-), or a long-chain-fatty-acyl-CoA reductase (EC 1.2.1.50) plus an alcohol dehydrogenase (EC 1.1.1.1), or a combination of an aldehyde dehydrogenase (EC 1.2.1.-) and an alcohol dehydrogenase. A polypeptide with fatty acyl-CoA reductase activity is provided by the fabG gene of *Acinetobacter* SP. ADP1, accession number YP_047869. A polypeptide with fatty-acyl reductase activity is provided by the FAR-N_SDR_e gene of *Bombyx mori*, accession number BAC79425. A polypeptide with aldehyde dehydrogenase is provided by the ALDH gene of *Geobacillus thermodenitrificans* NG80-2, accession number YP_001125970. A polypeptide with alcohol dehydrogenase activity is provided by the yqhD gene of *E. coli*, accession number AP_003562.1. Additional sources of these activities are known to the art and can be combined to generate a production strain that produces fatty alcohols.

Another chemical product may be an alpha olefin of any chain length from 4 to greater than 18 carbons.

Another chemical product may be an alkane of any chain length from 4 to greater than 18 carbons.

Another chemical product may be a diacid of any chain length from 4 to greater than 18 carbons. These fatty acid products may be produced from a fatty acid via omega or terminal oxidation by enzymes known in the art.

Any of these may be described herein as a selected chemical product, or a chemical product of interest. Also, any grouping, including any sub-group, of the above listing may be considered what is referred to by "selected chemical product." "chemical product of interest." and the like. For any of these chemical products a microorganism may inherently comprise a biosynthesis pathway to such chemical product and/or may require addition of one or more heterologous nucleic acid sequences to provide or complete such a biosynthesis pathway, in order to achieve a desired production of such chemical product.

As noted herein, various aspects of the present invention are directed to a microorganism cell that comprises a metabolic pathway from malonyl-CoA to a chemical product of interest, such as those described above, and means for modulating conversion of malonyl-CoA to acyl ACP molecules also are provided. Then, when the means for modulating modulate to decrease such conversion, a proportionally greater number of malonyl-CoA molecules are 1) produced and/or 2) converted via the metabolic pathway from malonyl-CoA to the chemical product.

Unexpected increases in specific productivity by a population of a genetically modified microorganism may be achieved in methods and systems in which that microorganism has a microbial production pathway from malonyl-CoA to a selected chemical product as well as a reduction in the enzymatic activity of a selected enzyme of the microorganism's fatty acid synthase system (more particularly, its malonyl-ACP dependent fatty acid elongation enzymes), in addition to the increase activity of an microorganisms malonyl-CoA dependent but malonyl-ACP independent fatty acyl-CoA production pathway. In various embodiments, specific supplements to a bioreactor vessel comprising such microorganism population may also be provided to further improve the methods and systems.

Other additional genetic modifications are disclosed herein for various embodiments.

I. Definitions

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, *Enzyme Nomenclature*, Academic Press. Inc., New York 2007.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption." or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

In various contexts, a gene disruption is taken to mean any genetic modification to the DNA, mRNA encoded from the DNA, and the corresponding amino acid sequence that results in reduced polypeptide activity. Many different methods can be used to make a cell having reduced polypeptide activity. For example, a cell can be engineered to have a disrupted regulatory sequence or polypeptide-encoding sequence using common mutagenesis or knock-out technology. See, e.g., *Methods in Yeast Genetics* (1997 edition). Adams et al., Cold Spring Harbor Press (1998). One particularly useful method of gene disruption is complete gene deletion because it reduces or eliminates the occurrence of genetic reversions in the genetically modified microorganisms of the invention. Accordingly, a disruption of a gene whose product is an enzyme thereby disrupts enzymatic function. Alternatively, antisense technology can be used to reduce the activity of a particular polypeptide. For example, a cell can be engineered to contain a cDNA that encodes an antisense molecule that prevents a polypeptide from being translated. Further, gene silencing can be used to reduce the activity of a particular polypeptide.

The term "antisense molecule" as used herein encompasses any nucleic acid molecule or nucleic acid analog (e.g., peptide nucleic acids) that contains a sequence that corresponds to the coding strand of an endogenous polypeptide. An antisense molecule also can have flanking sequences (e.g., regulatory sequences). Thus, antisense molecules can be ribozymes or antisense oligonucleotides.

As used herein, a ribozyme can have any general structure including, without limitation, hairpin, hammerhead, or axhead structures, provided the molecule cleaves RNA.

The term "reduction" or "to reduce" when used in such phrase and its grammatical equivalents are intended to encompass a complete elimination of such conversion(s).

Bio-production, as used herein, may be aerobic, microaerobic, or anaerobic.

As used herein, the language "sufficiently homologous" refers to proteins or portions thereof that have amino acid sequences that include a minimum number of identical or equivalent amino acid residues when compared to an amino acid sequence of the amino acid sequences provided in this application (including the SEQ ID Nos./sequence listings) such that the protein or portion thereof is able to achieve the respective enzymatic reaction and/or other function. To determine whether a particular protein or portion thereof is sufficiently homologous may be determined by an assay of enzymatic activity, such as those commonly known in the art.

Descriptions and methods for sequence identity and homology are intended to be exemplary and it is recognized that these concepts are well-understood in the art. Further, it is appreciated that nucleic acid sequences may be varied and still encode an enzyme or other polypeptide exhibiting a desired functionality, and such variations are within the scope of the present invention.

Further to nucleic acid sequences. "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. Hybridization temperatures can be as low as 5° C., but are typically greater than 22° C. more typically greater than about 30° C., and often are in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na Phosphate, 5 mM EDTA, pH 7.4) and a temperature of 25-30° C. are suitable for allele-specific probe hybridizations. For stringent conditions, see for example, Sambrook and Russell and Anderson "Nucleic Acid Hybridization" 1 Ed., BIOS Scientific Publishers Limited (1999), which are hereby incorporated by reference for hybridization protocols. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

The use of the phrase "segment of interest" is meant to include both a gene and any other nucleic acid sequence segment of interest. One example of a method used to obtain a segment of interest is to acquire a culture of a microorganism, where that microorganism's genome includes the gene or nucleic acid sequence segment of interest.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

In some embodiments a truncated respective polypeptide has at least about 90% of the full length of a polypeptide encoded by a nucleic acid sequence encoding the respective native enzyme, and more particularly at least 95% of the full length of a polypeptide encoded by a nucleic acid sequence encoding the respective native enzyme. By a polypeptide having an amino acid sequence at least, for example, 95% "identical" to a reference amino acid sequence of a polypeptide is intended that the amino acid sequence of the claimed polypeptide is identical to the reference sequence except that the claimed polypeptide sequence can include up to five amino acid alterations per each 100 amino acids of the reference amino acid of the polypeptide. In other words, to obtain a polypeptide having an amino acid sequence at least 95% identical to a reference amino acid sequence, up to 5% of the amino acid residues in the reference sequence can be deleted or substituted with another amino acid, or a number of amino acids up to 5% of the total amino acid residues in the reference sequence can be inserted into the reference sequence. These alterations of the reference sequence can occur at the amino or carboxy terminal positions of the reference amino acid sequence or anywhere between those terminal positions, interspersed either individually among residues in the reference sequence or in one or more contiguous groups within the reference sequence. In other embodiments truncation may be more substantial as described elsewhere herein.

Species and other phylogenic identifications are according to the classification known to a person skilled in the art of microbiology.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

Prophetic examples provided herein are meant to be broadly exemplary and not limiting in any way.

The meaning of abbreviations is as follows: "C" means Celsius or degrees Celsius, as is clear from its usage. DCW means dry cell weight, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-µ-D-thiogalactopyranoiside, "RBS" means ribosome binding site, "rpm" means revolutions per minute, "HPLC" means high performance liquid chromatography, and "GC" means gas chromatography.

II. Bioproduction Methods

A. Carbon Sources

Bio-production media, which is used in the present invention with recombinant microorganisms having a biosynthetic pathway for a fatty acid or fatty acid derived product, must contain suitable carbon sources or substrates for the intended metabolic pathways. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, carbon monoxide, or methanol for which metabolic conversion into key biochemical intermediates has been demonstrated. Additionally the carbon substrate may also be carbon dioxide and hydrogen or a combination thereof, such as syngas. In addition to one and two carbon substrates methylotrophic microorganisms are also known to utilize a number of other carbon containing compounds such as methylamine, glucosamine and a variety of amino acids for metabolic activity.

Although it is contemplated that all of the above mentioned carbon substrates and mixtures thereof are suitable in the present invention as a carbon source, common carbon substrates used as carbon sources are glucose, fructose, and sucrose, as well as mixtures of any of these sugars. Other suitable substrates include xylose, arabinose, other cellulose-based C-5 sugars, high-fructose corn syrup, and various other sugars and sugar mixtures as are available commercially. Sucrose may be obtained from feedstocks such as sugar cane, sugar beets, cassava, bananas or other fruit, and sweet sorghum. Glucose and dextrose may be obtained through saccharification of starch based feedstocks including grains such as corn, wheat, rye, barley, and oats. Also, in some embodiments all or a portion of the carbon source may be glycerol. Alternatively, glycerol may be excluded as an added carbon source.

In one embodiment, the carbon source is selected from glucose, fructose, sucrose, dextrose, lactose, glycerol, and mixtures thereof. Variously, the amount of these components in the carbon source may be greater than about 50%, greater than about 60%, greater than about 70%, greater than about 80%, greater than about 90%, or more, up to 100% or essentially 100% of the carbon source.

In addition, methylotrophic microorganisms are known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1 Compd. (Int. Symp.), 7th (1993), 415-32. Editor(s): Murrell, J. Collin; Kelly, Don P. Publisher: Intercept, Andover. UK). Similarly, various species of *Candida* will metabolize alanine or oleic acid (Sulter et al., Arch. Microbiol. 153:485-489 (1990)). Hence it is contemplated that the source of carbon utilized in embodiments of the present invention may encompass a wide variety of carbon-containing substrates.

In addition, fermentable sugars may be obtained from cellulosic and lignocellulosic biomass through processes of pretreatment and saccharification, as described, for example, in U.S. Patent Publication No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure. Any such biomass may be used in a bio-production method or system to provide a carbon source. Various approaches to breaking down cellulosic biomass to mixtures of more available and utilizable carbon molecules, including sugars, include: heating in the presence of concentrated or dilute acid (e.g., <1% sulfuric acid); treating with ammonia; treatment with ionic salts; enzymatic degradation; and combinations of these. These methods normally follow mechanical separation and milling, and are followed by appropriate separation processes.

In various embodiments, any of a wide range of sugars, including, but not limited to sucrose, glucose, xylose, cellulose or hemicellulose, are provided to a microorganism, such as in an industrial system comprising a reactor vessel in which a defined media (such as a minimal salts media including but not limited to M9 minimal media, potassium sulfate minimal media, yeast synthetic minimal media and many others or variations of these), an inoculum of a microorganism providing one or more of the fatty acid or fatty acid derived biosynthetic pathway alternatives, and the a carbon source may be combined. The carbon source enters the cell and is catabolized by well-known and common metabolic pathways to yield common metabolic intermediates, including phosphoenolpyruvate (PEP). (See Molecular Biology of the Cell, 3rd Ed., B. Alberts et al. Garland Publishing. New York, 1994, pp. 42-45, 66-74, incorporated by reference for the teachings of basic metabolic catabolic pathways for sugars; Principles of Biochemistry, 3rd Ed., D. L. Nelson & M. M. Cox, Worth Publishers. New York, 2000, pp 527-658, incorporated by reference for the teachings of major metabolic pathways; and Biochemistry, 4th Ed., L. Stryer, W. H. Freeman and Co., New York, 1995, pp. 463-650, also incorporated by reference for the teachings of major metabolic pathways.)

Bio-based carbon can be distinguished from petroleum-based carbon according to a variety of methods, including without limitation ASTM D6866, or various other techniques. For example, carbon-14 and carbon-12 ratios differ in bio-based carbon sources versus petroleum-based sources, where higher carbon-14 ratios are found in bio-based carbon sources. In various embodiments, the carbon source is not petroleum-based, or is not predominantly petroleum based. In various embodiments, the carbon source is greater than about 50% non-petroleum based, greater than about 60% non-petroleum based, greater than about 70% non-petroleum based, greater than about 80% non-petroleum based, greater than about 90% non-petroleum based, or more. In various embodiments, the carbon source has a carbon-14 to carbon-12 ratio of about $1.0\times10^{-14}$ or greater.

B. Microorganisms

Features as described and claimed herein may be provided in a microorganism selected from the listing herein, or another suitable microorganism, that also comprises one or more natural, introduced, or enhanced fatty acid or fatty acid derived product bio-production pathways. Thus, in some embodiments the microorganism comprises an endogenous fatty acid or fatty acid derived product production pathway (which may, in some such embodiments, be enhanced), whereas in other embodiments the microorganism does not comprise an endogenous fatty acid or fatty acid derived product production pathway.

Varieties of these genetically modified microorganisms may comprise genetic modifications and/or other system alterations as may be described in other patent applications of one or more of the present inventor(s) and/or subject to assignment to the owner of the present patent application.

The examples describe specific modifications and evaluations to certain bacterial and yeast microorganisms. The scope of the invention is not meant to be limited to such species, but to be generally applicable to a wide range of suitable microorganisms. Generally, a microorganism used for the present invention may be selected from bacteria, cyanobacteria, filamentous fungi and yeasts.

For some embodiments, microbial hosts initially selected for bio-production of a selected chemical product should also utilize sugars including glucose at a high rate. Most microbes are capable of utilizing carbohydrates. However, certain environmental microbes cannot utilize carbohydrates to high efficiency, and therefore would not be suitable hosts for such embodiments that are intended for glucose or other carbohydrates as the principal added carbon source.

As the genomes of various species become known, the present invention easily may be applied to an ever-increasing range of suitable microorganisms. Further, given the relatively low cost of genetic sequencing, the genetic sequence of a species of interest may readily be determined to make application of aspects of the present invention more readily obtainable (based on the ease of application of genetic modifications to a microorganism having a known genomic sequence).

More particularly, based on the various criteria described herein, suitable microbial hosts for the bio-production of a chemical product generally may include, but are not limited to, any gram negative microorganisms, more particularly a member of the family Enterobacteriaceae, such as *E. coli*, or *Oligotropha carboxidovorans*, or *Pseudomononas* sp.; any gram positive microorganism, for example *Bacillus subtilis, Lactobaccilus* sp. or *Lactococcus* sp.; a yeast, for example *Saccharomyces cerevisiae, Pichia pastoris* or *Pichia stipitis*; and other groups or microbial species. More particularly, suitable microbial hosts for the bio-production of a fatty acid or fatty acid derived product generally include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium. Pichia, Candida, Hansenula* and *Saccharomyces*. Hosts that may be particularly of interest include: *Oligotropha carboxidovorans* (such as strain OM5), *Escherichia coli, Alcaligenes eutrophus* (*Cupriavidus necator*), *Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae.*

More particularly, suitable microbial hosts for the bio-production of fatty acid or fatty acid derived product generally include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula* and *Saccharomyces.*

Hosts that may be particularly of interest include: *Oligotropha carboxidovorans* (such as strain $OM5^T$), *Escherichia coli, Alcaligenes eutrophus* (*Cupriavidus necator*), *Bacillus licheniformis. Paenibacillus macerans, Rhodococcus erythropolis. Pseudomonas putida, Lactobacillus plantarum. Enterococcus faecium, Enterococcus gallinarium, Enterococcus faecalis, Bacillus subtilis* and *Saccharomyces cerevisiae*. Also, any of the known strains of these species may be utilized as a starting microorganism, as may any of the following species including respective strains thereof—*Cupriavidus basilensis, Cupriavidus campinensis, Cupriavidus gilardi, Cupriavidus laharsis, Cupriavidus metallidurans, Cupriavidus oxalaticus, Cupriavidus pauculus, Cupriavidus pinatubonensis, Cupriavidus respiraculi*, and *Cupriavidus taiwanensis.*

In some embodiments, the recombinant microorganism is a gram-negative bacterium. In some embodiments, the recombinant microorganism is selected from the genera *Zymomonas, Escherichia, Pseudomonas, Alcaligenes*, and *Klebsiella*. In some embodiments, the recombinant microorganism is selected from the species *Escherichia coli. Cupriavidus necator, Oligotropha carboxidovorans*, and *Pseudomonas putida*. In some embodiments, the recombinant microorganism is an *E. coli* strain.

In some embodiments, the recombinant microorganism is a gram-positive bacterium. In some embodiments, the recombinant microorganism is selected from the genera *Clostridium, Salmonella, Rhodococcus, Bacillus, Lactobacillus, Enterococcus, Paenibacillus, Arthrobacter, Corynebacterium*, and *Brevibacterium*. In some embodiments, the recombinant microorganism is selected from the species *Bacillus licheniformis, Paenibacillus macerans, Rhodococcus erythropolis, Lactobacillus plantanrum, Enterococcus faecium, Enterococcus gallinarium, Enterococcus faecalis*, and *Bacillus subtilis*. In particular embodiments, the recombinant microorganism is a *B. subtilis* strain.

In some embodiments, the recombinant microorganism is a yeast. In some embodiments, the recombinant microorganism is selected from the genera *Pichia, Candida, Hansenula, Klebsiella, Issatchenkia*, and *Saccharomyces*. In particular embodiments, the recombinant microorganism is *Saccharomyces cerevisiae.*

It is further appreciated, in view of the disclosure, that any of the above microorganisms may be used for production of chemical products other than fatty acid or fatty acid derived product.

The ability to genetically modify the host is essential for the production of any recombinant microorganism. The mode of gene transfer technology may be by electroporation, conjugation, transduction or natural transformation. A broad range of host conjugative plasmids and drug resistance markers are available. The cloning vectors are tailored to the host microorganisms based on the nature of antibiotic resistance markers that can function in that host.

C. Media and Culture Conditions

In addition to an appropriate carbon source, such as selected from one of the herein-disclosed types, bio-production media must contain suitable minerals, salts, cofactors, buffers and other components, known to those skilled in the art, suitable for the growth of the cultures and promotion of the enzymatic pathway necessary for chemical product bio-production under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media in the present invention are common commercially prepared media such as Luria Bertani (LB) broth. Terrific Broth (TB), M9 minimal media, Sabouraud Dextrose (SD) broth. Yeast medium (YM) broth, (Ymin) yeast synthetic minimal media, and minimal media as described herein, such as M9 minimal media. Other defined or synthetic growth media may also be used, and the appropriate medium for growth of the particular microorganism will be known by one skilled in the art of microbiology or bio-production science. In various embodiments a minimal media may be developed and used that does not comprise, or that has a low level of addition of various components, for example less than 10, 5, 2 or 1 g/L of a complex nitrogen source including but not limited to yeast extract, peptone, tryptone, soy flour, corn steep liquor, or casein. These minimal medias may also have limited supplementation of vitamin mixtures including biotin, vitamin B12 and derivatives of vitamin B12, thiamin, pantothenate and other vitamins. Minimal media may also have limited simple inorganic nutrient sources containing less than 28, 17, or 2.5 mM phosphate, less than 25 or 4 mM sulfate, and less than 130 or 50 mM total nitrogen.

Bio-production media, which is used in embodiments of the present invention with genetically modified microorganisms, must contain suitable carbon substrates for the intended metabolic pathways. As described hereinbefore, suitable carbon substrates include carbon monoxide, carbon dioxide, and various monomeric and oligomeric sugars.

Suitable pH ranges for the bio-production are between pH 3.0 to pH 10.0, where pH 6.0 to pH 8.0 is a typical pH range for the initial condition. However, the actual culture conditions for a particular embodiment are not meant to be limited by these pH ranges.

Bio-productions may be performed under aerobic, microaerobic, or anaerobic conditions, with or without agitation.

The amount of a fatty acid or fatty acid derived product produced in a bio-production media generally can be determined using a number of methods known in the art, for example, high performance liquid chromatography (HPLC), gas chromatography (GC), or GC/Mass Spectroscopy (MS).

D. Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into a fatty acid or fatty acid derived product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Industrial bio-production systems and their operation are well-known to those skilled in the arts of chemical engineering and bio-process engineering.

Bio-productions may be performed under aerobic, microaerobic, or anaerobic conditions, with or without agitation. The operation of cultures and populations of microorganisms to achieve aerobic, microaerobic and anaerobic conditions are known in the art, and dissolved oxygen levels of a liquid culture comprising a nutrient media and such microorganism populations may be monitored to maintain or confirm a desired aerobic, microaerobic or anaerobic condition. When syngas is used as a feedstock, aerobic, microaerobic, or anaerobic conditions may be utilized. When sugars are used, anaerobic, aerobic or microaerobic conditions can be implemented in various embodiments.

Any of the recombinant microorganisms as described and/or referred to herein may be introduced into an industrial bio-production system where the microorganisms convert a carbon source into a selected chemical product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to the selected chemical product.

In various embodiments, syngas components or sugars are provided to a microorganism, such as in an industrial system comprising a reactor vessel in which a defined media (such as a minimal salts media including but not limited to M9 minimal media, potassium sulfate minimal media, yeast synthetic minimal media and many others or variations of these), an inoculum of a microorganism providing an embodiment of the biosynthetic pathway(s) taught herein, and the carbon source may be combined. The carbon source enters the cell and is catabolized by well-known and common metabolic pathways to yield common metabolic intermediates, including phosphoenolpyruvate (PEP) or acetyl-CoA. (See *Molecular Biology of the Cell,* $3^{rd}$ Ed., B. Alberts et al. Garland Publishing. New York, 1994, pp. 42-45, 66-74, incorporated by reference for the teachings of basic metabolic catabolic pathways for sugars; *Principles of Biochemistry,* $3^{rd}$ Ed., D. L. Nelson & M. M. Cox. Worth Publishers, New York, 2000, pp. 527-658, incorporated by reference for the teachings of major metabolic pathways; and *Biochemistry,* $4^{th}$ Ed., L. Stryer, W. H. Freeman and Co., New York, 1995, pp. 463-650, also incorporated by reference for the teachings of major metabolic pathways.).

Further to types of industrial bio-production, various embodiments of the present invention may employ a batch type of industrial bioreactor. A classical batch bioreactor system is considered "closed" meaning that the composition of the medium is established at the beginning of a respective bio-production event and not subject to artificial alterations and additions during the time period ending substantially with the end of the bio-production event. Thus, at the beginning of the bio-production event the medium is inoculated with the desired microorganism or microorganisms, and bio-production is permitted to occur without adding anything to the system. Typically, however, a "batch" type of bio-production event is batch with respect to the addition of carbon source and attempts are often made at controlling factors such as pH and oxygen concentration. In batch systems the metabolite and biomass compositions of the system change constantly up to the time the bio-production event is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of a desired end product or intermediate.

A variation on the standard batch system is the fed-batch system. Fed-batch bio-production processes are also suitable in the present invention and comprise a typical batch system with the exception that the nutrients, including the substrate, are added in increments as the bio-production progresses. Fed-Batch systems are useful when catabolite repression is apt to inhibit the metabolism of the cells and where it is desirable to have limited amounts of substrate in the media. Measurement of the actual nutrient concentration in Fed-Batch systems may be measured directly, such as by sample analysis at different times, or estimated on the basis of the changes of measurable factors such as pH, dissolved oxygen and the partial pressure of waste gases such as $CO_2$. Batch and fed-batch approaches are common and well known in the art and examples may be found in Thomas D. Brock in *Biotechnology: A Textbook of Industrial Microbiology*. Second Edition (1989) Sinauer Associates, Inc., Sunderland. Mass. Deshpande, Mukund V., Appl. Biochem. Biotechnol., 36:227, (1992), and *Biochemical Engineering Fundamentals,* $2^{nd}$ Ed. J. E. Bailey and D. F. Ollis, McGraw Hill, New York, 1986, herein incorporated by reference for general instruction on bio-production.

Although embodiments of the present invention may be performed in batch mode, or in fed-batch mode, it is contemplated that the invention would be adaptable to continuous bio-production methods. Continuous bio-production is considered an "open" system where a defined bio-production medium is added continuously to a bioreactor and an equal amount of conditioned media is removed simultaneously for processing. Continuous bio-production generally maintains the cultures within a controlled density range where cells are primarily in log phase growth. Two types of continuous bioreactor operation include a chemostat, wherein fresh media is fed to the vessel while simultaneously removing an equal rate of the vessel contents. The limitation of this approach is that cells are lost and high cell density generally is not achievable. In fact, typically one can obtain much higher cell density with a fed-batch process. Another continuous bioreactor utilizes perfusion culture, which is similar to the chemostat approach except that the stream that is removed from the vessel is subjected to a separation technique which recycles viable cells back to the vessel. This type of continuous bioreactor operation has been shown to yield significantly higher cell densities than fed-batch and can be operated continuously. Continuous bio-production is particularly advantageous for industrial operations because it has less down time associated with draining, cleaning and preparing the equipment for the next bio-production event. Furthermore, it is typically more economical to continuously operate downstream unit operations, such as distillation, than to run them in batch mode.

Continuous bio-production allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Methods of modulating nutrients and growth factors for continuous bio-production processes as well as techniques for maximizing the rate of product formation are well known in the art of industrial microbiology and a variety of methods are detailed by Brock, supra.

It is contemplated that embodiments of the present invention may be practiced using either batch, fed-batch or continuous processes and that any known mode of bio-production would be suitable. It is contemplated that cells may be immobilized on an inert scaffold as whole cell catalysts and subjected to suitable bio-production conditions for chemical product bio-production, or be cultured in liquid media in a vessel, such as a culture vessel. Thus, embodiments used in such processes, and in bio-production systems using these processes, include a population of genetically modified microorganisms of the present invention, a culture system comprising such population in a media comprising nutrients for the population, and methods of making a selected chemical product.

Embodiments of the invention include methods of making a selected chemical product in a bio-production system, some of which methods may include obtaining a fatty acid or fatty acid derived product after such bio-production event. For example, a method of making a fatty acid or fatty acid derived product may comprise: providing to a culture vessel a media comprising suitable nutrients; providing to the culture vessel an inoculum of a genetically modified microorganism comprising genetic modifications described herein such that the microorganism produces a selected chemical product from syngas and/or a sugar molecule; and maintaining the culture vessel under suitable conditions for the genetically modified microorganism to produce a selected chemical product.

It is within the scope of the present invention to produce, and to utilize in bio-production methods and systems, including industrial bio-production systems for production of a selected chemical product, a recombinant microorganism genetically engineered to modify one or more aspects effective to increase chemical product bio-production by at least 20 percent over control microorganism lacking the one or more modifications.

In various embodiments, the invention is directed to a system for bio-production of a chemical product as described herein, said system comprising: a fermentation tank suitable for microorganism cell culture; a line for discharging contents from the fermentation tank to an extraction and/or separation vessel; and an extraction and/or separation vessel suitable for removal of the chemical product from cell culture waste. In various embodiments, the system includes one or more pre-fermentation tanks, distillation columns, centrifuge vessels, back extraction columns, mixing vessels, or combinations thereof.

The following published resources are incorporated by reference herein for their respective teachings to indicate the level of skill in these relevant arts, and as needed to support a disclosure that teaches how to make and use methods of industrial bio-production of chemical product(s) produced under the invention, from sugar sources, and also industrial systems that may be used to achieve such conversion with any of the recombinant microorganisms of the present invention (Biochemical Engineering Fundamentals, $2^{nd}$ Ed. J. E. Bailey and D. F. Ollis, McGraw Hill, New York, 1986, entire book for purposes indicated and Chapter 9, pages 533-657 in particular for biological reactor design; Unit Operations of Chemical Engineering, $5^{th}$ Ed., W. L. McCabe et al., McGraw Hill, New York 1993, entire book for purposes indicated, and particularly for process and separation technologies analyses; Equilibrium Staged Separations, P. C. Wankat, Prentice Hall, Englewood Cliffs. N.J. USA, 1988, entire book for separation technologies teachings).

E. Genetic Modifications, Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host microorganisms based on the nature of antibiotic resistance markers that can function in that host. Also, as disclosed herein, a genetically modified (recombinant) microorganism may comprise modifications other than via plasmid introduction, including modifications to its genomic DNA.

It has long been recognized in the art that some amino acids in amino acid sequences can be varied without significant effect on the structure or function of proteins. Variants included can constitute deletions, insertions, inversions, repeats, and type substitutions so long as the indicated enzyme activity is not significantly adversely affected. Guidance concerning which amino acid changes are likely to be phenotypically silent can be found, inter alia, in Bowie, J. U., et al., "Deciphering the Message in Protein Sequences: Tolerance to Amino Acid Substitutions." Science 247:1306-1310 (1990). This reference is incorporated by reference for such teachings, which are, however, also generally known to those skilled in the art.

In various embodiments polypeptides obtained by the expression of the polynucleotide molecules of the present invention may have at least approximately 50%, 60%, 70%, 80%, 90%, 95%, 96%, 97%, 98%, 99% or 100% identity to one or more amino acid sequences encoded by the genes and/or nucleic acid sequences described herein for the fatty acid or fatty acid derived product tolerance-related and biosynthesis pathways.

As a practical matter, whether any particular polypeptide is at least 50%, 60%, 70%, 80%, 85%, 90%, 92%, 95%, 96%, 97%, 98% or 99% identical to any reference amino acid sequence of any polypeptide described herein (which may correspond with a particular nucleic acid sequence described herein), such particular polypeptide sequence can be determined conventionally using known computer programs such the Bestfit program (Wisconsin Sequence Analysis Package. Version 8 for Unix. Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set such that the percentage of identity is calculated over the full length of the reference amino acid sequence and that gaps in homology of up to 5% of the total number of amino acid residues in the reference sequence are allowed.

For example, in a specific embodiment the identity between a reference sequence (query sequence, i.e., a sequence of the present invention) and a subject sequence, also referred to as a global sequence alignment, may be determined using the FASTDB computer program based on the algorithm of Brutlag et al. (Comp. App. Biosci. 6:237-245 (1990)). Preferred parameters for a particular embodiment in which identity is narrowly construed, used in a FASTDB amino acid alignment, are: Scoring Scheme=PAM (Percent Accepted Mutations) 0, k-tuple=2. Mismatch Penalty=1, Joining Penalty=20. Randomization Group Length=0. Cutoff Score=1. Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are lateral to the N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence are considered for this manual correction. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli*, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. Examples of suitable promoters for directing transcription of the nucleic acid constructs, especially in an *E. coli* host cell, are the lac promoter (Gronenborn, 1976, MoI. Gen. Genet. 148: 243-250), tac promoter (DeBoer et al., 1983, Proceedings of the National Academy of Sciences USA 80: 21-25), trc promoter (Brosius et al, 1985, J. Biol. Chem. 260: 3539-3541). T7 RNA polymerase promoter (Studier and Moffatt, 1986, J. MoI. Biol. 189: 113-130), phage promoter $p_L$ (Elvin et al., 1990, Gene 87: 123-126), tetA promoter (Skerra, 1994. Gene 151: 131-135), araBAD promoter (Guzman et al., 1995, J. Bacteriol. 177: 4121-4130), and rha$P_{BAD}$ promoter (Haldimann et al., 1998, J. Bacteriol. 180: 1277-1286). Other promoters are described in "Useful proteins from recombinant bacteria" in Scientific American, 1980, 242: 74-94; and in Sambrook and Russell "Molecular Cloning: A Laboratory Manual," Third Edition 2001 (volumes 1-3). Cold Spring Harbor Laboratory Press, Cold Spring Harbor, N.Y.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in an *E. coli* cell may be used in the present invention. It may also be desirable to add regulatory sequences that allow regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to fatty acid or fatty acid derived product production. Specific methodologies and approaches to achieve such genetic modification are well known to one skilled in the art, and include, but are not limited to: increasing expression of an endogenous genetic element; decreasing functionality of a repressor gene; introducing a heterologous genetic element; increasing copy number of a nucleic acid sequence encoding a polypeptide catalyzing an enzymatic conversion step to produce fatty acid or a fatty acid derived product; mutating a genetic element to provide a mutated protein to increase specific enzymatic activity; over-expressing; under-expressing; over-expressing a chaperone; knocking out a protease; altering or modifying feedback inhibition; providing an enzyme variant comprising one or more of an impaired binding site for a repressor and/or competitive inhibitor; knocking out a repressor gene; evolution, selection and/or other approaches to improve mRNA stability as well as use of plasmids having an effective copy number and promoters to achieve an effective level of improvement. Random mutagenesis may be practiced to provide genetic modifications that may fall into any of these or other stated approaches. The genetic modifications further broadly fall into additions (including insertions), deletions (such as by a mutation) and substitutions of one or more nucleic acids in a nucleic acid of interest. In various embodiments a genetic modification results in improved enzymatic specific activity and/or turnover number of an enzyme. Without being limited, changes may be measured by one or more of the following: $K_M$; $K_{cat}$; and $K_{avidity}$.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), and pyruvate-formate lyase (pflB) may be disrupted, including deleted. Such gene disruptions, including deletions, are not meant to be limiting, and may be implemented in various combinations in various embodiments. Gene deletions may be accomplished by mutational gene deletion approaches, and/or starting with a mutant strain having reduced or no expression of one or more of these enzymes, and/or other methods known to those skilled in the art. Gene deletions may be effectuated by any of a number of known specific methodologies, including but not limited to the RED/ET methods using kits and other reagents sold by Gene Bridges (Gene Bridges GmbH. Dresden. Germany, <<www.genebridges.com>>).

More particularly as to the latter method, use of Red/ET recombination, is known to those of ordinary skill in the art and described in U.S. Pat. Nos. 6,355,412 and 6,509,156, issued to Stewart et al. and incorporated by reference herein for its teachings of this method. Material and kits for such method are available from Gene Bridges (Gene Bridges GmbH, Dresden, Germany, <<www.genebridges.com>>), and the method may proceed by following the manufacturer's instructions. The method involves replacement of the target gene by a selectable marker via homologous recombination performed by the recombinase from λ-phage. The host microorganism expressing X-red recombinase is transformed with a linear DNA product coding for a selectable marker flanked by the terminal regions generally ~50 bp, and alternatively up to about ~300 bp) homologous with the target gene. The marker could then be removed by another recombination step performed by a plasmid vector carrying the FLP-recombinase, or another recombinase, such as Cre.

Figure 5:
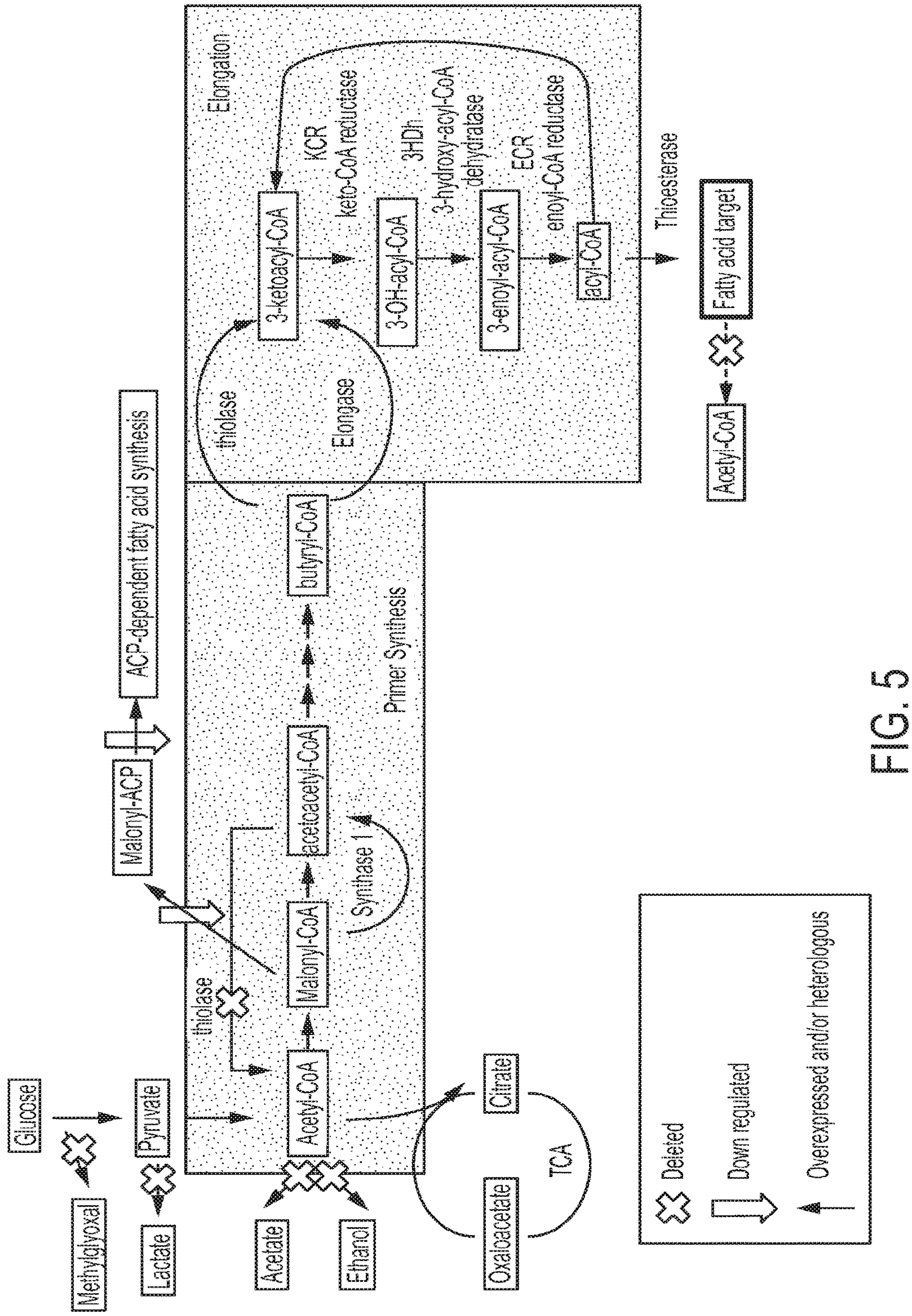
FIG. 5 depicts an embodiment of metabolic pathways provided by the present invention for fatty acid bio-production.
Figure 6:
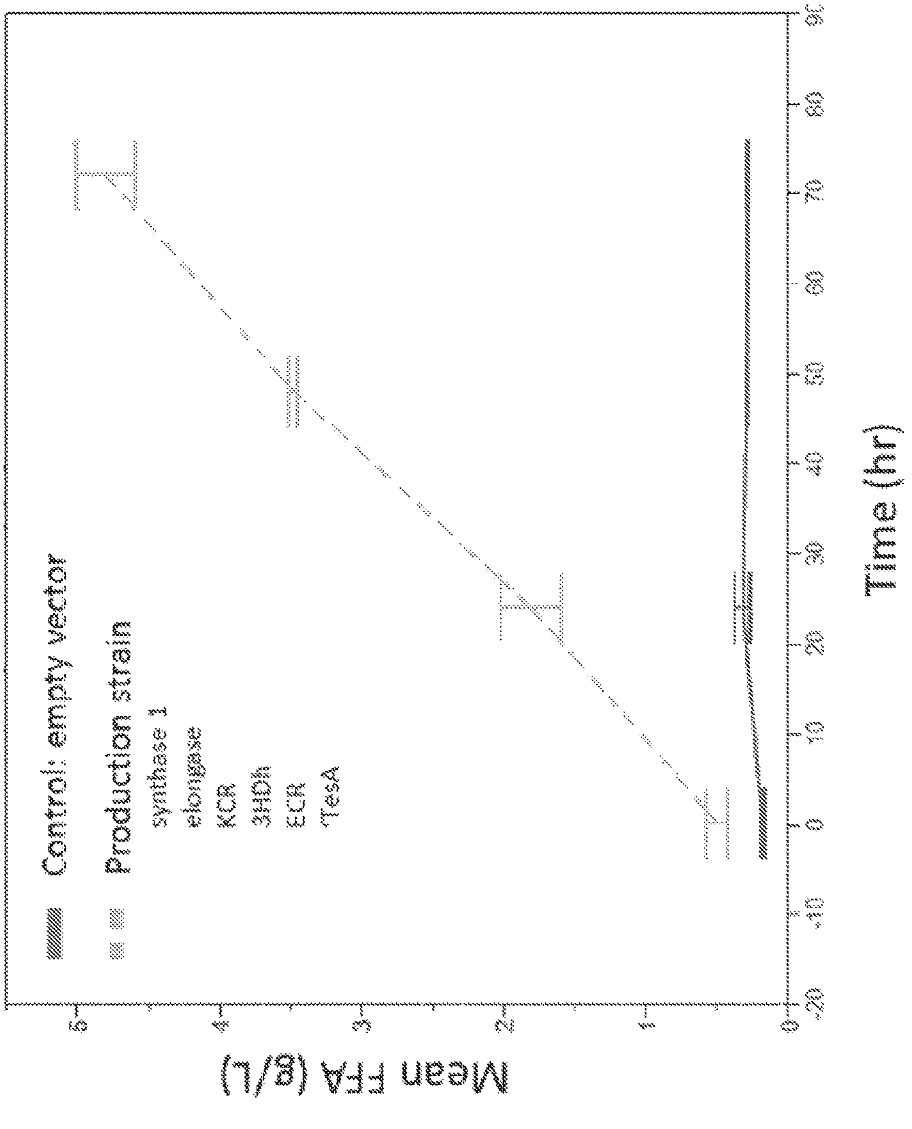
FIG. 6 depicts an embodiment of a microorganism carrying a combination of genetic modification that increases free fatty acid (FFA) bio-production activity.

Targeted deletion of parts of microbial chromosomal DNA or the addition of foreign genetic material to microbial chromosomes may be practiced to alter a host cell's metabolism so as to reduce or eliminate production of undesired metabolic products, such as the elimination of acetate, ethanol, lactate, and others or combination thereof (for example see FIG. 5). This may be used in combination with other genetic modifications such as described herein in this general example. In this detailed description, reference has been made to multiple embodiments and to the accompanying drawings in which are shown by way of illustration specific exemplary embodiments in which the invention may be practiced. These embodiments are described in sufficient detail to enable those skilled in the art to practice the invention, and it is to be understood that modifications to the various disclosed embodiments may be made by a skilled artisan.

Further, for a fatty acid or fatty acid derived product production, such genetic modifications may be chosen and/or selected for to achieve a higher flux rate through certain enzymatic conversion steps within the respective a fatty acid or fatty acid derived product production pathway and so may affect general cellular metabolism in fundamental and/or major ways. For example, in some embodiments the rate can be increased by genetic modifications that increase the flux from sugar to acetyl-CoA.

It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gin, with another residue bearing an amide group; exchange of a basic residue such as Lys or Arg with another basic residue; and replacement of an aromatic residue such as Phe or Tyr with another aromatic residue.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms. In various embodiments, nucleic acid sequences encoding sufficiently homologous proteins or portions thereof are within the scope of the invention. More generally, nucleic acids sequences that encode a particular amino acid sequence employed in the invention may vary due to the degeneracy of the genetic code, and nonetheless fall within the scope of the invention. The following table provides a summary of similarities among amino acids, upon which conservative and less conservative substitutions may be based, and also various codon redundancies that reflect this degeneracy.

TABLE 1

Similarities Among Amino Acids

| AMINO ACID | RELATIONSHIPS | DNA CODONS |
|---|---|---|
| Alanine | N, Ali | GCT, GCC, GCA, GCG |
| Proline | N | CCT, CCC, CCA, CCG |
| Valine | N, Ali | GTT, GTC, GTA, GTG |
| Leucine | N, Ali | CTT, CTC, CTA, CTG, TTA, TTG |
| Isoleucine | N, Ali | ATT, ATC, ATA |
| Methionine | N | ATG |
| Phenylalanine | N, Aro | TTT, TTC |
| Tryptophan | N | TGG |
| Glycine | PU | GGT, GGC, GGA, GGG |
| Serine | PU | TCT, TCC, TCA, TCG, AGT, AGC |
| Threonine | PU | ACT, ACC, ACA, ACG |
| Asparagine | PU, Ami | AAT, AAC |
| Glutamine | PU, Ami | CAA, CAG |
| Cysteine | PU | TGT, TGC |
| Aspartic acid | NEG, A | GAT, GAC |
| Glutamic acid | NEG, A | GAA, GAG |
| Arginine | POS, B | CGT, CGC, CGA, CGG, AGA, AUG |
| Lysine | POS, B | AAA, AAG |
| Histidine | POS | CAT, CAC |
| Tyrosine | Aro | TAT, TAC |
| Stop Codons | | TAA, TAG, TGA |

Legend: side groups and other related properties: A = acidic; B = basic; Ali = aliphatic; Ami = amine; Aro = aromatic; N = nonpolar; PU = polar uncharged; NEG = negatively charged; POS = positively charged.

Also, variants and portions of particular nucleic acid sequences, and respective encoded amino acid sequences recited herein may be exhibit a desired functionality, e.g., enzymatic activity at a selected level, when such nucleic acid sequence variant and/or portion contains a 15 nucleotide sequence identical to any 15 nucleotide sequence set forth in the nucleic acid sequences recited herein including, without limitation, the sequence starting at nucleotide number 1 and ending at nucleotide number 15, the sequence starting at nucleotide number 2 and ending at nucleotide number 16, the sequence starting at nucleotide number 3 and ending at nucleotide number 17, and so forth. It will be appreciated that the invention also provides isolated nucleic acid that contains a nucleotide sequence that is greater than 15 nucleotides (e.g., 16, 17, 18, 19, 20, 21, 22, 23, 24, 25, 26, 27, 28, 29, 30 or more nucleotides) in length and identical to any portion of the sequence set forth in nucleic acid sequences recited herein. For example, the invention provides isolated nucleic acid that contains a 25 nucleotide sequence identical to any 25 nucleotide sequence set forth in any one or more (including any grouping of) nucleic acid sequences recited herein including, without limitation, the sequence starting at nucleotide number 1 and ending at nucleotide number 25, the sequence starting at nucleotide number 2 and ending at nucleotide number 26, the sequence starting at nucleotide number 3 and ending at nucleotide number 27, and so forth. Additional examples include, without limitation, isolated nucleic acids that contain a nucleotide sequence that is 50 or more nucleotides (e.g., 100, 150, 200, 250, 300, or more nucleotides) in length and identical to any portion of any of the sequences disclosed herein. Such isolated nucleic acids can include, without limitation, those isolated nucleic acids containing a nucleic acid sequence represented in any one section of discussion and/or examples, such as regarding a fatty acid or fatty acid derived product production pathways, nucleic acid sequences encoding enzymes of the fatty acid synthase system, or a fatty acid or fatty acid derived product tolerance. For example, the invention provides an isolated nucleic acid containing a nucleic acid sequence listed herein that contains a single insertion, a single deletion, a single substitution, multiple insertions, multiple deletions, multiple substitutions, or any combination thereof (e.g., single deletion together with multiple insertions). Such isolated nucleic acid molecules can share at least 60, 65, 70, 75, 80, 85, 90, 95, 97, 98, or 99 percent sequence identity with a nucleic acid sequence listed herein (i.e., in the sequence listing).

Additional examples include, without limitation, isolated nucleic acids that contain a nucleic acid sequence that encodes an amino acid sequence that is 50 or more amino acid residues (e.g., 100, 150, 200, 250, 300, or more amino acid residues) in length and identical to any portion of an amino acid sequence listed or otherwise disclosed herein.

In addition, the invention provides isolated nucleic acid that contains a nucleic acid sequence that encodes an amino acid sequence having a variation of an amino acid sequence listed or otherwise disclosed herein. For example, the invention provides isolated nucleic acid containing a nucleic acid sequence encoding an amino acid sequence listed or otherwise disclosed herein that contains a single insertion, a single deletion, a single substitution, multiple insertions, multiple deletions, multiple substitutions, or any combination thereof (e.g., single deletion together with multiple insertions). Such isolated nucleic acid molecules can contain a nucleic acid sequence encoding an amino acid sequence that shares at least 60, 65, 70, 75, 80, 85, 90, 95, 97, 98, or 99 percent sequence identity with an amino acid sequence listed or otherwise disclosed herein.

Examples of properties that provide the bases for conservative and other amino acid substitutions are exemplified in Table 1. Accordingly, one skilled in the art may make numerous substitutions to obtain an amino acid sequence variant that exhibits a desired functionality. BLASTP, CLUSTALP, and other alignment and comparison tools may be used to assess highly conserved regions, to which fewer substitutions may be made (unless directed to alter activity to a selected level, which may require multiple substitutions). More substitutions may be made in regions recognized or believed to not be involved with an active site or other binding or structural motif. In accordance with Table 1, for example, substitutions may be made of one polar uncharged (PU) amino acid for a polar uncharged amino acid of a listed sequence, optionally considering size/molecular weight (i.e., substituting a serine for a threonine). Guidance concerning which amino acid changes are likely to be phenotypically silent can be found, inter alia, in Bowie, J. U., et Al., "Deciphering the Message in Protein Sequences: Tolerance to Amino Acid Substitutions," Science 247:1306-1310 (1990). This reference is incorporated by reference for such teachings, which are, however, also generally known to those skilled in the art. Recognized conservative amino acid substitutions comprise (substitutable amino acids following each colon of a set): ala:ser; arg:lys; asn:gln or his; asp:glu; cys:ser; gln:asn; glu:asp; gly:pro; his:asn or gln; ile:leu or val; leu:ile or val; lys:arg or gln or glu; met:leu or ile; phe:met or leu or tyr; ser:thr; thr:ser; trp:tyr; tyr:trp or phe; val:ile or leu.

It is noted that codon preferences and codon usage tables for a particular species can be used to engineer isolated nucleic acid molecules that take advantage of the codon usage preferences of that particular species. For example, the isolated nucleic acid provided herein can be designed to have codons that are preferentially used by a particular microorganism of interest. Numerous software and sequencing services are available for such codon-optimizing of sequences.

The invention provides polypeptides that contain the entire amino acid sequence of an amino acid sequence listed or otherwise disclosed herein. In addition, the invention provides polypeptides that contain a portion of an amino acid sequence listed or otherwise disclosed herein. For example, the invention provides polypeptides that contain a 15 amino acid sequence identical to any 15 amino acid sequence of an amino acid sequence listed or otherwise disclosed herein including, without limitation, the sequence starting at amino acid residue number 1 and ending at amino acid residue number 15, the sequence starting at amino acid residue number 2 and ending at amino acid residue number 16, the sequence starting at amino acid residue number 3 and ending at amino acid residue number 17, and so forth. It will be appreciated that the invention also provides polypeptides that contain an amino acid sequence that is greater than 15 amino acid residues (e.g., 16, 17, 18, 19, 20, 21, 22, 23, 24, 25, 26, 27, 28, 29, 30 or more amino acid residues) in length and identical to any portion of an amino acid sequence listed or otherwise disclosed herein For example, the invention provides polypeptides that contain a 25 amino acid sequence identical to any 25 amino acid sequence of an amino acid sequence listed or otherwise disclosed herein including, without limitation, the sequence starting at amino acid residue number 1 and ending at amino acid residue number 25, the sequence starting at amino acid residue number 2 and ending at amino acid residue number 26, the sequence starting at amino acid residue number 3 and ending at amino acid residue number 27, and so forth. Additional examples include, without limitation, polypeptides that contain an amino acid sequence that is 50 or more amino acid residues (e.g., 100, 150, 200, 250, 300 or more amino acid residues) in length and identical to any portion of an amino acid sequence listed or otherwise disclosed herein. Further, it is appreciated that, per above, a 15 nucleotide sequence will provide a 5 amino acid sequence, so that the latter, and higher-length amino acid sequences, may be defined by the above-described nucleotide sequence lengths having identity with a sequence provided herein.

In addition, the invention provides polypeptides that an amino acid sequence having a variation of the amino acid sequence set forth in an amino acid sequence listed or otherwise disclosed herein. For example, the invention provides polypeptides containing an amino acid sequence listed or otherwise disclosed herein that contains a single insertion, a single deletion, a single substitution, multiple insertions, multiple deletions, multiple substitutions, or any combination thereof (e.g., single deletion together with multiple insertions). Such polypeptides can contain an amino acid sequence that shares at least 60, 65, 70, 75, 80, 85, 90, 95, 97, 98 or 99 percent sequence identity with an amino acid sequence listed or otherwise disclosed herein. A particular variant amino acid sequence may comprise any number of variations as well as any combination of types of variations.

As indicated herein, polypeptides having a variant amino acid sequence can retain enzymatic activity. Such polypeptides can be produced by manipulating the nucleotide sequence encoding a polypeptide using standard procedures such as site-directed mutagenesis or various PCR techniques. As noted herein, one type of modification includes the substitution of one or more amino acid residues for amino acid residues having a similar chemical and/or biochemical property. For example, a polypeptide can have an amino acid sequence set forth in an amino acid sequence listed or otherwise disclosed herein comprising one or more conservative substitutions.

More substantial changes can be obtained by selecting substitutions that are less conservative, and/or in areas of the sequence that may be more critical, for example selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue. e.g., serine or threonine, is substituted for (or by) a hydrophobic residue. e.g., leucine, isoleucine, phenylalanine, valine or alanine: (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain. e.g., glycine. The effects of these amino acid substitutions (or other deletions or additions) can be assessed for polypeptides having enzymatic activity by analyzing the ability of the polypeptide to catalyze the conversion of the same substrate as the related native polypeptide to the same product as the related native polypeptide. Accordingly, polypeptides having 5, 10, 20, 30, 40, 50 or less conservative substitutions are provided by the invention.

Polypeptides and nucleic acids encoding polypeptides can be produced by standard DNA mutagenesis techniques, for example, M13 primer mutagenesis. Details of these techniques are provided in Sambrook and Russell, 2001. Nucleic acid molecules can contain changes of a coding region to fit the codon usage bias of the particular microorganism into which the molecule is to be introduced.

Alternatively, the coding region can be altered by taking advantage of the degeneracy of the genetic code to alter the coding sequence in such a way that, while the nucleic acid sequence is substantially altered, it nevertheless encodes a polypeptide having an amino acid sequence identical or substantially similar to the native amino acid sequence. For example, alanine is encoded in the open reading frame by the nucleotide codon triplet GCT. Because of the degeneracy of the genetic code, three other nucleotide codon triplets—GCA, GCC, and GCG—also code for alanine. Thus, the nucleic acid sequence of the open reading frame can be changed at this position to any of these three codons without affecting the amino acid sequence of the encoded polypeptide or the characteristics of the polypeptide. Based upon the degeneracy of the genetic code, nucleic acid variants can be derived from a nucleic acid sequence disclosed herein using standard DNA mutagenesis techniques as described herein, or by synthesis of nucleic acid sequences. Thus, for various embodiments the invention encompasses nucleic acid molecules that encode the same polypeptide but vary in nucleic acid sequence by virtue of the degeneracy of the genetic code.

The invention also provides an isolated nucleic acid that is at least about 12 bases in length (e.g., at least about 13, 14, 15, 16, 17, 18, 19, 20, 25, 30, 40, 50, 60, 100, 250, 500, 750, 1000, 1500, 2000, 3000, 4000, 5000, 6000, 7000, 8000, 9000, 10000, 11000, 12000, 13000, 14000, 15000, 16000, 17000, 18000, 19000 or 20000 bases in length) and hybridizes, under hybridization conditions, to the sense or antisense strand of a nucleic acid having a sequence listed or otherwise disclosed herein. The hybridization conditions can be moderately or highly stringent hybridization conditions.

F. Redirecting Malonyl-CoA from Native Malonyl-ACP Dependent Fatty Acid Synthesis to Malonyl-CoA Dependent Fatty Acid Synthesis Compositions of the present invention, such as genetically modified microorganisms, comprise a production pathway for a fatty acid or fatty acid derived product in which malonyl-CoA is a substrate, and may also comprise one or more genetic modifications to reduce the activity of enzymes encoded by one or more of the microorganisms malonyl-ACP dependent fatty acid synthetase system genes. The compositions may be used in the methods and systems of the present invention.

Regarding microbial fermentation of a number of fatty acid or fatty acid derived products in many microorganisms of commercial fermentation interest, malonyl-CoA is a metabolic intermediate that, under normal growth conditions, is converted to fatty acids and derivatives thereof, such as phospholipids, that are then used in cell membranes and for other key cellular functions. For example, in *Escherichia coli*, the fatty acid synthase system is a type II or dissociated fatty acid synthase system. In this system the enzymes of the malonyl-ACP dependent fatty acid production pathway are encoded by distinct genes, and, common for many critical metabolic pathways, is well-regulated, including by downstream products inhibiting upstream enzymes.

In various microorganisms conversion of the metabolic intermediate malonyl-CoA to fatty acids via a fatty acid synthesis system (i.e., pathway or complex) is the only or the major use of malonyl-CoA. It has been determined that when a production pathway to an alternative chemical product exists in a microorganism, reducing such conversion of malonyl-CoA to fatty acids can improve metrics for production of that alternative chemical product. For example, in many microorganism cells the fatty acid synthase system comprises polypeptides that have the following enzymatic activities: malonyl-CoA-acyl carrier protein (ACP) transacylase; β-ketoacyl-ACP synthase; β-ketoacyl-ACP reductase; β-hydroxyacyl-ACP dehydratase; 3-hydroxyacyl-ACP dehydratase; and enoyl-ACP reductase. In various embodiments nucleic acid sequences that encode temperature-sensitive forms of these polypeptides may be introduced in place of the native enzymes, and when such genetically modified microorganisms are cultured at elevated temperatures (at which these thermolabile polypeptides become inactivated, partially or completely, due to alterations in protein structure or complete denaturation), there is observed an increase in a chemical product. In *E. coli*, these temperature-sensitive mutant genes could include $fabI^{st}$(S241F), $fabB^{st}$(A329V) or $fabD^{ts}$(W257Q). In other embodiments other types of genetic modifications may be made to otherwise modulate, such as lower, enzymatic activities of one or more of these polypeptides. In various embodiments a result of such genetic modifications is to shift malonyl-CoA utilization so that there is a reduced conversion of malonyl-CoA to fatty acids via the native pathway, overall biomass, and proportionally greater conversion of carbon source to a chemical product including a fatty acid or fatty acid derived product via a malonyl-CoA dependent and malonyl-ACP independent route. In various embodiments, the specific productivity for the microbially produced chemical product is unexpectedly high. Also, additional genetic modifications, such as to increase malonyl-CoA production, may be made for certain embodiments. FIG. 1 depicts metabolic pathways of a microorganism related to genetic modifications for increasing flux through the intermediate malonyl-CoA.

One enzyme, enoyl-acyl carrier protein reductase (EC No. 1.3.1.9, also referred to as enoyl-ACP reductase) is a key enzyme for fatty acid biosynthesis from malonyl-CoA. In *Escherichia coli* this enzyme, FabI, is encoded by the gene fabI (See "Enoyl-Acyl Carrier Protein (fabI) Plays a Determinant Role in Completing Cycles of Fatty Acid Elongation in *Escherichia coli*." Richard J. Heath and Charles O. Rock, J. Biol. Chem. 270:44, pp. 26538-26543 (1995), incorporated by reference for its discussion of fabI and the fatty acid synthase system).

The present invention may utilize a microorganism that is provided with a nucleic acid sequence (polynucleotide) that encodes a polypeptide having enoyl-ACP reductase enzymatic activity that may be modulated during a fermentation event. For example, a nucleic acid sequence encoding a temperature-sensitive enoyl-ACP reductase may be provided in place of the native enoyl-ACP reductase, so that an elevated culture temperature results in reduced enzymatic activity, which then results in a shifting utilization of malonyl-CoA to production of a desired chemical product. At such elevated temperature the enzyme is considered non-permissive, as is the temperature. One such sequence is a mutant temperature-sensitive fabI ($fabI^{TS}$) of *E. coli* or the $fabI^{ts}$(S241F).

It is appreciated that nucleic acid and amino acid sequences for enoyl-ACP reductase in species other than *E. coli* are readily obtained by conducting homology searches in known genomics databases, such as BLASTN and BLASTP. Approaches to obtaining homologues in other species and functional equivalent sequences are described herein. Accordingly, it is appreciated that the present invention may be practiced by one skilled in the art for many microorganism species of commercial interest.

Other approaches than a temperature-sensitive enoyl-ACP reductase may be employed as known to those skilled in the art, such as, but not limited to, replacing a native enoyl-ACP or enoyl-CoA reductase with a nucleic acid sequence that includes an inducible promoter for this enzyme, so that an initial induction may be followed by no induction, thereby decreasing enoyl-ACP or enoyl-CoA reductase enzymatic activity after a selected cell density is attained.

In some aspects, the present invention comprises a genetically modified microorganism that comprises at least one genetic modification that provides, completes, or enhances a selected chemical product production pathway effective to convert malonyl-CoA to the selected chemical product, and further comprises a genetic modification of carbonic anhydrase to increase bicarbonate levels in the microorganism cell and/or a supplementation of its culture medium with bicarbonate and/or carbonate, and may further comprise one or more genetic modifications to increase enzymatic activity of one or more of acetyl-CoA carboxylase and NADPH-dependent transhydrogenase. Related methods and systems utilize such genetically modified microorganism.

In various embodiments the present invention is directed to a method of making a chemical product comprising: providing a selected cell density of a genetically modified microorganism population in a vessel, wherein the genetically modified microorganism comprises a production pathway for production of a chemical product from malonyl-CoA; and reducing enzymatic activity of at least one enzyme of the genetically modified microorganism's malonyl-ACP dependent fatty acid synthase pathway.

In various embodiments, reducing the enzymatic activity of an enoyl-ACP reductase in a microorganism host cell results in production of chemical product at elevated specific and volumetric productivity. In still other embodiments, reducing the enzymatic activity of an enoyl-ACP reductase in a microorganism host cell results in production of the chemical product at elevated specific and volumetric productivity.

Figure 2:
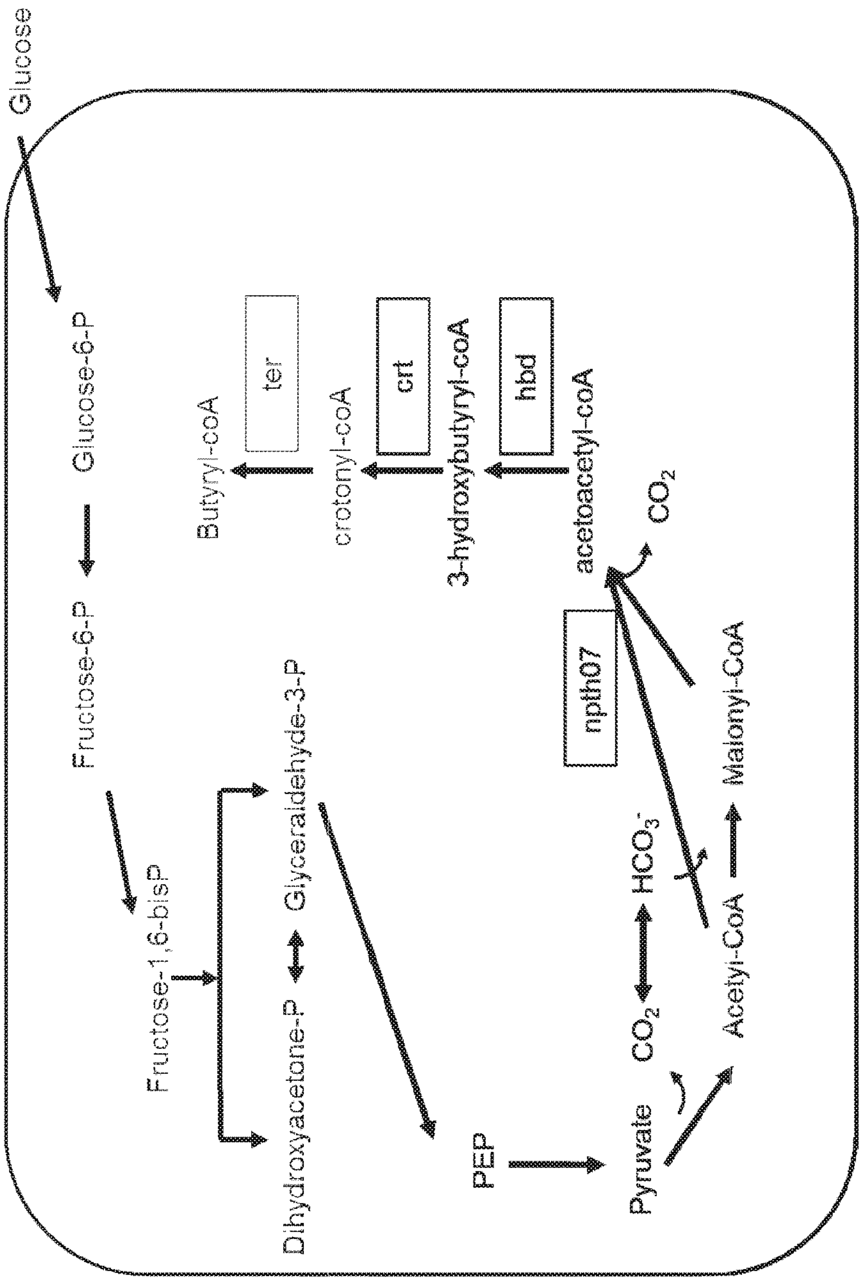
FIG. 2 depicts metabolic pathways of a microorganism related to aspects of the present invention, more particularly related to the production of butyryl-CoA and butyryl-CoA derived products.

FIG. 2 depicts metabolic pathways of a microorganism to produce a butyryl-CoA primer for fatty acyl-CoA synthesis via a malonyl-CoA dependent manner. This involves increasing activity of a malonyl-CoA dependent acetoacetyl-CoA synthase enzyme alone or in combination with decreasing an microorganism's acetoacetyl-CoA thiolase activity. The malonyl-CoA dependent production of acetoacetyl-CoA is then followed by the reduction to butyrate by increasing 3-hydroxybutyryl-CoA dehydrogenase or 3-ketoacyl-CoA reductase activity as well as enoyl-CoA hydratase and trans-2-enoyl-CoA reductase activity. The butyryl-CoA primer can then be used for to produce longer chain fatty acyl-CoAs or alternatively butyrate, butanol or other products.

Figure 3A:
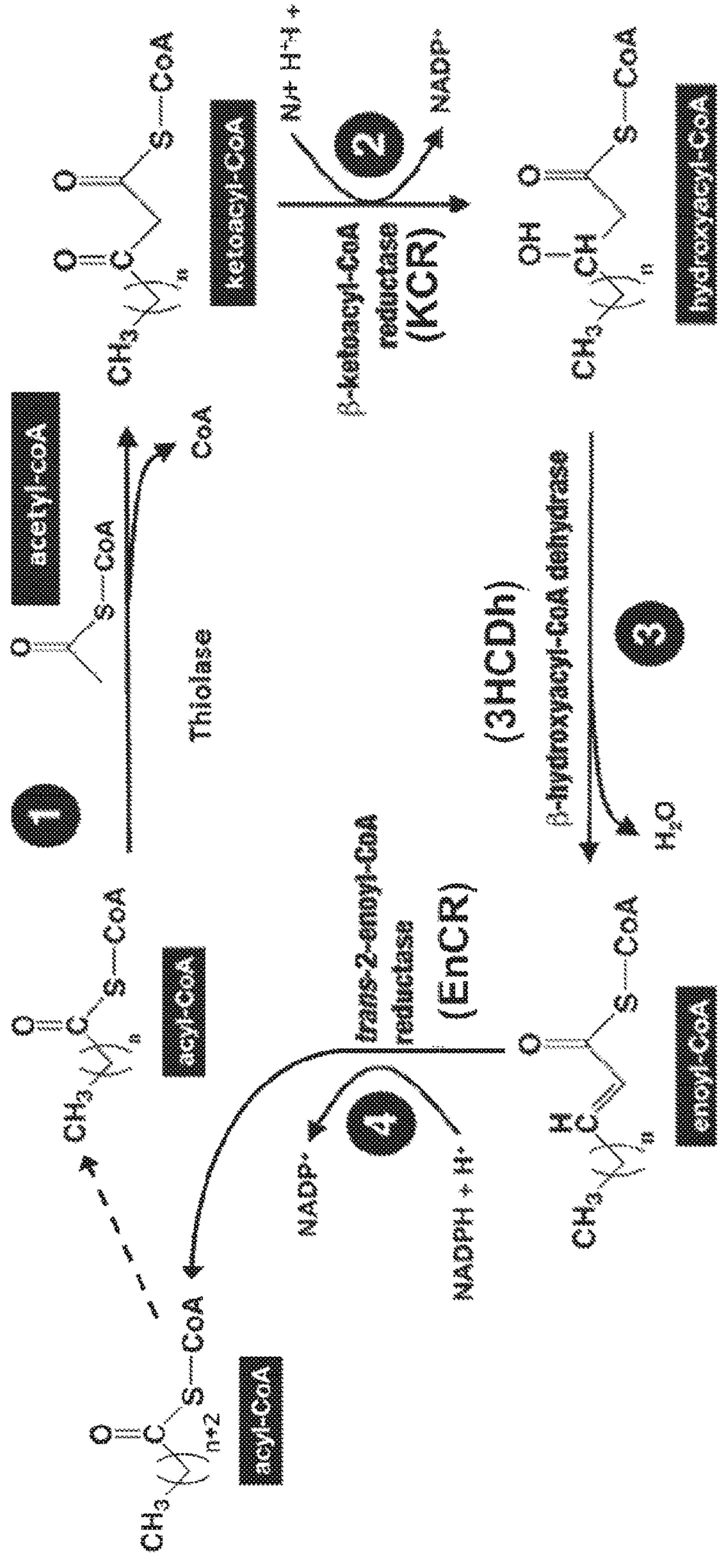
FIG. 3A depicts metabolic pathways of a microorganism related to aspects of the present invention, more particularly related to the production of fatty acyl-CoAs, fatty acids and fatty acid derived products.

FIG. 3A depicts metabolic pathways of a microorganism to produce a fatty acyl-CoA synthesis via a acetyl-CoA dependent manner, starting with the primer butyryl-CoA. This involves increasing activity of a 3-ketoacyl-CoA thiolase activity, 3-hydroxybutyryl-CoA dehydrogenase or 3-ketoacyl-CoA reductase activity as well as enoyl-CoA hydratase and trans-2-enoyl-CoA reductase activity.

Figure 3B:
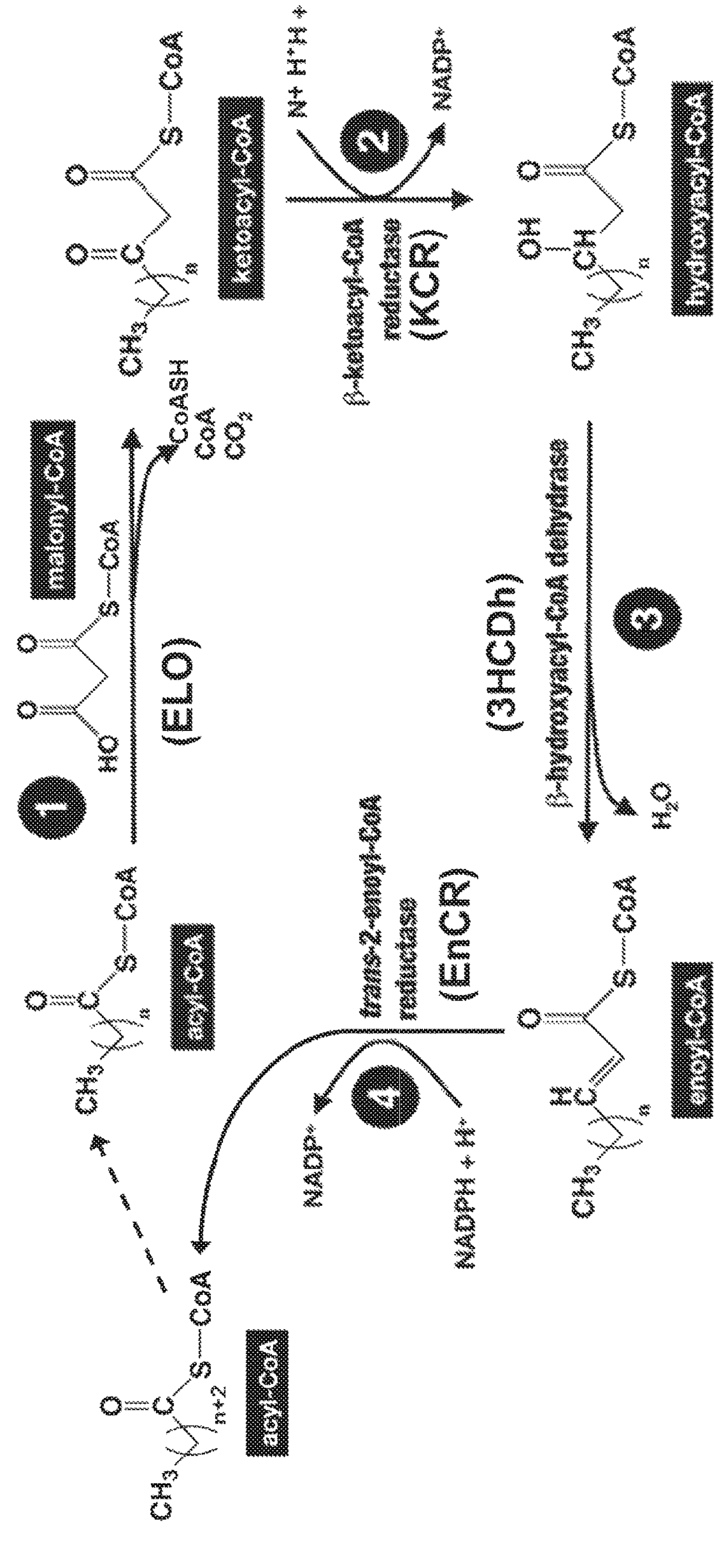
FIG. 3B depicts metabolic pathways of a microorganism related to aspects of the present invention, more particularly related to the production of fatty acyl-CoAs, fatty acids and fatty acid derived products

FIG. 3B depicts metabolic pathways of a microorganism to produce a fatty acyl-CoA synthesis via a malonyl-CoA dependent manner, starting with the primer butyryl-CoA. This involves increasing activity of a 3-ketoacyl-CoA synthase or elongase activity, 3-hydroxybutyryl-CoA dehydrogenase or 3-ketoacyl-CoA reductase activity as well as enoyl-CoA hydratase and trans-2-enoyl-CoA reductase activity.

Another approach to genetic modification to reduce enzymatic activity of these enzymes is to provide an inducible promoter that promotes one such enzyme, such as the enoyl-ACP reductase gene (e.g., fabI in *E. coli*). In such example this promoter may be induced (such as with isopropyl-μ-D-thiogalactopyranoiside (IPTG)) during a first phase of a method herein, and after the IPTG is exhausted, removed or diluted out the second step, of reducing enoyl-ACP reductase enzymatic activity, may begin. Other approaches may be applied to control enzyme expression and activity such as are described herein and/or known to those skilled in the art. For example promoters that are turned on in response to phosphate depletion may be used to controllably express desired genes. Such promoters could include the yibD or pstS gene promoters in *E. coli.*

While enoyl-CoA reductase is considered an important enzyme of the fatty acid synthase system, genetic modifications may be made to any combination of the polynucleotides (nucleic acid sequences) encoding the polypeptides exhibiting the enzymatic activities of this system, such as are listed herein. For example. FabB, β-ketoacyl-acyl carrier protein synthase I, is an enzyme in *E. coli* that is essential for growth and the biosynthesis of both saturated and unsaturated fatty acids. Inactivation of FabB results in the inhibition of fatty acid elongation and diminished cell growth as well as eliminating a futile cycle that recycles the malonate moiety of malonyl-ACP back to acetyl-CoA. FabF, β-ketoacyl-acyl carrier protein synthase II, is required for the synthesis of saturated fatty acids and the control membrane fluidity in cells. Both enzymes are inhibited by cerulenin.

It is reported that overexpression of FabF results in diminished fatty acid biosynthesis. It is proposed that FabF outcompetes FabB for association with FabD, malonyl-CoA:ACP transacylase. The association of FabB with FabD is required for the condensation reaction that initiates fatty acid elongation. (See Microbiological Reviews, September 1993, p. 522-542 Vol. 57, No. 3; K. Magnuson et al., “Regulation of Fatty Acid Biosynthesis in *Escherichia coli*.” American Society for Microbiology; W. Zha et al., “Improving cellular malonyl-CoA level in *Escherichia coli* via metabolic engineering.” Metabolic Engineering 11 (2009) 192-198). An alternative to genetic modification to reduce such fatty acid synthase enzymes is to provide into a culture system a suitable inhibitor of one or more such enzymes. This approach may be practiced independently or in combination with the genetic modification approach. Inhibitors, such as cerulenin, thiolactomycin, and triclosan (this list not limiting) or genetic modifications directed to reduce activity of enzymes encoded by one or more of the fatty acid synthetase system genes may be employed, singly or in combination.

Without being bound to a particular theory, it is believed that reducing the enzymatic activity of enoyl-ACP reductase (and/or of other enzymes of the fatty acid synthase system) in a microorganism leads to an accumulation and/or shunting of malonyl-CoA, a metabolic intermediate upstream of the enzyme, and such malonyl-CoA may then be converted to a chemical product for which the microorganism cell comprises a metabolic pathway that utilizes malonyl-CoA. In certain compositions, methods and systems of the present invention the reduction of enzymatic activity of enoyl-ACP reductase (or, more generally, of the fatty acid synthase system) is made to occur after a sufficient cell density of a genetically modified microorganism is attained. This biphasic culture approach balances a desired quantity of biocatalyst, in the cell biomass which supports a particular production rate, with yield, which may be partly attributed to having less carbon be directed to cell mass after the enoyl-ACP reductase activity (and/or activity of other enzymes of the fatty acid synthase system) is/are reduced. This results in a shifting net utilization of malonyl-CoA, thus providing for greater carbon flux to a desired chemical product.

In various embodiments of the present invention the specific productivity is elevated and this results in overall rapid and efficient microbial fermentation methods and systems. In various embodiments the volumetric productivity also is substantially elevated.

The improvements in both specific and volumetric productivity parameters based on the teachings and previous data, such as for fatty acids, are unexpected and advance the art.

The reduction of enoyl-ACP reductase activity and/or of other enzymes of the fatty acid synthase system may be achieved in a number of ways, as is discussed herein.

By “means for modulating” the conversion of malonyl-CoA to fatty acyl-ACP or fatty acyl-CoA molecules, and to fatty acid molecules, is meant any one of the following: 1) providing in a microorganism cell at least one polynucleotide that encodes at least one polypeptide having activity of one of the malonyl-ACP dependent fatty acid synthase system enzymes (such as recited herein), wherein the polypeptide so encoded has (such as by mutation and/or promoter substitution, etc., to lower enzymatic activity), or may be modulated to have (such as by temperature sensitivity, inducible promoter, etc.) a reduced enzymatic activity; 2) providing to a vessel comprising a microorganism cell or population an inhibitor that inhibits enzymatic activity of one or more of the malonyl-ACP dependent fatty acid synthase system enzymes (such as recited herein), at a dosage effective to reduce enzymatic activity of one or more of these enzymes. These means may be provided in combination with one another. When a means for modulating involves a conversion, during a fermentation event, from a higher to a lower activity of the fatty acid synthetase system, such as by increasing temperature of a culture vessel comprising a population of genetically modified microorganism comprising a temperature-sensitive fatty acid synthetase system polypeptide (e.g., enoyl-ACP reductase), or by adding an inhibitor, there are conceived two modes—one during which there is higher activity, and a second during which there is lower activity, of such fatty acid synthetase system. During the lower activity mode, a shift to greater utilization of malonyl-CoA to a selected chemical product may proceed via the increased activity of one or more malonyl-CoA dependent, malonyl-ACP independent fatty acyl-CoA metabolic pathways.

Once the modulation is in effect to decrease the noted enzymatic activity(ies), each respective enzymatic activity so modulated may be reduced by at least 10, at least 20, at least 30, at least 40, at least 50, at least 60, at least 70, at least 80, or at least 90 percent compared with the activity of the native, non-modulated enzymatic activity (such as in a cell or isolated). Similarly, the conversion of malonyl-CoA to fatty acyl-ACP or fatty acyl-CoA molecules may be reduced by at least 10, at least 20, at least 30, at least 40, at least 50, at least 60, at least 70, at least 80, or at least 90 percent compared with such conversion in a non-modulated cell or other system. Likewise, the conversion of malonyl-CoA to fatty acid molecules may be reduced by at least 10, at least 20, at least 30, at least 40, at least 50, at least 60, at least 70, at least 80, or at least 90 percent compared with such conversion in a non-modulated cell or other system.

G. Production Pathways from Malonyl-CoA to Fatty Acyl-CoA Dependent Products

In various embodiments the compositions, methods and systems of the present invention involve inclusion of a metabolic production pathway that converts malonyl-CoA to a fatty acid of fatty acid derived product.

Any of the above polypeptides may be NADH- or NADPH-dependent, and methods known in the art may be used to convert a particular enzyme to be either form. More particularly, any method can be used to convert a polypeptide that uses NADPH as a cofactor into a polypeptide that uses NADH as a cofactor such as those described by others (Eppink et al., J Mol. Biol., 292 (1): 87-96 (1999). Hall and Tomsett, Microbiology, 146 (Pt 6): 1399-406 (2000), and Dohr et al., Proc. Natl. Acad. Sci., 98 (1): 81-86 (2001)). (See e.g., WO 2002/042418).

In various embodiments, bio-production of a selected chemical product may reach at least 1, at least 2, at least 5, at least 10, at least 20, at least 30, at least 40, and at least 50 g/liter titer, such as by using one of the methods disclosed herein.

As may be realized by appreciation of the advances disclosed herein as they relate to commercial fermentations of selected chemical products, embodiments of the present invention may be combined with other genetic modifications and/or method or system modulations so as to obtain a microorganism (and corresponding method) effective to produce at least 10, at least 20, at least 30, at least 40, at least 45, at least 50, at least 80, at least 100, or at least 120 grams of a chemical product per liter of final (e.g., spent) fermentation broth while achieving this with specific and/or volumetric productivity rates as disclosed herein.

In some embodiments a microbial chemical bio-production event (i.e., a fermentation event using a cultured population of a microorganism) proceeds using a genetically modified microorganism as described herein, wherein the specific productivity is between 0.01 and 0.60 grams of selected chemical product produced per gram of microorganism cell on a dry weight basis per hour (g chemical product/g DCW-hr). In various embodiments the specific productivity is greater than 0.01, greater than 0.05, greater than 0.10, greater than 0.15, greater than 0.20, greater than 0.25, greater than 0.30, greater than 0.35, greater than 0.40, greater than 0.45, or greater than 0.50 g chemical product/g DCW-hr. Specific productivity may be assessed over a 2, 4, 6, 8, 12 or 24 hour period in a particular microbial chemical production event. More particularly, the specific productivity for a chemical product is between 0.05 and 0.10, 0.10 and 0.15, 0.15 and 0.20, 0.20 and 0.25, 0.25 and 0.30, 0.30 and 0.35, 0.35 and 0.40, 0.40 and 0.45, or 0.45 and 0.50 g chemical product/g DCW-hr., 0.50 and 0.55, or 0.55 and 0.60 g chemical product/g DCW-hr. Various embodiments comprise culture systems demonstrating such productivity.

Also, in various embodiments of the present invention the volumetric productivity achieved may be 0.25 g fatty acid (or other chemical product) per liter per hour (g (chemical product)/L-hr), may be greater than 0.25 g fatty acid (or other chemical product)/L-hr. may be greater than 0.50 g fatty acid (or other chemical product)/L-hr, may be greater than 1.0 g fatty acid (or other chemical product)/L-hr. may be greater than 1.50 g fatty acid (or other chemical product)/L-hr. may be greater than 2.0 g fatty acid (or other chemical product)/L-hr, may be greater than 2.50 g fatty acid (or other chemical product)/L-hr, may be greater than 3.0 g fatty acid (or other chemical product)/L-hr, may be greater than 3.50 g fatty acid (or other chemical product)/L-hr, may be greater than 4.0 g fatty acid (or other chemical product)/L-hr, may be greater than 4.50 g fatty acid (or other chemical product)/L-hr. may be greater than 5.0 g fatty acid (or other chemical product)/L-hr, may be greater than 5.50 g fatty acid (or other chemical product)/L-hr, may be greater than 6.0 g fatty acid (or other chemical product)/L-hr, may be greater than 6.50 g fatty acid (or other chemical product)/L-hr, may be greater than 7.0 g fatty acid (or other chemical product)/L-hr, may be greater than 7.50 g fatty acid (or other chemical product)/L-hr, may be greater than 8.0 g fatty acid (or other chemical product)/L-hr. may be greater than 8.50 g fatty acid (or other chemical product)/L-hr. may be greater than 9.0 g fatty acid (or other chemical product)/L-hr, may be greater than 9.50 g fatty acid (or other chemical product)/L-hr, or may be greater than 10.0 g fatty acid (or other chemical product)/L-hr.

In some embodiments, specific productivity as measured over a 24-hour fermentation (culture) period may be greater than 0.01, 0.05, 0.10, 0.20, 0.5, 1.0, 2.0, 3.0, 4.0, 5.0, 6.0, 7.0, 8.0, 9.0, 10.0, 11.0 or 12.0 grams of chemical product per gram DCW of microorganisms (based on the final DCW at the end of the 24-hour period).

In various aspects and embodiments of the present invention, there is a resulting substantial increase in microorganism specific productivity that advances the fermentation art and commercial economic feasibility of microbial chemical production, such as of a fatty acid (but not limited thereto).

Stated in another manner, in various embodiments the specific productivity exceeds (is at least) 0.01 g chemical product/g DCW-hr, exceeds (is at least) 0.05 g chemical product/g DCW-hr, exceeds (is at least) 0.10 g chemical product/g DCW-hr. exceeds (is at least) 0.15 g chemical product/g DCW-hr, exceeds (is at least) 0.20 g chemical product/g DCW-hr, exceeds (is at least) 0.25 g chemical product/g DCW-hr, exceeds (is at least) 0.30 g chemical product/g DCW-hr, exceeds (is at least) 0.35 g chemical product/g DCW-hr, exceeds (is at least) 0.40 g chemical product/g DCW-hr, exceeds (is at least) 0.45 g chemical product/g DCW-hr, exceeds (is at least) 0.50 g chemical product/g DCW-hr, exceeds (is at least) 0.60 g chemical product/g DCW-hr.

More generally, based on various combinations of the genetic modifications described herein, optionally in combination with supplementations described herein, specific productivity values for a fatty acid or fatty acid derived product, and for other chemical products described herein, may exceed 0.01 g chemical product/g DCW-hr, may exceed 0.05 g chemical product/g DCW-hr. may exceed 0.10 g chemical product/g DCW-hr. may exceed 0.15 g chemical product/g DCW-hr, may exceed 0.20 g chemical product/g DCW-hr, may exceed 0.25 g chemical product/g DCW-hr, may exceed 0.30 g chemical product/g DCW-hr, may exceed 0.35 g chemical product/g DCW-hr. may exceed 0.40 g chemical product/g DCW-hr. may exceed 0.45 g chemical product/g DCW-hr. and may exceed 0.50 g or 0.60 chemical product/g DCW-hr. Such specific productivity may be assessed over a 2, 4, 6, 8, 12 or 24 hour period in a particular microbial chemical production event.

The improvements achieved by embodiments of the present invention may be determined by percentage increase in specific productivity, or by percentage increase in volumetric productivity, compared with an appropriate control microorganism lacking the particular genetic modification combinations taught herein (with or without the supplements taught herein, added to a vessel comprising the microorganism population). For particular embodiments and groups thereof, such specific productivity and/or volumetric productivity improvements is/are at least 10, at least 20, at least 30, at least 40, at least 50, at least 100, at least 200, at least 300, at least 400, and at least 500 percent over the respective specific productivity and/or volumetric productivity of such appropriate control microorganism.

The specific methods and teachings of the specification, and/or cited references that are incorporated by reference, may be incorporated into the examples. Also, production of a chemical product may reach at least 1, at least 2, at least 5, at least 10, at least 20, at least 30, at least 40, and at least 50 g/liter titer in various embodiments.

The metrics may be applicable to any of the compositions, e.g., genetically modified microorganisms, methods, e.g., of producing chemical products, and systems. e.g., fermentation systems utilizing the genetically modified microorganisms and/or methods disclosed herein.

It is appreciated that iterative improvements using the strategies and methods provided herein, and based on the discoveries of the interrelationships of the pathways and pathway portions, may lead to even greater chemical product bio-production at the conclusion of a bio-production event.

H. Combinations of Genetic Modifications

In some embodiments, at least one genetic modification to decrease enzymatic activity is a gene disruption. In some embodiments, at least one genetic modification to decrease enzymatic activity is a gene deletion.

In some embodiments, the genetic modification increases microbial synthesis of a selected fatty acid or fatty acid derived chemical product above a rate or titer of a control microorganism lacking said at least one genetic modification to produce a selected chemical product. In some embodiments, the genetic modification is effective to increase enzymatic conversions to a selected chemical product by at least about 5 percent, at least about 10 percent, at least about 20 percent, at least about 30 percent, or at least about 50 percent above the enzymatic conversion of a control microorganism lacking the genetic modification. Several of these non-limiting genetic modifications to enzymes or enzymatic activities are listed below in Table 2.

TABLE 2

Genetic Modifications

| ENZYME FUNCTION | E.C. CLASSIFICATION No. | GENE NAME IN *E. COLI* | COMMENTS |
|---|---|---|---|
| Glucose transporter | N/A | galP | Increase function |
| Pyruvate dehydrogenase E1p | 1.2.4.1 | aceE | Increase function |
| lipoate acetyltransferase/ dihydrolipoamide acetyltransferase | 2.3.1.12 | aceF | Increase function |
| Pyruvate dehydrogenase E3 (lipoamide dehydrogenase) | 1.8.1.4 | lpd | Increase function or alter such as by mutation to increase resistance to NADH inhibition. |
| Lactate dehydrogenase | 1.1.1.28 | ldhA | Decrease function, including by mutation |
| Pyruvate formate lyase (B "inactive") | 2.3.1.- | pflB | Decrease function, including by mutation |
| Pyruvate oxidase | 1.2.2.2 | poxB | Decrease function, including by mutation |
| Phosphate acetyltransferase | 2.3.1.8 | Pta | Decrease function, including by mutation |
| acetate kinase | 2.7.2.15 2.7.2.1 | ackA | Decrease function, including by mutation |
| methylglyoxal synthase | 4.2.3.3 | mgsA | Decrease function, including by mutation |
| Heat stable, histidyl phosphorylatable protein (of PTS) | N/A | ptsH (HPr) | Decrease function, including by mutation |

TABLE 2-continued

Genetic Modifications

| ENZYME FUNCTION | E.C. CLASSIFICATION No. | GENE NAME IN *E. COLI* | COMMENTS |
|---|---|---|---|
| Phosphoryl transfer protein (of PTS) | N/A | ptsI | Decrease function, including by mutation |
| Polypeptide chain (of PTS) | N/A | Crr | Decrease function, including by mutation |
| 3-oxoacyl-ACP synthase I 3-oxoacyl-ACP synthase II monomer | 2.3.1.179 2.3.1.41 | fabF | Decrease function, including by mutation |
| β-ketoacyl-ACP synthase I, 3-oxoacyl-ACP-synthase I | 2.3.1.41 2.3.1.- | fabB | Decrease function, including by mutation |
| Malonyl-CoA-ACP transacylase | 2.3.1.39 | fabD | Decrease function, including by mutation |
| enoyl acyl carrier protein reductase | 13.1.9, 1.3.1.10 | fabI | Decrease function, including by mutation |
| β-ketoacyl-acyl carrier protein synthase III | 2.3.1.180 | fabH | Decrease function, including by mutation |
| Carboxyl transferase subunit α subunit | 6.4.1.2 | accA | Increase function |
| Biotin carboxyl carrier protein | 6.4.1.2 | accB | Increase function |
| Biotin carboxylase subunit | 6.3.4.14 | accC | Increase function |
| Carboxyl transferase subunit β subunit | 6.4.1.2 | accD | Increase function |
| long chain fatty acyl thioesterase I | 3.1.2.2, 3.1.1.5 | tesA | Increase function as well as alter by mutation to express in cytoplasm or deletion. |
| acyl-CoA synthase | 2.3.1.86 | fadD | Decrease via deletion or mutation |
| acetate CoA-transferase | 2.8.3.8 | atoD | Decrease via deletion or mutation |
| acetate CoA-transferase | 2.8.3.8 | atoA | Decrease via deletion or mutation |
| Transporter | N/A | atoE | Decrease via deletion or mutation |
| acetyl-CoA acetyltransferase | 2.3.1.9 | atoB | Decrease via deletion or mutation |
| pantothenate kinase | 2.7.1.33 | coaA | Increase via expression or feedback resistant mutation |
| lactose repressor | N/A | lacI | Decrease via deletion or mutation |
| γ-glutamyl-γ-aminobutyraldehyde dehydrogenase | 1.2.1.- | puuC | Decrease via deletion or mutation |
| malate synthase A | 2.3.3.9 | aceB | Decrease via deletion or mutation |
| isocitrate lyase | 4.1.3.1 | aceA | Decrease via deletion or mutation |
| isocitrate dehydrogenase phosphatase/isocitrate dehydrogenase kinase | 3.1.3.-2.7.11.5. | aceK | Decrease via deletion or mutation |
| pyruvate formate-lyase deactivase | 1.2.1.10 1.1.1.1 | adhE | Decrease via deletion or mutation |
| aldehyde dehydrogenase A, NAD-linked | 1.2.1.21 1.2.1.22 | aldA | Decrease via deletion or mutation |
| acetaldehyde dehydrogenase | 1.2.1.4 | aldB | Decrease via deletion or mutation |
| Lambda phage DE3 lysogen | N/A | λDE3 | Increase |
| T7 mRNA polymerase | N/A | T7pol | Increase |
| trigger factor | 5.2.1.8 | tig | Decrease via deletion or mutation |
| 3-ketoacyl-CoA thiolase | 2.3.1.16 | fad A | Increase |

TABLE 2-continued

Genetic Modifications

| ENZYME FUNCTION | E.C. CLASSIFICATION No. | GENE NAME IN *E. COLI* | COMMENTS |
|---|---|---|---|
| dodecenoyl-CoA δ-isomerase, enoyl-CoA hydratase, 3-hydroxybutyryl-CoA epimerase, 3-hydroxyacyl-CoA dehydrogenase | 5.3.3.8 1.1.1.35 5.1.2.3 4.2.1.17 | fadB | Increase |
| Sucrose permease | N/A | cscB | Increase |
| Invertase | 3.2.1.26 | cscA | Increase |
| fructokinase | 2.7.1.4 | cscK | Increase |
| carbonic anhydrase | 4.2.1.1 | cynT | Increase |
| carbonic anhydrase | 4.2.1.1 | can | Increase |
| pyridine nucleotide transhydrogenase | 1.6.1.2 | pntAB | Increase |
| pyridine nucleotide transhydrogenase | 1.6.1.1 | udhA | Increase |
| acyl-CoA thioesterase | 3.1.2.20 3.1.2.2 | yciA | Increase and or decrease |
| thioesterase II | 3.1.2.20 3.1.2.2 | tesB | Increase and or decrease |
| thioesterase III | 3.1.2.- | fadM | Increase and or decrease |
| hydroxyphenylacetyl-CoA thioesterase | N/A | paaI | Increase and or decrease |
| esterase/thioesterase | 3.1.2.28 | ybgC | increase and or decrease |
| proofreading thioesterase in enterobactin biosynthesis | | entH | Increase and or decrease |
| acetoacetyl-CoA synthase | 2.3.1.194 | npth07 | Increase |
| 3-ketoacyl-CoA synthase/elongase | 2.3.1 | Elo1 | Increase |
| 3-ketoacyl-CoA synthase/elongase | 2.3.1 | Elo2 | Increase |
| 3-Hydroxybutyryl-CoA dehydrogenase | 1.1.1.157 | hbd | Increase |
| 3-oxoacyl-CoA reductase | 1.1.1.100 | fabG | Increase |
| enoyl-CoA hydratase | 4.2.1.17 | crt | Increase |
| enoyl-CoA hydratase | 4.2.1.17 | ech2 | Increase |
| Trans-2-enoyl-reductase | 1.3.1.9 | ter | Increase |
| thioesterase | 3.1.2.20 | paaI | Decrease |

E.C. No. = "Enzyme Commission number"

Further with regard to decreasing enzyme function based on the teaching in Table 2, any one or a combination of enzyme functions of the following may be decreased in a particular embodiment combined with other genetic modifications described herein: β-ketoacyl-ACP synthase I, 3-oxoacyl-ACP-synthase I; Malonyl-CoA-ACP transacylase; enoyl ACP reductase; and β-ketoacyl-ACP synthase III.

Accordingly, as described in various sections above, some compositions, methods and systems of the present invention comprise providing a genetically modified microorganism that comprises both a production pathway to a selected chemical product, such as a fatty acid or fatty acid derived product, and a modified polynucleotide that encodes an enzyme of the malonyl-ACP dependent fatty acid synthase system that exhibits reduced activity, so that utilization of malonyl-CoA shifts toward the production pathway compared with a comparable (control) microorganism lacking such modifications. The methods involve producing the chemical product using a population of such genetically modified microorganism in a vessel, provided with a nutrient media. Other genetic modifications described herein, to other enzymes, such as acetyl-CoA carboxylase and/or NADPH-dependent transhydrogenase, may be present in some such embodiments. Providing additional copies of polynucleotides that encode polypeptides exhibiting these enzymatic activities is shown to increase a fatty acid or fatty acid derived product production. Other ways to increase these respective enzymatic activities is known in the art and may be applied to various embodiments of the present invention.

Also, without being limiting, a first step in some multi-phase method embodiments of making a chemical product may be exemplified by providing into a vessel, such as a culture or bioreactor vessel, a nutrient media, such as a minimal media as known to those skilled in the art, and an inoculum of a genetically modified microorganism so as to provide a population of such microorganism, such as a bacterium, and more particularly a member of the family Enterobacteriaceae, such as *E. coli*, where the genetically modified microorganism comprises a metabolic pathway that converts malonyl-CoA to a selected chemical product. This inoculum is cultured in the vessel so that the cell density increases to a cell density suitable for reaching a production level of a fatty acid or fatty acid derived product that meets overall productivity metrics taking into consideration the next step of the method. In various alternative embodiments, a population of these genetically modified microorganisms may be cultured to a first cell density in a first, preparatory vessel, and then transferred to the noted vessel so as to provide the selected cell density. Numerous multi-vessel culturing strategies are known to those skilled in the art. Any such embodiments provide the selected cell density according to the first noted step of the method.

Also without being limiting, a subsequent step may be exemplified by two approaches, which also may be practiced in combination in various embodiments. A first approach provides a genetic modification to the genetically modified microorganism such that its enoyl-ACP reductase enzymatic activity may be controlled. As one example, a genetic modification may be made to substitute a temperature-sensitive mutant enoyl-ACP reductase (e.g., $fabI^{TS}$ in *E. coli*) for the native enoyl-ACP reductase. The former may exhibit reduced enzymatic activity at temperatures above 30° C. but normal enzymatic activity at 30° C., so that elevating the culture temperature to, for example to 34° C. 35° C. 36° C. 37° C. or even 42° C. reduces enzymatic activity of enoyl-ACP reductase. In such case, more malonyl-CoA is converted to a fatty acid or fatty acid derived product or another chemical product than at 30° C., where conversion of malonyl-CoA to fatty acids is not impeded by a less effective enoyl-ACP reductase.

As to the production increase aspects of the invention, which may result in elevated titer of a selected chemical product in industrial bio-production, the genetic modifications comprise introduction of one or more nucleic acid sequences into a microorganism, wherein the one or more nucleic acid sequences encode for and express one or more production pathway enzymes (or enzymatic activities of enzymes of a production pathway). In various embodiments these improvements thereby combine to increase the efficiency and efficacy of, and consequently to lower the costs for, the industrial bio-production production of a selected chemical product.

In various embodiments, genetic modifications may be directed to transcriptional, translational, and post-translational modifications that result in a change of enzyme activity and/or selectivity under selected and/or identified culture conditions. Thus, in various embodiments, to function more efficiently, a microorganism may comprise one or more gene deletions.

Gene deletions may be accomplished by mutational gene deletion approaches, and/or starting with a mutant strain having reduced or no expression of one or more of these enzymes, and/or other methods known to those skilled in the art.

Aspects of the invention also regard provision of multiple genetic modifications to improve microorganism overall effectiveness in converting a selected carbon source into a selected chemical product such as a polyketide. Particular combinations are shown, such as in the Examples, to increase specific productivity, volumetric productivity, titer and yield substantially over more basic combinations of genetic modifications.

Additional genetic modifications may be provided in a microorganism strain of the present invention. Many such modifications may be provided to impart a particular phenotype.

For example, the ability to utilize sucrose may be provided, and this would expand the range of feed stocks that can be utilized to produce a fatty acid or fatty acid derived product or other chemical products. Common laboratory and industrial strains of *E. coli*, such as the strains described herein, are not capable of utilizing sucrose as the sole carbon source. Since sucrose, and sucrose-containing feed stocks such as molasses, are abundant and often used as feed stocks for the production by microbial fermentation, adding appropriate genetic modifications to permit uptake and use of sucrose may be practiced in strains having other features as provided herein. Various sucrose uptake and metabolism systems are known in the art (for example, U.S. Pat. No. 6,960,455), incorporated by reference for such teachings. These and other approaches may be provided in strains of the present invention. The examples provide at least two approaches.

Also, genetic modifications may be provided to add functionality for breakdown of more complex carbon sources, such as cellulosic biomass or products thereof, for uptake, and/or for utilization of such carbon sources. For example, numerous cellulases and cellulase-based cellulose degradation systems have been studied and characterized (see, for example, and incorporated by reference herein for such teachings, Beguin, P and Aubert. J-P (1994) FEMS Microbial. Rev. 13: 25-58; Ohima, K. et al. (1997) Biotechnol. Genet. Eng. Rev. 14: 365414).

In addition to the above-described genetic modifications, in various embodiments genetic modifications also are provided to increase the pool and availability of the cofactor NADPH, and/or, consequently, the NADPH/$NADP^+$ ratio. For example, in various embodiments for *E. coli*, this may be done by increasing activity, such as by genetic modification, of one or more of the following genes: pgi (in a mutated form), pntAB, overexpressed, gapA:gapN substitution/replacement, and disrupting or modifying a soluble transhydrogenase such as sthA, and/or genetic modifications of one or more of zwf, gnd, and edd.

Any such genetic modifications may be provided to species not having such functionality, or having a less than desired level of such functionality.

More generally, and depending on the particular metabolic pathways of a microorganism selected for genetic modification, any subgroup of genetic modifications may be made to decrease cellular production of fermentation product(s) selected from the group consisting of acetate, acetoin, acetone, acrylic, malate, fatty acid ethyl esters, isoprenoids, glycerol, ethylene glycol, ethylene, propylene, butylene, isobutylene, ethyl acetate, vinyl acetate, other acetates, 1,4-butanediol, 2,3-butanediol, butanol isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, and maleic acid. Gene deletions may be made as disclosed generally herein, and other approaches may also be used to achieve a desired decreased cellular production of selected fermentation products.

I. Disclosed Embodiments are Non-Limiting

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a figure), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. (See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986.) These published resources are incorporated by reference herein for their respective teachings of standard laboratory methods found therein. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls.

Subject matter in the Examples is incorporated into this section to the extent not already present.

III. Examples

The examples herein provide some examples, not meant to be limiting, of combinations of genetic modifications and supplement additions. The following examples include both actual examples and prophetic examples.

Unless indicated otherwise, temperature is in degrees Celsius and pressure is at or near atmospheric pressure at approximately 5.340 feet (1.628 meters) above sea level. It is noted that work done at external analytical and synthetic facilities is not conducted at or near atmospheric pressure at approximately 5,340 feet (1,628 meters) above sea level. All reagents, unless otherwise indicated, are obtained commercially. Species and other phylogenic identifications are according to the classification known to a person skilled in the art of microbiology.

The names and city addresses of major suppliers are provided herein. In addition, as to Qiagen products, the QIAprep® Spin ("mini prep"). Cat. No. 27106, is used for plasmid DNA purification, and the QIAquick® Gel Extraction Kit. Cat. No. 28706, is used for gel extractions as described herein.

Example 1

General Example of Genetic Modification to a Host Cell

This example is meant to describe a non-limiting approach to genetic modification of a selected microorganism to introduce a nucleic acid sequence of interest. Alternatives and variations are provided within this general example. The methods of this example are conducted to achieve a combination of desired genetic modifications in a selected microorganism species, such as a combination of genetic modifications as described in sections herein, and their functional equivalents, such as in other bacterial and other microorganism species.

A gene or other nucleic acid sequence segment of interest is identified in a particular species (such as *E. coli* as described herein) and a nucleic acid sequence comprising that gene or segment is obtained.

Based on the nucleic acid sequences at the ends of or adjacent the ends of the segment of interest, 5' and 3' nucleic acid primers are prepared. Each primer is designed to have a sufficient overlap section that hybridizes with such ends or adjacent regions. Such primers may include enzyme recognition sites for restriction digest of transposase insertion that could be used for subsequent vector incorporation or genomic insertion. These sites are typically designed to be outward of the hybridizing overlap sections. Numerous contract services are known that prepare primer sequences to order (e.g., Integrated DNA Technologies, Coralville, Iowa USA).

Once primers are designed and prepared, polymerase chain reaction (PCR) is conducted to specifically amplify the desired segment of interest. This method results in multiple copies of the region of interest separated from the microorganism's genome. The microorganism's DNA, the primers, and a thermophilic polymerase are combined in a buffer solution with potassium and divalent cations (e.g., Mg or Mn) and with sufficient quantities of deoxynucleoside triphosphate molecules. This mixture is exposed to a standard regimen of temperature increases and decreases. However, temperatures, components, concentrations, and cycle times may vary according to the reaction according to length of the sequence to be copied, annealing temperature approximations and other factors known or readily learned through routine experimentation by one skilled in the art.

In an alternative embodiment the segment of interest may be synthesized, such as by a commercial vendor, and prepared via PCR, rather than obtaining from a microorganism or other natural source of DNA.

The nucleic acid sequences then are purified and separated, such as on an agarose gel via electrophoresis. Optionally, once the region is purified it can be validated by standard DNA sequencing methodology and may be introduced into a vector. Any of a number of vectors may be used, which generally comprise markers known to those skilled in the art, and standard methodologies are routinely employed for such introduction. Commonly used vector systems are pSMART (Lucigen, Middleton, Wis.), pET *E. coli* EXPRESSION SYSTEM (Stratagene, La Jolla, Calif.), pSC-B StrataClone Vector (Stratagene, La Jolla, Calif.), pRANGER-BTB vectors (Lucigen. Middleton, Wis.), and TOPO vector (Invitrogen Corp, Carlsbad, Calif., USA). Similarly, the vector then is introduced into any of a number of host cells. Commonly used host cells are *E. coli* 10G (Lucigen, Middleton, Wis.). *E. coli* 10GF' (Lucigen, Middleton, Wis.), StrataClone Competent cells (Stratagene, La Jolla, Calif.), *E. coli* BL21, *E. coli* BW25113, and *E. coli* K12 MG1655. Some of these vectors possess promoters, such as inducible promoters, adjacent the region into which the sequence of interest is inserted (such as into a multiple cloning site), while other vectors, such as pSMART vectors (Lucigen, Middleton, Wis.), are provided without promoters and with dephosphorylated blunt ends. The culturing of such plasmid-laden cells permits plasmid replication and thus replication of the segment of interest, which often corresponds to expression of the segment of interest.

Various vector systems comprise a selectable marker, such as an expressible gene encoding a protein needed for growth or survival under defined conditions. Common selectable markers contained on backbone vector sequences include genes that encode for one or more proteins required for antibiotic resistance as well as genes required to complement auxotrophic deficiencies or supply critical nutrients not present or available in a particular culture media. Vectors also comprise a replication system suitable for a host cell of interest.

The plasmids containing the segment of interest can then be isolated by routine methods and are available for introduction into other microorganism host cells of interest. Various methods of introduction are known in the art and can include vector introduction or genomic integration. In various alternative embodiments the DNA segment of interest may be separated from other plasmid DNA if the former will be introduced into a host cell of interest by means other than such plasmid.

While steps of the general prophetic example involve use of plasmids, other vectors known in the art may be used instead. These include cosmids, viruses (e.g., bacteriophage, animal viruses, plant viruses), and artificial chromosomes (e.g., yeast artificial chromosomes (YAC) and bacteria artificial chromosomes (BAC)).

Host cells into which the segment of interest is introduced may be evaluated for performance as to a particular enzymatic step, and/or tolerance or bio-production of a chemical compound of interest. Selections of better performing genetically modified host cells may be made, selecting for overall performance, tolerance, or production or accumulation of the chemical of interest.

It is noted that this procedure may incorporate a nucleic acid sequence for a single gene (or other nucleic acid sequence segment of interest), or multiple genes (under control of separate promoters or a single promoter), and the procedure may be repeated to create the desired heterologous nucleic acid sequences in expression vectors, which are then supplied to a selected microorganism so as to have, for example, a desired complement of enzymatic conversion step functionality for any of the herein-disclosed metabolic pathways. However, it is noted that although many approaches rely on expression via transcription of all or part of the sequence of interest, and then translation of the transcribed mRNA to yield a polypeptide such as an enzyme, certain sequences of interest may exert an effect by means other than such expression.

The specific laboratory methods used for these approaches are well-known in the art and may be found in various references known to those skilled in the art, such as Sambrook and Russell, Molecular Cloning: A Laboratory Manual, Third Edition 2001 (volumes 1-3), Cold Spring Harbor Laboratory Press, Cold Spring Harbor, N.Y. (hereinafter, Sambrook and Russell, 2001).

As an alternative to the above, other genetic modifications may also be practiced, such as a deletion of a nucleic acid sequence of the host cell's genome. One non-limiting method to achieve this is by use of Red/ET recombination, known to those of ordinary skill in the art and described in U.S. Pat. Nos. 6,355,412 and 6,509,156, issued to Stewart et al. and incorporated by reference herein for its teachings of this method. Material and kits for such method are available from Gene Bridges (Gene Bridges GmbH, Dresden, Germany. <<www.genebridges.com>>), and the method may proceed by following the manufacturer's instructions. Targeted deletion of genomic DNA may be practiced to alter a host cell's metabolism so as to reduce or eliminate production of undesired metabolic products. This may be used in combination with other genetic modifications such as described herein in this general example.

Example 2

Utilization of Sucrose as the Feedstock for Production of Fatty Acids and Other Fatty Acid Derived Products Common laboratory and industrial strains of *E. coli*, such as the strains described herein, are not capable of utilizing sucrose as the sole carbon source, although this property is found in a number of wild strains, including pathogenic *E. coli* strains. Sucrose, and sucrose-containing feedstocks such as molasses, are abundant and often used as feedstocks for the production by microbial fermentation of organic acids, amino acids, vitamins, and other products. Thus further derivatives of the fatty acyl-CoA-producing strains that are capable of utilizing sucrose would expand the range of feedstocks that can be utilized to fatty acids and fatty acid derived products.

Various sucrose uptake and metabolism systems are known in the art (for example, U.S. Pat. No. 6,960,455), incorporated by reference for such teachings. We describe the construction of *E. coli* strains that harbor the csc genes conferring the ability to utilize sucrose via a non-phosphotransferase system, wherein the csc genes constitute cscA, encoding a sucrose hydrolase, cscB, encoding a sucrose permease, cscK, encoding a fructokinase, and cscR, encoding a repressor. The sequences of these genes are annotated in the NCBI database as accession No. X81461 AF473544. To allow efficient expression utilizing codons that are highly abundant in *E. coli* genes, an operon containing cscB, cscK, and cscA was designed and synthesized using the services of a commercial synthetic DNA provider (DNA 2.0, Menlo Park. Calif.). The amino acid sequences of the genes are set forth as, respectively, cscB—SEQ. ID. No. 014; cscK—SEQ. ID. No. 015: cscA—SEQ. ID. No. 016. The synthetic operon consisted of 60 base pairs of the region of the *E. coli* genome immediately 5' (upstream) of the aldA gene, a consensus strong promoter to drive expression of the csc genes, the coding regions for cscB, cscK, and cscA with short intergenic regions containing ribosome binding sites but no promoters, and 60 bp immediately 3' (downstream) of the aldA gene. The segments homologous to sequences flanking the aldA gene will be used to target insertion of the csc operon genes into the *E. coli* chromosome, with the concomitant deletion of aldA. The synthetic csc operon is constructed in plasmid pJ214 (DNA 2.0, Menlo Park. Calif.) that provides an origin of replication derived from plasmid p15A and a gene conferring resistance to ampicillin. A suitable host cell, such as *E. coli* strain BX_595, is transformed simultaneously with the above plasmid pTrc_kan_mcr or other suitable plasmid, and transformed strains selected for on LB medium plates containing ampicillin and kanamycin. Transformants carrying both plasmids are grown and evaluated for fatty acid or fatty acid derived product production in shake flasks as described elsewhere, except that the glucose in the medium is replaced with an equal concentration of sucrose.

Genes that confer functions to enable utilization of sucrose by *E. coli* can also be obtained from the natural isolate pUR400 (Cowan, P. J., et al. J. Bacteriol. 173:7464-7470, 1991) which carries genes for the phosphoenolpyruvate-dependent carbohydrate uptake phosphotransferase system (PTS). These genes consist of scrA, encoding the enzyme II component of the PTS transport complex, scrB, encoding sucrose-6 phosphate hydrolase, scrK, encoding fructokinase, and scrY, encoding a porin. These genes may be isolated or synthesized as described above, incorporated on a plasmid, and transformed into a suitable host cell, such as *E. coli* strain BX_845 (Table 3.1), simultaneously with other suitable plasmid, and transformed strains selected for on LB medium plates containing the appropriate antibiotics. Transformants carrying both plasmids are grown and evaluated for fatty acid production in shake flasks, except that the glucose in SM3 medium is replaced with an equal concentration of sucrose.

Example 3

Construction and Evaluation of Fatty Acid Production Strains

Other strains are produced that comprise various combinations of the genetic elements (additions, deletions and modifications) described herein are evaluated for and used for fatty acid production, including commercial-scale production. The following 2 tables illustrate a number of these strains. Table 3.1 provides for the parental genotypes of several genetically modified host strains of *E. coli*, whereas Table 3.2 provides genotypes for specific genetically modified fatty acid producing strains, including those incorporating plasmids for gene overexpression. All of the below described strains were constructed via standard methodologies for plasmid construction and chromosomal modifications as described in the common methods section. The genotype of BW25113 is F-, Δ(araD-araB)567, ΔlacZ4787 (::rrnB-3), LAM-, rph-1, Δ(rhaD-rhaB)568, hsdR514.

TABLE 3.1

| Strains | | |
|---|---|---|
| STRAIN DESIGNATION | PARENT | ADDITIONAL MODIFICATIONS |
| BW25113* | NA | NA |
| BX_845 | BW25113 | ΔldhA::FRT, ΔpflB::FRT, ΔmgsA::FRT, ΔpoxB::FRT, Δpta-ackA::FRT, fabI$^{st}$, ΔfadD::FRT, λDE3; ΔatoDAEB::FRT |
| BX_854 | BW25113 | ΔldhA::FRT, ΔpflB::FRT, ΔmgsA::FRT, ΔpoxB::FRT, Δpta-ack::FRT, fabI$^{st}$, fabB$^{ts}$, ΔfabF:FRT, coaA*, fabD$^{ts}$, ΔlacI::frt, ΔpuuC::P$_{T5}$-aceEF-lpd*::loxP, ΔaceBAK::FRT, lpd*::loxP, ΔaldB:: P$_{yibD}$-T7pol::loxP, ΔadhE::FRT, ΔaldA::CSC, λDE3, ΔfadD::FRT |
| BX_860 | BX_845 | fabB$^{ts}$, ΔfabF::FRT, coaA*, fabD$^{ts}$, ΔlacI::frt, ΔpuuC::T5-aceEF-<br>lpd*::loxP, ΔaceBAK::FRT, lpd*::loxP, ΔaldB::P$_{yibD}$-T7pol::loxP, ΔadhE::FRT, ΔaldA::CSC, Δtig::FRT |
| BX_864 | BX_860 | ΔtesB |
| BX_874 | BX_864 | ΔfadA::FRT |
| BX_875 | BX_864 | ΔfadB::FRT |
| BX_876 | BX_864 | ΔyciA::FRT |
| BX_878 | BX_854 | ΔtesB::FRT |
| BX_879 | BX_845 | fabB$^{ts}$, ΔfabF::FRT, coaA*, fabD$^{ts}$, ΔlacI::FRT, ΔpuuC::PT5-aceEF-lpd*::loxP, ΔaceBAK::FRT, lpd*::loxP, ΔaldB::P$_{yibD}$-T7pol::loxP, ΔadhE::FRT, ΔaldA::CSC, ΔtesB::FRT |
| BX_881 | BX_864 | ΔfadAB::frt |

Lpd* and coaA* denote feedback-resistance variants of the lpd and coaA gene products

TABLE 3.2

| Free fatty Acid Production Strains | | | |
|---|---|---|---|
| STRAIN DESIG-NATION | HOST | PLASMIDS | SEQ ID No.s |
| BXF_0007 | BX_845 | 1) pACYCDuet-1 (empty vector),<br>2) pET-28b (empty vector) | 002<br>001 |
| BXF_0008 | BX_845 | 1) pACYCDuet-1 (empty vector),<br>2) pET-28b-ptb-buk | 002<br>003 |
| BXF_0009 | BX_845 | 1) pACYC_PT7-phaA-hdb-crt-ter<br>2) pET-28b-ptb-buk | 004<br>003 |
| BXF_0010 | BX_845 | 1) pACYC_PT7-nphT7-hdb-crt-ter<br>2) pET-28b-ptb-buk | 013<br>003 |
| BXF_0011 | BX_864 | 1) pET-28-ELO1<br>2) pBMT3-PT7-'tesA_P$_{T7}$-nphT7-hdb-crt-ter | 005<br>006 |
| BXF_0012 | BX_864 | 1) pBMT-3_ccdAB | 007 |
| BXF_0013 | BX_864 | 1) pBMT-3_ccdAB_P$_{T7}$-'tesA | 008 |
| BXF_0014 | BX_864 | 1) pBMT-3_ccdAB_P$_{T7}$-nphT7-hbd-crt-ter | 017 |
| BXF_0015 | BX_864 | 1) pBMT-3_ccdAB_P$_{T7}$-'tesA_PT7-nph$_{T7}$-hbd-crt-ter | 006 |
| BXF_0016 | BX_864 | 1) pBMT-4_ccdAB_P$_{T7}$-'tesA_PT7-nph$_{T7}$-hbd-crt-ter<br>2) pACYC184(empty vector) | 006<br>009 |
| BXF_0017 | BX_864 | 1) pBMT-4_ccdAB_P$_{T7}$-'tesA_PT7-nph$_{T7}$-hbd-crt-ter 2)<br>2) pACYC_PyibD-rbsADBC | 010<br>011 |
| BXF_0018 | BX_864 | 1) pBMT-3_ccdAB_P$_{T7}$-nphT7-hbd-crt-ter<br>2) pET-AtTE | 017<br>012 |
| BXF_0019 | BX_864 | 1) pBMT-3_ccdAB_PT7-'tesA_PT7-nphT7-hbd-crt-ter<br>2) pET-AtTE | 006<br>012 |
| BXF_0020 | BX_860 | 1) pBMT-3_ccdAB_PT7-'tesA_PT7-nphT7-hbd-crt-ter | 006 |
| BXF_0021 | BX_876 | 1) pBMT-3_ccdAB_PT7-'tesA_PT7-nphT7-hbd-crt-ter | 006 |
| BXF_0022 | BX_874 | 1) pBMT-3_ccdAB | 007 |
| BXF_0023 | BX_874 | 1) pBMT-3_ccdAB_PT7-'tesA | 008 |
| BXF_0024 | BX_874 | 1) pBMT-3_ccdAB_PT7-'tesA_PT7-nphT7-hbd-crt-ter | 006 |
| BXF_0025 | BX_875 | 1) pBMT-3_ccdAB | 007 |
| BXF_0026 | BX_875 | 1) pBMT-3_ccdAB_PT7-'tesA | 008 |
| BXF_0027 | BX_875 | 1) pBMT-3_ccdAB_PT7-'tesA_PT7-nphT7-hbd-crt-ter | 006 |
| BXF_0028 | BX_878 | 1) pBMT-3ccdAB_T7-'tesA_PT7-nphT7-hbd-crt-ter | 006 |

TABLE 3.2-continued

| Free fatty Acid Production Strains | | | |
|---|---|---|---|
| STRAIN DESIG-NATION | HOST | PLASMIDS | SEQ ID No.s |
| BXF_0028 | BX_878 | 1) pBMT-3_ccdAB_PT7-'tesA_PT7-nphT7-hbd-crt-ter | 006 |
| BXF_0029 | BX_879 | 1) pBMT-3_ccdAB_PT7-'tesA_PT7-nphT7-hbd-crt-ter | 006 |
| BXF_0030 | BX_881 | 1) pBMT-3_ccdAB_PT7-'tesA_PT7-nphT7-hbd-crt-ter | 006 |
| BXF_0031 | BX_864 | 1) pBMT-3_ccdAB_PT7-'tesA_PT7-nphT7-hbd-crt-ter<br>2) pET-25b (empty vector) | 006<br>001 |
| BXF_0033 | BX_878 | 1) pBMT-3_ccdAB_PT7-nphT7-hbd-crt-ter | 017 |
| BXF_0034 | BX_879 | 1) pBMT-3_ccdAB_PT7-nphT7-hbd-crt-ter | 017 |

Example 4

Genetic Modification to Increase the Production of Malonyl-CoA Dependent Products, Via Fatty Acid Synthesis Inhibition Inhibition of fatty acid synthesis can lead to the removal of feedback inhibition of malonyl-CoA production, leading to increased intracellular malonyl-CoA pools and increased rates of product formation from the intermediate malonyl-CoA. (See e.g., U.K. Patent Number GB2473755. International Patent Application Numbers PCT/US2010/050436 PCT/US2011/022790, which are incorporated herein by reference.) One non-limiting example of the production of malonyl-CoA derived products is as follows: Any of the strains listed in Table 3.1 can be transformed with a vector encoding the controllable expression of a 1,3,6,8-tetrahydroxynaphthalene (THN) synthase enzyme. This can be accomplished via the transformation of the ptrc_THNS plasmid (SEQ ID NO. 018). These strains can then be evaluated in shake flasks for the production of THN or its purple colored oxidation derivative flaviolin. Briefly, overnight starter cultures can be made in 50 mL of Terrific Broth (TB) including the appropriate antibiotics and incubated 16-24 hours are 30° C., while shaking at 225 rpm. These cultures can be used to inoculate 150 mL cultures of each strain in SM11 minimal medium to an $OD_{600}$ of 0.8 and 5% TB culture carryover as starting inoculum, and antibiotics. After 2 hours, IPTG can be added to a final concentration of 0.5 mM IPTG to each flask. The cultures can be grown at 30° C. for approximately another 2 h to an $OD_{600}$ of 1.8-2.0 after 2 h cells are shifted to 37° C. and monitored for up to 72 hours for THN or flaviolin (purple product) formation.

Example 5

Fatty Acid Production Via Malonyl-CoA and Acetyl-CoA Via a Thiolase in Genetically Modified *E. coli*-1

Genetically modified *E. coli* strains were constructed according to the well known methods in the art described in the common methods section. These strains whose genotypes are given in Table 3.1 and 3.2 are listed below in Tables 5.1 and 5.2. Results including the time point of measurement, the concentration (titers g/L) are given in Table 5.1 and 5.2. Strains were evaluated according to one or more shake flask production protocols described in the common methods section. Broth samples were taken at 24, 48 and or 72 hrs post production initiation and evaluated for the production of free fatty acids ranging in chain length from 4 to 18. In Table 5.1 a protocol comparison is shown wherein the temperature of the shake flasks were either maintained constant at 30° C. or shifted according to the protocol to 37° C. This enabled the assessment of the effect of inhibition of normal malonyl-ACP dependent fatty acid synthesis and increased malonyl-CoA pools. (refer to Example 4) In Table 5.2 several other strains were evaluated to better define the genetic requirements for increased fatty acid production.

TABLE 5.1

Assessment of temperature change on the production of FFA > C4

| STRAIN | SHAKE FLASK METHOD | TIME POINT | C4 (G/L) | TITER (G/L) (C6-C18:1) |
|---|---|---|---|---|
| BXF_011, with temperature shift to 37° C. | 3 | 72 hrs | 0.82 +/− .08 | 2.91 +/− 0.17 |
| BXF_011, without temperature shift | 3 | 72 hrs | 0.06 +/− 0.02 | 0.65 +/− 0.09 |

TABLE 5.2

Assessment of genetic requirements for the production of FFA > C4

| Strain | Shake Flask Method | Time Point | C4 (g/L) | Titer (g/L) (C6-C18:1) |
|---|---|---|---|---|
| BXF_029 | 1 | 72 hrs | 1.56 ± 0.18 | 0.26 ± 0.007 |
| BXF_028 | 1 | 72 hrs | 1.44 ± 0.08 | 0.26 ± 0.018 |
| BXF_015 | 1 | 72 hrs | 0.60 ± 0.16 | 1.16 ± 0.48 |
| BXF_037 | 3 | 24 hrs | 1.65 ± 0.174 | 0.484 ± 0.067 |
| BXF_015 | 3 | 24 hrs | 0.165 ± 0.015 | 0.68 ± 0.095 |
| BXF_012 | 1 | 48 hrs | 0 ± 0 | 0.117 ± 0.071 |
| BXF_013 | 1 | 48 hrs | 0 ± 0 | 0.213 ± 0.069 |
| BXF_014 | 1 | 48 hrs | 0.555 ± 0.159 | 0.123 ± 0.019 |
| BXF_015 | 1 | 48 hrs | 0.595 ± 0.009 | 0.376 ± 0.044 |

Example 6

Fatty Acid Production Via Malonyl-CoA Via a Synthase in Genetically Modified *E. coli*-1

Genetically modified *E. coli* strains were constructed. Several of these strains were constructed to evaluate the use of a ketoacyl-CoA synthase or elongase for free fatty acid production. The particular elongase enzyme, ELO1, used in this example is from *Trypanosoma brucei*, a eukaryotic human parasite (Lee et al. Cell 126, 691-699, 2006).

Figure 4:
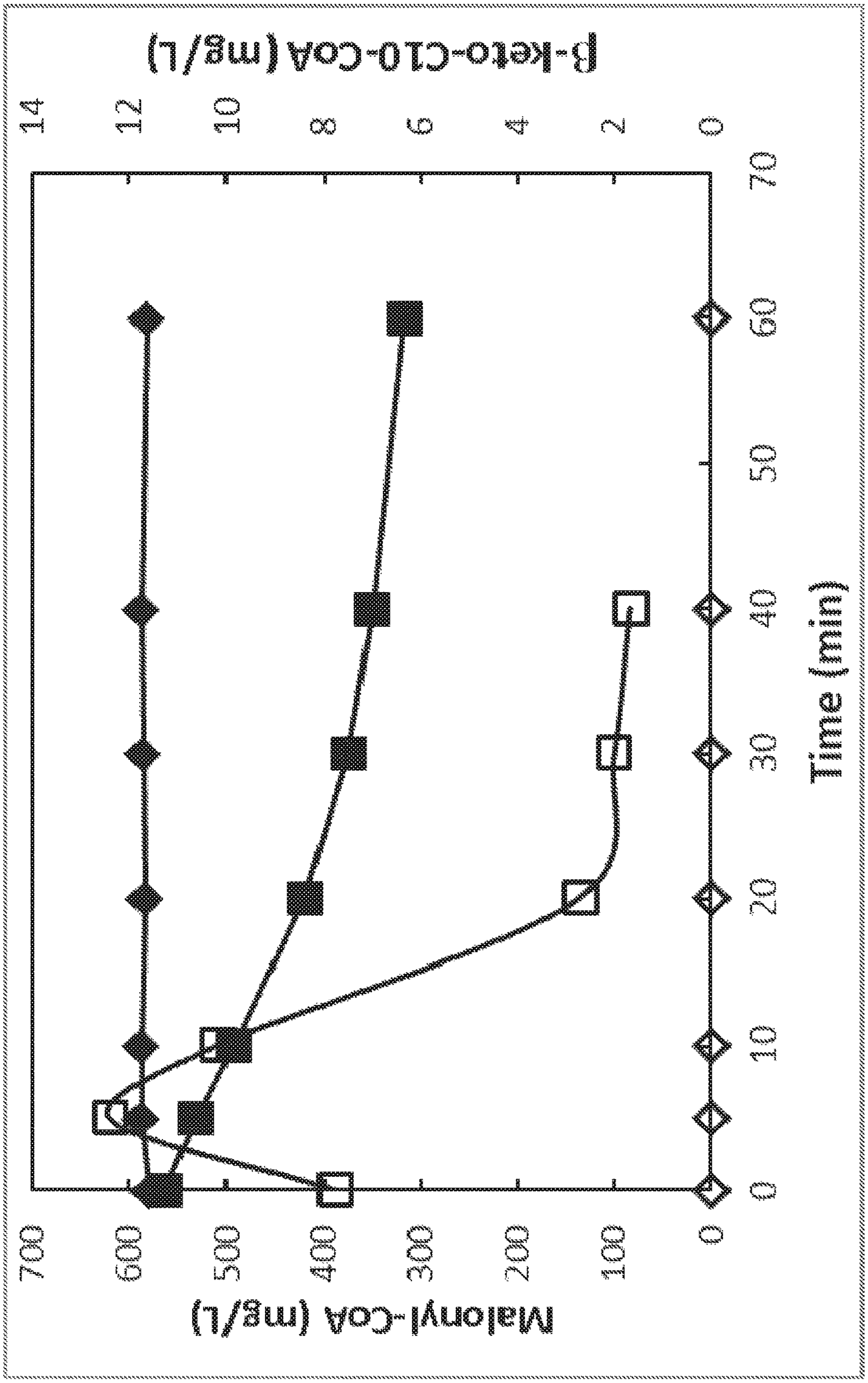
FIG. 4 depicts the activity of the elongase gene ELO1 in *E. coli*

ELO1 (*T. brucei*) was successfully expressed heterologously in *E. coli*. A recombinant ELO1 gene was synthesized using GenScript (Piscataway, N.J.). The synthesized DNA was based on published gene sequence (accession number XM_840948) and codon optimized for expression in *E. coli*. The synthetic ELO1 gene was then sub-cloned into plasmid pET28b (Novagen, SEQ ID 001), generating SEQ ID 005. Total membrane fraction prepared from an *E. coli* strain carrying ELO1 under conditions as described in Method 5 was shown to condense malonyl-CoA with an octanoyl-CoA and produced β-keto-decanoyl-CoA. Specific ELO1 activity was estimated to be 3.4 nmole/min-mg membrane protein, based on malonyl-CoA consumption. Meanwhile, total membrane fraction prepared from an *E. coli* strain without ELO1 neither consumed any malonyl-CoA nor produced β-keto-decanoyl-CoA. Data is shown in FIG. 4. Several strains were constructed to assess the effect of ELO1 activity on free fatty acid production. These strains whose genotypes are given in Table 3.1 and 3.2 are listed below in Table 6.1. Strains were evaluated according to one or more shake flask production protocols described in the common methods section. Broth samples were taken and evaluated for the production of free fatty acids ranging in chain length from 4 to 18. Results including concentration (Titers g/L) as well as percentage of particular chain length of the fatty acid produced are given in Table 6.1. These data also include the rate of FFA accumulation (C6-C18:1) which is based off of 4 datapoints (0, 24, 48, and 72 h).

TABLE 6.1

ELO1 dependent Fatty Acid Production

| Strain | Shake Flask Method | Time Point | Rate (G/L-h) (C6-C18:1) | C4 (g/L) | Titer (g/L) (C6-C18:1) |
|---|---|---|---|---|---|
| BXF_035 | 4 | 72 hrs | 0.003 | 0 ± 0 | 0.35 ± 0.02 |
| BXF_031 | 4 | 72 hrs | 0.009 | 1.7 ± 0.02 | 0.97 ± 0.04 |
| BXF_011 | 4 | 72 hrs | 0.013* | 1.4 ± 0.06 | 1.23 ± 0.08 |

Example 7

Fatty Acid Production Via Malonyl-CoA and Acetyl-CoA Via a Thiolase in Genetically Modified Microorganisms A genetically modified microorganism of the invention can be, for example, *Bacillus subtilis, Cupriavidus necator* (formerly known as *Ralstonia* or *Alcaligenes eutropha*), *Corynebacterium glutamicum, Zymnomonas mobilis, Streptomyces coelicolor, Clostridium acetobutylicum*, or *Pseudomonas putida*. Such microorganisms can serve as bacterial hosts that may be genetically modified to produce free fatty acids. In addition, *Saccharomyces cerevisiae, Schizosaccharomyces pombe, Kluyveromyces marxianus, Yarrowia lipolytica, Aspergillus niger, Pichia pastoris*, and *Issatchenkia orientalis* are exemplary yeasts or fungi that may be genetically modified microorganisms of the invention and can be constructed to produce free fatty acids.

Heterologous genes encoding ELO1, nphT7, hbd, crt, and/or ter can be introduced into these hosts by recombination into the chromosome or as self-replicating plasmids or episomal elements. Alternative synthases, thiolases, 3-keto-acyl-CoA reductases, 3-hydroxy-acyl-CoA dehydratases, and/or enoyl-CoA reductase, may be introduced into these hosts using similar approaches. Genes designed for heterologous expression may be synthesized using codons that are preferentially utilized in the particular host for increased expression efficiency. To maximize production of free fatty acids via malonyl-CoA and acetyl-CoA, certain genetic changes in the hosts are contemplated. These include increasing the availability of malonyl-CoA by increasing the activity of acetyl-CoA carboxylase, and by decreasing the activity of competing pathways such as the acyl carrier protein (ACP)-dependent fatty acid synthesis (FAS) pathway. Conditionally decreasing the activity of the FAS pathway may be accomplished using temperature-sensitive alleles and increasing the growth temperature, using chemical inhibitors, or by regulating expression of the FAS genes. Also of benefit is the elimination of acyl-CoA thioesterase activities on short chain substrates such as butyryl-CoA. This may be accomplished in the genetically modified production hosts by deletion of the specific thioesterase genes identified by homology to, for example the *E. coli* tesB gene product or by enzymatic assays for thioesterase activity in lysates of the host strain, thioesterase enzyme purification, and characterization of the polypeptide using, for example, mass spectrometry. In addition, elimination of the reconsumption of free fatty acids, for example by the β-oxidation pathway, will prevent degradation of the free fatty acid product and will maximize product formation. This may be accomplished in the genetically modified production hosts by deletion of specific fatty acid uptake and degradation functions.

Example 8

Butyrate Production Via Malonyl-CoA in Genetically Modified *E. coli*-1

Genetically modified *E. coli* strains were constructed according to the well known methods in the art described in the common methods section. These strains whose genotypes are given in Table 3.1 and 3.2 are listed below in Table 8.1. Strains were evaluated according to one or more shake flask production protocols described in the common methods section. Broth samples were taken at 24 hrs post production initiation and evaluated for the production of free fatty acids including butyrate ranging in chain length from 4 to 18. Results including concentration (titers g/L) as well as percentage of particular chain length of the fatty acid produced are given in Table 8.1.

TABLE 8.1

| Butyrate Production | | | | |
|---|---|---|---|---|
| Strain | Shake Flask Method | time (h) | C4 (g/L) | % C4 |
| BXF_037 | 3 | 24 | 1.65 ± 0.174 | 84% |
| BXF_029 | 1 | 24 | 1.41 ± 0.0794 | 89% |
| BXF_031 | 4 | 24 | 1.24 ± 0.0304 | 65% |
| BXF_028 | 1 | 24 | 1.22 ± 0.0954 | 89% |
| BXF_015 | 2 | 24 | 0.99 ± 0.0309 | 79% |
| BXF_011 | 2 | 24 | 0.85 ± 0.0152 | 80% |
| BXF_018 | 2 | 24 | 0.68 ± 0.046 | 87% |
| BXF_020 | 1 | 24 | 0.68 ± 0.073 | 61% |
| BXF_011 | 4 | 24 | 0.66 ± 0.044 | 59% |

TABLE 8.1-continued

| Butyrate Production | | | | |
|---|---|---|---|---|
| Strain | Shake Flask Method | time (h) | C4 (g/L) | % C4 |
| BXF_027 | 1 | 24 | 0.56 ± 0.070 | 80% |
| BXF_014 | 1 | 24 | 0.41 ± 0.036 | 83% |
| BXF_019 | 2 | 24 | 0.40 ± 0.040 | 74% |
| BXF_015 | 1 | 24 | 0.34 ± 0.163 | 46% |
| BXF_024 | 1 | 24 | 0.26 ± 0.046 | 42% |
| BXF_021 | 1 | 24 | 0.22 ± 0.006 | 38% |
| BXF_030 | 1 | 24 | 0.21 | 33% |
| BXF_011 | 3 | 24 | 0.20 ± 0.031 | 11% |
| BXF_031 | 3 | 24 | 0.19 ± 0.060 | 10% |
| BXF_015 | 3 | 24 | 0.17 ± 0.015 | 18% |
| BXF_013 | 1 | 24 | 0.00 ± 0 | 0.00 |
| BXF_036 | 3 | 24 | 0.00 ± 0 | 0.00 |
| BXF_012 | 3 | 24 | 0.00 ± 0 | 0.00 |
| BXF_035 | 4 | 24 | 0.00 ± 0 | 0.00 |
| BXF_035 | 3 | 24 | 0.00 ± 0 | 0.00 |

Example 9

Hexanoic Production Via Malonyl-CoA in Genetically Modified *E. coli*-1

Genetically modified *E. coli* strains were constructed according to the well known methods in the art described in the common methods section. These strains whose genotypes are given in Table 3.1 and 3.2 are listed below in Table 9.1. Strains were evaluated according to one or more shake flask production protocols described in the common methods section. Broth samples were taken at 24 hrs post production initiation and evaluated for the production of free fatty acids including butyrate ranging in chain length from 4 to 18. Results including concentration (titers g/L) as well as percentage of particular chain length of the fatty acid produced are given in Table 9.1.

TABLE 9.1

| Hexanoic Acid Production | | | | |
|---|---|---|---|---|
| Strain | Shake Flask Method | time (h) | Mean(C6 (g/L), 48) | Mean(% C6 total, 48) |
| BXF_018 | 2 | 48 | 0.019 ± 0.002 | 1.91% |
| BXF_031 | 4 | 48 | 0.019 ± 0.001 | 0.87% |
| BXF_015 | 2 | 48 | 0.015 ± 0.004 | 0.97% |
| BXF_011 | 3 | 48 | 0.015 ± 0.002 | 0.42% |
| BXF_031 | 3 | 48 | 0.013 ± 0.001 | 0.39% |
| BXF_011 | 4 | 48 | 0.012 ± 0 | 0.75% |
| BXF_011 | 2 | 48 | 0.011 ± 0.001 | 0.76% |
| BXF_019 | 2 | 48 | 0.011 ± 0.001 | 1.20% |
| BXF_021 | 1 | 48 | 0.011 ± 0.001 | 1.39% |
| BXF_029 | 1 | 48 | 0.005 ± 0.001 | 0.32% |
| BXF_015 | 1 | 48 | 0.003 ± 0.003 | 0.33% |
| BXF_014 | 1 | 48 | 0.002 ± 0.003 | 0.28% |
| BXF_013 | 1 | 48 | 0.000 ± 0 | 0.00% |
| BXF_020 | 1 | 48 | 0.000 ± 0 | 0.00% |
| BXF_024 | 1 | 48 | 0.000 ± 0 | 0.00% |
| BXF_027 | 1 | 48 | 0.000 ± 0 | 0.00% |
| BXF_028 | 1 | 48 | 0.000 ± 0 | 0.00% |
| BXF_030 | 1 | 48 | 0.000 ± 0 | 0.00% |
| BXF_036 | 3 | 48 | 0.000 ± 0 | 0.00% |
| BXF_037 | 3 | 48 | 0.000 ± 0 | 0.00% |
| BXF_012 | 3 | 48 | 0.000 ± 0 | 0.00% |
| BXF_015 | 3 | 48 | 0.000 ± 0 | 0.00% |
| BXF_035 | 4 | 48 | 0.000 ± 0 | 0.00% |
| BXF_035 | 3 | 48 | 0.000 ± 0 | 0.00% |

Example 10

Octanoic Production Via Malonyl-CoA in Genetically Modified *E. coli*-1

Genetically modified *E. coli* strains were constructed according to the well known methods in the art described in the common methods section. These strains whose genotypes are given in Table 3.1 and 3.2 are listed below in Table 10.1. Strains were evaluated according to one or more shake flask production protocols described in the common methods section. Broth samples were taken and evaluated for the production of free fatty acids including butyrate ranging in chain length from 4 to 18. Results including concentration (titers g/L) as well as percentage of particular chain length of the fatty acid produced are given in Table 10.1.

TABLE 10.1

Octanoic Acid Production

| Strain | Shake Flask Method | time (h) | C8 (g/L) | % C8 |
|---|---|---|---|---|
| BXF_018 | 2 | 96 | 0.050 ± 0.011 | 19.12% |
| BXF_109 | 2 | 96 | 0.067 ± 0.027 | 10.19% |
| BXF_015 | 2 | 96 | 0.021 ± 0.003 | 1.17% |
| BXF_011 | 2 | 96 | 0.019 ± 0.004 | 2.71% |
| BXF_013 | 1 | 96 | N.D | N.D |
| BXF_014 | 1 | 96 | N.D | N.D |
| BXF_015 | 1 | 96 | N.D | N.D |
| BXF_020 | 1 | 96 | N.D | N.D |
| BXF_021 | 1 | 96 | N.D | N.D |
| BXF_024 | 1 | 96 | N.D | N.D |
| BXF_027 | 1 | 96 | N.D | N.D |
| BXF_028 | 1 | 96 | N.D | N.D |
| BXF_029 | 1 | 96 | N.D | N.D |
| BXF_030 | 1 | 96 | N.D | N.D |
| BXF_031 | 3 | 96 | N.D | N.D |
| BXF_036 | 3 | 96 | N.D | N.D |
| BXF_037 | 3 | 96 | N.D | N.D |
| BXF_011 | 4 | 96 | N.D | N.D |
| BXF_011 | 3 | 96 | N.D | N.D |
| BXF_012 | 3 | 96 | N.D | N.D |
| BXF_015 | 3 | 96 | N.D | N.D |
| BXF_031 | 4 | 96 | N.D | N.D |
| BXF_035 | 4 | 96 | N.D | N.D |
| BXF_035 | 3 | 96 | N.D | N.D |

(N.D.—non determined)

Example 11

Dodecanoic Acid (C12 Fatty Acid) Production Via Malonyl-CoA in Genetically modified *E. coli*-1

Genetically modified *E. coli* strains were constructed according to the well known methods in the art described in the common methods section. These strains whose genotypes are given in Table 3.1 and 3.2 are listed below in Table 11.1. Strains were evaluated according to one or more shake flask production protocols described in the common methods section. Broth samples were taken and evaluated for the production of free fatty acids ranging in chain length from 4 to 18. Results including concentration (titers g/L) as well as percentage of particular chain length of the fatty acid produced are given in Table 11.1.

TABLE 11.1

Dodecanoic Acid Production in *E. coli*

| Strain | Shake flask method | Time point (h) | C12 (g/L) | % C12 |
|---|---|---|---|---|
| BXF_011 | 3 | 48 | 0.108 ± 0.004 | 3.10% |
| BXF_031 | 3 | 48 | 0.093 ± 0.001 | 2.88% |

TABLE 11.1-continued

Dodecanoic Acid Production in *E. coli*

| Strain | Shake flask method | Time point (h) | C12 (g/L) | % C12 |
|---|---|---|---|---|
| BXF_015 | 3 | 48 | 0.038 ± 0.006 | 3.10% |
| BXF_031 | 4 | 48 | 0.038 ± 0.002 | 1.70% |
| BXF_011 | 2 | 48 | 0.029 ± 0.001 | 1.92% |
| BXF_011 | 4 | 48 | 0.029 ± 0.001 | 1.78% |
| BXF_030 | 1 | 48 | 0.028 ± 0.002 | 2.16% |
| BXF_024 | 1 | 48 | 0.024 ± 0.014 | 1.82% |
| BXF_015 | 1 | 48 | 0.023 ± 0.012 | 1.79% |
| BXF_015 | 2 | 48 | 0.021 ± 0.002 | 1.37% |
| BXF_020 | 1 | 48 | 0.017 ± 0.002 | 1.24% |
| BXF_012 | 3 | 48 | 0.013 ± 0.001 | 5.05% |
| BXF_035 | 4 | 48 | 0.013 ± 0.001 | 3.82% |
| BXF_037 | 3 | 48 | 0.011 ± 0.001 | 1.89% |
| BXF_035 | 3 | 48 | 0.011 ± 0.001 | 3.82% |
| BXF_021 | 1 | 48 | 0.011 ± 0.001 | 1.39% |
| BXF_019 | 2 | 48 | 0.010 ± 0 | 1.07% |
| BXF_036 | 3 | 48 | 0.010 ± 0 | 3.83% |
| BXF_027 | 1 | 48 | 0.006 ± 0 | 0.53% |
| BXF_028 | 1 | 48 | 0.006 ± 0 | 0.41% |
| BXF_029 | 1 | 48 | 0.006 ± 0 | 0.36% |
| BXF_013 | 1 | 48 | 0.002 ± 0.003 | 0.75% |
| BXF_014 | 1 | 48 | 0.000 ± 0 | 0.00% |
| BXF_018 | 2 | 48 | 0.000 ± 0 | 0.00% |

Example 12

Myristic Acid (C14 Fatty Acid) Production Via Malonyl-CoA in Genetically Modified *E. coli*-1

Genetically modified *E. coli* strains were constructed according to the well known methods in the art described in the common methods section. These strains whose genotypes are given in Table 3.1 and 3.2 are listed below in Table 12.1. Strains were evaluated according to one or more shake flask production protocols described in the common methods section. Broth samples were taken and evaluated for the production of free fatty acids including butyrate ranging in chain length from 4 to 18. Results including concentration (titers g/L) as well as percentage of particular chain length of the fatty acid produced are given in Table 12.1.

TABLE 12.1

Myristic Acid Production in *E. coli*

| STRAIN | SHAKE FLASK METHOD | TIMEPOINT (h) | C14 (g/L) | % C14 |
|---|---|---|---|---|
| BXF_011 | 3 | 72 | 1.704 ± 0.064 | 35.45% |
| BXF_031 | 3 | 72 | 1.679 ± 0.196 | 35.77% |
| BXF_015 | 1 | 72 | 0.500 ± 0.039 | 28.35% |
| BXF_024 | 1 | 72 | 0.497 ± 0.034 | 25.99% |
| BXF_030 | 1 | 72 | 0.477 ± 0.032 | 23.28% |
| BXF_015 | 3 | 72 | 0.430 ± 0.019 | 31.81% |
| BXF_011 | 4 | 72 | 0.315 ± 0.025 | 11.97% |
| BXF_031 | 4 | 77 | 0.306 ± 0.014 | 11.58% |
| BXF_037 | 3 | 72 | 0.058 ± 0.002 | 8.09% |
| BXF_027 | 1 | 72 | 0.048 ± 0.002 | 3.70% |
| BXF_035 | 3 | 72 | 0.047 ± 0.001 | 16.05% |
| BXF_035 | 4 | 72 | 0.039 ± 0.001 | 10.77% |
| BXF_029 | 1 | 72 | 0.037 ± 0.006 | 1.98% |
| BXF_028 | 1 | 72 | 0.035 ± 0.002 | 2.09% |
| BXF_036 | 3 | 72 | 0.032 ± 0.009 | 9.38% |
| BXF_012 | 3 | 72 | 0.030 ± 0.003 | 11.44% |
| BXF_011 | 2 | 77 | N.D. | N.D. |
| BXF_013 | 1 | 72 | N.D. | N.D. |
| BXF_014 | 1 | 72 | N.D. | N.D. |
| BXF_015 | 2 | 72 | N.D. | N.D. |
| BXF_018 | 7 | 72 | N.D. | N.D. |
| BXF_019 | 2 | 72 | N.D. | N.D. |

TABLE 12.1-continued

| Myristic Acid Production in *E. coli* | | | | |
|---|---|---|---|---|
| STRAIN | SHAKE FLASK METHOD | TIMEPOINT (h) | C14 (g/L) | % C14 |
| BXF_020 | 1 | 72 | N.D. | N.D. |
| BXF_021 | 1 | 72 | N.D. | N.D. |

N.D.—non determined

Example 13

Palmitic (C16:0 Fatty Acid) Production Via Malonyl-CoA in Genetically Modified *E. coli*-1

Genetically modified *E. coli* strains were constructed according to the well known methods in the art described in the common methods section. These strains whose genotypes are given in Table 3.1 and 3.2 are listed below in Table 13.1. Strains were evaluated according to one or more shake flask production protocols described in the common methods section. Broth samples were taken and evaluated for the production of free fatty acids including butyrate ranging in chain length from 4 to 18. Results including concentration (titers g/L) as well as percentage of particular chain length of the fatty acid produced are given in Table 13.1.

TABLE 13.1

| Palmitic Acid Production in *E. coli* | | | | |
|---|---|---|---|---|
| STRAIN | SHAKE FLASK METHOD | TIMEPOINT (h) | C16 (g/L) | % C16 |
| BXF_011 | 3 | 72 | 0.729 ± 0.044 | 15.16% |
| BXF_031 | 3 | 72 | 0.717 ± 0.046 | 15.33% |
| BXF_024 | 1 | 72 | 0.300 ± 0.025 | 15.67% |
| BXF_015 | 3 | 72 | 0.294 ± 0.014 | 21.74% |
| BXF_015 | 1 | 72 | 0.283 ± 0.032 | 15.99% |
| BXF_030 | 1 | 72 | 0.269 ± 0.005 | 13.21% |
| BXF_011 | 4 | 72 | 0.259 ± 0.014 | 9.87% |
| BXF_031 | 4 | 72 | 0.211 ± 0.01 | 8.00% |
| BXF_035 | 4 | 72 | 0.187 ± 0.006 | 51.96% |
| BXF_035 | 3 | 72 | 0.177 ± 0.003 | 61.01% |
| BXF_036 | 3 | 72 | 0.175 ± 0.051 | 51.35% |
| BXF_012 | 3 | 72 | 0.125 ± 0.02 | 47.41% |
| BXF_027 | 1 | 72 | 0.118 ± 0.006 | 9.08% |
| BXF_028 | 1 | 72 | 0.088 ± 0.026 | 5.20% |
| BXF_029 | 1 | 72 | 0.087 ± 0.02 | 4.64% |
| BXF_037 | 3 | 72 | 0.069 ± 0.001 | 9.57% |
| BXF_011 | 2 | 72 | N.D | N.D |
| BXF_013 | 1 | 72 | N.D | N.D |
| BXF_014 | 1 | 72 | N.D | N.D |
| BXF_015 | 2 | 72 | N.D | N.D |
| BXF_018 | 2 | 72 | N.D | N.D |
| BXF_019 | 2 | 72 | N.D | N.D |
| BXF_020 | 1 | 72 | N.D | N.D |
| BXF_021 | 1 | 72 | N.D | N.D |

N.D.—non determined

Example 14

Palmitoleioc (C16:1 Fatty Acid) Production Via Malonyl-CoA in Genetically Modified *E. coli*-1

Genetically modified *E. coli* strains were constructed according to the well known methods in the art described in the common methods section. These strains whose genotypes are given in Table 3.1 and 3.2 are listed below in Table 14.1. Strains were evaluated according to one or more shake flask production protocols described in the common methods section. Broth samples were taken and evaluated for the production of free fatty acids including butyrate ranging in chain length from 4 to 18. Results including concentration (titers g/L) as well as percentage of particular chain length of the fatty acid produced are given in Table 14.1.

TABLE 14.1

| Palmitoleic Acid Production in *E. coli* | | | | |
|---|---|---|---|---|
| Strain | shake flask method | Time point (h) | C16:1 (g/L) | % C16:1 |
| BXF_011 | 3 | 72 | 1.059 ± 0.026 | 22.04% |
| BXF_031 | 3 | 72 | 1.034 ± 0.102 | 22.06% |
| BXF_011 | 4 | 72 | 0.329 ± 0.03 | 12.53% |
| BXF_030 | 1 | 72 | 0.251 ± 0.019 | 12.33% |
| BXF_024 | 1 | 72 | 0.247 ± 0.008 | 12.94% |
| BXF_015 | 3 | 72 | 0.247 ± 0.035 | 18.14% |
| BXF_015 | 1 | 72 | 0.231 ± 0.046 | 13.01% |
| BXF_031 | 4 | 72 | 0.181 ± 0.012 | 6.84% |
| BXF_037 | 3 | 72 | 0.143 ± 0.001 | 20.00% |
| BXF_029 | 1 | 72 | 0.084 ± 0.005 | 4.55% |
| BXF_028 | 1 | 72 | 0.082 ± 0.003 | 4.84% |
| BXF_036 | 3 | 72 | 0.054 ± 0.016 | 15.80% |
| BXF_035 | 4 | 72 | 0.046 ± 0.004 | 12.79% |
| BXF_012 | 3 | 72 | 0.022 ± 0.002 | 8.41% |
| BXF_027 | 1 | 72 | 0.017 ± 0.001 | 1.33% |
| BXF_035 | 3 | 72 | 0.012 ± 0 | 4.13% |
| BXF_011 | 2 | 72 | N.D | N.D |
| BXF_013 | 1 | 72 | N.D | N.D |
| BXF_014 | 1 | 72 | N.D | N.D |
| BXF_015 | 2 | 72 | N.D | N.D |
| BXF_018 | 2 | 72 | N.D | N.D |
| BXF_019 | 2 | 72 | N.D | N.D |
| BXF_020 | 1 | 72 | N.D | N.D |
| BXF_021 | 1 | 72 | N.D | N.D |

N.D.—non determined

Example 15

Oleic and Stearic Acid (C18:1 Fatty Acid) Production Via Malonyl-CoA in Genetically Modified *E. coli*-1

Genetically Modified *E. coli* Strains were constructed according to the well known methods in the art described in the common methods section. These strains whose genotypes are given in Table 3.1 and 3.2 are listed below in Table 15.1. Strains were evaluated according to one or more shake flask production protocols described in the common methods section. Broth samples were taken and evaluated for the production of free fatty acids including butyrate ranging in chain length from 4 to 18. Results including concentration (titers g/L) as well as percentage of particular chain length of the fatty acid produced are given in Table 15.1.

TABLE 15.1

| Oleic Acid Production in *E. coli* | | | | |
|---|---|---|---|---|
| STRAIN | SHAKE FLASK METHOD | TIMEPOINT (h) | C18:1 (g/L) | % C18:1 |
| BXF_031 | 3 | 72 | 0.417 ± 0.045 | 8.94% |
| BXF_011 | 3 | 72 | 0.408 ± 0.026 | 8.48% |
| BXF_011 | 4 | 72 | 0.239 ± 0.012 | 9.08% |
| BXF_031 | 4 | 72 | 0.178 ± 0.002 | 6.74% |
| BXF_015 | 3 | 72 | 0.177 ± 0.018 | 13.04% |
| BXF_024 | 1 | 72 | 0.113 ± 0.006 | 5.89% |
| BXF_015 | 1 | 72 | 0.101 ± 0.023 | 5.68% |
| BXF_030 | 1 | 72 | 0.094 ± 0.01 | 4.65% |
| BXF_035 | 4 | 72 | 0.044 ± 0.003 | 12.23% |
| BXF_029 | 1 | 72 | 0.031 ± 0.006 | 1.65% |
| BXF_037 | 3 | 72 | 0.030 ± 0.002 | 4.18% |
| BXF_036 | 3 | 72 | 0.029 ± 0.006 | 8.49% |
| BXF_012 | 3 | 72 | 0.029 ± 0.003 | 10.95% |
| BXF_028 | 1 | 72 | 0.028 ± 0.002 | 1.65% |
| BXF_035 | 3 | 72 | 0.028 ± 0 | 9.64% |

TABLE 15.1-continued

| Oleic Acid Production in *E. coli* | | | | |
|---|---|---|---|---|
| STRAIN | SHAKE FLASK METHOD | TIMEPOINT (h) | C18:1 (g/L) | % C18:1 |
| BXF_027 | 1 | 72 | 0.027 ± 0.001 | 2.10% |
| BXF_011 | 2 | 72 | N.D. | N.D. |
| BXF_013 | 1 | 72 | N.D. | N.D. |
| BXF_014 | 1 | 72 | N.D. | N.D. |
| BXF_015 | 2 | 72 | N.D. | N.D. |
| BXF_018 | 2 | 72 | N.D. | N.D. |
| BXF_019 | 2 | 72 | N.D. | N.D. |
| BXF_020 | 1 | 72 | N.D. | N.D. |
| BXF_021 | 1 | 72 | N.D. | N.D. |

N.D.—non determined

Example 16

Altering Chain Length Specificity of Fatty Acid Production in Genetically Modified *E. coli*-1

The distribution of free fatty acid product chain length is determined by the combination of synthetic and release activities. Synthetic activities such as that catalyzed by elongase have product chain length preferences, such that the *T. brucei* ELO1 produces C10-CoA product and ELO2 produces C14-CoA product (Lee, et al., 2006; Cell 126:691-699; Denic and Weissman, 2007, Cell 130:663-677). The immediate product of the ELO1 reaction is 3-keto-hexanoyl-CoA. The successive actions of a keto-acyl-CoA reductase (KCR), 3-hydroxy-acyl-CoA dehydratase (3HDh), and an enoyl-CoA reductase (ECR) generate hexanoyl-CoA which serves as primer for the subsequent elongation by 2-carbon units from malonyl-CoA. Chain length specificity of these activities also determines the distribution of the final products and may be engineered to preferentially generate a product of desired and specified chain length.

Thioesterases catalyze the hydrolysis of acyl-CoAs or acyl-ACPs to the free fatty acids and coenzyme A or ACP, respectively, thus releasing the free fatty acid product. A large number of thioesterases from diverse sources are known and their chain length specificities for acyl-ACP substrates has been documented (e.g. Jing et al. 2011. BMC Biochemistry 12: 1-16). We have expressed and assayed a number of thioesterases to determine their chain length specificities on acyl-CoA substrates. Thioesterase activities and chain length preferences for these proteins were determined by expressing these proteins in *E. coli* as described in Common Methods. Lysates were prepared by extrusion of the cells through a Microfluidizer and the lysates were de-salted using G-25 Spin Columns (GE 27-5325-01), 200-μl assays contained 7 mM Potassium Phosphate, pH 8.0, 20% (v/v) glycerol, 0.04% Triton X100, 0.10 mM DTNB (5,5'-Dithiobis-(2-nitrobenzoic acid), Sigma D8130, 25 mM in ETOH), 0.40 mM acyl-CoA substrate, and the reaction initiated with addition of G-25 purified lysate. Formation of the 5-thio-2-nitrobenzoic acid (TNB) product was monitored kinetically at 412 nm, and the results tabulated in Table 16.1.

TABLE 16.1

| Specific Activities (U/mg) of Thioesterases in Lysates | | | | | | | | |
|---|---|---|---|---|---|---|---|---|
| SOURCE | ACCESSION NUMBER | C4 | C6 | C8 | C10 | C12 | C14 | C16 |
| *Cuphea palustris* | AAC49179 | 0.03 | 0.05 | 0.05 | 0.06 | 0.10 | 0.10 | 0.06 |
| *Anaerococcus tetradius* | EEI82564 | 0.02 | 0.03 | 0.08 | 0.10 | 0.09 | 0.10 | not tested |
| *E. coli* YciA | | 1.05 | 2.87 | 4.54 | 2.22 | 2.69 | 2.64 | not tested |
| *E. coli* tesB | | 1.24 | 2.78 | 2.61 | 3.44 | 5.39 | 4.73 | 3.59 |
| *E. coli* tesA (soluble) | | 0.00 | 0.00 | 0.00 | 0.06 | 0.74 | 1.21 | 0.81 |
| *E. coli* YbgC | | 0.16 | 0.05 | 0.04 | 0.10 | 0.20 | 0.17 | not tested |
| *E. coli* YbfF | | 0.06 | 0.05 | 0.09 | 0.08 | 0.34 | 0.24 | not tested |

As shown in Table 16.1, these thioesterases exhibit different and marked chain length preferences. AtTE prefers short chain acyl-CoA substrates starting with C8-CoA, whereas soluble 'tesA is most active on C12 and longer substrates. Additional thioesterase genes and gene products may be evaluated in a similar manner. Potential genes include thioesterase from *Ulmus americana* (AAB71731), *Lactobacillus plantarum* (CAD63310), *Lactobacillus brevis* (ABJ63754), *Clostridium perfringens* (ABG82470). *Pseudomonas aeruginosa* (PA2801), among others. Chain length specificities for acyl-CoA may be altered by the application of protein engineering or directed evolution techniques to generate variants which have higher preferences for a particular chain length. For example, thioesterase-encoding genes may be shuffled (Stemmer, 1994, Proc. Natl. Acad., Sci. USA 91:10747-10751) to generate a library of variants. Isolation of a variant with increased activity towards a particular chain length acyl-CoA is achieved by screening for activity towards that particular chain length acyl-CoA, and for decreased activity towards acyl-CoAs of undesired chain lengths.

Example 17

Improvement of Fatty Acid or Fatty Acid Derived Product Bio-Production in *B. licheniformis*

Most of the plasmids and shuttle vectors that replicate in *B. subtilis* are used to transform *B. licheniformis* by either protoplast transformation or electroporation. The nucleic acid sequences required for free fatty acid biosynthesis are isolated from various sources, codon optimized as appropriate, and cloned in plasmids pBE20 or pBE60 derivatives (Nagarajan et al., Gene 114:121-126 (1992)). Methods to transform *B. licheniformis* are known in the art (for example see Fleming et al. Appl. Environ. Microbiol., 61(11):3775-3780 (1995)). These published resources are incorporated by reference for their respective indicated teachings and compositions. The plasmids constructed for expression of heterologous enzymes in *B. subtilis* are transformed into *B.*

*licheniformis* to produce a recombinant microorganism that then demonstrates improved of fatty acid or fatty acid derived product production.

Example 18

Improvement of Fatty Acid or Fatty Acid Derived Product Bio-Production in *Paenibacillus macerans*

Plasmids are constructed as described herein for expression of heterologous enzymes in *B. subtilis* and used to transform *Paenibacillus macerans* by protoplast transformation to produce a recombinant microorganism that demonstrates improved of fatty acid or fatty acid derived product production.

Example 19

Improvement of Fatty Acid or Fatty Acid Derived Product Bio-Production in *Alcaligenes* (*Ralstonia*) *eutrophus* (Currently Referred to as *Cupriavidus necator*)

Methods for gene expression and creation of mutations in *Alcaligenes eutrophus* are known in the art (see for example Taghavi et al., Appl. Environ. Microbiol., 60(10):3585-3591 (1994)). This published resource is incorporated by reference for its indicated teachings and compositions. Any of the nucleic acid sequences identified to improve fatty acid biosynthesis are isolated from various sources, codon optimized as appropriate, and cloned in any of the broad host range vectors described herein, and electroporated to generate recombinant microorganisms that demonstrate improved of fatty acid or fatty acid derived product production. Importantly, using *C. necator* strains, fatty acid or fatty acid derived products can be produced from carbon dioxide and hydrogen as the sole sources of carbon and reducing equivalents as this microorganism can grow chemolithotrophically.

Example 20

Improvement of Fatty Acid or Fatty Acid Derived Product Bio-Production in *Pseudomonas putida*

Methods for gene expression in *Pseudomonas putida* are known in the art (see for example Ben-Bassat et al., U.S. Pat. No. 6,586,229, which is incorporated herein by reference for these teachings). Any of the nucleic acid sequences identified to improve fatty acid or fatty acid derived product biosynthesis are isolated from various sources, codon optimized as appropriate, and cloned in any of the broad host range vectors described herein, and electroporated to generate recombinant microorganisms that demonstrate fatty acid or fatty acid derived product biosynthetic production. For example, these nucleic acid sequences are inserted into pUCP18 and this ligated DNA are electroporated into electrocompetent *Pseudomonas putida* KT2440 cells to generate recombinant *P. putida* microorganisms that exhibit increased fatty acid or fatty acid derived product formation.

Example 21

Improvement of Fatty Acid or Fatty Acid Derived Product Bio-Production in *Lactobacillus plantarum*

The *Lactobacillus* genus belongs to the Lactobacillales family and many plasmids and vectors used in the transformation of *Bacillus subtilis* and *Streptococcus* are used for *Lactobacillus*. Non-limiting examples of suitable vectors include pAM.beta.1 and derivatives thereof (Renault et al., Gene 183:175-182 (1996); and O'Sullivan et al., Gene 137:227-231 (1993)); pMBB1 and pHW800, a derivative of pMBB1 (Wyckoff et al. Appl. Environ. Microbiol 62:1481-1486 (1996)); pMG1, a conjugative plasmid (Tanimoto et al., J. Bacteriol. 184:5800-5804 (2002)); pNZ9520 (Kleerebezem et al., Appl. Environ. Microbiol. 63:4581-4584 (1997)); pAM401 (Fujimoto et al., Appl. Environ. Microbiol. 67:1262-1267 (2001)); and pAT392 (Arthur et al., Antimicrob. Agents Chemother. 38:1899-1903 (1994)). Several plasmids from *Lactobacillus plantarum* have also been reported (e.g., van Kranenburg R. Golic N. Bongers R. Leer R J, de Vos W M, Siezen R J. Kleerebezem M. Appl. Environ. Microbiol. 2005 March; 71(3): 1223-1230). Any of the nucleic acid sequences identified to improve fatty acid or fatty acid derived product biosynthesis are isolated from various sources, codon optimized as appropriate, and cloned in any of the vectors described herein, and introduced to generate recombinant microorganisms that demonstrate fatty acid or fatty acid derived product biosynthetic production.

Example 22

Production of Fatty Alcohols

Production strains making fatty acids may also be used to produce fatty alcohols by expressing genes encoding enzymes that convert fatty acyl-CoA or free fatty acids to fatty alcohols. Examples of these enzymes include an alcohol-forming acyl-CoA reductase (EC 1.2.1.-), or a long-chain-fatty-acyl-CoA reductase (EC 1.2.1.50) plus an alcohol dehydrogenase (EC 1.1.1.1), or a combination of an aldehyde dehydrogenase (EC 1.2.1.-) and an alcohol dehydrogenase. A polypeptide with fatty acyl-CoA reductase activity is provided by the fabG gene of *Acinetobacter* SP. ADP1, accession number YP_047869. A polypeptide with fatty-acyl reductase activity is provided by the FAR-N_SDR_e gene of *Bombyx mori*, accession number BAC79425. A polypeptide with aldehyde dehydrogenase is provided by the ALDH gene of *Geobacillus thermodenitrificans* NG80-2, accession number YP_001125970. A polypeptide with alcohol dehydrogenase activity is provided by the yqhD gene of *E. coli*, accession number AP_003562.1. Additional sources of these activities are known to the art and can be combined to generate a production strain that produces fatty alcohols.

IV. Common Methods Section

All methods in this Section are provided for incorporation into the Examples where so referenced.

Subsection A. Microorganism Species and Strains, Cultures, and Growth Media

Bacterial species, that may be utilized as needed, are as follows:

*Acinetobacter calcoaceticus* (DSMZ #1139) is obtained from the German Collection of Microorganisms and Cell Cultures (Braunschweig. Germany) as a vacuum dried culture. Cultures are then resuspended in Brain Heart Infusion (BHI) Broth (RPI Corp, Mt. Prospect, Ill., USA). Serial dilutions of the resuspended *A. calcoaceticus* culture are made into BHI and are allowed to grow for aerobically for 48 hours at 37° C. at 250 rpm until saturated.

*Bacillus subtilis* is a gift from the Gill lab (University of Colorado at Boulder) and is obtained as an actively growing culture. Serial dilutions of the actively growing *B. subtilis* culture are made into Luria Broth (RPI Corp, Mt. Prospect, Ill., USA) and are allowed to grow for aerobically for 24 hours at 37° C. at 250 rpm until saturated.

*Chlorobium limicola* (DSMZ#245) is obtained from the German Collection of Microorganisms and Cell Cultures (Braunschweig. Germany) as a vacuum dried culture. Cultures are then resuspended using Pfennig's Medium I and II (#28 and 29) as described per DSMZ instructions. *C. limicola* is grown at 25° C. under constant vortexing.

*Citrobacter braakii* (DSMZ #30040) is obtained from the German Collection of Microorganisms and Cell Cultures (Braunschweig, Germany) as a vacuum dried culture. Cultures are then resuspended in Brain Heart Infusion (BHI) Broth (RPI Corp. Mt. Prospect. Ill. USA). Serial dilutions of the resuspended *C. braakii* culture are made into BHI and are allowed to grow for aerobically for 48 hours at 30° C. at 250 rpm until saturated.

*Clostridium acetobutylicum* (DSMZ #792) is obtained from the German Collection of Microorganisms and Cell Cultures (Braunschweig. Germany) as a vacuum dried culture. Cultures are then resuspended in *Clostridium acetobutylicum* medium (#411) as described per DSMZ instructions. *C. acetobutylicum* is grown anaerobically at 37° C. at 250 rpm until saturated.

*Clostridium aminobutyricum* (DSMZ #2634) is obtained from the German Collection of Microorganisms and Cell Cultures (Braunschweig. Germany) as a vacuum dried culture. Cultures are then resuspended in *Clostridium aminobutyricum* medium (#286) as described per DSMZ instructions. *C. aminobutyricum* is grown anaerobically at 37° C. at 250 rpm until saturated.

*Clostridium kluyveri* (DSMZ #555) is obtained from the German Collection of Microorganisms and Cell Cultures (Braunschweig. Germany) as an actively growing culture. Serial dilutions of *C. kluyveri* culture are made into *Clostridium kluyveri* medium (#286) as described per DSMZ instructions. *C. kluyveri* is grown anaerobically at 37° C. at 250 rpm until saturated.

*Cupriavidus metallidurans* (DMSZ #2839) is obtained from the German Collection of Microorganisms and Cell Cultures (Braunschweig. Germany) as a vacuum dried culture. Cultures are then resuspended in Brain Heart Infusion (BHI) Broth (RPI Corp, Mt. Prospect. Ill. USA). Serial dilutions of the resuspended *C. metallidurans* culture are made into BHI and are allowed to grow for aerobically for 48 hours at 30° C. at 250 rpm until saturated.

*Cupriavidus necator* (DSMZ #428) is obtained from the German Collection of Microorganisms and Cell Cultures (Braunschweig. Germany) as a vacuum dried culture. Cultures are then resuspended in Brain Heart Infusion (BHI) Broth (RPI Corp. Mt. Prospect. Ill., USA). Serial dilutions of the resuspended *C. necator* culture are made into BHI and are allowed to grow for aerobically for 48 hours at 30° C. at 250 rpm until saturated. As noted elsewhere, previous names for this species are *Alcaligenes eutrophus* and *Ralstonia eutrophus.*

*Desulfovibrio fructosovorans* (DSMZ #3604) is obtained from the German Collection of Microorganisms and Cell Cultures (Braunschweig, Germany) as a vacuum dried culture. Cultures are then resuspended in *Desulfovibrio fructosovorans* medium (#63) as described per DSMZ instructions. *D. fructosovorans* is grown anaerobically at 37° C. at 250 rpm until saturated.

*Escherichia coli* Crooks (DSMZ#1576) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill. USA). Serial dilutions of the resuspended *E. coli* Crooks culture are made into BHI and are allowed to grow for aerobically for 48 hours at 37° C. at 250 rpm until saturated.

*Escherichia coli* K12 is a gift from the Gill lab (University of Colorado at Boulder) and is obtained as an actively growing culture. Serial dilutions of the actively growing *E. coli* K12 culture are made into Luria Broth (RPI Corp, Mt. Prospect, Ill., USA) and are allowed to grow for aerobically for 24 hours at 37° C. at 250 rpm until saturated.

*Halobacterium salinarum* (DSMZ#1576) is obtained from the German Collection of Microorganisms and Cell Cultures (Braunschweig. Germany) as a vacuum dried culture. Cultures are then resuspended in *Halobacterium* medium (#97) as described per DSMZ instructions. *H. salinarum* is grown aerobically at 37° C. at 250 rpm until saturated.

*Lactobacillus delbrueckii* (#4335) is obtained from WYEAST USA (Odell, Oreg., USA) as an actively growing culture. Serial dilutions of the actively growing *L. delbrueckii* culture are made into Brain Heart Infusion (BHI) broth (RPI Corp. Mt. Prospect. Ill. USA) and are allowed to grow for aerobically for 24 hours at 30° C. at 250 rpm until saturated.

*Metallosphaera sedula* (DSMZ #5348) is obtained from the German Collection of Microorganisms and Cell Cultures (Braunschweig. Germany) as an actively growing culture. Serial dilutions of *M. sedula* culture are made into *Metallosphaera* medium (#485) as described per DSMZ instructions. *M. sedula* is grown aerobically at 65° C. at 250 rpm until saturated.

*Propionibacterium freudenreichii* subsp. *shermanii* (DSMZ#4902) is obtained from the German Collection of Microorganisms and Cell Cultures (Braunschweig, Germany) as a vacuum dried culture. Cultures are then resuspended in PYG-medium (#104) as described per DSMZ instructions. *P. freudenreichii* subsp. *shermanii* is grown anaerobically at 30° C. at 250 rpm until saturated.

*Pseudomonas putida* is a gift from the Gill lab (University of Colorado at Boulder) and is obtained as an actively growing culture. Serial dilutions of the actively growing *P. putida* culture are made into Luria Broth (RPI Corp, Mt. Prospect, Ill. USA) and are allowed to grow for aerobically for 24 hours at 37° C. at 250 rpm until saturated.

*Streptococcus mutans* (DSMZ#6178) is obtained from the German Collection of Microorganisms and Cell Cultures (Braunschweig, Germany) as a vacuum dried culture. Cultures are then resuspended in Luria Broth (RPI Corp, Mt. Prospect, Ill., USA). *S. mutans* is grown aerobically at 37° C. at 250 rpm until saturated.

The following non-limiting strains may also be used as starting strains in the Examples: DF40 [Hfr(PO2A), garB10, fhuA22, ompF627(T2R), fadL701(T2R), relA1, pitA10, spoT1, rrnB-2, pgi-2, mcrB1, creC510], BW25113 [F-, Δ(araD-araB)567, ΔlacZ4787(::rrnB-3), &lambda-, rph-1. Δ(rhaD-rhaB)568, hsdR514]. JP111 [Hfr(PO1), galE45 (GalS), $fabI^{ts}$, relA1, spoT1, thi-1]. These strains possess recognized genetic modifications, and are available from public culture sources such as the Yale Coli Genetic Stock Collection (New Haven, Conn. USA). Strains developed from these strains are described in the Examples.

Common laboratory media include commercially prepared media such as Luria Bertani (LB) broth, Terrific Broth (TB), and M9 minimal media. The contents of SM11 medium are (per 1000 mL):

2 mL FM10 Trace Mineral Stock
2.26 mL 1M $MgSO_4$
30 g glucose
200 mM MOPS (pH 7.4)

1 g/L yeast extract
1.25 mL VM1 Vitamin Mix
0.329 g $K_2HPO_4$
0.173 g $KH_2PO_4$
3 g $(NH_4)_2SO_4$
0.15 g citric acid (anhydrous)

FM10 Trace Mineral Stock consists of:
1 mL of concentrated HCl
4.9 g $CaCl_2*2H_2O$
0.97 g $FeCl_3*6H_2O$
0.04 g $CoCl_2*6H_2O$
0.27 g $CuCl_2*2H_2O$
0.02 g ZnCl2
0.024 g $Na_2MoO_4*2H_2O$
0.007 g $H_3BO_3$
0.036 g $MnCl_2*4H_2O$
Q.S. with DI water to 100 mL VM1 Vitamin Mix Solution consists of:
5 g Thiamine
5.4 g Pantothenic acid
6.0 g Niacin
0.06 g
Q.S. with DI water to 1000 mL Subsection B: Gel Preparation, DNA Separation, Extraction, Ligation, and Transformation Methods Molecular biology grade agarose (RPI Corp. Mt. Prospect. Ill. USA) is added to 1×TAE to make a 1% Agarose in TAE. To obtain 50×TAE add the following to 900 mL distilled $H_2O$: 242 g Tris base (RPI Corp, Mt. Prospect, Ill., USA), 57.1 mL Glacial Acetic Acid (Sigma-Aldrich, St. Louis. Mo., USA), 18.6 g EDTA (Fisher Scientific, Pittsburgh, Pa. USA), and adjust volume to 1 L with additional distilled water. To obtain 1×TAE, add 20 mL of 50×TAE to 980 mL of distilled water. The agarose-TAE solution is then heated until boiling occurred and the agarose is fully dissolved. The solution is allowed to cool to 50° C. before 10 mg/mL ethidium bromide (Acros Organics, Morris Plains, N.J., USA) is added at a concentration of 5 μl per 100 mL of 1% agarose solution. Once the ethidium bromide is added, the solution is briefly mixed and poured into a gel casting tray with the appropriate number of combs (Idea Scientific Co., Minneapolis, Minn., USA) per sample analysis. DNA samples are then mixed accordingly with 5×TAE loading buffer, 5×TAE loading buffer consists of 5×TAE (diluted from 50×TAE as described herein), 20% glycerol (Acros Organics, Morris Plains, N.J., USA), 0.125% Bromophenol Blue (Alfa Aesar, Ward Hill. Mass. USA), and adjust volume to 50 mL with distilled water. Loaded gels are then run in gel rigs (Idea Scientific Co., Minneapolis, Minn., USA) filled with 1×TAE at a constant voltage of 125 volts for 25-30 minutes. At this point, the gels are removed from the gel boxes with voltage and visualized under a UV transilluminator (FOTODYNE Inc., Hartland, Wis., USA).

The DNA isolated through gel extraction is then extracted using the QIAquick Gel Extraction Kit following manufacturer's instructions (Qiagen (Valencia Calif. USA)). Similar methods are known to those skilled in the art.

Plasmid construction was carried out using either restriction enzyme/ligation methodologies known to those skilled in the art or homologous recombination methods such as Gibson Assembly (New England BioLabs Inc., Ipswich, Mass. USA) or GeneArt Seamless Cloning (Invitrogen Inc., Carlsbad, Calif. USA)

General Transformation and Related Culture Methodologies:

Chemically competent transformation protocols are carried out according to the manufacturer's instructions or according to the literature contained in *Molecular Cloning* (Sambrook and Russell, 2001). Generally, plasmid DNA or ligation products are chilled on ice for 5 to 30 min. in solution with chemically competent cells. Chemically competent cells are a widely used product in the field of biotechnology and are available from multiple vendors, such as those indicated in this Subsection. Following the chilling period cells generally are heat-shocked for 30 seconds at 42° C. without shaking, re-chilled and combined with 250 microliters of rich media, such as S.O.C. Cells are then incubated at 37° C. while shaking at 250 rpm for 1 hour. Finally, the cells are screened for successful transformations by plating on media containing the appropriate antibiotics.

Alternatively, selected cells may be transformed by electroporation methods such as are known to those skilled in the art.

Genetic manipulation in the chromosome of *E. coli* was achieved using Lambda-Red recombinase technology known to those skilled in the art (Datsenko and Wanner, 2000 and Gene Bridges GmbH, Dresden, Germany). This included gene deletions, insertions and mutations.

Plasmid construction was carried out using either restriction enzyme/ligation methodologies known to those skilled in the art or homologous recombination methods such as Gibson Assembly (New England Biolabs Inc. Ipswich. Mass. USA) or GeneArt Seamless Cloning (Invitrogen Inc. Carlsbad, Calif. USA) according to manufacturer's instructions.

The choice of an *E. coli* host strain for plasmid transformation is determined by considering factors such as plasmid stability, plasmid compatibility, plasmid screening methods and protein expression. Strain backgrounds can be changed by simply purifying plasmid DNA as described herein and transforming the plasmid into a desired or otherwise appropriate *E. coli* host strain such as determined by experimental necessities, such as any commonly used cloning strain (e.g., DH5α, Top10F', *E. coli* 10G, etc.).

Plasmid DNA was prepared using the commercial miniprep kits from Qiagen (Valencia, Calif. USA) according to manufacturer's instructions.

The embodiments, variations, sequences, and figures described herein should provide an indication of the utility and versatility of the present invention. Other embodiments that do not provide all of the features and advantages set forth herein may also be utilized, without departing from the spirit and scope of the present invention. Such modifications and variations are considered to be within the scope of the invention.

Subsection C. Shake Flask Strain Evaluation Protocols

Shake Flask Method 1:

Strains were evaluated in shake flasks for the production of free fatty acids (FFA). Triplicate evaluations were performed. Briefly, overnight starter cultures were made in 50 mL of Terrific Broth including the appropriate antibiotics and incubated 16-24 hours at 30° C., while shaking at 225 rpm. These cultures were used to inoculate 150 mL cultures of each strain in SM11 minimal medium to an $OD_{600}$ of 0.8 and 5% TB culture carryover as starting inoculum, and antibiotics. Cultures were incubated for 2 hours at 30° C., while shaking at 225 rpm. After 2 hours, the cells were washed with SM11 (no phosphate). Cells were twice spun down (4,000 rpm, 15 min), the supernatant decanted, the pellet re-suspended in 150 ml of SM11 (no phosphate). The cultures were used to inoculate 3×50 mL of each strain in SM11 (no phosphate). The cultures were grown at 30° C. for approximately 2 h to an $OD_{600}$ of 1.0-1.5 after 2 h cells and shifted to 37° C. and samples removed periodically for fatty acid measurement over the course of 72 hrs.

Shake Flask Method 2:

Strains were evaluated in shake flasks for the production of FFA. Triplicate evaluations are performed. Briefly, overnight starter cultures were made in 50 mL of Terrific Broth including the appropriate antibiotics and incubated 16-24 hours are 30° C., while shaking at 225 rpm. These cultures were used to inoculate 150 mL cultures of each strain in SM11 minimal medium to an $OD_{600}$ of 0.8 and 5% TB culture carryover as starting inoculum, and antibiotics. After 2 hours, the cells were washed with SM11 (no phosphate). Cells were twice spun down (4,000 rpm, 15 min), the supernatant decanted, the pellet re-suspended in 150 ml of SM11 (no phosphate). The cultures were used to inoculate 3×50 mL of each strain in SM11 (no phosphate) and 0.5 mM IPTG was added to each. The cultures were grown at 30° C. for approximately 2 hr to an $OD_{600}$ of 1.8-2.0 after which the cultures are shifted to 37° C. and samples removed periodically for fatty acid measurement over the course of 72 hrs.

Shake Flask Method 3:

Strains were evaluated in shake flasks for the production of FFA. Triplicate evaluations were performed. Briefly, overnight starter cultures were made in 50 mL of Terrific Broth including the appropriate antibiotics and incubated 16-24 hours are 30° C., while shaking at 225 rpm. These cultures were used to inoculate 300 mL cultures of each strain in Terrific Broth medium to an $OD_{600}$ of 0.8 and 5% TB culture carryover as starting inoculum, and antibiotics. Cultures were incubated for 4-6 hours at 30° C., while shaking at 225 rpm until they reached an $OD_{600}$ of 1.8-2.0. After 4-6 hours, the cells were washed with SM11 (no phosphate). Cells were twice spun down (4.000 rpm, 15 min), the supernatant decanted, the pellet re-suspended in 300 ml of SM11 (no phosphate). The cultures were used to inoculate 3×100 mL of each strain in SM11 (no phosphate). The cultures were grown at 25° C. for approximately 16 hr and are then shifted to 37° C. and samples removed periodically for fatty acid measurement over the course of 72 hours.

Shake Flask Method 4:

Strains were evaluated in shake flasks for the production of FFA. Triplicate evaluations were performed. Briefly, overnight starter cultures were made in 50 mL of Terrific Broth including the appropriate antibiotics and incubated 16-24 hours are 30° C. while shaking at 225 rpm. These cultures were used to inoculate 300 mL cultures of each strain in Terrific Broth medium to an $OD_{600}$ of 0.8 and 5% TB culture carryover as starting inoculum, and antibiotics. Cultures were incubated for 4-6 hours at 30° C., while shaking at 225 rpm until they reached an $OD_{600}$ of 1.8-2.0. After 4-6 hours, the cells were washed with SM11 (no phosphate). Cells are twice spun down (4,000 rpm, 15 min), the supernatant decanted, the pellet re-suspended in 300 mL of SM11 (no phosphate). The cultures were used to inoculate 3×100 mL of each strain in SM11 (no phosphate) and 0.5 mM IPTG was added to each. The cultures were grown at 25° C. for approximately 16 hr and are then shifted to 37° C. and samples removed periodically for fatty acid measurement over the course of 72 hrs.

Subsection D. Analyte Quantification Protocols

Quantitation of fatty acids was performed by esterifying the fatty acids in the fermentation media to make methyl esters (FAME) before analysis by gas chromatography using a Stabilwax column. The esterification was with methanol in hydrochloric acid at 100° C. for 2 hours. The FAMEs were separated on the GC column and detected by flame ionization detection (FID). FAMEs were quantified using a standard curve of each component at the beginning of the run. Data are reported in amount (mg) of each FAME in the media.

Solvents and Buffers

Methyl esterification solution (83% Methanol/8.3% hydrochloric acid/8.3% chloroform) is made by: Add 100 mL methanol to 100 mL glass bottle, Add 10 mL hydrochloric acid. Add 10 mL chloroform and Mix thoroughly (store at room temperature)

Extraction solution (80% hexane/20% chloroform) is made by: Add 80 mL hexane to 100 mL glass bottle. Add 20 mL chloroform, and Mix thoroughly (store at room temperature)

Procedure

The GC is operated under a gradient: 50° C. for 4 minute, 7° C./minute to 150° C. hold 3 min. 40° C./minute to 220° C. and hold 2 min with a total Run time of 25 minutes. The carrier gas is Helium with a Flow rate 4.0 mL/min. the makeup gas is helium with a Flow rate 30 mL/min. Hydrogen Flow rate 35 mL/min, Air Flow rate 340 ml/min, Velocity 55.3 cm/sec, Pressure 16.3 psi @ 50° C., Split Ratio 17:1. Split Flow 68 mL/min, Injection volume 1 μL, Inlet temperature 250° C. and Detector temperature 300° C.

Pentadecane is used as an internal standard. Prepare standard curves for each fatty acid based on concentration of standards using the GC software and linear regression function. Determine the amount (mg) of each fatty acid in each sample and the control using the GC calibration software. The assay acceptance criteria require the correlation coefficient for the fatty acid standard curves to be greater than 0.99. The concentration of the standard must be within historical range.

Samples are prepared as follows: Add <2 mL culture to a reaction vial. Dry samples in the SpeedVac with heat for approximately 60 mins. Add 3 mL methyl esterification solution. Add 10 μL internal standard solution. Incubate at 85° C. for 2 hrs. Remove from incubator and cool to room temperature. Add 1 mL deionized water. Add 2 mL extraction solution. Vortex vigorously for 1 minute and let mixture settle and separate. Remove organic layer (TOP) and place into vial insert within amber GC vial.

Using the mass spectrometer detector consists of using the same method of sample preparation as per the GC-FID. Additional tools of chemical entity identification are via the NIST08 library to verify free fatty acids (FFA). This is to match not only retention time with a standard, but target and qualifier ions to the standard using the mass spectrometer.

What is claimed is:

1. A genetically modified microorganism that produces a fatty acid or fatty acid derived product comprising (i) a genetic modification to overexpress a gene encoding an acetoacetyl-CoA synthase enzyme comprising Npht7, (ii) a deletion of a tesB gene and (iii) a genetic modification to overexpress a gene encoding AtTE thioesterase enzyme, wherein:

the fatty acid or fatty acid derived product is produced via a growing acetyl-CoA or fatty acyl-CoA chain;

the acetyl-CoA or fatty acyl-CoA chain is extended with at least one malonyl-CoA molecule;

and the fatty acid or fatty acid derived product is a mixture enriched for chain length C8 wherein the C8 chain comprises >10% of the total fatty acid product on mass (g) basis.

2. The genetically modified microorganism of claim 1, wherein a butyryl-CoA intermediate is made from acetyl-CoA and malonyl-CoA.

3. The genetically modified microorganism of claim 1, wherein the microorganism comprises a genetic modification to convert an acyl-CoA into a fatty acid derived product, including an alcohol, aldehyde, alkene, alkane or diacid.

4. The genetically modified microorganism of claim 1, wherein the microorganism comprises a genetic modification to overexpress an enzyme selected from the group consisting of an enoyl-CoA reductase, a ketoacyl-CoA reductase and a 3-hydroxyacyl-CoA dehydratase.

5. The genetically modified microorganism of claim 4, wherein the microorganism comprises a genetic modification to overexpress an enoyl-CoA reductase that can utilize the cofactor NADH, NADPH or both NADH and NADPH, or a ketoacyl-CoA reductase that can utilize the cofactor NADH, NADPH or both NADH and NADPH.

6. The genetically modified microorganism of claim 4, wherein the enoyl-CoA reductase is E.C. No. 1.3.1.9, the ketoacyl-CoA reductase is E.C. No. 1.1.1.157, and the 3-hydroxyacyl-CoA dehydratase is E.C. No. 4.2.1.17.

7. The genetically modified microorganism of claim 4, wherein the enoyl-CoA reductase comprises a trans-2-enoyl-CoA reductase, the ketoacyl-CoA reductase comprises a 3-hydroxybutyryl-CoA dehydrogenase, and the 3-hydroxyacyl-CoA dehydratase comprises an enoyl-CoA hydratase.

8. The genetically modified microorganism of claim 1, wherein:

the microorganism produces a fatty acid and the microorganism comprises a genetic modification to overexpress a fatty acyl-CoA thioesterase, or a fatty acyl-CoA phosphotransferase and a fatty acid kinase;

the microorganism produces a fatty aldehyde and the microorganism comprises a genetic modification to overexpress a fatty acyl-CoA reductase;

the microorganism produces a fatty alcohol and the microorganism comprises a genetic modification to overexpress an alcohol-forming acyl-CoA reductase, a long-chain-fatty-acyl-CoA reductase and an alcohol dehydrogenase, or an aldehyde dehydrogenase and an alcohol dehydrogenase; or the microorganism produces a diacid and the microorganism comprises a genetic modification to overexpress one or more enzymes capable of catalyzing the conversion of a fatty acid to a diacid via omega or terminal oxidation.

9. The genetically modified microorganism of claim 1, wherein the microorganism is selected from bacteria, cyanobacteria, filamentous fungi and yeasts.

* * * * *